US008067001B2

(12) United States Patent
Zhou et al.

(10) Patent No.: US 8,067,001 B2
(45) Date of Patent: *Nov. 29, 2011

(54) ANTIBODY SELECTIVE FOR A TUMOR NECROSIS FACTOR-RELATED APOPTOSIS-INDUCING LIGAND RECEPTOR AND USES THEREOF

(75) Inventors: Tong Zhou, Birmingham, AL (US); Kimishisa Ichikawa, Yokohama (JP); Robert P. Kimberly, Birmingham, AL (US); William J. Koopman, Indian Springs, AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/822,732

(22) Filed: Jun. 24, 2010

(65) Prior Publication Data

US 2011/0008324 A1 Jan. 13, 2011

Related U.S. Application Data

(63) Continuation of application No. 11/760,491, filed on Jun. 8, 2007, now Pat. No. 7,790,165, which is a continuation of application No. 10/275,180, filed as application No. PCT/US01/14151 on May 2, 2001, now Pat. No. 7,244,429.

(60) Provisional application No. 60/201,344, filed on May 2, 2000.

(51) Int. Cl.
*A61K 39/395* (2006.01)
*C07K 16/28* (2006.01)
*C07K 16/30* (2006.01)

(52) U.S. Cl. .............. 424/143.1; 424/138.1; 530/387.1; 530/388.22; 530/388.8; 530/350; 530/388.85

(58) Field of Classification Search .................. None
See application file for complete search history.

(56) References Cited

U.S. PATENT DOCUMENTS

| | | | |
|---|---|---|---|
| 6,072,047 A | 6/2000 | Rauch et al. |
| 6,252,050 B1 | 6/2001 | Ashkenazi et al. |
| 6,294,546 B1 | 9/2001 | Rosen et al. |
| 6,313,269 B1 | 11/2001 | Deen et al. |
| 6,342,363 B1 | 1/2002 | Ni et al. |
| 6,342,369 B1 | 1/2002 | Ashkenazi |
| 6,433,147 B1 | 8/2002 | Ni et al. |
| 6,461,823 B1 | 10/2002 | Ni et al. |
| 6,534,061 B1 | 3/2003 | Goddard et al. |
| 6,635,482 B1 | 10/2003 | Yu et al. |
| 6,872,568 B1 | 3/2005 | Ni et al. |
| 6,965,023 B2 | 11/2005 | Reed et al. |
| 7,105,640 B2 | 9/2006 | Desnoyers et al. |
| 7,279,160 B2 | 10/2007 | Zhou et al. |
| 7,476,383 B2 | 1/2009 | Zhou et al. |
| 7,704,502 B2 | 4/2010 | Zhou et al. |

| | | |
|---|---|---|
| 2002/0072091 A1 | 6/2002 | Ni et al. |
| 2002/0098550 A1 | 7/2002 | Ni et al. |
| 2003/0228309 A1 | 12/2003 | Salcedo et al. |

FOREIGN PATENT DOCUMENTS

| | | |
|---|---|---|
| EP | 0125023 | 11/1984 |
| WO | WO9907861 | 7/1990 |
| WO | WO9832856 | 7/1998 |
| WO | WO9835986 | 8/1998 |
| WO | WO9841629 | 9/1998 |
| WO | WO9846643 | 10/1998 |
| WO | WO9851793 | 11/1998 |
| WO | WO9902653 | 1/1999 |
| WO | WO9903992 | 1/1999 |
| WO | WO9909165 | 2/1999 |
| WO | WO9911791 | 3/1999 |
| WO | WO9912963 | 3/1999 |
| WO | WO9937684 | 7/1999 |
| WO | WO0066156 | 11/2000 |
| WO | WO0067793 | 11/2000 |
| WO | WO0073349 | 12/2000 |
| WO | WO0075191 | 12/2000 |
| WO | WO0119861 | 3/2001 |
| WO | WO0177342 | 10/2001 |
| WO | WO0183560 | 11/2001 |
| WO | WO02079377 | 10/2002 |

OTHER PUBLICATIONS

Mayer et al., Mitochondrial regulation of apoptosis, News Physiol. Sci. 18: 89-94, 2003.*
Ostrow et al., "Determination of complimentary therapy use in HIV-infected individuals receiving antiretroviral or anti-opportunistic agents," J. Acquir. Immune Defic. Syndr. Hum. Retrovirol. 15(2):115-20 (1997).
Pan et al., "The receptor for the cytotoxic ligand TRAIL," Science 276(5309):111-3 (1997).
Pan et al., "An antagonist decoy receptor and a death domain-containing receptor for TRAIL," Science 277 (5327):815-8 (1997).
Reichel et al., "Radiological changes in the cervical spine in rheumatoid arthritis-prognostic factors obtained by a cross-sectional study," Z. Rheumatol. 61(6):710-7 (2000). Rudikoff et al., "Single amino acid substitution altering antigen-binding specificity," Proc. Natl. Acad. Sci. USA 79:1979-83 (1982).
Schneider et al., "TRAIL receptors 1 (DR4) and 2 (DR5) signal FADD-dependent apoptosis and activate NF-kB," Immunity 7(6):831-6 (1997).
Seitz et al., "Pretreatment cytokine profiles of peripheral blood mononuclear cells and serum from patients with rheumatoid arthritis in different American college of rheumatology response groups to methotrexate," Rhemuatol. 30(1):28-35 (2003).
Sheridan et al., "Control of TRAIL-induced apoptosis by a family of signaling and decoy receptors," Science 277 (5327):818-21 (1997).
Silvestris et al., "Recent advances in understanding the pathogenesis of anemia in multiple myeloma" Int. J. Hematol. 78(2):121-5 (2003).

(Continued)

*Primary Examiner* — Lorraine Spector
*Assistant Examiner* — Claire Kaufman
(74) *Attorney, Agent, or Firm* — McKeon, Meunier, Carlin & Curfman

(57) ABSTRACT

An antibody of the invention interacts with human DR5 to produce agonistic or antagonistic effects downstream of the receptor including inhibition of cell proliferation and apoptosis. Nucleic acid sequences and amino acid sequences of anti-DR5 antibodies have been elucidated and vectors and cells containing and expressing these sequences have been generated. Methods and uses for the antibodies are detailed including treatment of apoptosis-related disease and treatment of dysregulated cell growth.

20 Claims, 38 Drawing Sheets

OTHER PUBLICATIONS

Solomon et al., "Management of glucocorticoid-induced osteoporosis in patients with rheumatoid arthritis: rates and predictors of care in an academic rheumatology practice," Arthritis Rheum. 46(12):3136-42 (2002).
Song et al., "Tumor necrosis factor-related apoptosis inducing ligand (TRAIL) is an inhibitor of autoimmune inflammation and cell cycle progression," 191(7):1095-1103 (2000).
Sprick et al., "FADD/MORTI and caspase-8 are recruited to TRAIL receptors 1 and 2 and are essential for apoptosis mediated by TRAIL receptor 2," Immunity 12:599-609 (2000).
Srivastava, "TRAIL/Apo-2L:Mechanism and clinical applications in cancer," Neoplasia 3(6):535-46 (2001).
Steiner et al., "Novel autoantibodies for the diagnosis of rheumatoid arthritis," Z. Rheumatol. 61(6):667-73 (2002).
Stites et al., eds. Basic and Clinical Immunology, 8th Ed., (Appleton & Lange:Norwalk, CT), p. 137 (1994).
Straughn et al., "Anti-tumor activity of TRA-8 anti-death receptor 5 (DRS) monoclonal antibody in combination with chemotherapy and radiation therapy in a cervical cancer model," Gynecol. Oncology 101(1):46-54 (2006).
Sun et al., "Specific cytotoxicity and immuno-regulation by EBV-specific CD4+ T cells," 42nd Abstract of Ann. Meet. Amer. Canc. Soc. Hematol., The Moscone Center, San Fran., CA Dec. 1-5, 2000.
Vane, "Aspirin and other anti-inflammatory drugs," Thorax 55(Suppl. 5):S3-S9 (2000).
Wajant et al., "Dominant-negative FADD inhibits TNFR60-, Fas/Apol-, and TRAIL-R/Apo2-mediated cell death but not gene induction," Curr. Biol. 8:113-6 (1998).
Walczak et al., "TRAIL-R2: a novel apoptosis-mediating receptor for TRAIL," EMBO 16(17):5386-97 (1997).
Walczak et al., "Tumoricidal activity of tumor necrosis factor-related apoptosis-inducing ligand in vivo," Nat. Med. 5:157-63 (1999).
Wiley et al., "Identification and characterization of a new member of the TNF family that induces apoptosis," Immunity 3(6):673-82 (1995).
Winter and Harris, "Humanized antibodies," Immunology Today 14(6):243-246 (1993).
Yamada et al., "TRAIL causes cleavage of bid by caspase-8 and loss of mitochondrial membrane potential resulting in apoptosis in BJAB cells," Biochem. Biophys. Res. Commun. 265:130-3 (1999).
Zamai et al., "Natural killer (NK) cell-mediated cytotoxicity: differential use of TRAIL and Fas ligand by immature and mature primary human NK cells," J. Exp. Med. 188(12):2375-80 (1998).
Zhang et al., "Rising level of serum sTRAIL and its recipient DR4 in patients with lupus-nephritis," Disi. Junyi. Daxue Xuebao. 24(11):1040-1 (2003).
Zhou et al., "Targeted radiotherapy potentiates the cytotoxicity of a novel anti-human DR5 monoclonal antibody in prostate cancer," Internat. J. Radiation Oncol. Biol. Phys. 54(2 Suppl.):224 (2002).
Adams et al., "Structural and funcational analysis of the interaction between agonist monoclonal antibody Apomab and the proapoptotic receptor DR5," Cell Death Diff. 15:751-61 (2008).
Lamminmaki et al., "Crystal structure of a recombinant anti-estradiol Fab fragment in complex with 17 Beta-estradiol," J. Biol. Chem. 276:36687-94 (2001).
MacCallum et al., "Antibody-antigen interactions: contact analysis and binding site topology," J. Mol. Biol. 262:732-45 (1996).
Arai et al., "Genomic organization and mutation analyses of the DR5/TRAIL receptor 2 gene in colorectal carcinomas," Cancer Letters 13392):197-204 (1998).
Ashkenzai et al., "Safety and antitumor activity of recombinant soluble Apo2 ligand," J. Clin. Invest. 104:155-62 (1999).
Bendele et al., "Effects of PEGylated soluble tumor necrosis factor receptor type I (PEG sTNF-RI) alone and in combination with methotrexate in adjuvant arthritic rats," Clin. Exp. Rheumatol. 17(5):553-60 (1999).
Berckmans et al., "Cell-derived microparticles in synovial fluid from inflamed arthritic joints support coagulation exclusively via a factor VII-dependent mechanism," Arthritis Rheum. 46(11):2857-66 (2002).
Bodmer et al., "TRAIL receptor-2 signals apoptosis through FADD and caspase-8," Nat. Cell Biol. 2:241-3 (2000).

Bonavida et al., "Selectivity of TRAIL-mediated apoptosis of cancer cells nd synergy with drugs: the trail to non-toxic cancer therapeutics (Review)" Int. J. Oncol. 15:793-802 (1999).
Bretz, et al., "Inflammatory cytokine regulation of TRAIL-mediated apoptosis in thyroid epithelial cells," Cell Death Diff. 9:274-86 (2002).
Buchsbaum et al., "Treatment of human breast cancer xenografts with monoclonal antibody against DR5 with or without chemotherapy inhibits tumor growth in nude mice," Proceed. Annual Meet. Amer. Assoc. Cancer Res. 43:1005-6 (Mar. 2002) (Abstract).
Buchsbaum et al., "Antitumor efficacy of TRA-8 anti-DR5 monoclonal antibody alone or in combination with chemotherapy and/or radiation therapy in a human breast cancer model," Clin. Canc. Res.9(10 Pt.1):3731-41 (2003).
Chaudhary et al., "Death receptor 5, a new member of the TNFR family, and DR4 induce FADD-dependent apoptosis and activate the NFkB pathway," Immunity 7(6):821-30 (1997).
Chinnaiyan et al., "Combined effect of tumor necrosis-factor related apoptosis-inducing ligand and ionizing radiation in breast cancer therapy," Proc. Natl. Acad. Sci. USA 97(4):1754-9 (2000).
Choy et al., "Therapeutic benefit of blocking interleukin-6 activity with an anti-interleukin-1 receptor monoclonal antibody in rheumatoid arthritis: A randomized, double blind, placebo-controlled, dose-escalation trial," Arthritis Rheum. 46(12):3143-50 (2002).
Chuntharapai et al., "Isotype-dependent inhibition of tumor growth in vivo by monoclonal antibodies to death receptor 4," J. Immunol. 166:4891-8 (2001).
Ciranni et al., "The 'Braids Lady' of Arezzo: a case of rheumatoid arthritis in a 16th century mummy," Clin. Exp. Rheumatol. 20(6):745-52 (2002).
Clarke et al., "reovirus-induced apoptosis is mediated by TRAIL," J. Virol. 74(17):8135-9 (2000).
Czuczman et al., "Treatment of patients with low-grade B-cell lymphoma with the combination of chimeric anti-CD20 monoclonal antibody and CHOP chemotherapy," J. Clin. Oncol. 17(1):268-76 (1999).
Degli-Esposti et al., "Cloning and characterization of TRAIL-R3, a novel member of the emerging TRAIL receptor family," J. Exp. Med. 186(7):1165-70 (1997).
Degli-Esposti et al., "The nvoel receptor TRAIL-R4 induces NF-kappaB and protects against TRAIL mediated apoptosis, yet retains an incomplete death domain," Immunity 7:813-20 (1997).
Desrosier et al., "Treatment with gemcitabine and TRA-8 anti-death-receptor-5 mAb reduces pancreatic adenocarcinoma cell viability in vitro and growth in vivo," J. Gastrointestinal Surg. 10(9):1291-1300 (2006).
Emery et al., "Osteoprotegerin is a receptor for the cytotoxic ligand TRAIL," J. Biol. Chem. 273(23):14363-7 (1998).
Fanger et al., "Human dendritic cells mediate cellular apoptosis via tumor-necrosis factor related apoptosis-inducing ligand (TRAIL)," J. Exp. Med. 190(8):1155-64 (1999).
Foote and Winter, "Antibody framework residues affecting the conformation of the hypervariable loops." J Mol. Biol. 224(2):487-99 (1992).
Fujisawa et al., "Therapeutic effect of the anti-fas antibody on arthritis in HTLV-1 tax transgenic mice," J. Clin. Invest. 98(2):271-8 (1996).
Gazada et al., "Gene expression changes in bone marrow cells from Diamond-Backfan anemia patients" Blood 104(11 pt.1):206A-207A (2004).
Gibson et al., "Increased expression of death receptors 4 and 5 synergizes the apoptosis response to combined treatment with etoposide and TRAIL," Mol. Cell. Biol. 20(1):205-12 (2000).
Griffith et al., "Functional analysis of TRAIL receptors using monoclonal antibodies," J. Immunol. 162:2597-2605 (1999).
Herr et al., "JNK/SAPK activity contributes to TRAIL-induced apoptosis," Cell Death Diff. 6:130-5 (1999).
Ichikawa et al., "Tumoricidal activity of a novel anti-human DR5 monoclonal antibody without hepatocyte cytotoxicity," Nature Med. 7(8):954-60 (2001).
Ichikawa et al., "Tumoricidal activity in the absence of hepatocyte cytotoxicity of a novel antihuman DR5 monoclonal antibody," FASEB J. 15(5):A1198 (2001).

Ichikawa et al., "TRAIL-R2 (DR5) mediates apoptosis of synovial fibroblasts in rheumatoid arthritis," J. Immunol. 171(2):1061-9 (2003).

Jeremias et al., "TRAIL induces apoptosis and activation of NF-kappaB," Eur. Cytokine Netw. 9:687-8 (1998).

Jo et al., "Apoptosis induced in normal human hepatocytes by tumor necrosis factor-related apoptosis-inducing ligand," Nat. Med. 6:564-7 (2000).

Keane et al., "Chemotherapy augments TRAIL-induced apoptosis in breast cell lines," Canc. Res. 59:734-41 (1999).

Kischkel et al., "Apo2L/TRAIL-dependent recruitment of endogenous FADD and caspase-8 to death receptors 4 and 5," Immunity 12:611-20 (2000).

Kuang et al., "FADD is required for DR4- and DR5-mediated apoptosis:lack of TRAIL-induced apoptosis in FADD-deficient mouse embryonic fibroblasts," J. Biol. Chem. 275:25065-8 (2000).

Lee et al., "Alterations of the DR5/TRAIL receptor 2 gene in non-small cell lung cancers," Canc. Res. 59:5683-6 (1999).

Lindbland et al., "Patients' view of priority setting for new medicines. A qualitative study of patients with rheumatoid arthritis," Scan. J. Rheumatol. 31(6):324-9 (2002).

Liu et al., "Trail R2 (DR5) is a novel, selective therapeutic target for rheumatoid arthritis," FASEB J. 16(5):A1047 (2002).

Lum et al., "Induction of cell death in human immunodeficiency virus-infected macrophages and resting memory CD4 T-cells by TRAIL/Apo2L," J. Virol. 75(22):11128-36 (2001).

MacFarlane et al., "Identification and molecular cloning of two novel receptors for the cytotoxic ligand TRAIL," J. Biol. Chem. 272(41):25417-20 (1997).

Madland et al., "Leukocyte protein calprotectin and outcome in rheumatoid arthritis. A longitudinal study," Scand. J. Rheumatol. 31(6):351-4 (2002).

Marsters et al., "A novel receptor for Apo2L/TRAIL contains a truncated death domain," Curr. Biol. 7(12):1003-6 (1997).

Meng et al., "Induction of cell death in breast cancer cells by anti-TRAIL R2/DR5 antibody alone and in combination with TRAIL," Amer. Assoc. Canc. Res., 91st Annual Meeting, Apr. 1-5, 2000: Abstract LB-27.

Merkesdal et al., "Current aspects of cost effectiveness of TNF-alpha blocking agents in patients with rheumatoid arthritis," Z. Rheumatol. 61(Supp. 2)II29-II32 (2002).

Mitsiades et al., "Ewing's sarcoma family tumors are sensitive to tumor necrosis factor-related apoptosis-inducing ligand and express death receptor 4 and death receptor 5," Canc. Res. 61:2704-12 (2001).

Mizutani et al., "Synergistic cytotoxicity and apoptosis by Apo-2 ligand and adriamycin against bladder cancer cells," Clin. Canc. Res. 5:2605-12 (1999).

Muhlenbeck et al., "TRAIL/Apo2L activates c-Jun NH2-terminal kinase (JNK) via caspase-dependent and caspase-independent pathways," J. Biol. Chem. 273:33091-8 (1998).

Ohtsuka et al., "Role of JNK/p38 signaling pathway in DR5-mediated apoptosis," FASEB J. 15(4):A709 (2001).

Ohtsuka et al., "Bisindolymalemide VIII enhances DR5-mediated apoptosis through the MKK4/JNK/p38 kinase and the mitochondrial pathways," J. Biol. Chem. 277(32):29294-303 (2002).

Ohtsuka et al., "Synergistic induction of tumor cell apoptosis by death receptor antibody and chemotherapy agent through JNK/p38 and mitochondrial death pathway," Oncogene 22(13):2034-44 (2003).

* cited by examiner

FIG - 1A
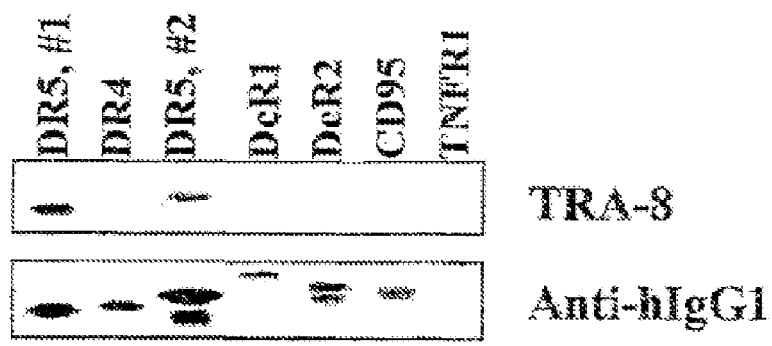
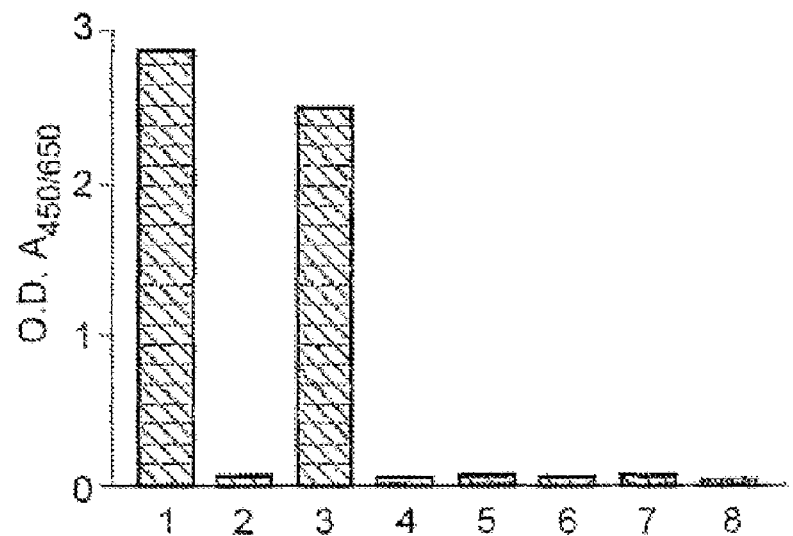
FIG - 1C
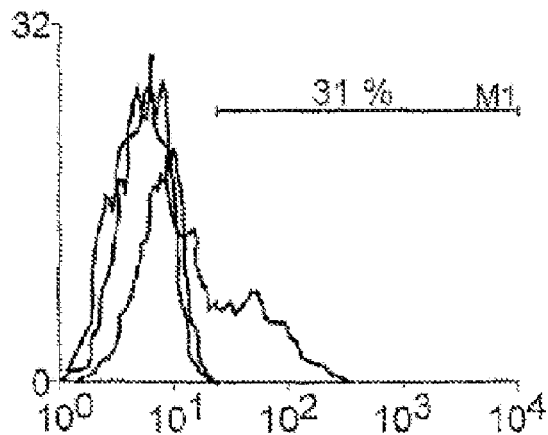

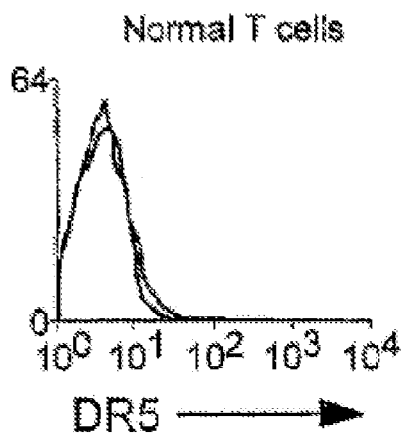
FIG - 2A-1 Normal T cells
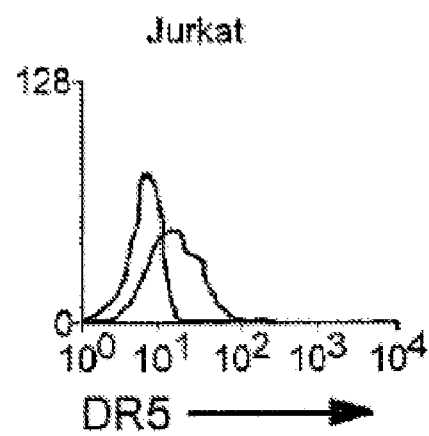
FIG - 2A-2 Jurkat
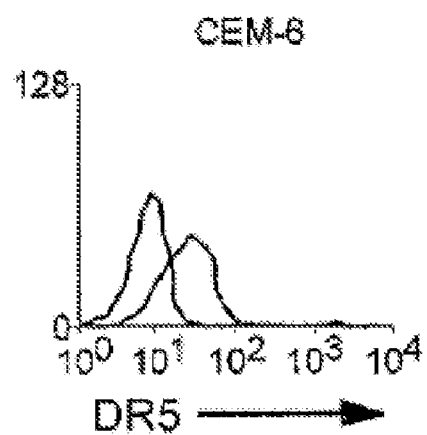
FIG - 2A-3 CEM-6
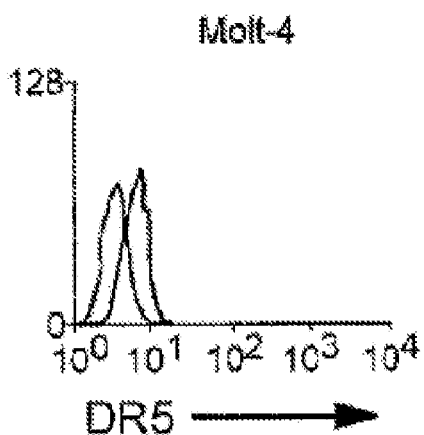
FIG - 2A-4 Molt-4
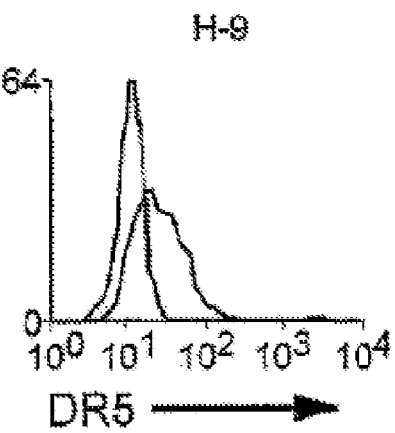
FIG - 2A-5 H-9

Normal astrocytes

SH683

U87

D54

1321N1

U-373MG

CH-235MG

U87

SMK1

1321N1

FIG - 5A
*Normal tissue homogenates*
FIG - 5B
*Cancer tissue homogenates*
FIG - 5C
Breast
Lung
Spleen
FIG - 5D
Breast carcinoma
Lung cancer
Lymphoma

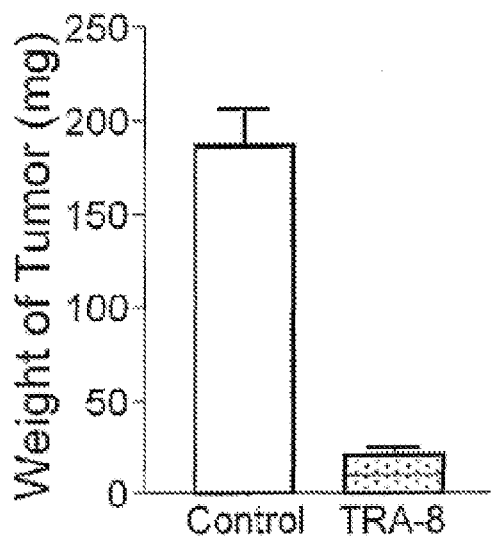
FIG - 6A
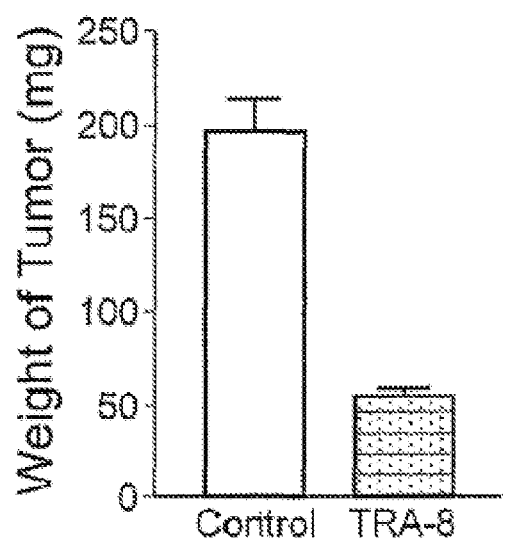
FIG - 6B
FIG - 6C
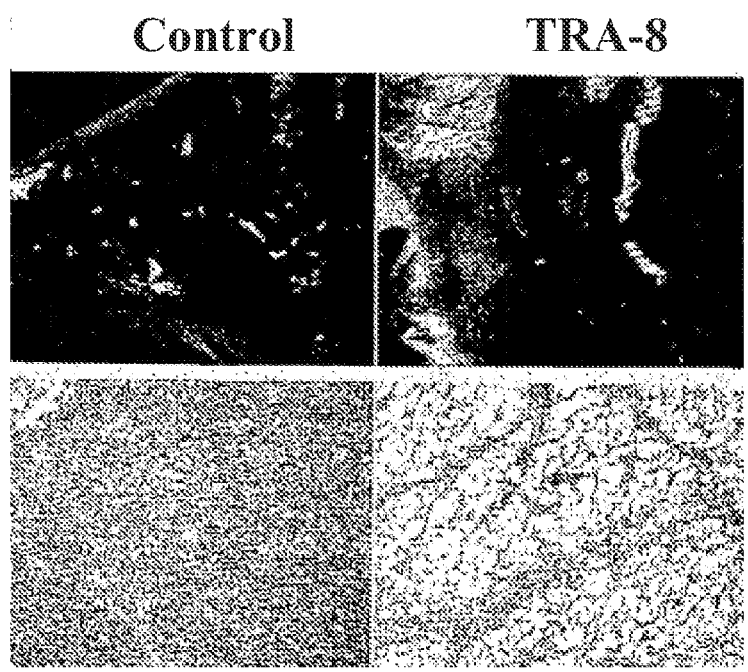

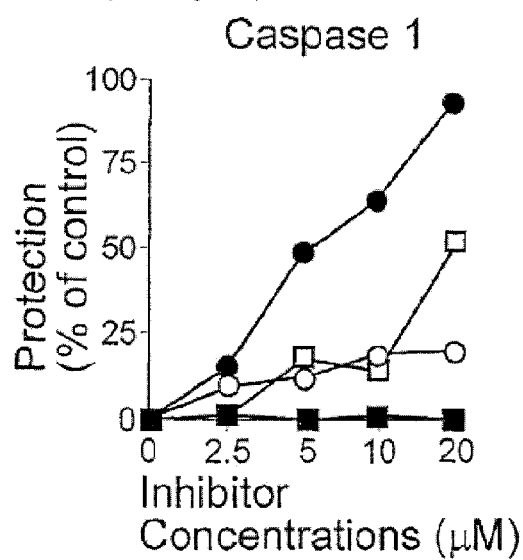
FIG - 9A Caspase 1
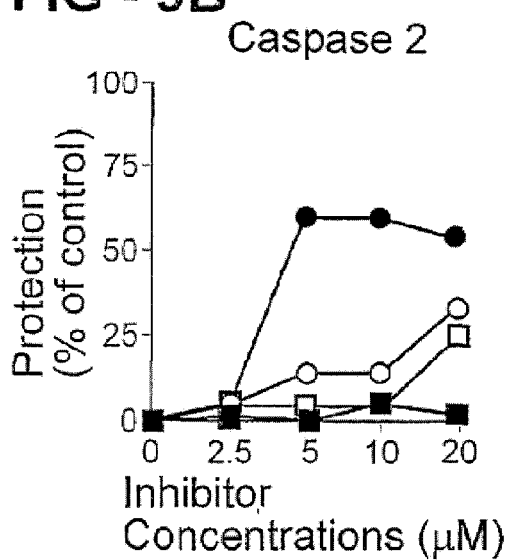
FIG - 9B Caspase 2
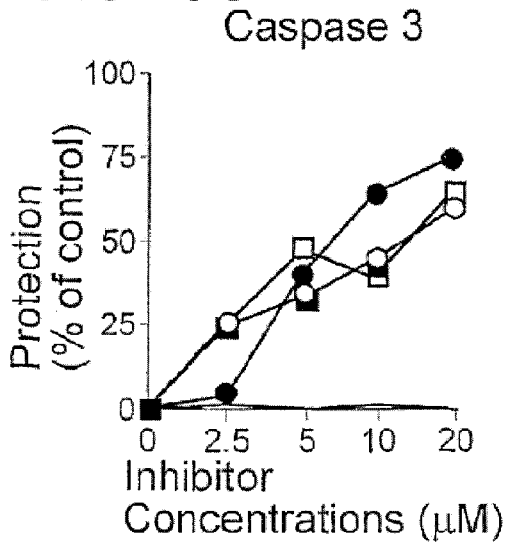
FIG - 9C Caspase 3
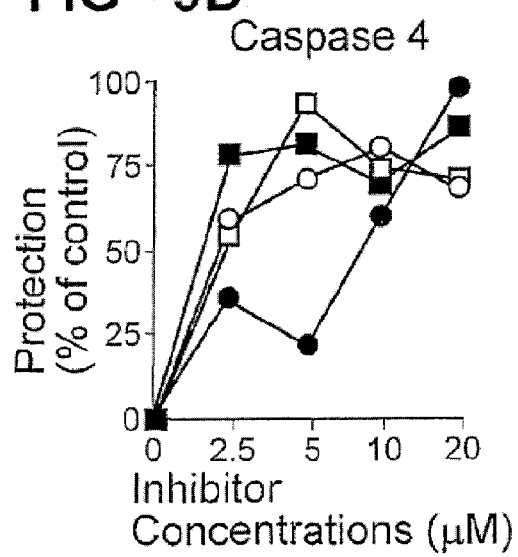
FIG - 9D Caspase 4

Concentration of TNF-α (x1), TRAIL (x5), TRA-8 (x5). (ng/ml)

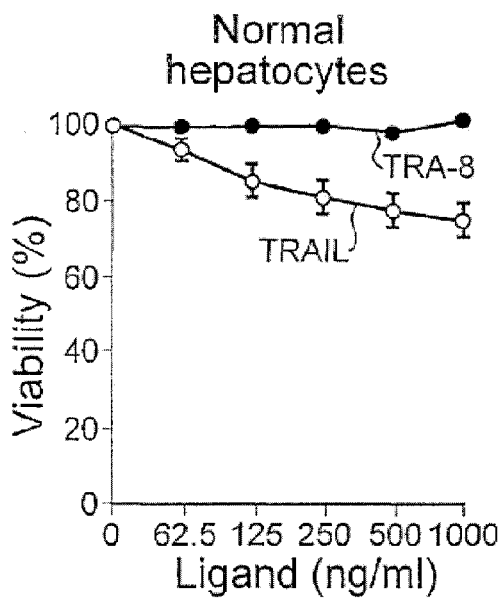
FIG - 12D-1 Normal hepatocytes
FIG - 12D-2 Hepatocellular carcinoma
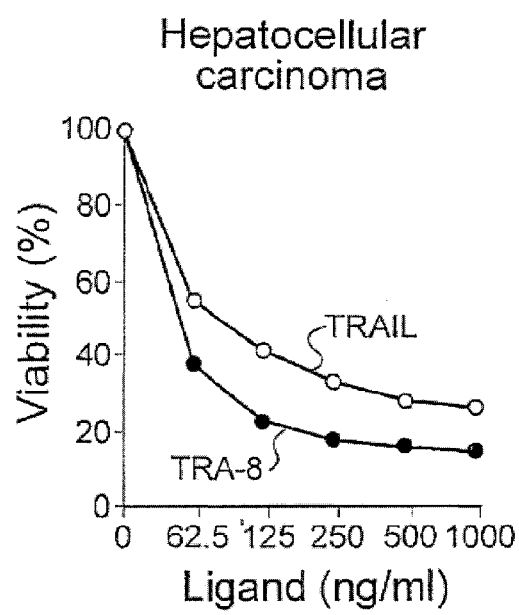
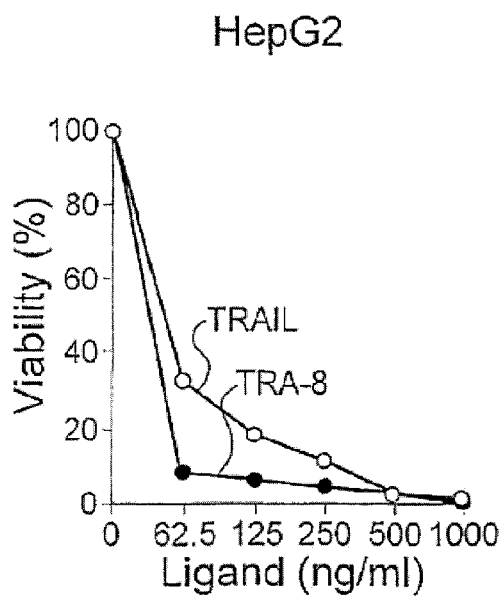
FIG - 12D-3 HepG2
FIG - 12D-4
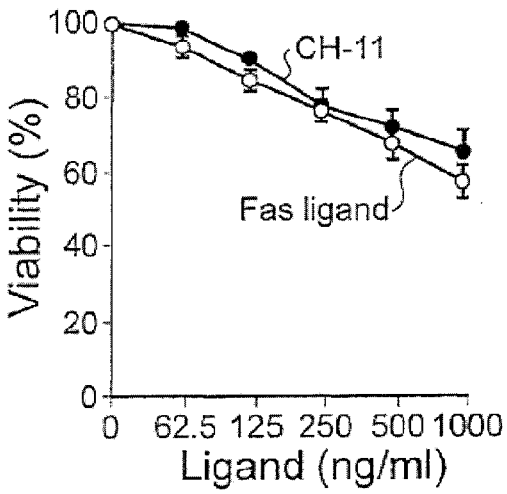

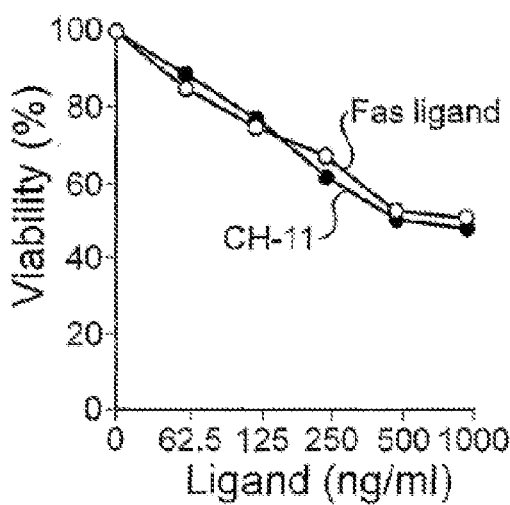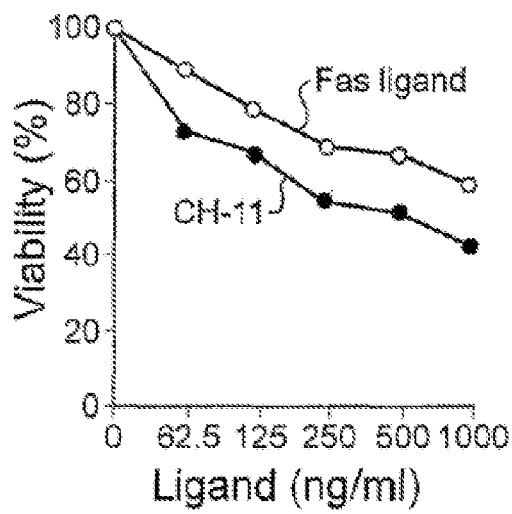
FIG - 12D-5
FIG - 12D-6
FIG - 13A
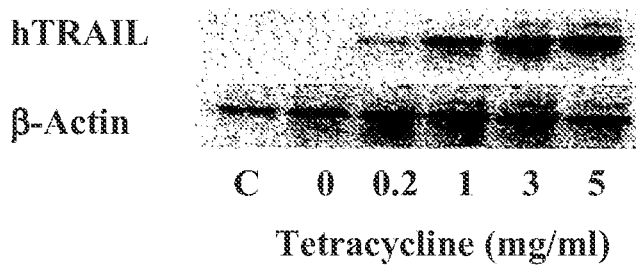
FIG - 13B
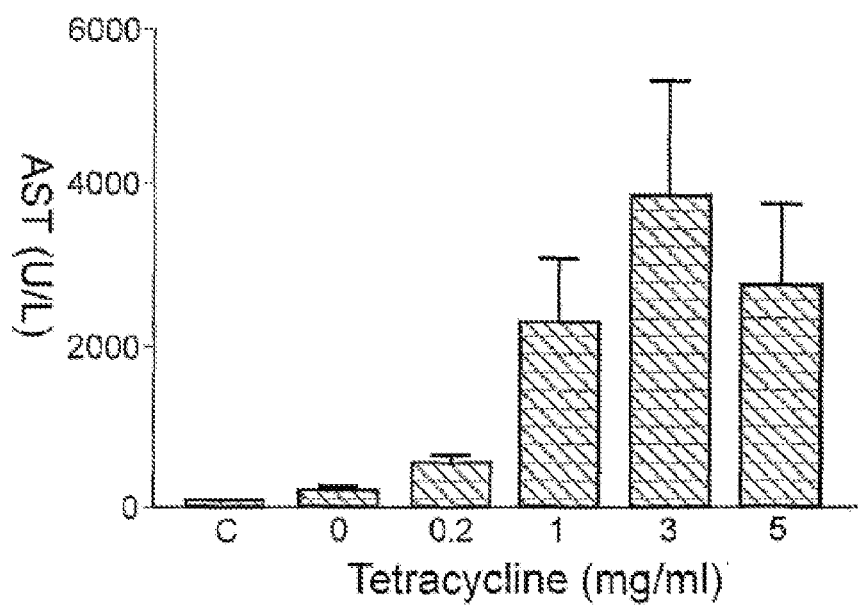

FIG - 13C-1
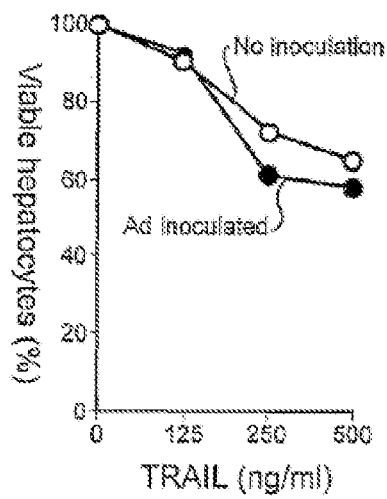
FIG - 13C-2
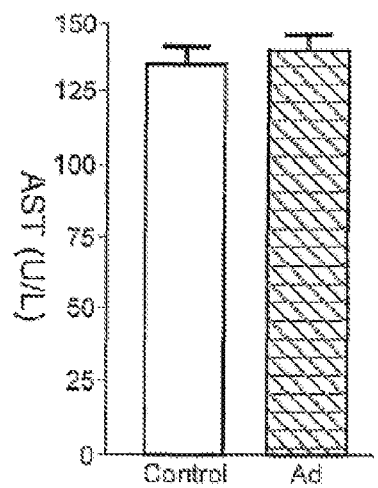
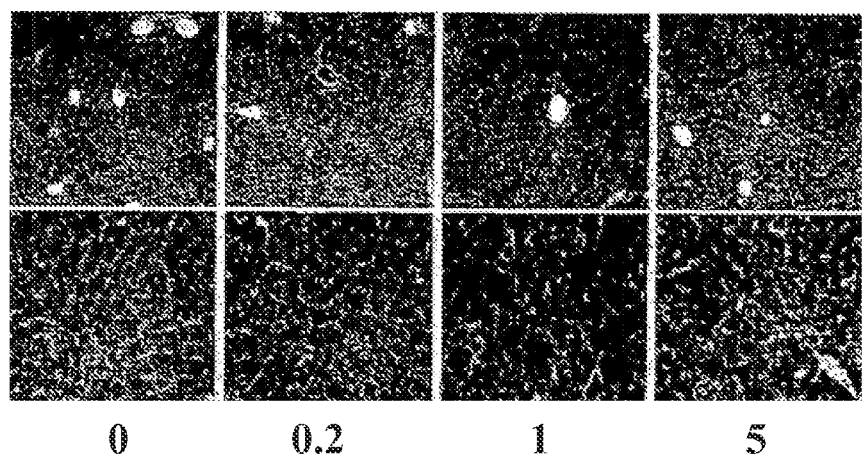
FIG - 13D  Tetracycline (mg/ml)
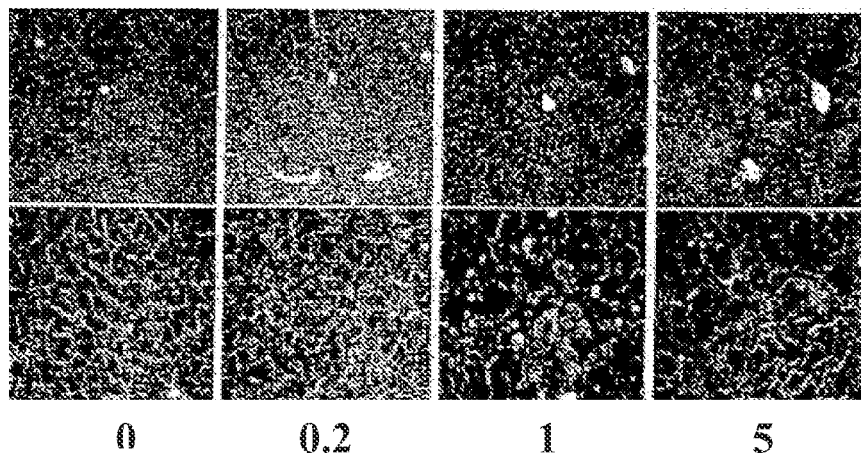
FIG - 13E  Tetracycline (mg/ml)

Primary

Anti-CD3

Con-A

Primary

Anti-µ

LPS

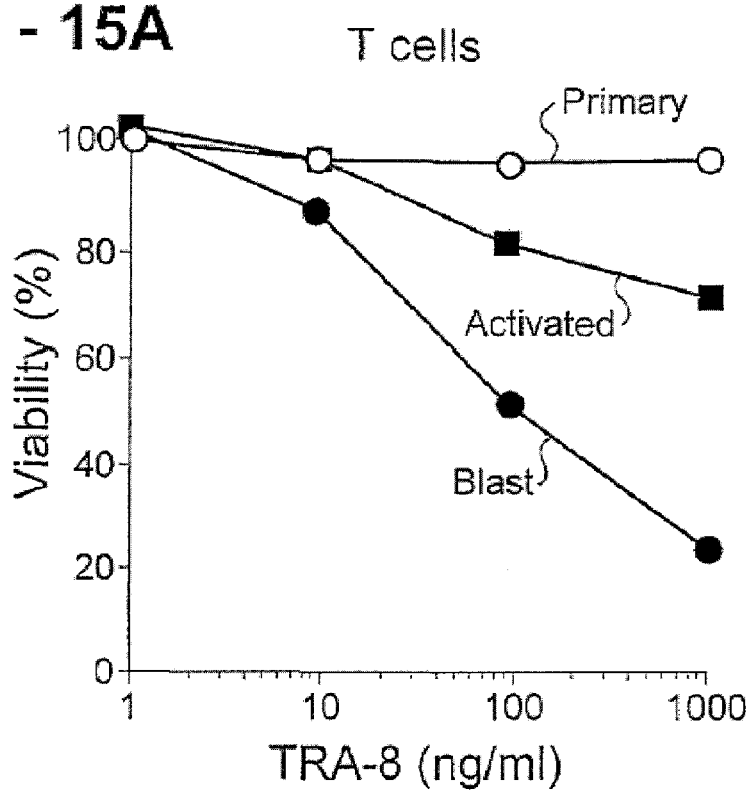
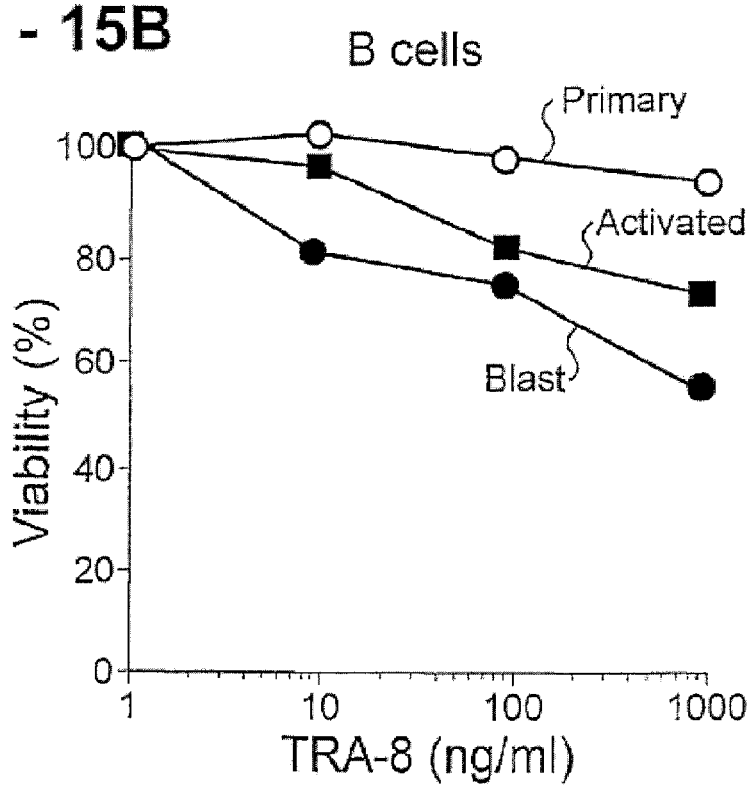

FIG - 16
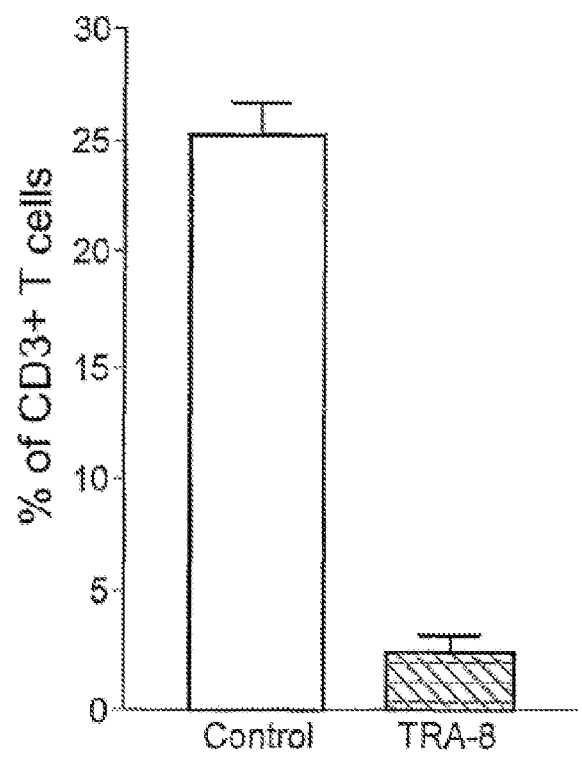
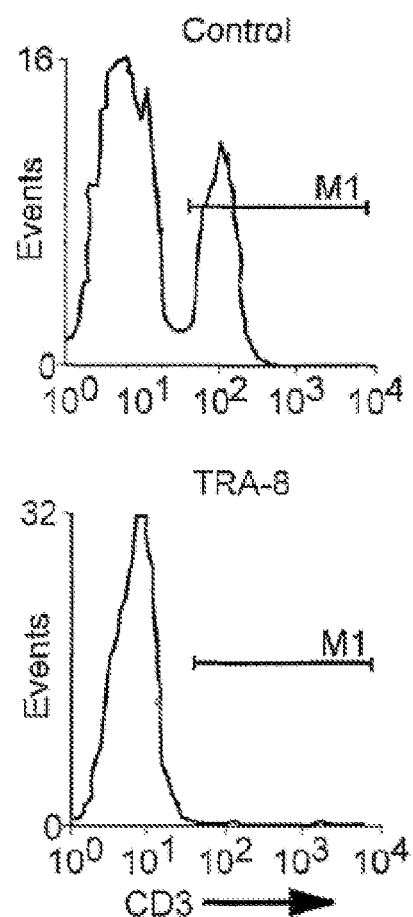
FIG - 17
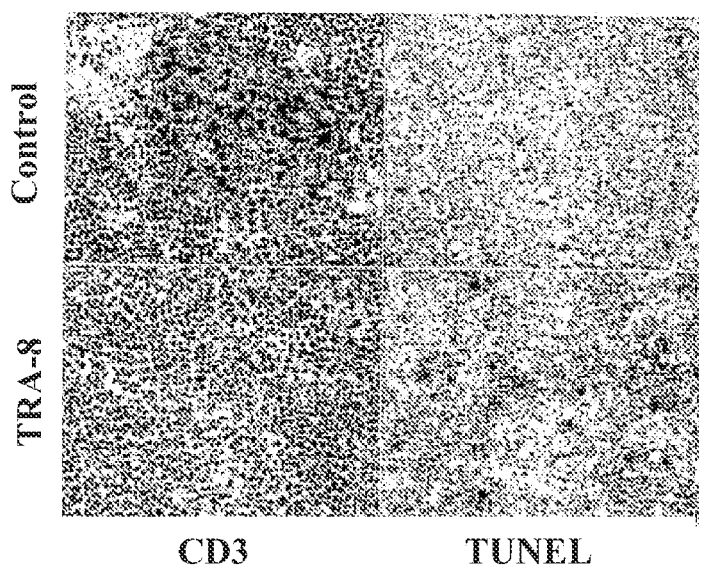

SEQUENCE LISTING

```
<160> NUMBER OF SEQ ID NOS: 102

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 1
gacgatgccc gatctacttt aaggg                                          25

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 2
```

```
ccactgggtg atgttggatg gg                                              22
```

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 3

```
ggatccgtgg acacattcga tgtc                                            24
```

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 4

```
Glu Val Met Leu Val Glu Ser Gly Gly Gly Leu Val Lys Pro Gly Gly
1               5                   10                  15

Ser Leu Lys Leu
            20
```

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 5

```
Asp Ile Val Met Thr Gln Ser His Lys Phe Met Ser Thr Ser Val Gly
1               5                   10                  15

Asp Arg Val Ser
            20
```

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 6

```
cagcactgaa cacggacccc                                                 20
```

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 7

```
aaaggtaatt tattgagaag                                                 20
```

<210> SEQ ID NO 8
<211> LENGTH: 20
<212> TYPE: DNA

```
<213> ORGANISM: Artificial Sequence
<220> FEATURE:
<223> OTHER INFORMATION: Description of Artificial Sequence:/Note =
      Synthetic Construct

<400> SEQUENCE: 8
cctcaccatg aacttcgggc                                                     20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 9
ctgttgtatg cacatgagac                                                     20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 10
gaagtgatgc tggtggagtc                                                     20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 11
agtgtgaagt gatgctggtg                                                     20

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 12
tttaccagga gagtgggaga g                                                   21

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 13
tgcagagaca gtgaccagag                                                     20

<210> SEQ ID NO 14
<211> LENGTH: 20
<212> TYPE: DNA
<213> ORGANISM: Artificial Sequence
<220> FEATURE:
```

```
<223> OTHER INFORMATION: Description of Artificial Sequence:/Note =
      Synthetic Construct

<400> SEQUENCE: 14
tgttcaggac cagcatgggc                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 15
aagacatttt ggattctaac                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 16
tatcatgaag tctttgtatg                                              20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 17
gatggagaca cattctcagg                                              20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 18
gacattgtga tgacccagtc                                              20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 19
ttaacactca ttcctgttga                                              20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:/Note =
      Synthetic Construct
```

```
<400> SEQUENCE: 20
gactgggtca tcacaatgtc                                                    20

<210> SEQ ID NO 21
<211> LENGTH: 1398
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 21
atgaacttcg ggctcagctt gattttcctt gtccttgttt taaaaggtgt ccagtgtgaa        60
gtgatgctgg tggagtctgg gggaggctta gtgaagcctg gagggtccct gaaactctcc      120
tgtgcagcct ctggattcac tttcagtagc tatgtaatgt cttgggttcg ccagactccg      180
gagaagaggc tggagtgggt cgcaaccatt agtagtggtg gtagttacac ctactatcca      240
gacagtgtga aggggcgatt caccatctcc agagacaatg ccaagaacac cctgtacctg      300
caaatgagca gtctgaggtc tgaggacacg gccatgtatt actgtgcaag acgggggac      360 tctatgatta cgacggacta ctggggccaa ggcaccactc tcacagtctc ctcagccaaa      420
acgacacccc catctgtcta tccactggcc cctggatctg ctgcccaaac taactccatg      480
gtgaccctgg gatgcctggt caagggctat ttccctgagc cagtgacagt gacctggaac      540
tctggatccc tgtccagcgg tgtgcacacc ttcccagctg tcctgcagtc tgacctctac      600
actctgagca gctcagtgac tgtcccctcc agcacctggc ccagcgagac cgtcacctgc      660
aacgttgccc acccgccag cagcaccaag gtggacaaga aaattgtgcc cagggattgt       720
ggttgtaagc cttgcatatg tacagtccca gaagtatcat ctgtcttcat cttcccccca      780
aagcccaagg atgtgctcac cattactctg actcctaagg tcacgtgtgt tgtggtagac      840
atcagcaagg atgatcccga ggtccagttc agctggtttg tagatgatgt ggaggtgcac      900
acagctcaga cgcaaccccg ggaggagcag ttcaacagca cttccgctc agtcagtgaa       960 cttcccatca tgcaccagga ctggctcaat ggcaaggagt tcaaatgcag ggtcaacagt     1020
gcagctttcc ctgcccccat cgagaaaacc atctccaaaa ccaaaggcag accgaaggct     1080
ccacaggtgt acaccattcc acctcccaag gagcagatgg ccaaggataa agtcagtctg     1140
acctgcatga taacagactt cttccctgaa gacattactg tggagtggca gtggaatggg     1200
cagccagcgg agaactacaa gaacactcag cccatcatgg acacagatgg ctcttacttc     1260
gtctacagca agctcaatgt gcagaagagc aactgggagg caggaaatac tttcacctgc     1320
tctgtgttac atgagggcct gcacaaccac catactgaga gagcctctc ccactctcct      1380 ggtaaaaatc actagtga                                                   1398

<210> SEQ ID NO 22
<211> LENGTH: 705
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 22
atgaagtctt tgtatgtgtt agtgtataca cattatctgt ttctgtttgc aggtgttgaa       60
ggagacattg tgatgaccca gtctcacaaa ttcatgtcca catcagtagg agacagggtc      120
agcatcacct gcaaggccag tcaggatgtg gtactgctg tagcctggta tcaacagaaa       180
```

```
ccagggcaat tcctaaaact actgatttac tgggcatcca cccggcacac tggagtccct    240
gatcgcttca caggcagtgg atctgggaca gatttcactc tcaccattag caatgtgcag    300
tctgaagact tggcagatta tttctgtcag caatatagca gctatcggac gttcggtgga    360
ggcaccaagc tggaaatcaa acgggctgat gctgcaccaa ctgtatccat cttcccacca    420
tccagtgagc agttaacatc tggaggtgcc tcagtcgtgt gcttcttgaa caacttctac    480
cccaaagaca tcaatgtcaa gtggaagatt gatggcagtg aacgacaaaa tggcgtcctg    540
aacagttgga ctgatcagga cagcaaagac agcacctaca gcatgagcag cacccctcacg    600 ttgaccaagg acgagtatga acgacataac agctatacct gtgaggccac tcacaagaca    660
tcaacttcac ccattgtcaa gagcttcaac aggaatgagt gttaa                    705
```

```
<210> SEQ ID NO 23
<211> LENGTH: 464
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 23
```

```
Met Asn Phe Gly Leu Ser Leu Ile Phe Leu Val Leu Val Leu Lys Gly
1               5                   10                  15

Val Gln Cys Glu Val Met Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Ser Tyr Val Met Ser Trp Val Arg Gln Thr Pro Glu Lys Arg Leu
    50                  55                  60

Glu Trp Val Ala Thr Ile Ser Ser Gly Gly Ser Tyr Thr Tyr Tyr Pro
65                  70                  75                  80

Asp Ser Val Lys Gly Arg Phe Thr Ile Ser Arg Asp Asn Ala Lys Asn
                85                  90                  95

Thr Leu Tyr Leu Gln Met Ser Ser Leu Arg Ser Glu Asp Thr Ala Met
            100                 105                 110

Tyr Tyr Cys Ala Arg Arg Gly Asp Ser Met Ile Thr Thr Asp Tyr Trp
        115                 120                 125

Gly Gln Gly Thr Thr Leu Thr Val Ser Ser Ala Lys Thr Thr Pro Pro
    130                 135                 140

Ser Val Tyr Pro Leu Ala Pro Gly Ser Ala Ala Gln Thr Asn Ser Met
145                 150                 155                 160

Val Thr Leu Gly Cys Leu Val Lys Gly Tyr Phe Pro Glu Pro Val Thr
                165                 170                 175

Val Thr Trp Asn Ser Gly Ser Leu Ser Ser Gly Val His Thr Phe Pro
            180                 185                 190

Ala Val Leu Gln Ser Asp Leu Tyr Thr Leu Ser Ser Ser Val Thr Val
        195                 200                 205

Pro Ser Ser Thr Trp Pro Ser Glu Thr Val Thr Cys Asn Val Ala His
    210                 215                 220

Pro Ala Ser Ser Thr Lys Val Asp Lys Lys Ile Val Pro Arg Asp Cys
225                 230                 235                 240

Gly Cys Lys Pro Cys Ile Cys Thr Val Pro Glu Val Ser Ser Val Phe
                245                 250                 255

Ile Phe Pro Pro Lys Pro Lys Asp Val Leu Thr Ile Thr Leu Thr Pro
            260                 265                 270
```

-continued

```
Lys Val Thr Cys Val Val Asp Ile Ser Lys Asp Asp Pro Glu Val
            275                 280                 285

Gln Phe Ser Trp Phe Val Asp Asp Val Glu Val His Thr Ala Gln Thr
290                 295                 300

Gln Pro Arg Glu Glu Gln Phe Asn Ser Thr Phe Arg Ser Val Ser Glu
305                 310                 315                 320

Leu Pro Ile Met His Gln Asp Trp Leu Asn Gly Lys Glu Phe Lys Cys
            325                 330                 335

Arg Val Asn Ser Ala Ala Phe Pro Ala Pro Ile Glu Lys Thr Ile Ser
            340                 345                 350

Lys Thr Lys Gly Arg Pro Lys Ala Pro Gln Val Tyr Thr Ile Pro Pro
            355                 360                 365

Pro Lys Glu Gln Met Ala Lys Asp Lys Val Ser Leu Thr Cys Met Ile
            370                 375                 380

Thr Asp Phe Phe Pro Glu Asp Ile Thr Val Glu Trp Gln Trp Asn Gly
385                 390                 395                 400

Gln Pro Ala Glu Asn Tyr Lys Asn Thr Gln Pro Ile Met Asp Thr Asp
            405                 410                 415

Gly Ser Tyr Phe Val Tyr Ser Lys Leu Asn Val Gln Lys Ser Asn Trp
            420                 425                 430

Glu Ala Gly Asn Thr Phe Thr Cys Ser Val Leu His Glu Gly Leu His
            435                 440                 445

Asn His His Thr Glu Lys Ser Leu Ser His Ser Pro Gly Lys Asn His
            450                 455                 460

<210> SEQ ID NO 24
<211> LENGTH: 234
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 24

Met Lys Ser Leu Tyr Val Leu Val Tyr Thr His Tyr Leu Phe Leu Phe
1               5                   10                  15

Ala Gly Val Glu Gly Asp Ile Val Met Thr Gln Ser His Lys Phe Met
            20                  25                  30

Ser Thr Ser Val Gly Asp Arg Val Ser Ile Thr Cys Lys Ala Ser Gln
        35                  40                  45

Asp Val Gly Thr Ala Val Ala Trp Tyr Gln Gln Lys Pro Gly Gln Ser
    50                  55                  60

Pro Lys Leu Leu Ile Tyr Trp Ala Ser Thr Arg His Thr Gly Val Pro
65                  70                  75                  80

Asp Arg Phe Thr Gly Ser Gly Ser Gly Thr Asp Phe Thr Leu Thr Ile
            85                  90                  95

Ser Asn Val Gln Ser Glu Asp Leu Ala Asp Tyr Phe Cys Gln Gln Tyr
            100                 105                 110

Ser Ser Tyr Arg Thr Phe Gly Gly Gly Thr Lys Leu Glu Ile Lys Arg
            115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175
```

```
Asn Gly Val Leu Asn Ser Trp Thr Asp Gln Asp Ser Lys Asp Ser Thr
            180                 185                 190
Tyr Ser Met Ser Ser Thr Leu Thr Leu Thr Lys Asp Glu Tyr Glu Arg
        195                 200                 205
His Asn Ser Tyr Thr Cys Glu Ala Thr His Lys Thr Ser Thr Ser Pro
    210                 215                 220
Ile Val Lys Ser Phe Asn Arg Asn Glu Cys
225                 230

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 25

Ser Tyr Val Met Ser
1               5

<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 26

Thr Ile Ser Ser Gly Gly Ser Tyr Thr Tyr Tyr Pro Asp Ser Val Lys
1               5                   10                  15

Gly

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 27

Arg Gly Asp Ser Met Ile Thr Thr Asp Tyr
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 28

Lys Ala Ser Gln Asp Val Gly Thr Ala Val Ala
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence:/Note =
      Synthetic Construct
```

```
<400> SEQUENCE: 29

Trp Ala Ser Thr Arg His Thr
1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 30

Gln Gln Tyr Ser Ser Tyr Arg Thr
1               5

<210> SEQ ID NO 31
<211> LENGTH: 119
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 31

Glu Val Met Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Val Met Ser Trp Val Arg Gln Ala Pro Gly Lys Gly Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Asp Ser Met Ile Thr Thr Asp Tyr Trp Gly Gln Gly
            100                 105                 110

Thr Leu Val Thr Val Ser Ser
        115

<210> SEQ ID NO 32
<211> LENGTH: 80
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 32
ttggataagc ttggcttgac ctcaccatgg gatggagctg tatcatcctc ttcttggtag    60
caacagctac aggtgtccac                                                80

<210> SEQ ID NO 33
<211> LENGTH: 80
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 33
```

```
tctgaagtaa tgctggtgga gtctgggga ggcttagtac agcctggagg gtccctgaga    60
ctctcctgtg cagcctctgg                                              80
```

<210> SEQ ID NO 34
<211> LENGTH: 80
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 34

```
attcactttc agtagttatg taatgtcttg ggttcggcag gcaccaggga agggtctgga    60
gtgggttgca accattagta                                               80
```

<210> SEQ ID NO 35
<211> LENGTH: 80
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 35

```
gtggtggtag ttacacctac tatccagaca gtgtgaaggg ccgattcacc atctccagag    60
acaatgccaa gaacaccctg                                               80
```

<210> SEQ ID NO 36
<211> LENGTH: 80
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 36

```
tatctgcaaa tgaacagtct gagagcagag gacacggctg tttattactg tgcaagaagg    60
ggtgactcta tgattacgac                                               80
```

<210> SEQ ID NO 37
<211> LENGTH: 64
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 37

```
ggactactgg ggccaaggga ccctggtcac agtctcctca gcctccacca agggcccatc    60
ggtc                                                                64
```

<210> SEQ ID NO 38
<211> LENGTH: 60
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 38

```
ctaccaagaa gaggatgata cagctccatc ccatggtgag gtcaagccaa gcttatccaa    60
```

<210> SEQ ID NO 39
<211> LENGTH: 80

```
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 39
tctcagggac cctccaggct gtactaagcc tcccccagac tccaccagca ttacttcaga    60
gtggacacct gtagctgttg                                                80

<210> SEQ ID NO 40
<211> LENGTH: 80
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 40
tccagaccct ccctggtgc ctgccgaacc caagacatta cataactact gaaagtgaat    60
ccagaggctg cacaggagag                                                80

<210> SEQ ID NO 41
<211> LENGTH: 80
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 41
ctctggagat ggtgaatcgg cccttcacac tgtctggata gtaggtgtaa ctaccaccac    60
tactaatggt tgcaacccac                                                80

<210> SEQ ID NO 42
<211> LENGTH: 80
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 42
ccttcttgca cagtaataaa cagccgtgtc ctctgctctc agactgttca tttgcagata    60
cagggtgttc ttggcattgt                                                80

<210> SEQ ID NO 43
<211> LENGTH: 84
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 43
gaccgatggg cccttggtgg aggctgagga gactgtgacc aggtcccctt ggccccagta    60
gtccgtcgta atcatagagt cacc                                           84

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence:/Note =
      Synthetic Construct
```

<400> SEQUENCE: 44
ttggataagc ttggcttgac                                                    20

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 45
gaccgatggg cccttggtgg a                                                  21

<210> SEQ ID NO 46
<211> LENGTH: 213
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 46

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Arg Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 47
<211> LENGTH: 34
<212> TYPE: DNA
<213> ORGANISM: Artificial Sequence
<220> FEATURE:
<223> OTHER INFORMATION: Description of Artificial Sequence:/Note =
      Synthetic Construct

```
<400> SEQUENCE: 47
cccaagctta agaagcatcc tctcatctag ttct                              34

<210> SEQ ID NO 48
<211> LENGTH: 45
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 48
cccgaattct tactaacact ctcccctgtt gaagctcttt gtgac                  45

<210> SEQ ID NO 49
<211> LENGTH: 60
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 49
gtcccccaca gatgcagaca aagaacttgg agattgggtc atcacaatgt caccagtgga  60

<210> SEQ ID NO 50
<211> LENGTH: 48
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 50
ccaagttctt tgtctgcatc agtaggagac agggtcacca tcacctgc               48

<210> SEQ ID NO 51
<211> LENGTH: 57
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 51
agtgtgccgg gtggatgccc agtaaatcag tagtttagga gctttccctg gtttctg     57

<210> SEQ ID NO 52
<211> LENGTH: 48
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 52
tgggcatcca cccggcacac tggggtccca agcaggttta gtggcagt               48

<210> SEQ ID NO 53
<211> LENGTH: 63
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 53
```

```
ataactacta tattgctgac agtaataggt tgcaaaatcc tccggctgca gactagagat    60
ggt                                                                 63
```

<210> SEQ ID NO 54
<211> LENGTH: 63
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 54

```
cagcaatata gcagctatcg gacgttcggt caaggcacca aggtggaaat caaacggact    60
gtg                                                                 63
```

<210> SEQ ID NO 55
<211> LENGTH: 711
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 55

```
atggagacag acacaatcct gctatgggtg ctgctgctct ggttccagg ctccactggt     60 gacattgtga tgacccaatc tccaagttct ttgtctgcat ctgtggggga cagggtcacc   120
atcacctgca aggccagtca ggatgtgggt actgctgtag cctggtatca acagaaacca   180
gggaaagctc ctaaactact gatttactgg gcatccaccc ggcacactgg ggtcccaagc   240
aggtttagtg gcagtgggtc tgggacagac ttcacccctca ccatctctag tctgcagccg   300
gaggattttg caacctatta ctgtcagcaa tatagtagtt atcggacgtt cggtcaaggc   360
accaaggtgg aaatcaaacg gactgtggct gcaccatctg tcttcatctt cccgccatct   420
gatgagcagt tgaaatctgg aactgcctct gttgtgtgcc tgctgaataa cttctatccc   480
agagaggcca agtacagtg gaaggtggat aacgccctcc aatcgggtaa ctcccaggag   540
agtgtcacag agcaggacag caaggacagc acctacagcc tcagcagcac cctgacgctg   600
agcaaagcag actacgagaa acacaaagtc tacgcctgcg aagtcaccca tcagggcctg   660
agctcgcccg tcacaaagag cttcaacagg ggagagtgtt agtaagaatt c           711
```

<210> SEQ ID NO 56
<211> LENGTH: 119
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 56

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Val Met Ser Trp Val Arg Gln Ala Pro Gly Lys Gly Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Arg Gly Asp Ser Met Ile Thr Thr Asp Tyr Trp Gly Gln Gly
            100                 105                 110

Thr Leu Val Thr Val Ser Ser
        115
```

<210> SEQ ID NO 57
<211> LENGTH: 80
<212> TYPE: DNA
<213> ORGANISM: Artificial Sequence
<220> FEATURE:
<223> OTHER INFORMATION: Description of Artificial Sequence:/Note = Synthetic Construct

<400> SEQUENCE: 57

```
tctgaagtac agctggtgga gtctggggga ggcttagtac agcctggagg gtccctgaga      60
ctctcctgtg cagcctctgg                                                  80
```

<210> SEQ ID NO 58
<211> LENGTH: 80
<212> TYPE: DNA
<213> ORGANISM: Artificial Sequence
<220> FEATURE:
<223> OTHER INFORMATION: Description of Artificial Sequence:/Note = Synthetic Construct

<400> SEQUENCE: 58

```
tctcagggac cctccaggct gtactaagcc tcccccagac tccaccagct gtacttcaga      60
gtggacacct gtagctgttg                                                  80
```

<210> SEQ ID NO 59
<211> LENGTH: 119
<212> TYPE: PRT
<213> ORGANISM: Artificial Sequence
<220> FEATURE:
<223> OTHER INFORMATION: Description of Artificial Sequence:/Note = Synthetic Construct

<400> SEQUENCE: 59

```
Glu Val Met Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Val Met Ser Trp Val Arg Gln Ala Pro Gly Lys Gly Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Arg Arg Gly Asp Ser Met Ile Thr Thr Asp Tyr Trp Gly Gln Gly
            100                 105                 110

Thr Leu Val Thr Val Ser Ser
        115
```

<210> SEQ ID NO 60
<211> LENGTH: 119
<212> TYPE: PRT
<213> ORGANISM: Artificial Sequence
<220> FEATURE:

<223> OTHER INFORMATION: Description of Artificial Sequence:/Note =
      Synthetic Construct

<400> SEQUENCE: 60

Glu Val Met Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Val Met Ser Trp Val Arg Gln Thr Pro Glu Lys Arg Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Arg Arg Gly Asp Ser Met Ile Thr Thr Asp Tyr Trp Gly Gln Gly
            100                 105                 110

Thr Leu Val Thr Val Ser Ser
        115

<210> SEQ ID NO 61
<211> LENGTH: 119
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 61

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Val Met Ser Trp Val Arg Gln Thr Pro Glu Lys Arg Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Arg Gly Asp Ser Met Ile Thr Thr Asp Tyr Trp Gly Gln Gly
            100                 105                 110

Thr Thr Leu Thr Val Ser Ser
        115

<210> SEQ ID NO 62
<211> LENGTH: 80
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 62
tatctgcaaa tgagcagtct gagagcagag gacacggctg tttattactg tgcaagaagg    60
ggtgactcta tgattacgac                                                80

```
<210> SEQ ID NO 63
<211> LENGTH: 80
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 63
ccttcttgca cagtaataaa cagccgtgtc ctctgctctc agactgttca tttgcagata    60
cagggtgttc ttggcattgt                                                80

<210> SEQ ID NO 64
<211> LENGTH: 80
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 64
attcactttc agtagttatg taatgtcttg ggttcggcag actccagaga agaggctgga    60
gtgggttgca accattagta                                                80

<210> SEQ ID NO 65
<211> LENGTH: 80
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 65
tccagcctct tctctggagt ctgccgaacc caagacatta cataactact gaaagtgaat    60
ccagaggctg cacaggagag                                                80

<210> SEQ ID NO 66
<211> LENGTH: 80
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 66
tctgaagtaa tgctggtgga gtctggggga ggcttagtaa agcctggagg gtccctgaaa    60
ctctcctgtg cagcctctgg                                                80

<210> SEQ ID NO 67
<211> LENGTH: 80
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 67
tatctgcaaa tgagcagtct gagatctgag gacacggcta tgtattactg tgcaagaagg    60
ggtgactcta tgattacgac                                                80

<210> SEQ ID NO 68
<211> LENGTH: 64
<212> TYPE: DNA
<213> ORGANISM: Artificial Sequence
<220> FEATURE:
```

<223> OTHER INFORMATION: Description of Artificial Sequence:/Note =
      Synthetic Construct

<400> SEQUENCE: 68
ggactactgg ggccaaggga ccactctcac agtctcctca gcctccacca agggcccatc    60
ggtc                                                                64

<210> SEQ ID NO 69
<211> LENGTH: 80
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 69
tttcagggac cctccaggct ttactaagcc tcccccagac tccaccagca ttacttcaga    60
gtggacacct gtagctgttg                                                80

<210> SEQ ID NO 70
<211> LENGTH: 80
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 70
ccttcttgca cagtaataca tagccgtgtc ctcagatctc agactgctca tttgcagata    60
cagggtgttc ttggcattgt                                                80

<210> SEQ ID NO 71
<211> LENGTH: 70
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 71
gaccgatggg cccttggtgg aggctgagga gactgtgaga gtggtccctt ggccccagta    60
gtccgtcgta                                                           70

<210> SEQ ID NO 72
<211> LENGTH: 212
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln Tyr Ser Ser Tyr Arg Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu
        210

<210> SEQ ID NO 73
<211> LENGTH: 213
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 73

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Arg Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
        210
```

<210> SEQ ID NO 74
<211> LENGTH: 213
<212> TYPE: PRT
<213> ORGANISM: Artificial Sequence
<220> FEATURE:
<223> OTHER INFORMATION: Description of Artificial Sequence:/Note = Synthetic Construct

<400> SEQUENCE: 74

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Ser Ser Tyr Arg Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 75
<211> LENGTH: 213
<212> TYPE: PRT
<213> ORGANISM: Artificial Sequence
<220> FEATURE:
<223> OTHER INFORMATION: Description of Artificial Sequence:/Note = Synthetic Construct

<400> SEQUENCE: 75

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Ser Leu Gln Pro
65                  70                  75                  80

Glu Asp Phe Ala Asp Tyr Phe Cys Gln Gln Tyr Ser Ser Tyr Arg Thr

```
                        85                  90                  95
Phe Gly Gly Gly Thr Lys Val Glu Ile Lys Arg Thr Val Ala Ala Pro
                100                 105                 110
Ser Val Phe Ile Phe Pro Pro Ser Asp Glu Gln Leu Lys Ser Gly Thr
                115                 120                 125
Ala Ser Val Val Cys Leu Leu Asn Asn Phe Tyr Pro Arg Glu Ala Lys
            130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
                180                 185                 190
Cys Glu Val Thr His Gln Gly Leu Ser Ser Pro Val Thr Lys Ser Phe
            195                 200                 205
Asn Arg Gly Glu Cys
            210

<210> SEQ ID NO 76
<211> LENGTH: 213
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 76

Asp Ile Val Met Thr Gln Ser His Lys Phe Met Ser Thr Ser Val Gly
1               5                   10                  15
Asp Arg Val Ser Ile Thr Cys Lys Ala Ser Gln Asp Val Gly Thr Ala
            20                  25                  30
Val Ala Trp Tyr Gln Gln Lys Pro Gly Gln Ser Pro Lys Leu Leu Ile
        35                  40                  45
Tyr Trp Ala Ser Thr Arg His Thr Gly Val Pro Asp Arg Phe Thr Gly
    50                  55                  60
Ser Gly Ser Gly Thr Asp Phe Thr Leu Thr Ile Ser Asn Val Gln Ser
65                  70                  75                  80
Glu Asp Leu Ala Asp Tyr Phe Cys Gln Gln Tyr Ser Ser Tyr Arg Thr
                85                  90                  95
Phe Gly Gly Gly Thr Lys Leu Glu Ile Lys Arg Ala Val Ala Ala Pro
                100                 105                 110
Ser Val Phe Ile Phe Pro Pro Ser Asp Glu Gln Leu Lys Ser Gly Thr
                115                 120                 125
Ala Ser Val Val Cys Leu Leu Asn Asn Phe Tyr Pro Arg Glu Ala Lys
            130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Gly Thr Tyr Ser Leu Ser Ser
                165                 170                 175
Thr Leu Thr Leu Ser Lys Ala Asp Tyr Glu Lys His Lys Val Tyr Ala
                180                 185                 190
Cys Glu Val Thr His Gln Gly Leu Ser Ser Pro Val Thr Lys Ser Phe
            195                 200                 205
Asn Arg Gly Glu Cys
            210
```

<210> SEQ ID NO 77
<211> LENGTH: 60
<212> TYPE: DNA
<213> ORGANISM: Artificial Sequence
<220> FEATURE:
<223> OTHER INFORMATION: Description of Artificial Sequence:/Note =
    Synthetic Construct

<400> SEQUENCE: 77
gtcccccaca gatgcagaca aagaacttgg agattgggtc atctgaatgt caccagtgga    60

<210> SEQ ID NO 78
<211> LENGTH: 65
<212> TYPE: DNA
<213> ORGANISM: Artificial Sequence
<220> FEATURE:
<223> OTHER INFORMATION: Description of Artificial Sequence:/Note =
    Synthetic Construct

<400> SEQUENCE: 78
atctagttct cagagatgga gacagacaca atcctgctat gggtgctgct gctctgggtt    60
ccagg                                                                65

<210> SEQ ID NO 79
<211> LENGTH: 69
<212> TYPE: DNA
<213> ORGANISM: Artificial Sequence
<220> FEATURE:
<223> OTHER INFORMATION: Description of Artificial Sequence:/Note =
    Synthetic Construct

<400> SEQUENCE: 79
cagcacccat agcaggattg tgtctgtctc catctctgag aactagatga gaggatgctt    60
cttaagctt                                                            69

<210> SEQ ID NO 80
<211> LENGTH: 67
<212> TYPE: DNA
<213> ORGANISM: Artificial Sequence
<220> FEATURE:
<223> OTHER INFORMATION: Description of Artificial Sequence:/Note =
    Synthetic Construct

<400> SEQUENCE: 80
ctccactggt gacattgtga tgacccaatc tccaagttct ttgtctgcat ctgtggggga    60
cagggtc                                                              67

<210> SEQ ID NO 81
<211> LENGTH: 54
<212> TYPE: DNA
<213> ORGANISM: Artificial Sequence
<220> FEATURE:
<223> OTHER INFORMATION: Description of Artificial Sequence:/Note =
    Synthetic Construct

<400> SEQUENCE: 81
acttggagat tgggtcatca caatgtcacc agtggagcct ggaacccaga gcag          54

<210> SEQ ID NO 82
<211> LENGTH: 67
<212> TYPE: DNA
<213> ORGANISM: Artificial Sequence
<220> FEATURE:
<223> OTHER INFORMATION: Description of Artificial Sequence:/Note =
    Synthetic Construct

<400> SEQUENCE: 82

```
accatcacct gcaaggccag tcaggatgtg ggtactgctg tagcctggta ccaacagaaa    60
ccaggaa                                                              67

<210> SEQ ID NO 83
<211> LENGTH: 72
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 83
tacagcagta cccacatcct gactggcctt gcaggtgatg gtgaccctgt ccccacaga     60 tgcagacaaa ga                                                        72

<210> SEQ ID NO 84
<211> LENGTH: 71
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 84
aagcacccaa actcctcatc tattgggcat ccacccggca cactggggtc ccagataggt    60
ttacaggcag t                                                         71

<210> SEQ ID NO 85
<211> LENGTH: 72
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 85
cccagtgtgc cgggtggatg cccaatagat gaggagtttg ggtgcttttc ctggtttctg    60
ttggtaccag gc                                                        72

<210> SEQ ID NO 86
<211> LENGTH: 63
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 86
gggtctggga cagacttcac cctcaccatc tctagtctgc agccggagga ttttgcaacc    60
tat                                                                  63

<210> SEQ ID NO 87
<211> LENGTH: 60
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 87
actagagatg gtgagggtga agtctgtccc agacccactg cctgtaaacc tatctgggac    60

<210> SEQ ID NO 88
```

<210> SEQ ID NO 88
<211> LENGTH: 57
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 88
tactgtcagc aatatagcag ctatcggacg ttcggtcaag gcaccaaggt ggaaatc        57

<210> SEQ ID NO 89
<211> LENGTH: 57
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 89
cgtccgatag ctgctatatt gctgacagta ataggttgca aaatcctccg gctgcac        57

<210> SEQ ID NO 90
<211> LENGTH: 51
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 90
aaacggactg tggctgcacc atctgtcttc atcttcccgc catctgatga g              51

<210> SEQ ID NO 91
<211> LENGTH: 63
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 91
gaagatgaag acagatggtg cagccacagt ccgtttgatt ccaccttggt gccttgacc    60 gaa                                                                 63

<210> SEQ ID NO 92
<211> LENGTH: 57
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 92
ttctgtcagc aatatagcag ctatcggacg ttcggtcaag gcaccaaggt ggaaatc        57

<210> SEQ ID NO 93
<211> LENGTH: 57
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 93
cgtccgatag ctgctatatt gctgacagaa ataggttgca aaatcctccg gctgcag        57

<210> SEQ ID NO 94

<211> LENGTH: 63
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 94
gggtctggga cagacttcac cctcaccatc tctagtctgc agccggagga ttttgcagat    60
tat                                                                  63

<210> SEQ ID NO 95
<211> LENGTH: 57
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 95
ttctgtcagc aatatagcag ctatcggacg ttcggtggag gcaccaaggt ggaaatc       57

<210> SEQ ID NO 96
<211> LENGTH: 57
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 96
cgtccgatag ctgctatatt gctgacagaa ataatctgca aaatcctccg gctgcag       57

<210> SEQ ID NO 97
<211> LENGTH: 51
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 97
tgatgtggac atgaatttgt gagactgggt catcacaatg tcaccagtgg a             51

<210> SEQ ID NO 98
<211> LENGTH: 51
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 98
tgggttccag gctccactgg tgacattgtg atgacccagt ctcacaaatt c             51

<210> SEQ ID NO 99
<211> LENGTH: 49
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 99
aagacagatg gtgcagccac agcccgtttg atttccagct tggtgcctc                49

<210> SEQ ID NO 100

```
-continued

<211> LENGTH: 45
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 100
aagctggaaa tcaaacgggc tgtggctgca ccatctgtct tcatc                45

<210> SEQ ID NO 101
<211> LENGTH: 30
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 101
agatttcaac tgctcatcag atggcgggaa                                 30

<210> SEQ ID NO 102
<211> LENGTH: 63
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 102
gaagatgaag acagatggtg cagccacagt ccgtttgatt tccaccttgg tgcctccacc   60
gaa                                                              63
```

ANTIBODY SELECTIVE FOR A TUMOR NECROSIS FACTOR-RELATED APOPTOSIS-INDUCING LIGAND RECEPTOR AND USES THEREOF

CROSS-REFERENCE TO RELATED APPLICATIONS

This application is a continuation of and claims priority to U.S. Ser. No. 11/760,491, filed Jun. 8, 2007, which is a continuation of U.S. Ser. No. 10/275,180, filed Mar. 5, 2003, now U.S. Pat. No. 7,244,429, which is a §371 of International Application No. PCT/US2001/14151 filed May 2, 2001, now expired. International Application No. PCT/US2001/14151 claims priority to U.S. Ser. No. 60/201,344 filed May 2, 2000. The applications to which the present application claims benefit are herein incorporated by reference in their entireties.

FIELD OF THE INVENTION

The present invention relates to an antibody capable of specifically binding a single type of tumor necrosis factor (hereinafter referred to as "TNF")-related apoptosis-inducing ligand (hereinafter referred to as "TRAIL") receptor, more particularly, to a monoclonal antibody that induces apoptosis in in vivo and in vitro cells expressing the single type receptor and therapies based thereon.

BACKGROUND OF THE INVENTION

TRAIL is a member of the TNF family of proteins, which also includes TNF-α and Fas ligand (1). These proteins are potent inducers of apoptosis. To date, five receptors for TRAIL have been identified, two of which, DR4 (TRAIL-R1) and DR5 (TRAIL-R2) (2-7), are capable of transducing the apoptosis signal while the other three DcR1 (TRAIL-R3), DcR2 (TRAIL-R4), and osteoprotegerin (OPG) do not transduce the apoptosis signal (8-12). All five receptors for TRAIL share significant homology in their extracellular ligand binding domains. Similar to Fas and TNF receptor I (hereinafter referred to as "TNFRI"), the intracellular segments of both DR4 and DR5 contain a death domain, and transduce an apoptosis signal through a pathway that involves the Fas-associated death domain protein (hereinafter referred to as "FADD") and caspase 8 (6,7). In addition to transducing the apoptosis signal, the DR4 and DR5 receptors can also activate a pathway involving NFκb (6,7).

The biological functions of TRAIL that have been demonstrated include the capability of TRAIL to selectively induce apoptosis of transformed tumor cells, with normal cells being relatively resistant to TRAIL-mediated apoptosis (13-15). This selectivity suggests that, in contrast to Fas ligand, the administration of TRAIL is associated with very low levels of toxicity as demonstrated by systemic administration of TRAIL in an animal model without inducing significant toxicity (13). Thus, TRAIL has been proposed as a potent apoptosis inducing agent that would be a suitable therapeutic agent for the treatment of cancer and other diseases associated with abnormal cell proliferation. TRAIL also has been proposed to be a potent apoptosis-inducing agent that would be suitable for the treatment of autoimmune and inflammatory diseases. It has been demonstrated that TRAIL-mediated apoptosis is involved in activation-induced cell death of T cells, thereby serving as an alternative mechanism to Fas ligand (16,17). TRAIL-mediated apoptosis may also function in the induction of apoptosis of T cells and other inflammatory cells (18), and plays a role in the killing activity of NK cells (19-21), and in the immunomodulatory function of dendritic cells (22,23). Thus, TRAIL-mediated apoptosis may also function in immunoprivilege and immunosurveillance.

The TRAIL receptor system is complex, and includes at least two death receptors, DR4 and DR5, and at least two non-apoptotic receptors, DcR1 and DcR2. All of these receptors not only share a high amino acid sequence homology, but also exhibit a similar binding affinity to TRAIL (2-12). The ability of the DcR1 and DcR2 receptors to compete for binding of TRAIL without inducing apoptosis suggests that they may act as decoy receptors that block or modulate the activity of the TRAIL ligand. Moreover, it has been reported that untransformed cells express higher levels of decoy receptors than do transformed cells. Thus, it has been proposed that the differential modulation of the expression of the death and decoy receptors may represent a key regulatory mechanism that determines the susceptibility of cells to TRAIL-mediated apoptosis, but due to the lack of receptor-specific antibodies (2). Although the expression and function of DR4 and DR5 have been studied extensively, progress has been impeded by the lack of receptor-specific monoclonal antibodies. The cell surface expression of DR5 has not been documented. It has been reported that a panel of anti-TRAIL receptor antibodies have been generated that are capable of inducing apoptosis of melanoma cells in vitro but only upon immobilization of the antibodies, to promote cross-linking, and, in some cases, the cells require culturing with actinomycin D (24). Several anti-DR5 antibodies have been generated (24). However, these previously generated anti-DR5 monoclonal antibodies have low apoptosis-inducing activity in vitro, even under the conditions of crosslinking. No in vivo activity has been reported. These antibodies have not been used for examining cell surface expression of TRAIL receptors (24). Thus, there exists a need for a monoclonal antibody selective for each specific TRAIL receptor that is not only able to bind to cell surface receptor but also to strongly induce apoptosis of various types of abnormal cells, including tumor cells, both in vivo and vitro without the requirement for crosslinking or immobilization. Such an antibody would not only provide potential therapeutic agent but also a diagnostic tool for functional analysis of TRAIL receptor. There exists a particular need for an antibody specific against each of the death inducing receptors DR4 and DR5.

In the development, or progression, of many diseases it is often the case that cells are not deleted. In many autoimmune diseases and inflammatory conditions, the surviving activated cells attack normal tissues or cells. Further, progression of tumorigenesis and the proliferative panus formation of rheumatoid arthritis are characterized by the unchecked proliferation of cells. Thus, insufficient apoptosis leads to the development of disease, and the uses of apoptosis-inducing ligand or agonistic monoclonal antibody to enhance apoptosis are considered as a potential therapeutic strategy for eliminating those unwanted cells.

For example, rheumatoid arthritis (hereinafter referred to as "RA") is a common human autoimmune disease. The current understanding of the pathophysiology of RA is that autoimmune T cells and B cells initiate an inflammatory response in the joints, which drives hyperproliferation of the synoviocytes. As a consequence of the hyperproliferation of synovial cells, metalloproteinases (hereinafter referred to as "MMPs") are over-produced, which further leads to the erosive destruction of the cartilage and bone that is characteristic of RA (25). Thus, the control of hyperproliferation of inflammatory synovial cells is a key step in the treatment of RA. The molecular mechanisms leading to the hyperproliferation of synovial cells are still unknown. Although the hyperproliferative synovial cells are non-malignant and non-transformed, many studies have suggested that they share some common features with transformed cells (46). These cells, the so-called, "transformed-appearing synoviocytes", are characterized by a dense rough endoplasmic reticulum, numerous irregular nuclei, and changes in the normally spindle-shaped cell skeleton. It has been proposed that the incorporation of the oncogenes and virus-derived genes might be the primary triggers for the transformed appearance of RA synovial cells (46).

At least two aspects of RA suggest that dysregulated apoptosis may contribute to the disease process and that therapeutic elicitation of apoptosis may be an effective treatment: the failure of the deletion of the activated T cells suggests that there is defective activation-induced cell death of these T cells, which is a process that involves Fas-mediated apoptosis and TRAIL-mediated apoptosis, and the hyperproliferative nature of the RA synovial cells is a contributing factor in the later stages of RA pathophysiology. Indeed, it has been shown that the administration of anti-Fas antibody into the inflammatory joint inhibits the development of chronic arthritis in tax transgenic mice, which are an animal model for human RA (26). Moreover, localized transduction with the fas ligand gene by an adenoviral vector is effective in prevention of collagen-induced arthritis (27). Inhibition of the proliferation of inflammatory synovial cells by enhancement of Fas-mediated apoptosis is observed in both cases. Although Fas ligand is a strong apoptosis inducer in RA synovial cells, the application of Fas ligand-mediated apoptosis as a therapy for humans has been limited by lethal liver toxicity. Thus, TRAIL receptor induced apoptosis represents a safer and more effective therapeutic for the treatment of RA than Fas-ligand induced apoptosis.

TRAIL receptor induced apoptosis also represents a safer and more effective therapeutic for the treatment of cancer than Fas-ligand induced apoptosis. TRAIL-mediated apoptosis is known to specifically induce apoptosis of transformed tumor cells without affecting normal cells. It has been shown that the systemic administration of the trimerized soluble TRAIL did not cause toxicity in experimental animals yet was able to induce regression of implanted tumors (13,28). Its potential as an adjunctive therapy for traditional treatments was underscored by the recent finding that the expression of DR5 and susceptibility to TRAIL-induced apoptosis of breast cancer cells is enhanced by the radiation, suggesting that combined with radiation, the efficiency of TRAIL would be increased in cancer therapy (29).

In addition, the gene encoding the TRAIL receptor DR5 has been mapped to chromosome 8p21-22, loci with a high frequency of mutation in some cancer cells (30). It has been reported that at least two kinds of tumor cells, small lung cancer (31) and head and neck cancer (32) exhibit mutations in the death domain of the DR5 gene. Thus, there exists a need for an anti-DR5 antibody in cancer research to determine the effect of receptor epitope variation on the development and progression of cancers. Further, the functionality of TRAIL receptor mutations would prove a useful clinical diagnostic tool when used in conjunction with other biomarkers in the early detection of cancers and as a predictor of the tumor aggressiveness.

SUMMARY OF THE INVENTION

An antibody is disclosed which recognizes a TRAIL receptor DR5 and which induces apoptosis in a DR5-expressing cell in vivo. Further disclosed is an antibody that recognizes DR5 but not DR4, DcR1, or DcR2. Specifically detailed is a monoclonal antibody to DR5 produced by a hybridoma.

A method provided by the invention allows inhibition of cell proliferation by exposing a cell to a therapeutic quantity of an antibody capable of binding to DR5. Also disclosed is a pharmacological composition that includes a therapeutic amount of monoclonal antibody active against a DR5, a pharmaceutically acceptable carrier and a container enclosing the antibody and the carrier. Further provided by the invention is the use of an antibody recognizing DR5 for preparing a therapeutic for selective apoptosis of abnormal or dysregulated cells.

An antibody of the present invention interacts with a tumor necrosis factor ligand receptor such as DR4, DR5, DrR1, DrR2 and OPG, inducing apoptosis in a cell expressing such a receptor. Disclosed is an antibody of the invention capable of selectively binding an agonistic or antagonistic tumor necrosis factor ligand receptor epitope.

The present invention provides a treatment for an apoptosis related disease by a method that includes exposing a target tissue having an apoptosis related disease to a therapeutic quantity of an antibody of the invention.

Further described is a fusion protein that includes an antigenic TRAIL receptor amino acid sequence having at least ten bases, coupled to an immunoglobulin protein or fragment thereof capable of eliciting an immune response within a subject.

The present invention provides a method of gene therapy in which a target cell is transfected with a TRAIL receptor nucleic acid sequence in an expression vector so that the TRAIL receptor is expressed on the target cell. The target cell is then exposed to an antibody that selectively binds the TRAIL receptor.

Provided are nucleic acid sequences and amino acid sequences encoding the heavy and light chain immunoglobulins of an antibody selective for DR5. Also detailed are vectors that include a nucleic acid sequence of the invention and host cells transformed with a vector of the invention.

The present invention provides a host cell producing a humanized TRA-8.

A process for producing a humanized DR5 antibody is described in which a host is transformed with nucleic acid sequences encoding a humanized immunoglobulin light chain and a humanized immunoglobulin heavy chain after which the transformed host is incubated for a predetermined period of time.

Also described is a process for inhibiting cell proliferation that includes contacting a target cell with a pharmaceutically effective amount of a humanized DR5 antibody.

A commercial kit is provided for inducing apoptosis that includes a humanized TRA-8 antibody selective for DR5; packaged in a suitable container together with instructions for use.

BRIEF DESCRIPTION OF THE DRAWINGS

FIG. 13. TRAIL induces hepatitis. B6 mice were intravenously inoculated with $10^9$ pfu of adenoviral vector encoding the full length of human TRAIL under the control of the "Tet-on" transcriptional element. TRAIL expression was induced by the indicated dose of tetracycline. (A) Northern blot analysis of human TRAIL expression in the liver. 24 hours after inoculation of vector and induction with tetracycline, total RNA was isolated from the livers and probed with human TRAIL cDNA or β-actin. (B) Serum levels of AST. 24 hours after transduction of TRAIL, serum levels of AST were determined. (C) TRAIL-mediated cell death of adenoviral vector infected hepatocytes: B6 mice were intravenously inoculated with tetracycline-inducible adenoviral vector. 48 hours after inoculation, hepatocytes from inoculated and non-inoculated control mice were isolated and incubated with indicated concentrations of TRAIL for 8 hours (left panel). Cell viability of hepatocytes was determined by the ATPLite® assay. Mice, inoculated with adenoviral vector as above, were intravenously injected with 10 µg of soluble human TRAIL 48 hours later. Serum levels of AST were measured at 24 hours after TRAIL injection (right panel). (D and E) Histology analysis of liver damage induced by TRAIL. The livers were collected at 24 hours (D) or 7 days (E) after transduction with TRAIL. The paraffin sections were H&E stained, and photographed at 100× (top panel) and 400× (lower panel).

FIG. 14 is a series of graphs showing that activated T cells and B cells purified from human PBMC express increased levels of DR5 as determined by flow cytometry for resting and activated cells.

FIG. 15 is viability graphs as a function of TRA-8 concentration for the purified T cells (FIG. 15A) and B cells (FIG. 15B) depicted in FIG. 14 that have been stimulated for 48 hours with anti-CD3 (FIG. 15A) or anti-µ (FIG. 15B), with activated and blast cells collected by different density of Ficoll-Paque. Viability is determined by ATPLite® assay.

FIG. 16 is a histogram and flow cytometry plots showing CD3 expression in a gated lymphocyte population for NK cell depleted NOD/SCID mice injected with human PBMC and TRA-8 or IgG (control).

FIG. 17 shows CD3 and TUNEL stained cellular micrographs for mouse spleen tissue as detailed in Example 13.

DETAILED DESCRIPTION OF THE INVENTION

Figures 1, 1B:
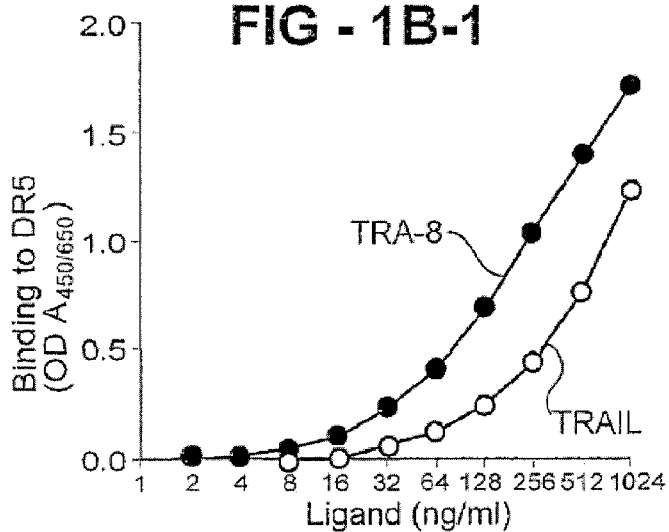
FIG. 1. Characterization of TRA-8. (A) Binding specificity of TRA-8: Western blot analysis (upper panel): Recombinant fusion proteins of the TNFR family probed with TRA-8 or anti-human IgG. Lane 1: DR5/hIgG1 fusion protein (immunogen); Lane 2: DR4/hIgG1 (TRAIL-R1); Lane 3: DR5/hIgG1; Lane 4: TRAIL-R3 (DcR-1)/hIgG1; Lane 5: TRAIL-R4 (DcR-2)/hIgG1; Lane 6, CD95/hIgG1; Lane 7: soluble TNFRI. ELISA analysis (lower panel): The well numbers match those of the Western blot except well 8 which is a murine DR5/hIgG1 fusion protein. (B) Binding activity of soluble TRAIL and TRA-8 to DR5 and DR4: ELISA plates were coated with DR5/hIgG1 or DR4/hIgG1 and then incubated with TRAIL or TRA-8. (C) Flow cytometry analysis of the surface expression of DR5. Cos-7 cells transfected with pcDNA3 expression vector containing the full-length DR5 cDNA, DR4 cDNA or empty vector. Forty-eight hours after transfection, cells were stained with TRA-8 followed by PE-conjugated anti-mouse IgG1. (D) in situ immunohistochemistry reactivity for DR5: Cytospin slides of Cos-7 cells transfected with DR5 expression or control vector were stained with TRA-8 at 48 hours after transfection, (E) Killing activity of TRA-8: Jurkat cells were incubated with the indicated concentrations of TRA-8. Cell viability was determined by ATPLite®, MTT, and PI exclusion assays after overnight culture. The results of ATPLite® and MTT assays are presented as percent of medium control, and PI assay are presented as percent of PI negative cells (F) Western blot analysis of caspase activation: Jurkat cells were incubated with 500 ng/ml TRA-8 for indicated time. Cell lysates were separated by 15% SDS-PAGE, blotted, and probed with anti-caspase antibodies. The arrows indicate the cleaved subunits of each caspase. (G) Caspase inhibition assay: Jurkat cells were incubated with 50 ng/ml TRA-8 overnight in the presence of various concentrations of indicated caspase inhibitors. Cell viability was determined by the ATPLite® assay.
Figures 1, 1B, 2:
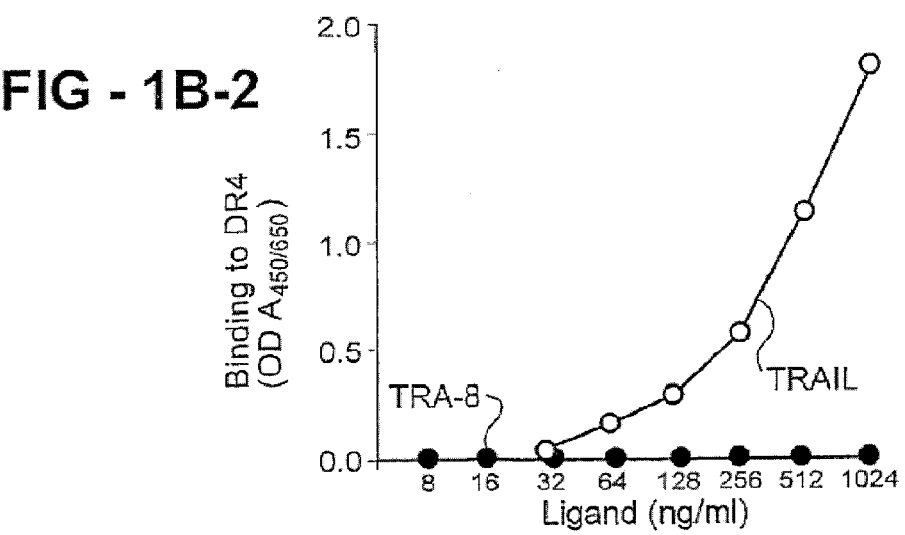
FIG. 2. Cell surface expression of DR5 and susceptibility to DR5-mediated apoptosis. Normal T and B cells, freshly isolated from peripheral blood, T cell (A and A'), glioma (B and B'), prostate cancer cell (C) and B cell (D) cell lines were incubated with TRA-8 or murine IgG1 isotype control antibody followed by PE-conjugated goat anti-mouse IgG1. Apoptosis was determined by the ATPLite® assay after overnight incubation with soluble TRAIL (open circles) or TRA-8 (closed circles) as shown in A, B' and D.
Figures 1, 1B, 2, 3:
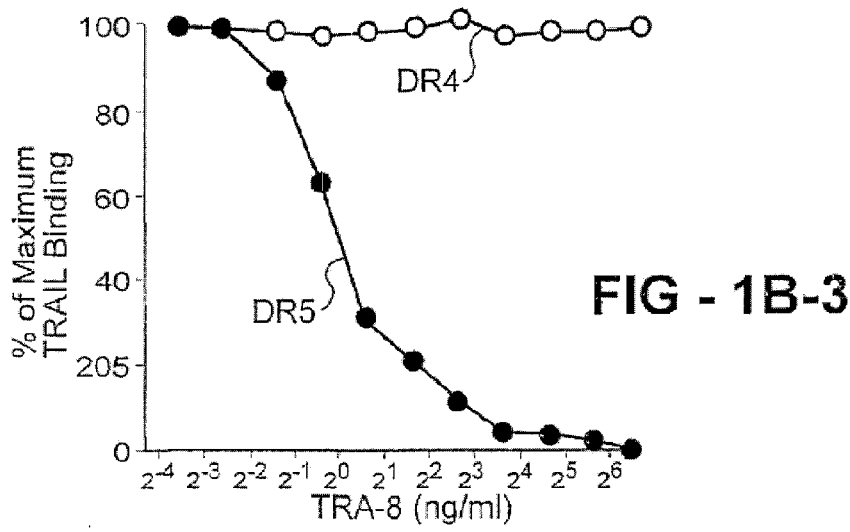
FIG. 3 Glioma (B) and prostate cancer (C) cell lines were incubated with TRA-8 or murine IgG1 isotype control antibody. Apoptosis was determined by the ATPLite® assay after overnight incubation with soluble TRAIL (open circles) or TRA-8 (closed circles)

The failure to delete cells is due to defects in the apoptosis inducing system which are associated with defects illustratively including expression or function of the ligand, the receptor, or the intracellular regulatory and effector molecules. The present invention affords a method to correct a deficient apoptosis inducing system as well as to elucidate the specific defects inherent in a given defective apoptosis inducing system.

The present invention relates to a new class of monoclonal antibodies that have selective in vivo and in vitro apoptosis inducing activity against specific TRAIL receptors, including DR5, DR4, DcR1 and DcR2. The present invention has utility as a reagent for apoptosis signaling research, as well as a therapeutic effective against cells expressing TRAIL receptors illustratively including broad classes of cancer cells, dysregulation of the apoptosis system and abnormally proliferating synovial cells of autoimmune diseases. Antibodies according to the present invention are specific in binding particular types of TRAIL receptors in spite of the homology therebetween. The inventive antibodies afford targeted apoptosis of only those cells expressing a target TRAIL receptor or alternatively, blocking TRAIL apoptosis of cells expressing a target receptor.

An anti-DR5 monoclonal antibody of the present invention serves as a potent inducer of apoptosis in cells expressing DR5 in vitro and as a potent inducer of apoptosis in vivo. Humanized fragmentary CDR sequences engrafted on humanized antibody backbones and fusion protein anti-DR5 antibodies of the present invention exhibit similar apoptotic properties.

To date, no monoclonal antibody is available which binds to cell surface DR5 and induces apoptosis of cells expressing DR5 both in vitro and in vivo in the absence of a crosslinker. The present invention includes a DR5 antibody operative as a therapeutic agent in animal models of disease, such as xenografted animals, or in vivo. Although soluble TRAIL has been shown to be effective in induction of apoptosis of tumor cells in vivo, the killing activity appeared to be very low with the large and repeated doses often being required (13). TRA-8, one of a series of DR5 antibodies according to the present invention, is pharmaceutically effective in animals carrying a human DR5 transgene and also has utility in establishing a model for the investigation of the role of DR5 and TRAIL.

An antibody according to the present invention raised against a TRAIL receptor is harvested according to the present invention from an experimental animal. By humanizing the antibody according to the present invention to maintain receptor binding activity while eliciting a diminished and therapeutically tolerable immune response within a human subject, a humanized anti-TRAIL receptor antibody according to the present invention is used as therapeutic agonist or antagonist for a given TRAIL receptor. The present invention being operative as an in vivo therapeutic since secondary crosslinking of the anti-TRAIL receptor antibody, optionally, is not required.

The present invention extends beyond a single anti-TRAIL receptor antibody having agonist or antagonistic apoptotic effects. Rather, two or more anti-TRAIL receptor antibodies are brought into contact with a cell culture in vitro or a subject body tissue in vivo to create a synergistic treatment. For example, glioma cell line U87 and hematopoietic cell lines U937 and Molt-4 are responsive to exposure to a synergistic exposure to agonistic anti-DR4 and anti-DR5 antibodies whereas exposure to agonistic anti-DR5 antibody alone shows only limited success in inducing apoptosis.

Additionally, antagonistic anti-TRAIL receptor antibodies have particular utility in the present invention when an antibody is specific to binding one of the decoy receptors DcR1, DcR2 or OPG. Selective blocking of a decoy receptor with an antibody according to the present invention has the effect in cell types expressing decoy receptors of shifting the TRAIL binding equilibrium towards those TRAIL receptors capable of transducing the apoptosis signal. Thus, in another combined therapy according to the present invention, a decoy receptor binding antibody sensitizes an expressing cell towards agonistic apoptosis signal transducing TRAIL receptor binding.

In another embodiment, the present invention affords a method of elucidating agonistic and antagonistic epitopes of a given TRAIL receptor. Further, polymorphisms between individuals associated with a given TRAIL receptor are elucidated according to the present invention through the use of a panel of monoclonal antibodies each having a differing variable or CDR region. A characterized panel of monoclonal antibodies provides the ability to define agonistic and antagonistic epitopes and polymorphisms. Thus, a panel of monoclonal antibodies according to the present invention has utility in drug discovery and/or subject screening for disease proclivity.

Still another embodiment of the present invention involves fusion proteins including an antigenic fragment of a TRAIL receptor coupled to an immunoglobulin protein, polypeptide or fragment thereof. A TRAIL receptor fragment being defined as containing a sufficient number of bases to elicit an immunogenic response to a native TRAIL receptor expressed on a subject cell surface. A TRAIL receptor fusion fragment including at least ten amino acids. An immunoglobulin fusion protein or fragment thereof is defined herein to include a native or synthetic protein or polypeptide segment having a sufficient number of amino acid bases to activate an immunogenic cascade response within a subject. An immunogen of the present invention including a fusion of a TRAIL receptor fragment coupled to an immunoglobin fragment has utility as an in vivo therapeutic to elicit an anti-TRAIL receptor antibody in situ within a subject.

In still a further embodiment, the present invention is operative as a gene therapy. In a gene therapy aspect of the present invention, targeted cells are transfected with a vector carrying an expressible sequence corresponding to a TRAIL receptor. The vector being conventional and chosen on the basis of the targeted cell susceptibility to the vector. Gene therapy vectors illustratively include adenovirus, pAdCMV5. Upon the targeted cells or tissue expressing the transfected TRAIL receptor, the cells or tissue are exposed to an antibody according to the present invention specific for binding the transfected TRAIL receptor. It is appreciated that the anti-TRAIL receptor antibody is either agonistic or antagonistic thereto consistent with the desired therapeutic result.

The antibodies of the present invention are also operative in conjunction with a sensitizer. A sensitizer as used herein is defined to include any stimulus that induces apoptosis, including ultraviolet light, organic molecules specifically including the class of bisindolmaleimides, heavy metals and free radical species.

In the context of a malignancy therapy, TRA-8, is able to induce apoptosis of most TRAIL-sensitive tumor cells in a caspase-dependent fashion in the absence of the secondary crosslinking. TRA-8 exhibits a strong tumoricidal activity in vivo. The ability of TRA-8 to induce apoptosis of most TRAIL-sensitive cells confirms that DR5 alone is sufficient to trigger apoptosis. The majority of tumor cells detailed herein express cell surface DR5 and their susceptibility to TRA-8 induced cell death paralleled their susceptibility to TRAIL, indicating that DR5 is a primary death receptor for TRAIL-mediated apoptosis in most tumor cells. Thus, differential expression of DR5 by normal and cancer cells is operative in the selectivity of TRAIL-mediated apoptosis. TRA-8 bypasses the decoy receptors to induce TRAIL-mediated apoptosis. Only a minority of TRAIL resistant tumor cells are sensitive to TRA-8, however, indicating that the decoy receptors do not appear to play a major role in the resistance of tumor cells to TRAIL-mediated apoptosis.

Although previous studies have indicated that systemic administration of the soluble form of TRAIL in animals does induce tumor regression without causing toxicity[3,4,22], the membrane-bound form of human TRAIL induces liver damage in mice as shown herein. However, the hepatic toxicity of TRAIL is much less potent than that of Fas ligand as demonstrated by the lesser susceptibility of normal hepatocytes to TRAIL-induced injury compared to Fas ligand and by the lack of lethality of TRAIL in vivo. Thus, titration of TRAIL has utility in cancer therapy.

As detailed herein, the absence of significant levels of DR5 protein expression by normal hepatocytes is shown and is associated with hepatocyte resistance to TRA-8 induced apoptosis. Crosslinking of DR5 with monoclonal antibody is insufficient to organize the homopolymeric forms of the death receptor able to trigger apoptosis. Experiments in marmoset indicate no evidence of hepatic toxicity of TRA-8 administration. Thus, an agonistic monoclonal anti-DR5 antibody is likely to be more selective and safer than soluble TRAIL as a therapeutic agent.

As a screening assay, the present invention is well suited for detecting small clusters of malignant cells which may still exhibit normal cell morphology. In situ cell section staining of human cancer cells including lung, prostate and liver cancers with labeled antibodies according to the present invention readily identifies cancerous cells. These cancer cells are observed to express very high levels of DR5 as compared to normal cells of the same type. Thus, the present invention has utility as a sensitive screening method for early stage malignancies within tissue including at least lung, prostate and liver. A therapeutic process is detailed herein for the inhibition of abnormal cell proliferation associated with diseases illustratively malignant cancers and lymphatic leukemias.

The present invention is detailed herein with particularity to an anti-human DR5 monoclonal antibody designated as TRA-8, having ATCC Accession Number PTA-1428. It is appreciated that the techniques and results detailed with regard to the agonistic anti-human DR5 monoclonal antibody TRA-8 are wholly extendable and applicable to antagonistic DR5 antibodies, as well as antibodies raised against DR4, DcR1 and DcR2 acting in both agonistic and antagonistic manners.

The levels of expression of an apoptosis receptor, such as Fas, do not necessarily correlate with the susceptibility of the cells to apoptosis. For TRAIL-mediated apoptosis, it has been suggested that the expression of the decoy receptors for TRAIL influences the susceptibility of the cells. Moreover, it has been suggested that DR5 must be associated with DR4 for effective transduction of the apoptosis signal through FADD and the caspase 8 pathway. The availability of agonistic monoclonal anti-DR5 antibody allowed evaluation of the regulation of DR5 signaling and its relative role in TRAIL-mediated apoptosis. Comparison of the susceptibility of the cells to TRA-8-mediated apoptosis with their susceptibility to TRAIL-mediated apoptosis offers insight into the role of DR5 in TRAIL-mediated apoptosis and the mechanisms that may affect susceptibility.

This advantage generally extends to humanized anti-DR5 antibodies of the present invention. A molecular clone of an antibody to DR-5 is prepared by known techniques as detailed with respect to the following Examples. Recombinant DNA methodology (33) is operative herein to construct nucleic acid sequences which encode a monoclonal antibody molecule or antigen binding region thereof.

The present invention allows the construction of humanized anti-TRAIL receptor antibodies that are unlikely to induce a human anti-mouse antibody (hereinafter referred to as "HAMA") response (34), while still having an effective antibody effector function. As used herein, the terms "human" and "humanized," in relation to antibodies, relate to any antibody which is expected to elicit a therapeutically tolerable weak immunogenic response in a human subject.

The present invention provides for an anti-DR5 antibody, a humanized anti-DR5 antibody, TRA-8 heavy and light chain immunoglobulins and humanized heavy and light chain immunoglobulins. Certain truncations of these proteins or genes perform the regulatory or enzymatic functions of the full sequence protein or gene. For example, the nucleic acid sequences coding therefor can be altered by substitutions, additions, deletions or multimeric expression that provide for functionally equivalent proteins or genes. Due to the degeneracy of nucleic acid coding sequences, other sequences which encode substantially the same amino acid sequences as those of the naturally occurring proteins may be used in the practice of the present invention. These include, but are not limited to, nucleic acid sequences including all or portions of the nucleic acid sequences encoding the above polypeptides, which are altered by the substitution of different codons that encode a functionally equivalent amino acid residue within the sequence, thus producing a silent change. It is appreciated that the nucleotide sequence of an immunoglobin according to the present invention tolerates sequence homology variations of up to 25% as calculated by standard methods ("Current Methods in Sequence Comparison and Analysis," *Macromolecule* Sequencing and Synthesis, Selected Methods and Applications, pp. 127-149, 1998, Alan R. Liss, Inc.) so long as such a variant forms an operative antibody which recognizes a TRAIL receptor DR5. For example, one or more amino acid residues within a polypeptide sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the present invention are proteins or fragments or derivatives thereof which are differentially modified during or after translation, e.g., by glycosylation, proteolytic cleavage, linkage to an antibody molecule or other cellular ligands, etc. In addition, the recombinant vector encoding nucleic acid sequences of the anti-DR5 antibodies of the present invention may be engineered so as to modify processing or expression of a vector.

Additionally, an inhibitor encoding nucleic acid sequence can be mutated in vitro or in vivo to create and/or destroy translation, initiation, and/or termination sequences or to create variations in coding regions and/or form new restriction endonuclease sites or destroy pre-existing ones, to facilitate further in vitro modification. Any technique for mutagenesis known in the art can be used, including but not limited to in vitro site directed mutagenesis, *J. Biol. Chem.* 253:6551, use of Tab linkers (Pharmacia), and the like.

X-ray crystallography data indicate that the antibody immunoglobulin fold generally forms a long cylindrical structure comprising two layers of antiparallel b-sheets, each consisting of three or four b-chains. In a variable region, three loops from each of the V domains of H and L chains cluster together to form an antigen-binding site. Each of these loops is termed a complementarity determining region (CDR). The CDRs have the highest variability in amino acid sequence with the antibody. The portions of the variable region that are not part of a CDR are called "framework regions" ("FR" regions) and generally play a role in maintaining CDR structure. Preferably, all the CDRs from a given antibody are grafted into an acceptor antibody, in order to preserve the binding region for the TRAIL receptor epitope region. It is appreciated that grafting a portion of the total amount of CDRs into a donor is operative herein. It is understood that grafting generally entails the replacement, residue for residue, of one amino acid or region, for another. However, occasionally, especially with the transfer of a region, one or more residues may be added or omitted or substituted therefor, as desired, and that such deletions and insertions, as well as appropriate replacements and inversions, are within the skill of those in the art.

An antibody of the present invention is obtained by, for example, grafting each CDR of L chain and H chain subunit of an anti-TRAIL receptor monoclonal antibody into a corresponding CDR region of a human antibody, thereby humanizing a mouse monoclonal antibody effective against a TRAIL-receptor.

Antibody fragments which contain the idiotype of the molecule are also generated and operative herein using known techniques. For example, such fragments illustratively include the anti-TRAIL receptor (AB')2 fragment which can be produced by pepsin digestion of the antibody molecule, the TRAIL receptor antibody AB' fragments generated through reduction of the disulfide bridges of the TRAIL receptor (AB')2 fragment, and the antibody fragment which are generated by treating the antibody molecule with papain and a reducing agent.

In particular, the anti-DR5 monoclonal antibody TRA-8 may be obtained by culturing a hybridoma which, in turn, may be obtained by immunizing a mouse with human DR5 and subsequently fusing the spleen cells or lymph node cells from the mouse with mouse myeloma cells.

Preparation of a monoclonal antibody illustratively involves the following steps:
  a) purification of a biomacromolecule for use as an antigen;
  b) preparation of antibody producing cells, after first immunizing an animal using injections of the antigen, bleeding the animal and assaying the antibody titer, in order to determine when to remove the spleen;
  c) preparation of myeloma cells;
  d) fusing the antibody producing cells and myeloma cells;
  e) selecting a hybridoma producing a desired antibody;
  f) preparing a single cell clone (cloning);

g) optionally, culturing the hybridoma cells, or growing animals into which the hybridoma cells have been transplanted, for large scale preparation of the monoclonal antibody; and h) testing the biological activities and the specificity, or assaying marker agent properties, of the monoclonal antibody thus prepared.

The procedure for the preparation of an anti-DR5 monoclonal antibody is detailed below with reference to the above-described steps. This method for preparing an antibody of the present invention is intended only to be illustrative of the methods of preparation and is not limited thereto. Other known procedures may be followed, or the following method modified, for instance by using antibody producing cells other than spleen cells and myeloma.

(a) Preparation of Antigen

A recombinant protein (hereinafter referred to as "recombinant human DR5"), effective as the antigen, is obtained by transfecting QBI-293A cells with the expression vector pAdDR5-IgG for a fusion protein comprising the extracellular domain of human DR5 and the Fc region of human IgG1 antibody (hereinafter referred to as "IgG"), (cf. PTA-1428) to express it by using the ADENO-Quest kit (Quantum Biotechnologies Inc., Canada), and collecting and partially purifying the expression product. The plasmid pAdDR5-IgG is constructed by inserting DNA encoding a human DR5 and human IgG fusion protein into pAdCMV5, which is an expression vector for animal cells. Other materials, such as the DNA encoding DR5, the vector, and the host, are operative herein.

The human DR5 and IgG fusion protein produced in the culture supernatant of the QBI-293A cells transfected with the vector pAdDR5-IgG may be partially purified by ProteinA-Sepharose affinity chromatography or ProteinG-Sepharose affinity chromatography, or ion-exchange chromatography using a Resource Q column (trade name; Pharmacia).

Alternatively, purified DR5 obtained from the cell membranes of human cell lines is used as the antigen. Further, since the primary structures of DR5 is known (cf. PTA-1428), a peptide comprising the amino acid sequence of SEQ ID NO. 1, may be chemically synthesized by a known method such as the Sanger method, and used as the antigen.

(b) Preparation of Antibody Producing Cells

A mouse is immunized with the immunogen produced in step (a), mixed with an adjuvant, such as Freund's complete or incomplete adjuvant or alum. Other suitable experimental animals illustratively include rats, guinea pigs, rabbits, dogs, chickens, horses, pigs, cows and sheep.

Suitable administration routes to immunize an experimental animal include the subcutaneous, intraperitoneal, intravenous, intradermal, and intramuscular injection routes, with subcutaneous and intraperitoneal injections being preferred.

Immunizations are optionally performed by a single dose or, by several repeated doses at appropriate intervals (preferably 1 to 5 weeks). Immunized animals are monitored for antibody titer in their sera, and an animal with a sufficiently high antibody titer is selected as the source of antibody producing cells. Selecting an animal with a high titer makes the subsequent process more efficient. Cells for the subsequent fusion are generally harvested from the animal 3 to 5 days after the final immunization.

Methods for assaying antibody titer include various well known techniques such as radioimmunoassay (hereinafter, referred to as "RIA"), solid-phase enzyme immunoassay (hereinafter, referred to as "ELISA"), fluorescent antibody assay and passive hemagglutination assay, with RIA and ELISA preferred for reasons of detection sensitivity, rapidity, accuracy and potential for automation.

Determination of antibody titer may be performed, for example, by ELISA, as follows. First, purified or partially purified DR5 is adsorbed onto the surface of a solid phase, such as a 96-well ELISA plate, followed by blocking any remaining surface, to which DR5 has not been bound, with a protein unrelated to the antigen, such as bovine serum albumin (BSA). After washing, the well surfaces are contacted with serially diluted samples of mouse sera to enable binding of the anti-DR5 antibody in the samples to the antigen. An enzyme-labeled, anti-mouse antibody, as the secondary antibody, is added to be bound to the mouse antibody. After washing, the enzyme substrate is added, and antibody titer is estimated by determining absorbance change due to color development caused by the alteration of the substrate or the like.

(c) Preparation of Myeloma Cells

Cells from established mouse cell lines serve as the source of myeloma cells, including for example 8-azaguanine resistant mouse, derived from BALB/c myeloma strains P3X63Ag8U.1 (P3-U1) (35), P3/NSI/1-Ag4-1(NS-1) (36). Sp2/0-Ag14 (SP-2) (37), P3X63Ag8.653 (653) (38) and P3X63Ag8 (X63) (39). The cell line selected is serially transferred into an appropriate medium, such as 8-azaguanine medium. 8-azaguanine medium includes Iscove's Modified Dulbecco's Medium (hereinafter referred to as "IMDM") or Dulbecco's, Modified Eagle Medium (hereinafter referred to as "DMEM"). RPMI-1640 medium supplemented with glutamine, 2-mercaptoethanol, gentamicin, fetal calf serum (hereinafter referred to as "FCS"), and 8-azaguanine. The cells are then transferred to a normal medium, such as ASF104 medium (Ajinomoto, K. K.) containing 10% FCS, 3 to 4 days prior to fusion, in order to ensure that at least $2 \times 10^7$ cells are available on the day of fusion.

(d) Cell Fusion

Lymphocytes and plasma cells obtained from any suitable part of the animal are precursor cells to produce the antibody. Lymphocyte or plasma cell sources illustratively include spleen, lymph nodes, peripheral blood, or any appropriate combination thereof, with spleen cells being the most common source.

After the last booster injection, tissue in which antibody producing cells are present is removed from a mouse having the predetermined antibody titer. The currently favored technique for fusion of spleen cells with myeloma cells prepared in step c), employs polyethylene glycol.

The fusion technique includes washing spleen and myeloma cells with serum-free medium (such as RPMI 1640) or phosphate buffered saline (hereinafter referred to as "PBS") so that the number ratio of spleen cells to myeloma cells is approximately between 5:1 and 10:1, and then centrifuged. After the supernatant has been discarded and the pelleted cells sufficiently loosened, 1 ml of serum-free medium containing 50% (w/v) polyethylene glycol (m.w. 1,000 to 4,000) is added dropwise with mixing. Subsequently, 10 ml of serum-free medium is slowly added and then centrifuged. The supernatant is discarded again, and the pelleted cells are suspended in an appropriate amount of HAT medium containing a solution of hypoxanthine, aminopterin and thymidine (hereinafter referred to as "HAT") and mouse interleukin-2 (hereinafter referred to as "IL-2"). The suspension is then dispensed into the wells of culture plates (also referred herein simply as "plates") and incubated in the presence of 5% v/v $CO_2$ at 37° C. for about 2 weeks, with the supplementary addition of HAT medium as appropriate.

(e) Selection of Hybridomas

When the myeloma strain used is resistant to 8-azaguanine, i.e., it is deficient in the hypoxanthine guanine phosphoribosyl transferase (HGPRT) enzyme, any unfused myeloma cells and any myeloma-myeloma fusions are unable to survive in HAT medium. On the other hand, fusions of antibody producing cells with each other, as well as hybridomas of antibody producing cells with myeloma cells can survive, the former only having a limited life. Accordingly, continued incubation in HAT medium results in selection of only the desired hybridomas.

The resulting hybridomas grow into colonies that are then transferred into HAT medium lacking aminopterin (HT medium). Thereafter, aliquots of the culture supernatant are removed to determine anti-Fas antibody titer by, for example, ELISA. When the above-mentioned fusion protein is used as the ELISA antigen, it is also necessary to eliminate clones producing an antibody which is specifically bound to the Fc region of human IgG1. The presence or absence of such a clone may be verified, for example, by ELISA using Fas-IgG1 or IgG1, as the antigen.

(f) Cloning

Hybridomas which have been shown to produce specific antibodies, using a method similar to that described in step b) to determine antibody titer, are then transferred to another plate for cloning. Suitable cloning methods include: the limiting dilution method, in which hybridomas are diluted to contain one cell per well of a plate and then cultured; the soft agar method in which colonies are recovered after culturing in soft agar medium; a method of using a micromanipulator to separate a single cell for culture; and "sort-a-clone," in which single cells are separated by a cell sorter.

The cloning procedure according to, for example, the limiting dilution method is repeated 2 to 4 times for each well demonstrating an antibody titer, and clones having stable antibody titers are selected as anti-DR5 monoclonal antibody producing hybridomas. Hybridomas producing an anti mouse DR5 antibody are selected by a similar method to obtain an anti-DR5 monoclonal antibody producing cell line.

The mouse-mouse hybridoma TRA-8 which is a basis for antibodies of the present invention was deposited with American Type Culture Collection, 10801 University Boulevard, Manassas, Va. 20110-2209 in accordance with the Budapest Treaty on Mar. 1, 2000, and has the accession number PTA-1428. Accordingly, when preparing an antibody using the mouse-mouse hybridoma TRA-8 or any other established hybridoma, the preparation may be performed by following a procedure starting from the step (g) below, with the steps (a) to (f) omitted.

(g) Culture of Hybridoma to Prepare Monoclonal Antibody

The hybridoma obtained by the cloning is then cultured in normal medium, not in HT medium. Large-scale culture is performed by roller bottle culture, using large culture bottles, or by spinner culture. The supernatant from the large-scale culture is then harvested and purified by a suitable method, such as gel filtration, which is well known to those skilled in the art, to obtain an anti-DR5 monoclonal antibody which is a basis for antibodies of the present invention. The hybridoma may also be grown intraperitoneally in a syngeneic mouse, such as a BALB/c mouse or a nu/nu mouse, to obtain ascites containing an anti-DR5 monoclonal antibody in large quantities. Commercially available monoclonal antibody purification kits (for example, MAbTrap GII Kit; Pharmacia) are conveniently used to purify the harvested antibodies.

Monoclonal antibodies prepared as above have a high specificity for human DR5.

(h) Assay of Monoclonal Antibody

Suitable identification methods of the isotype and the subclass of the monoclonal antibody include the Ouchterlony method, ELISA and RIA. Preferably, a commercial kit is used for identification, such as a Mouse Typer Kit (trade name; BioRad).

Quantification of protein may be performed by the Folin-Lowry method, or by calculation based on the absorbance at 280 nm (1.4 (OD280)=Immunoglobulin 1 mg/ml).

Identification of the epitope that the monoclonal antibody recognizes is performed as follows. First, various partial structures of the molecule that the monoclonal antibody recognizes are prepared. The partial structures are prepared by the method wherein various partial peptides of the molecule are synthetically prepared by known oligopeptide synthesis technique, or the method wherein DNA encoding the desired partial polypeptide is incorporated in a suitable expression plasmid, and is expressed in a suitable host, such as $E.\ coli$, to produce the peptides. Generally, both methods are frequently used in combination for the above object. For example, a series of polypeptides having appropriately reduced lengths, working from the C- or N-terminus of the antigen protein, can be prepared by established genetic engineering techniques. By establishing which fragments react with the antibody, an approximate idea of the epitope site is obtained.

The epitope is more closely identified by synthesizing a variety of smaller oligopeptides corresponding thereto or mutants of the peptide using established oligopeptide synthesis techniques to determine a binding property of the peptides to the anti-DR5 monoclonal antibody, for example, which is a basis for preparation of the antibody of the present invention and a competitive inhibition of binding of the peptide to an antigen with the monoclonal antibody. Commercially available kits, such as the SPOTs Kit (Genosys Biotechnologies, Inc.) and a series of multipin peptide synthesis kits based on the multipin synthesis method (Chiron Corp.) may be conveniently used to obtain a large variety of oligopeptides.

An antibody of the present invention has the various functional properties a) to f) described below, each of which is verified by, for example, a method described herein below.

a) Specific Binding of TRA-8 to Cells Expressing Human DR5.

A unique feature of the present invention is the ability to bind cell surface DR5. This is demonstrated by flow cytometry analysis of cells expressing DR5. First, specific cell surface binding of DR5 is confirmed by the COS-7 cells transfected with the full-length cDNA encoding human DR5. Specifically, TRA-8 only recognizes COS-7 cells transfected with DR5 but not empty control vector or vector encoding DR4. Second, three different origins: hematopoietic, glioma, and prostate cancer of human malignant tumor cells are tested. The majority of these transformed tumor cells expressed significant levels of cell surface DR5, although expression levels varied largely. Third, two panels of human primary synovial fibroblast cells from RA and OA patients are examined. All RA synovial cells expressed significantly higher levels of DR5 compared to OA cells.

b) Induction of Apoptosis of Human Malignant Tumor Cells in Vitro in the Absence of Crosslinking.

The ability of an antibody raised according to the present invention to recognize TRAIL receptor and to directly induce apoptosis of malignant human tumor cells is determined by cell viability assay (ATPLite®) during in vitro culture of cells with various concentrations of an antibody, specifically TRA-8. The majority of tumor cells are susceptible to TRA-8 induced apoptosis. For some cells, TRA-8 exhibited a strong apoptosis-inducing activity, for example, TRA-8 is able to induce apoptosis of human Jurkat cells within the pg/ml levels. Importantly, TRA-8 induced apoptosis did not require crosslinking, and in most cells, TRA-8 exhibited a stronger apoptosis-inducing activity than the recombinant soluble TRAIL in the presence of the enhancer.

c) Tumoricidal Activity of TRA-8 in Vivo.

Tumoricidal activity of TRA-8 is evaluated in two SCID/human tumor cell models. First, SCID mice are intravenously inoculated with human leukemia Jurkat cells, and treated with a single dose (100 μg) of TRA-8. The results show that the majority of implanted Jurkat cells are eliminated from the peripheral blood and spleen by the treatment with TRA-8, as determined by flow cytometry analysis and in situ immunohistochemical straining of Jurkat cells. Second, human astrocytoma cells, 1321N1, are subcutaneously inoculated in SCID mice, and the tumor-bearing mice are treated with a single dose of TRA-8. The growth of implanted 1321N1 cells is significantly inhibited in TRA-8 treated mice as determined by the sizes of tumor and histological analysis.

d) Identification of RA Synovial Cells by TRA-8

The primary synovial cells isolated from 8 RA and 4 OA patients are tested for cell surface expression of DR5. TRA-8 is able to positively strain all RA cells but negatively stain all OA cells. Thus, RA is differentiated from OA by the surface expression of DR5 as detected by TRA-8.

e) Induction of Apoptosis in RA Synovial Fibroblast Cells by TRA-8

The ability of TRA-8 to induce apoptosis of RA synovial cells is determined by cell viability assay during in vitro culture in the presence of various concentrations of TRA-8. All RA cells exhibited high to intermediate levels of susceptibility to 100 ng/ml of TRA-8. In contrast, all OA cells are essentially resistant to TRA-8 induced apoptosis. Importantly, TRA-8 exhibited a better apoptosis-inducing activity to RA synovial cells than soluble TRAIL with the enhancer. Moreover, compared to anti-Fas antibody (CH-11), TRA-8 exhibited a better selectivity to RA synovial cells.

f) TRA-8 Does Not Induce Production of MMPs in RA Synovial Cells

Since TRA-8 is able to induce NF-kb activation in RA synovial cells as TNF-a, the effect of TRA-8 on the production of MMP1 and MMP3 of synovial cells is determined. While TNF-a induced a dose-dependent increase of MMPs, TRA-8 is unable to induce any production of MMPs, and in some concentrations, TRA-8 slightly decreased the production of MMPs in RA synovial cells.

g) TRA-8 Induces Multiple Caspase Activation.

Since caspases play a crucial role in induction of apoptosis. The ability of TRA-8 to induce caspase activation is determined in human Jurkat cells. When Jurkat cells are incubated with a low dose (50 ng/ml) of TRA-8, the activation of caspase 8, caspase 9, and caspase 3 is observed as early as 15 minutes after incubation as demonstrated by Western blot analysis and caspase cleavage analysis. In term of timing, number and strength of caspase activation, antibodies of the present invention including the demonstrative antibody TRA-8 exhibited a much better activity than any other known apoptosis-inducing antibodies, such as anti-human Fas antibody (CH-11).

Thus, an antibody of the present invention is a substance having a property to selectively induce apoptosis in pathogenic cells as shown in effect (a) and (g). Accordingly, it is useful as a prophylactic and therapeutic agent for diseases associated with inappropriate survival of cells or inappropriate proliferation of cells, such as those attributable to dysregulation of apoptosis systems including the Fas/Fas ligand system.

The ability of an antibody of the present invention to induce apoptosis is confirmed by culturing cells such as the human leukemia cell line Jurkat (American Type Culture No. TIB-152) and astrocytoma cell line 1321N1 in medium in which the test sample has been added, and determining the survival rate by, for example, an ATPLite® assay.

Antibody of the present invention, especially anti-DR5 antibodies having almost the same immunogenicity to human as that of human antibodies, is used as an agent for prophylaxis or treatment of diseases associated with inappropriate survival or proliferation of cells, including those attributable to dysregulation of the apoptosis systems in autoimmune diseases illustratively including systemic lupus erythematosus, Hashimoto's disease, rheumatoid arthritis, graft-versus-host disease, Sjögren's syndrome, pernicious anemia, Addison disease, scleroderma, Goodpasture's syndrome, Crohn's disease, autoimmune hemolytic anemia, sterility, myasthenia gravis, multiple sclerosis, Basedow's disease, thrombopenia purpura, insulin-dependent diabetes mellitus, allergy; asthma, atopic disease; arteriosclerosis; myocarditis; cardiomyopathy; glomerular nephritis; hypoplastic anemia; rejection after organ transplantation and numerous malignancies of lung, prostate, liver, ovary, colon, cervix, lymphatic and breast tissues.

Such a prophylactic or therapeutic agent may be administered in various forms. Suitable modes of administration include oral administration, such as by tablets, capsules, granules, powders and syrups, or parenteral administration, such as by injection or suppositories.

The antibody or therapeutic agent may be administered orally, rectally, intracisternally, intraventricular, intracranial, intrathecal, intravaginally, parenterally (intravenously, intramuscularly, or subcutaneously), locally (powders, ointments, or drops), by intraperitoneal injection, transdermally, by inhalation or as a buccal or nasal spray. The exact amount of the antibody or therapeutic agent required will vary from subject to subject, depending on the age, weight and general condition of the subject, the severity of the disease that is being treated, the location and size of the tumor, the particular compounds used, the mode of administration, and the like. An appropriate amount may be determined by one of ordinary skill in the art using only routine experimentation given the teachings herein. Typical single dosages of antibody range from 0.1-10,000 micrograms, preferably between 1 and 100 micrograms. Typical antibody concentrations in a carrier range from 0.2 to 2000 nanograms per delivered milliliter.

Depending on the intended mode of administration, the antibody or therapeutic agent can be in pharmaceutical compositions in the form of solid, semi-solid or liquid dosage forms, such as, for example, tablets, suppositories, pills, capsules, powders, liquids, or suspensions, preferably in unit dosage form suitable for single administration of a precise dosage. The compositions will include an effective amount of the selected substrate in combination with a pharmaceutically acceptable carrier and, in addition, may include other medicinal agents, pharmaceutical agents, carriers, or diluents. By "pharmaceutically acceptable" is meant a material that is not biologically or otherwise undesirable, which can be administered to an individual along with the selected substrate without causing significant undesirable biological effects or interacting in a deleterious manner with any of the other components of the pharmaceutical composition in which it is contained.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solution are also contemplated as being within the scope of this invention.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate and laurylsulphonate salts, and the like. These may include cations based on the alkali and alkaline earth metals, such as sodium, lithium, potassium, calcium, magnesium, and the like, as well as non-toxic ammonium, quaternary ammonium and amine cations including, but not limited to ammonium, tetramethylammonium, tetraethylammonium, methylamine, dimethylamine, trimethylamine, triethylamine, ethylamine, and the like. (See, for example, S. M. Barge et al., "Pharmaceutical Salts," *J. Pharm. Sci.*, 1977, 66:1-19 which is incorporated herein by reference.)

The term "prodrug" refers to compounds that are rapidly transformed in vivo to yield the parent compounds of the above formula, for example, by hydrolysis in blood. A thorough discussion is provided in T. Higuchi and V. Stella, "Prodrugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987.

A target cell is a cell of an animal illustratively including human, non-human primate, rat, mouse, guinea pig, rabbit, goat, sheep, cow, horse, chicken, pig, marmoset and ferret.

In addition, the antibody or therapeutic agent of the present invention can exist in unsolvated as well as solvated forms with pharmaceutically acceptable solvents such as water, ethanol, and the like. In general, the solvated forms are considered equivalent to the unsolvated forms for the purposes of the present invention.

Antibody molecules are purified by known techniques illustratively including amino absorption or amino affinity chromatography, chromatographic techniques such as high pressure liquid chromatography, or a combination thereof.

Another aspect of the present invention includes a pharmaceutical product for use in delivering biologically active anti-TRAIL receptor antibody or humanized anti-TRAIL receptor antibody to a vertebrate. The pharmaceutical product includes a pharmaceutically effective quantity of anti-TRAIL receptor antibody or fragment thereof, a pharmaceutically acceptable carrier, and a container enclosing the carrier and the antibody in a sterile fashion.

In a preferred embodiment of the invention, a pharmaceutically effective amount of an anti-DR5 antibody inhibits cell proliferation by contact with a target cell. A pharmaceutically effective amount of an antibody recognizing DR5 or a humanized antibody recognizing DR5 is an amount administered to an individual sufficient to cause a desired effect. Desired effects of administration of a pharmaceutically effective amount of DR5 recognizing antibodies include death of a target cell, growth inhibition of a target cell, stimulation of DR5, binding to DR5 and increased NFkB levels or activity in a target cell. A target cell is a cell that expresses DR5 and illustratively includes abnormally growing cells and tumor cells such as papillomas and warts; breast cancer, colon cancer, hepatomas, leukemias, lung cancer, melanoma, myelomas, osteosarcomas, ovarian cancer, pancreatic cancer, prostate cancer, cancer of the head and neck, thyroid cancer, uterine cancer and tumors of the brain such as astrocytomas. In vivo, the target cell is a cell of an individual with a pathological condition, including those where cell proliferation is abnormal or dysregulated such as malignant or benign cancer and rheumatoid arthritis.

In another preferred embodiment, the target cell is also contacted by a therapeutic agent.

A therapeutic agent is a compound or composition effective in ameliorating a pathological condition. An illustrative example of a therapeutic agent includes an anti-cancer compound.

An anti-cancer compound is a compound or composition effective in inhibiting or arresting the growth of an abnormally growing cell. A pharmaceutically effective amount of an anti-cancer compound is an amount administered to an individual sufficient to cause inhibition or arrest of the growth of an abnormally growing cell. Illustrative examples of anti-cancer compounds include: bleomycin, carboplatin, chlorambucil, cisplatin, colchicine, cyclophosphamide, daunorubicin, dactinomycin, diethylstilbestrol doxorubicin, etoposide, 5-fluorouracil, floxuridine, melphalan, methotrexate, mitomycin, 6-mercaptopurine, teniposide, 6-thioguanine, vincristine and vinblastine. Further examples of anti-cancer compounds and therapeutic agents are found in The Merck Manual of Diagnosis and Therapy, 15th Ed., Berkow et al., eds., 1987, Rahway, N. J. and Sladek et al. Metabolism and Action of Anti-Cancer Drugs, 1987, Powis et al. eds., Taylor and Francis, New York, N.Y.

Antibody of the present invention can be further combined with other therapies, such as chemotherapy and radiotherapy in the treatment of malignance, and therapeutic efficacy can be enhanced by apoptosis-inducing compounds such as bis-indolylmaleimide VIII.

Compared to previously published anti-DR5 antibody (24), the apoptosis-inducing activity of the demonstrative TRA-8 antibody of the present invention is very strong, and is able to induce apoptosis of Jurkat cells with the pg/ml levels in vitro and demonstrates superior in vivo tumoricidal activity as compared to previously reported soluble TRAIL. The intravenous administration of a single dose of TRA-8 is sufficient to inhibit the growth of both solid tumor and hematopoietic tumor cells, whereas induction of in vivo tumor regression with the soluble TRAIL requires much high dose (500 µg every day for 10 days). The anti-TRAIL receptor antibodies of the present invention appear to be as safe as soluble TRAIL since exemplary antibody TRA-8 does not induce apoptosis of non-transformed fibroblast cells.

Vectors of the present invention include a nucleic acid sequence encoding a heavy or light chain immunoglobulin of an anti-DR5 antibody operably linked to a regulatory element such as a promoter or enhancer. "Operably linked" refers to an arrangement of nucleotide sequences configured so as to perform their usual function. Thus, a regulatory element operably linked to a nucleotide sequence encoding a polypeptide is capable of directing the transcription, replication and/or translation of the polypeptide. It will be recognized by those skilled in the art that a single vector optionally includes coding sequences for both a heavy and a light chain immunoglobulin of an anti-DR5 antibody.

The following examples are set forth below to illustrate the methods and results according to the present invention. These examples are not intended to be inclusive of all aspects of the present invention, but rather to illustrate representative methods and results. These examples are not intended to exclude equivalents and variations of the present invention which are apparent to one skilled in the art.

Example 1

Preparation of DR5 Antigen 1.1 Cloning of DR5 cDNA

DNA encoding the human DR5 protein is cloned by the following RT-PCR method using:

a) Template

The total RNA of HeLa cells is extracted by using TRIzol Reagent (GIBCO BRL). The template for the PCR reaction used cDNA that is obtained by using the First-Strand cDNA synthesis kit (Amersham Pharmacia Biotech) according to the instruction manual provided with the kit.

b) PCR Primers

The following oligonucleotide primers are synthesized for the PCR:

```
                              (DR5p1: SEQ ID No. 1)
     5'-gacgatgcccgatctactttaaggg-3';

(DR5p2: SEQ ID No. 2)
     5'-ccactgggtgatgttggatggg-3';
```

Unless otherwise specified, all oligonucleotides in these Examples are synthesized by Lifetechnologies. All oligonucleotides are stored at −20° C. after being dissolved in distilled water.

c) PCR Reaction

Composition of the PCR reaction solution:
template cDNA, 5 µl of total 33 µl reaction
primer DR5p1, 10 pmol;
primer DR5p2, 10 pmol;
10× concentrated PCR buffer (provided with the kit), 10 µl;

dNTPs (each 2.5 mM), 4 µl; and

Tag polymerase (Promega), 5 units.

Sterile distilled water is added to the solution to a total volume of 100 µl. Unless otherwise specified, dNTPs are an equimolar mixture of dATP, dCTP, dGTP and dTTP (2.5 mM each).

The PCR reaction is conducted as follows. The solution is first heated at 94° C. for 2 minutes, after which a cycle of heating to 94° C. for 30 sec, 52° C. for 1 minute and 72° C. for 3 minutes, is repeated 40 times. After completion of this procedure, the reaction solution is heated at 72° C. for 10 minutes.

The amplified DNA fragments, thus obtained, are separated on a 1% agarose gel containing 0.25 ug/ml ethidium bromide. The bands determined to contain the desired DNA fragments are cut out using a razor blade and the DNA is recovered therefrom using the Gene Clean kit (BIO101). The DNA fragment is cloned using the TA Cloning Kit (Invitrogen, CA). This is performed as follows.

The DNA fragment recovered from the PCR reaction solution, together with 50 ng of pCR2.1 vector which is provided with the TA Cloning kit, is mixed with 1 µl of 10× ligase reaction buffer (6 mM Tris-HCl (pH 7.5), 6 mM magnesium chloride, 5 mM sodium chloride, 7 mM β-mercaptoethanol, 0.1 mM ATP, 2 mM DTT, 1 mM spermidine, and 0.1 mg/ml bovine serum albumin), to which 4 units of T4 DNA ligase (1 µl) has been added. The total volume of the mixture is adjusted to 10 µl with sterile deionized water, and the resulting ligase solution is incubated at 14° C. for 15 hours. After this time, 2 µl of the ligase reaction solution is added to 50 µl of competent *E. coli* strain TOP10F', which is provided with the TA cloning kit and brought to competence in accordance with the instruction manual, to which 2 µl of 0.5 M β-mercaptoethanol has been added, and the resulting mixture is kept on ice for 30 minutes, then at 42° C. for 30 seconds, and again on ice for 5 minutes. Next, 500 µl of medium containing 2% v/v tryptone, 0.5% w/v yeast extract, 0.05% w/v sodium chloride, 2.5 mM potassium chloride, 1 mM magnesium chloride, and 20 mM glucose (hereinafter referred to as "SOC" medium) is added to the culture, and the mixture is incubated for 1 hour at 37° C. with shaking. After this time, the culture is spread on an L-broth agar plate (1% v/v tryptone, 0.5% w/v yeast extract, 0.5% w/v sodium chloride, 0.1% w/v glucose, and 0.6% w/v bacto-agar (Difco)), containing 100 µg/ml. Ampicillin resistant colonies appearing on the plate are selected and scraped off with a platinum transfer loop, and cultured in L-broth medium containing 100 µg/ml ampicillin at 37° C., overnight, with shaking at 200 r.p.m. After incubation, the cells are harvested by centrifugation, from which plasmid DNA is prepared by the alkali method. EcoRI-EcoRI DR5cDNA fragment from the thus obtained plasmid is subcloned into pCDNA3 plasmid (Invitrogen, CA). The full length of the DR5 gene in pCDNA3 are sequenced and matched the published sequence. The thus obtained plasmid is designated as plasmid pCDNA3-DR5.

1.2 Construction of DR5-IgG Expression Vector

In order to obtain a soluble form of human DR5 lacking the transmembrane domain, an expression plasmid vector is constructed. This vector is designed to encode a fusion protein comprising the extracellular domain of human DR5 fused to the human IgG1 Fc DNA (41). DNA encoding the human DR5 lacking the transmembrane domain is obtained by the following PCR reaction.

a) Template

The template for the PCR reaction used pcDNA3-DR5.

b) PCR Primers

The following oligonucleotide primers are synthesized for the PCR:

```
                               (DR5p1: SEQ ID No. 1)
5'-gacgatgcccgatctactttaaggg-3';

(DR5p3: SEQ ID No. 3)
5'-ggatccgtggacacattcgatgtc-3';
```

Unless otherwise specified, all oligonucleotides in these Examples are synthesized by Lifetechnologies. All oligonucleotides are stored at −20° C. after being dissolved in distilled water.

c) PCR Reaction

The PCR reaction is conducted and amplified DNA isolated as per Example 1.1(c).

The thus obtained plasmid is designated as plasmid pCR-ΔDR5. The BamHI-EcoRI fragment encoded human Fc fragment which is recovered from pmFas-hIgG1Fc is subcloned into BamHI and EcoRI multi-cloning sites of pcDNA3. The plasmid thus obtained is designated pcDNAFc. Furthermore, the BamHI-BamHI fragment encoding the human soluble DR5 region which is recovered from pCR-ΔDR5 is subcloned into the BamHI site of pcDNAFc plasmid. The thus obtained plasmid is designated as plasmid pcDNAΔDR5-Fc. The EcoRI fragment encoding the human soluble DR5-human IgG Fc region which is recovered from the pcDNAΔDR5-Fc plasmid is blunt ended by using the DNA polymerase Klenow fragment (GIBCO BRL) and then subcloned into the shuttle vector pAdCMV5 (Quantum Biotechnologies Inc., Canada) which is blunt ended after cutting by BamHI. The plasmid thus obtained is designated pAdΔDR5-Fc.

1.3 Expression and Purification of the Human DR5-IgG1 Fusion Protein

QBI-293A cells (provided with the ADENO-Quest Kit) are co-transfected with pAdΔDR5-Fc and QBI-viral DNA (provided with the ADENO-Quest Kit) using the ADENO-Quest kit (Quantum Biotechnologies Inc., Canada) according to the instruction manual. The recombinant virus plaques are cultured and screened for expression of DR5-IgG fusion protein by ELISA analysis of the supernatant. The positive plaques are amplified in QBI-293A cells and stored at −80° C. as virus stock. Fifty dishes (150 mm) of QBI-293A cells are transfected with pAdΔDR5-Fc recombinant virus at 10 m.o.i. (Multiplicity of Infection). The culture media are harvested after transfection for 48 hours.

The transfected cells having the DR5-IgG gene are grown to a cell density of $1 \times 10^6$ cells/ml by incubation in 500 ml of DMEM (GIBCO) medium, containing 10% v/v FCS, at 37° C. in an atmosphere of 5% v/v $CO_2$ for 2 days. The culture is then centrifuged (1,000 r.p.m., 5 minutes) and the supernatant collected. The purification of DR5-IgG from the supernatant is achieved using ProteinA-Sepharose CL-4B affinity chromatography (Pharmacia) under the following conditions:

column: ProteinA-Sepharose CL-4B column (column size 2 ml; Pharmacia);

elution buffer: 0.1 M glycine (pH 2.4), 0.15 M NaCl;

neutralization buffer: 1M Tris-HCl (pH 8.5).

After all of the supernatant is applied to the column, it is washed three times with 20 ml of PBS and then 1 ml of elution buffer is added 10 times. The optical density of each eluted fraction (1 ml) is measured. The second fraction through the fifth fraction (with $OD_{280} \geq 0.1$) are collected and after addition of 100 µl of neutralization buffer, the eluates are placed separately in dialysis tubing, and the eluates dialyzed against 1 liter of PBS (pH 7.5) at 4° C. The dialysis buffer being changed twice.

The eluates are then assayed for expression of the DR5-IgG gene product by ELISA. First, 100 µl of each fraction are placed separately into wells of a 96-well microplate (Costar) and incubated at 37° C. for 1 hour. After this time, the solution in the wells is removed, and the plate is washed 3 times with 100 µl/well of PBS containing 0.1% v/v Tween® 20 (hereinafter referred to as "PBS-Tween"). After washing, PBS containing 2% w/v bovine serum albumin (hereinafter referred to as "BSA") is added in quantities of 100 µl/well, and the plate is then incubated at 37° C. for 1 hour. After this time, the wells are washed a further 3 times with 100 µl/well of PBS-Tween, after which 100 µl/well of a solution of anti-human IgG1 monoclonal antibody diluted 1000-fold with PBS-Tween is added to each well, and the plate is once again incubated at 37° C. for 1 hour. The wells are then washed 3 times with 100 µl/well of PBS-Tween. 3,3',5,5'-Tetramethyl-benzidine (hereinafter referred to as "TMB") liquid substrate system (Sigma) is then added in an amount of 100 µl/well and the plate is allowed to stand at room temperature for 5 minutes and then the reaction stopped by adding 100 µl/well of 0.2N $H_2SO_4$. The absorbance of each well is read at 450 nm to estimate the concentration of the bound antibody, using the absorbance at 650 nm as the control reading. The absorbance is measured using a microplate reader (Molecular Devices). The production of DR5-IgG1 is confirmed using this ELISA method. The molecular weight of the expressed DR5-IgG1 fusion protein is determined using western blotting analysis in which anti-human IgG1 mAb (Sigma) is used to detect the antibody on the gel. The molecular weight of the expressed DR5-IgG1 fusion protein has an approximate molecular weight of 50 kDa. The purity achieved being greater than 90% as evaluated by analysis on SDS-PAGE and detection of the protein by Coomassie blue staining.

Example 2

Generation of Monoclonal Antibodies Against Human DR5

2.1 Immunization

Female, Balb/c mice (Jackson Laboratory, Bar Harbor, Me.) of 6-8 weeks of age, are immunized with the affinity-purified human DR5/hIgG1 fusion protein. For the initial foot-pad immunization, the fusion protein (50 µg) is emulsified in Freund's complete adjuvant (Difco, Detroit, Mich.). The mice are then boosted with four injections of 50 µg of fusion protein administered without adjuvant every other day. Three days after the last injection, lymphocytes from the local lymph nodes are fused with NS-1 myeloma cells, and the hybridomas are cultured in F104 media supplemented with 10% fetal calf serum. Positive hybridomas are selected by ELISA in which the plates are coated either with 1 µg/ml DR5/hIgG1 or the same amount of Fas/hIgG1 as a control. The isotype of the hybridomas is determined by ELISA using a panel of mouse Ig isotype-specific goat antibodies (Southern Biotechnology, Birmingham, Ala.). Monoclonal antibodies are purified by affinity chromatography using immobilized anti-mouse IgG1 or protein G (Sigma).

2.2 Cell Fusion

On the third day after the booster injection, the local lymph nodes are removed from the mouse and placed into 10 ml of serum-free RPMI 1640 medium (GIBCO BRL) containing 50 units/ml penicillin, 50 µg/ml streptomycin, and 300 µg/ml L-glutamic acid, and disrupted by passing the organ through a mesh (Cell Strainer; Falcon) using a spatula. The resulting cell suspension is centrifuged to pellet the local lymph nodes cells which are then washed twice with serum-free RPMI medium. The washed cells are then resuspended in serum-free RPMI medium and counted.

In the meantime, myeloma NS1 cells (American Type Culture Collection TIB-18) had been grown to a cell density not exceeding $1 \times 10^8$ cells/ml in ASF104 medium (Ajinomoto, K. K.) containing 10% v/v FCS (Gibco BRL) ("ASF medium with serum") at 37° C. under 5% v/v $CO_2$, and these are likewise disrupted, washed, resuspended and counted.

An amount of the NS1 cell suspension calculated to contain $3 \times 10^7$ cells is mixed with an amount of the spleen cell suspension calculated to contain $3 \times 10^8$ cells. The resulting mix is centrifuged and the supernatant discarded. The following steps of the cell fusion are performed whilst at all times keeping the plastic tube containing the pellet at 37° C. in a beaker of warm water.

One ml of 50% (w/v) polyethylene glycol 1500 (Boehringer Manheim) is then slowly added to the tube, all the while stirring the pellet using the tip of a pipette. Subsequently, 1 ml of serum-free RPMI medium, prewarmed to 37° C., is slowly added in 2 portions, followed by the addition of a further 7 ml of serum-free RPMI medium. The resulting mix is then centrifuged, the supernatant discarded and 10 ml of HAT medium containing 10% v/v FCS are added while stirring gently with the tip of a pipette. A further 20 ml of HAT medium containing 10% v/v FCS is added, and the suspension is dispensed into 96-well cell culture microplates at 100 µl/well and incubated at 37° C. in an atmosphere of 5% v/v $CO_2$. After 7 or 8 days, 100 µl/well of fresh HAT medium are used to replace medium in any wells exhibiting a yellowish hue. The fusion cells from these wells are cloned by limiting dilution as described below.

2.3 Cloning by Limiting Dilution

Thymuses from 4 to 10 week-old female BALB/c mice (from Japan SLC, Inc.) are removed, disrupted on a mesh (Cell Strainer; Falcon) as described above, and the disrupted cells are washed twice with HT medium containing 10% v/v FCS. An amount of thymus cells corresponding to those from one mouse is suspended in 30 ml of HT medium containing 10% v/v FCS to produce a feeder cell suspension. The fusion cell preparation obtained above in Example 2.2 is diluted with this feeder cell suspension 10- to 100-fold, and further diluted serially with the feeder cell suspension to make suspensions having fusion cell densities of 5, 1 and 0.5 cells/ml. The thus prepared samples are dispensed into wells of 96-well cell culture microplates at 100 µl/well and incubated for 5 days at 37° C. under 5% v/v $CO_2$.

2.4 Screening

The culture supernatants from the growing hybridomas are screened by ELISA using plates coated either with 1 µg/ml DR5/hIgG1 or the same amount of Fas/hIgG1 (41) as a control. The bound antibodies are detected using horseradish peroxidase (HRP)-conjugated anti-mouse immunoglobulins (Southern Biotechnology. Birmingham, Ala.) with TMB (Sigma, St Louis, Mich.) as the substrate. Purified DR5-IgG1 at a concentration of 1 µg/ml or the same amount of Fas-hIgG1 are introduced into a well of a 96-well ELISA/RIA STRIP PLATE (Costar, N.Y.). The plate is kept standing at 4° C. overnight to allow adsorption of the protein onto the well surface. After this time, the solution in the wells is discarded and each well is washed 3 times with PBS-Tween. Then, 100 µl of PBS containing 1% (w/v) bovine serum albumin (A3803; Sigma Chemicals Co.) is added to each well and the plate is incubated at 37° C. for 1 hour. The wells are then washed a further 3 times with PBS-Tween, and then 50 µl of each culture supernatants from the growing hybridomas is added to each well. The plate is then incubated at 37° C. for 1 hour, and the wells are again washed 4 times with PBS- Tween. After washing, 50 µl of horseradish peroxidase labeled goat anti-mouse immunoglobulin antibody (Southern Biotechnology, Birmingham, Ala.), diluted 1000-fold with PBS, is added per well, and the plate is again incubated at 37° C. for 1 hour, after which the wells are washed 4 times with PBS-Tween. 3,3',5,5'-Tetramethyl-benzidine (TMB) liquid substrate system (Sigma) is then added in an amount of 100 µl/well and the plate is allowed to stand at room temperature for 5 minutes and then the reaction stopped by addition of 100 µl/well of 0.2N $H_2SO_4$. The absorbance of each well at 450 nm (control 650 nm) is measured using a microplate reader (Molecular Devices) and fusion cells are selected from the sample which had the absorbance (450 nm-650 nm, OD values; >0.5) clearly higher than those to which no fusion cells supernatant had been added (OD values; ≈0.03).

Furthermore, the culture supernatants from the growing hybridomas are also functionally screened by measuring the apoptosis-inducing activity using Jurkat cell. Fifty µl of RPMI medium containing Jurkat cells (1000 cells per well) and 5 uM Bisindolylmaleimide VIII (BisVIII, Alexis, San Diego, Calif.) are added in 96-well plates in the presence of 50 µl of the culture supernatants from the growing hybridomas. The cells are cultured in a humidified incubator at 37° C. overnight. Apoptosis is determined by cell viability using the ATPLite® kit as instructed by the manufacturer (Packard Instruments), and the samples are counted using the Top-Counter (Packard Instruments).

2.5 ELISA Binding of TRAIL and TRA-8 to the Receptors

ELISA plates are coated with 2 µg/ml of DR4-Ig or DR5-Ig fusion protein overnight. After blocking with 3% BSA, the soluble TRAIL-FLAG or TRA-8 is added at indicated concentrations and incubated at 37° C. for one hour. The binding of TRAIL or TRA-8 is detected by HRP-conjugated anti-Flag antibody (Alexis) or HRP-conjugated anti-murine IgG1 (Southern Biotechnology), respectively. The reactions are developed by TMB substrate buffer and measured by the Benchmark Microplate Reader (BioRad). The Kd values are estimated by the one-site binding model of non-linear regression using GraphPad Prism® software (GraphPad Software, San Diego, Calif.). For competitive ELISA, 100 ng/ml TRAIL-FLAG is added and incubated in the presence of various concentrations of TRA-8. The binding of TRAIL is determined as above.

2.6 Cloning

The steps described in Examples 2.3 and 2.4 above are repeated 5 times for the cells selected in 2.4, thereby enabling the selection of several hybridoma clones each of which produced a single antibody that bound DR5-IgG but did not bind Fas-IgG. As a result of this selection procedure, a mouse-mouse hybridoma, designated TRA-8 and producing an antibody binding to DR5-IgG, but not Fas-IgG, is obtained. This hybridoma, TRA-8, was deposited with the American Type Culture Collection on Mar. 1, 2000, and has been assigned accession No. PTA-1428.

The subclass of the antibody produced by the mouse-mouse hybridoma TRA-8 (hereinafter referred to simply as "TRA-8") is demonstrated to be IgG1, κ, after testing with a monoclonal antibody isotyping kit (Pierce).

Using our human DR5-IgG1 fusion protein as immunogen, seven hybridoma clones are obtained by initial ELISA screening, all of which are strongly positive for DR5-IgG but not the Fas-IgG fusion protein, indicating that the obtained hybridomas produce antibodies that recognize the extracellular portion of DR5 but not the Fc portion of IgG1 (data not shown).

2.7 Western Blot Analysis

Filters for Western blot analysis of normal human and cancer tissue homogenates are purchased from Geno Technology (St Louis, Mo.). Each lane is loaded with an equal amount of protein as determined by an anti-β-actin antibody. The blots are probed with 1 µg/ml TRA-8 overnight, and followed by HRP-conjugated goat anti-mouse IgG1 (Southern Biotechnology) at room temperature for one hour, and developed by chemiluminescence.

2.8 In Situ Immunohistochemistry

Human tissues are obtained from the Tissue Procurement Center of UAB. Frozen sections are fixed in 70% ethanol, blocked with 10% horse serum in PBS, and then incubated with 10 µg/ml of affinity-purified TRA-8 at room temperature for 60 minutes. The anti-mouse IgG ABC kit with diaminobenzidine (Vector, Burlingame, Calif.) as the colorimetric substrate is used to visualize the reactivity.

2.9 Analysis of Caspase Activation

Jurkat cells ($1 \times 10^6$/ml) are incubated with 500 ng/ml TRA-8. Aliquots (30 µg of protein) of the cell lysate are separated on 15% SDS-PAGE, blotted onto a nylon membrane, and the blots are probed with anti-caspase 8, 9, and 3 antibodies (BD Pharmingen, San Diego, Calif.) followed by HRP-conjugated secondary antibody and chemiluminescence visualization of cleaved products. The caspase inhibitor set is purchased from R&D Systems (Minneapolis, Minn.). Each caspase inhibitor is added into culture at indicated concentrations.

Example 3

Purification of TRA-8 Monoclonal Antibody

The mouse-mouse hybridoma, TRA-8, is grown to a cell density of $1 \times 10^6$ cells/ml by incubation in 500 ml of ASF medium, containing 10% v/v FCS, at 37° C. under 5% v/v $CO_2$ for 5 days. The culture is then centrifuged (1,000 r.p.m., 5 minutes) and the supernatant collected. The purification of TRA-8 from the supernatant is achieved using ProteinG-Sepharose CL-4B affinity chromatography (Pharmacia) under the following conditions:

column: ProteinG-Sepharose CL-4B column (column size 2 ml; Pharmacia);

elution buffer: 0.1 M Glycine (pH 2.4), 0.15 M NaCl;

neutralization buffer: 1M Tris-HCl (pH 8.5).

After all of the supernatant is applied to column, 20 ml of PBS is washed three times and then elution buffer is added in 1 ml volumes for 10 times. The optical density of each eluted fraction (1 ml) is measured. The fractions from No. 2 to No. 5 (>$OD_{280}$=0.1) are collected separately.

After adding 100 µl of neutralization buffer, the eluates are placed in dialysis tubing separately, and the eluates dialyzed against 1 liter of PBS (pH 7.5) at 4° C. The dialysis buffer being changed twice. This sample is assayed for anti-DR5 antibody activity by ELISA using the human DR5-IgG fusion protein prepared above using the technique described above.

Example 4

Preparation of DR4 Antigen, DR4-IgG Expression Vector and Anti-DR4 Monoclonal Antibody The procedures of Examples 1-3 are repeated with DR4 template cDNA and primers in place of those detailed in Example 1 to obtain a DR4 antigen which is utilized as per Examples 1.2-3 to obtain a monoclonal antibody specific against DR4.

Example 5

Monoclonal Antibodies Against DcR1 and DcR2

Monoclonal antibodies are raised against decoy receptors DcR1 and DcR2 by substituting the corresponding cDNA and primers to create the respective antigens as per Example 1. Expression vectors for DcR1 or DcR2-fusions with immune globulin G and resulting purified monoclonal antibodies are created as per Examples 2 and 3.

Example 6

The Specificity of a Monoclonal Antibody

As all of the receptors for TRAIL and other proteins of the TNFR family share significant homology, the specificity of exemplary antibody TRA-8 for DR5 is determined by western blot analysis using two different human DR5-IgG fusion proteins and soluble, recombinant forms of other related proteins. A first DR5-Ig fusion protein is constructed by fusing cDNA from residues 1-180 of the extracellular portion of DR5 and cDNA encoding the constant region of human IgG1. The fused cDNA is cloned into a recombinant adenoviral vector (Quantum Biotechnologies, Inc., Montreal, Canada). The expressed DR5/hIgG1 fusion protein, which had a relative molecular weight of 50 kDa, is purified using an anti-human IgG affinity column (Sigma, St Louis, Mo.). For western blot analysis of specificity, a second recombinant human DR5/IgG1 fusion protein (aa. 52-212), as well as TRAIL-R1, R3 and R4 fusion proteins, are purchased from Alexis. The soluble forms of human Fas and TNFR1 are kindly provided by Dr. Carl Edwards of Amgen, Inc., Thousands Oaks, Calif., USA. The soluble recombinant human DR4, DcR1, DcR2, TNFR1, R4, and Fas molecules used are human IgG1 fusion proteins. 0.5 µg of each protein is separated by 10% SDS-PAGE and blotted onto a nitrocellulose membrane. The blots are blocked with 5% dry milk in PBS at room temperature for one hour, and probed with 1 µg/ml of purified monoclonal anti-DR5 antibody (clone: TRA-8) or 0.1 µg/ml of HRP-conjugated goat anti-human IgG at 4° C. overnight. Horse-radish-peroxidase (HRP)-conjugated goat anti-mouse IgG is used as secondary antibody to detect bound TRA-8. The blots are developed by chemiluminescence.

Cos-7 cells transfected with the pcDNA3 vector (Clontech, Palo Alto, Calif.) containing the full-length DR5 or DR4 or empty vector are used for flow cytometry analysis. The full-length cDNA encoding human TRAIL or murine Fas ligand is cloned into the pTRE vector down-stream of the tetracycline-controllable promoter (Clontech). The XhoI-HindIII fragments of pTRE-hTRAIL or pTRE-mFasL are further cloned into the adenoviral shuttle vector pAdBN (Quantum Biotechnologies, Inc.). The 293 host cells are co-transfected with the linearized pAd-TRE-hTRAIL or pAd-TRE-mFasL and the large fragment DNA of adenovirus. The expression of functional human TRAIL or murine Fas ligand from the recombinant virus plaques is screened using a $^{51}$Cr-release assay with Jurkat as the targets.

TRA-8 reacted strongly with the DR5-IgG fusion protein (~50 kDa), which is used for immunization as shown in FIG. 1a, DR5, #1, and weakly with the second DR5-IgG fusion protein (~60 kD) as shown in FIG. 1a, DR5, #2. There is no significant binding of TRA-8 to DR4, DcR1, DcR2, Fas (CD95) or TNFRI. These results indicate that TRA-8 recognizes the epitopes that are specific for DR5 but not shared by the other members of the family.

TRA-8 does not react with other members of the TNF receptor superfamily, such as Fas (CD95) and TNF receptor I, nor does TRA-8 cross-react with the murine homologue of DR5 as shown by optical absorbance ratios for 450 nm and 650 nm, wherein lower panel numbers 1-7 (FIG. 1a, the column 8 of lower panel). Soluble TRAIL and TRA-8 bound comparably to immobilized DR5 (FIG. 1b, left panel). In contrast, TRAIL bound to DR4, but TRA-8 did not exhibit any binding activity to DR4 (FIG. 1b, middle panel). The Kd values for the binding of TRAIL and TRA-8 to DR5 are estimated at 59 nM and 3 nM, respectively. Importantly, TRA-8 efficiently competing with TRAIL for binding to DR5 but not for binding to DR4, as shown in competitive ELISA (FIG. 1b, right panel). These results establish the specificity of TRA-8 for human DR5.

Figures 1, 1D:
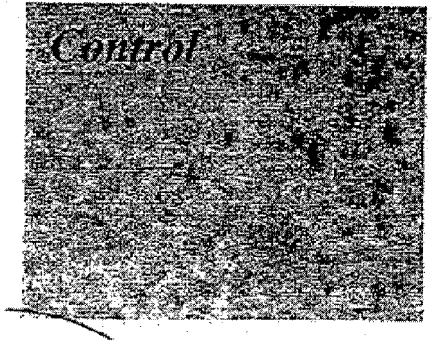
Figures 1, 1D, 2:
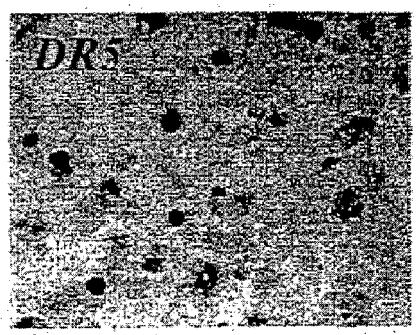
Figure 1E:
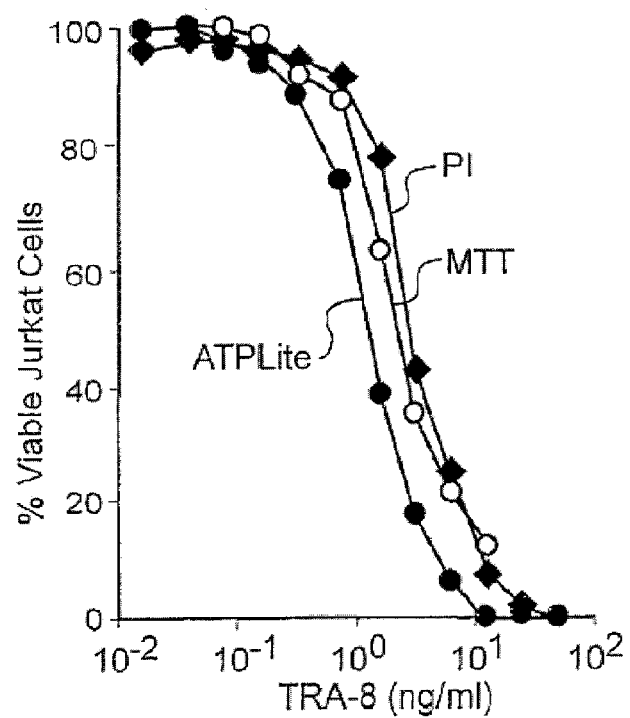
Figure 1F:
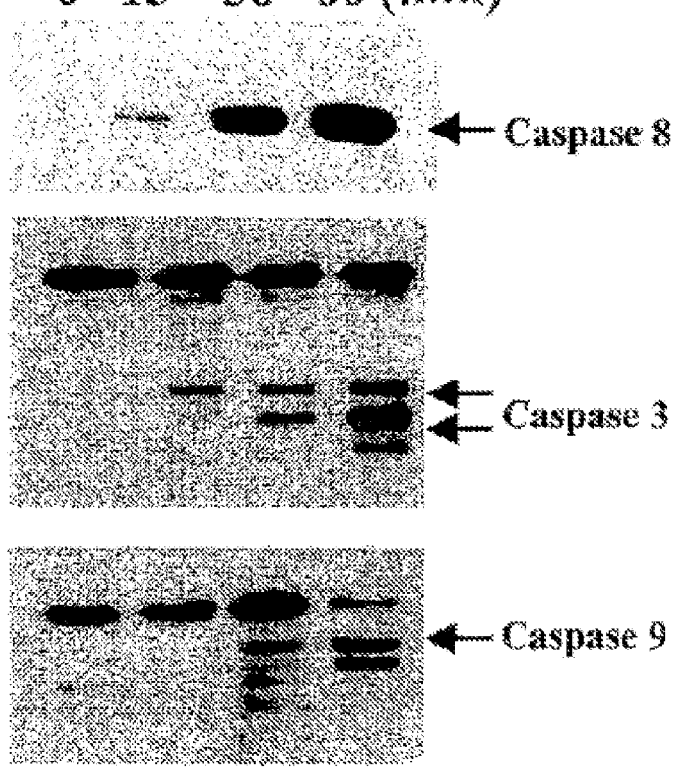
Figure 1G:
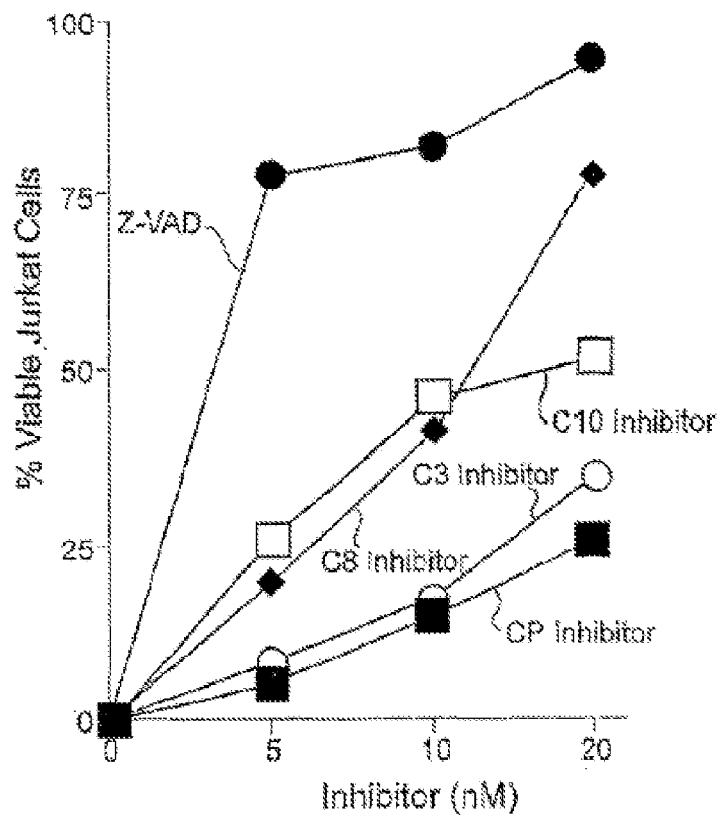

TRA-8 is able to detect cell surface expression of DR5, with flow cytometric analysis indicating specific binding to the cell surface of Cos-7 cells transfected with full-length human DR5, but not of Cos-7 cells transfected with DR4 or empty vector (FIG. 1c). Similarly, in situ immunohistochemistry with TRA-8 demonstrated reactivity with Cos-7 cells transfected with full-length DR5 DNA but not with those transfected with control vector (FIG. 1d). TRA-8 does not induce apoptosis of untransfected Cos-7 cells, and RT-PCR of RNA from Cos-7 cells using paired primers encoding human DR5 showed that no specific PCR products. Further functional analysis using human Jurkat cells as targets showed that, in the absence of crosslinking, TRA-8 strongly induces cell death, demonstrated by three different assays for cell viability including ATPLite®, MTT and PI exclusion (FIG. 1e). Greater than 50% of Jurkat cells are killed by nanogram levels of TRA-8 as shown by ATPLite® assay. The killing activity of TRA-8 is specific for DR5 as it could be blocked by DR5-Ig but not DR4-Ig fusion protein (data not shown). Cleavage of caspases 8, 9, and 3 could be detected by western blot analysis as early as 30 minutes after TRA-8 treatment of Jurkat cells (FIG. 1f), and cell death of Jurkat cells is completely inhibited by the general caspase inhibitor (Z-VAD) (FIG. 1g). Individual caspase inhibitors for caspase 8, 3, 9, and 10 partially inhibited cell death, further indicating that TRA-8-mediated cell death is primarily through a caspase-dependent apoptotic mechanism.

Example 7

Flow Cytometric Analysis of the Expression of Cell Surface DR5: A Major Death Receptor on Many Tumor Cells but Not on Normal Cells The ability of TRA-8 to bind DR5 expressed on the cell surface and the specificity of this reaction is then assessed using COS-7 (American Type Culture Collection No. CRL-1651) cells transfected with the expression vector containing the full-length human DR5 or DR4 cDNA or empty vector as control. Phycoerythrin (PE)-conjugated anti-mouse IgG1 (Pharmingen) is used as the second antibody to detect the bound TRA-8. The fluorescence of $1 \times 10^4$ cells is measured, using a flow cytometer (FACSVantage™) under the following conditions:

Excitation wave length: 488 nm;
Detection wave length; 600 nm.

Flow cytometry analysis showed that TRA-8 stained approximately 30% of COS-7 cells transfected with the DR5 vector as shown in the solid histogram of FIG. 1c. This percentage parallels the transfection efficiency as determined by analysis of transfection using green fluorescent protein (GFP) (data not shown). TRA-8 did not significantly stain cells transfected with either DR4 (the open histogram) or control vector (the dotted histogram), indicating that TRA-8 is specific for cell surface DR5.

Although DR5 expression in tumor cells has been studied extensively at the mRNA level (Rieger J. et al. 1:FEBS Lett 1998 May 1; 427(1):124-8), the surface expression of DR5 is not well understood. Gibson S. B. et al. 1:Mol Cell Biol 2000 January; 20(1):205-12; Kim K. et al. 1: Clin Cancer Res 2000 February; 6(2):334-46. Thus, the availability of monoclonal anti-DR5 antibody allows us to examine the surface levels of DR5, and to correlate the expression with the susceptibility of the cells to TRAIL-mediated apoptosis. The following panel of cells ($1\times10^6$) is incubated with 10 µg/ml of affinity purified TRA-8 at room temperature for 30 min, and then stained with PE-conjugated anti-mouse IgG1 (Pharmingen) for another 30 min. 10,000 viable cells are analyzed using the FACS vantage™ flow cytometer under the following conditions:

Excitation wave length: 488 nm;
Detection wave length: 600 nm.

Figures 2, 2A, 3, 4, 5, 6:
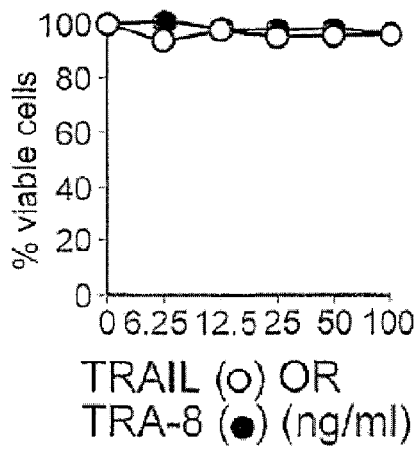
FIG. 4 is a series of graphs showing cell viability for human Jurkat cells after exposure to indicated concentrations of (A) antibody strains TRA-1, -8 and -10 and (B) TRAIL in the presence of a fixed concentration of the inventive antibody strains depicted in FIG. 4A.
FIG. 5. Expression of DR5 in normal and cancer tissues: Normal and cancer tissue homogenates were probed with TRA-8 and developed by chemiluminescence. (A) Western blot analysis of DR5 protein in normal tissues: lane 1: liver, lane 2: brain, lane 3: lung, lane 4: kidney, lane 5: spleen, lane 6: testes. Lane 7: ovary, lane 8: heart, lane 9: pancreas. (B) Western blot analysis of DR5 protein in cancer tissues. The cancer tissue blot containing cancers from the ovary (lane 1), lung (lane 2), liver (lane 3), rectum (lane 4), cervix (lane 5), skin (lane 6), testes (lane 7), thyroid (lane 8), uterus (lane 10), stomach (lane 11), laryngopharynx (lane 12), and pancreas (lane 13) was probed. In situ immunohistochemistry of normal human tissues (C) and of cancer tissues (D). Frozen sections were immunostained with TRA-8.
FIG. 6. Tumoricidal activity of TRA-8. SCID mice were inoculated subcutaneously with 1321N1 cells. Mice were injected intravenously with a single dose of 100 μg TRA-8 on the second day after tumor inoculation (A), or with three doses of 100 μg TRA-8 beginning 7 days after tumor inoculation (B). Tumor growth was determined by the weight and examined histologically with H&E staining. The photographs show viable tumor growth in control mice but not in TRA-8 treated mice (C, upper panel), and H&E staining of tumor (C, lower panel). SCID mice were injected intravenously with $10^6$ Jurkat cells and treated with a single dose of TRA-8 on the second day after injection. Seven days later, spleen cells were harvested, stained with anti-human CD3 antibody and analyzed by flow cytometry (D), or by immunohistochemistry (E).
Figures 2, 2A, 3, 4, 5, 6, 7:
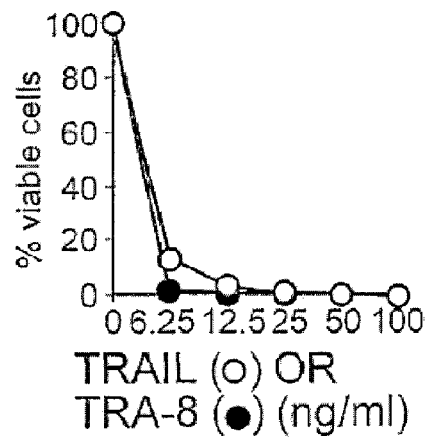
FIG. 7 shows expression of cell surface DR5 in RA (A) and OA (B) synovial cells. $1\times10^6$ primary cultured synovial cells were stained with affinity-purified TRA-8 and followed by PE-conjugated goat anti-mouse IgG1 antibody. 10,000 viable cells analyzed by FACSvantage™.
Figures 2, 2A, 3, 4, 5, 6, 7, 8:
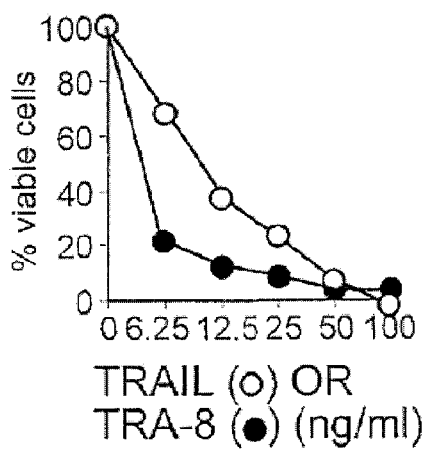
FIG. 8 is a series of graphs showing cell viability as a function of TRAIL and TRA-8 concentration induced apoptosis of representative strains of RA (A) and OA (B) synovial cells with various concentrations of the recombinant soluble TRAIL (the open circles) or affinity-purified TRA-8 (the closed circles). Cell viability is the percentage of the cpm of treated cells versus the cpm of untreated cells.

The five hematopoietic cell lines tested are Jurkat, CEM-6, Molt-4, H-9 and U937 cells. DR5 expression is detectable on the surface of Jurkat, CEM-6, H-9, and U937 cells but is almost undetectable on Molt-4 cells as shown in FIGS. 2a and 2a'. Although high levels of DR5 RNA expression has been described previously (43), the FACs analysis indicated that these cells do not express high levels of the surface DR5. These results indicate that cell surface expression of DR5 does not correlate with the transcriptional expression of DR5, which is not unexpected for such a receptor. The level of cell surface expression of DR5 may be cell lineage-specific since most of the cells of hematopoietic origin expressed low levels whereas most glioma and prostate cells expressed high levels of DR5.

TRA-8 monoclonal antibody is used determine the role of DR5 in induction of TRAIL-mediated apoptosis by examining its cell surface expression among a panel of different types of human tumor cells as well as the susceptibility of these cells to both TRAIL and TRA-8-mediated apoptosis. Primary peripheral blood T cells did not express significant levels of cell surface DR5 and are resistant to both TRAIL and TRA-8-mediated apoptosis (FIGS. 2a, 2a' and 3a'). Although all five of the human T-leukemia cell lines tested expressed detectable albeit relatively low levels of cell surface DR5, two of them (Jurkat and CEM-6) are highly susceptible to both TRAIL-mediated and TRA-8-mediated apoptosis, indicating that DR5 alone is sufficient to induce apoptosis of these cells. Molt-4 and U937 cells are partially susceptible to TRAIL-mediated apoptosis but are relatively resistant to TRA-8-mediated apoptosis, suggesting that other TRAIL receptors might be involved in transduction of an apoptosis signal. H-9 cells are resistant to both TRAIL and TRA-8-mediated apoptosis, implicating a block mediated by an intracellular anti-apoptosis pathway.

The panel of cells included the human malignant glioma cell lines, Hs683, U251MG, D37MG, D54MG, U373MG, CH235MG, U87 and normal human astrocytes, which were provided by Dr. Yancey Gillespie of the Neurosurgery Department of the University of Alabama at Birmingham. The human prostate cancer cell lines, Du154, PC3 and LnCap, were provided by Dr. William Grizzle of the Pathology Department of the University of Alabama at Birmingham who had obtained the cell lines from the American Type Culture Collection. The human leukemia T cell lines, B-cell lymphoma, HepG2 Jurkat (American Type Culture Collection TIB-152) and CCRF-CEM CEM-6 (American Type Culture Collection CCL-119); monocyte cell lines, U937 (American Type Culture Collection CRL-2367); were purchased from the American Type Culture Collection. All above cell lines are cultured in RPMI 1640 supplemented with 10% FCS. The human astrocytoma cell line, 1321N1, was kindly provided by Dr. Richard Jope of Psychiatry Department of the University of Alabama at Birmingham, and cultured in DMEM supplemented with 5% FCS.

Soluble recombinant human TRAIL, purchased from Alexis Corporation (San Diego, Calif.), is a fusion protein comprised of the extracellular domain of human TRAIL (aa residues 95 to 281) fused at N-terminus to a FLAG-tag and an 8 amino acid linker peptide. Unlike previously reported His-tagged TRAIL, this preparation of TRAIL alone does not induce a strong apoptotic response in Jurkat cells and requires an anti-FLAG antibody as a crosslinker to enhance apoptosis. The anti-FLAG antibody was also purchased from Alexis.

Figures 2, 2A, 3, 4, 5, 6, 7, 8, 9:
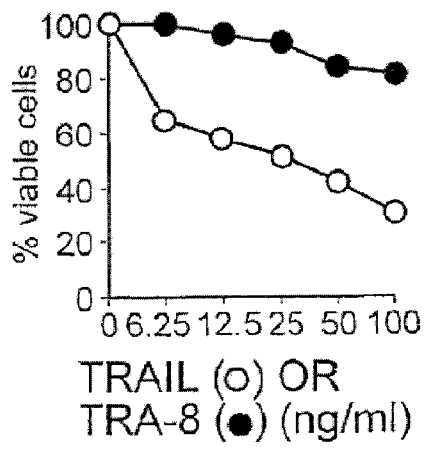
FIG. 9 is a series of graphs showing the caspase dependence of DR5-mediated apoptosis of RA synovial cells. RA synovial cells (RA512) are incubated with 50 ng/ml of soluble Fas ligand (open squares), anti-Fas antibody (CH-11) (closed squares), soluble TRAIL (open circles), or anti-DR5 antibody (TRA-8) (closed circles) in the presence of variable concentrations of caspase 1 inhibitor (FIG. 9A), caspase 2 inhibitor (FIG. 9B), caspase 3 inhibitor (FIG. 9C), caspase 4 inhibitor (FIG. 9D), caspase 6 inhibitor (FIG. 9E), caspase 8 inhibitor (FIG. 9F), caspase 9 inhibitor (FIG. 9G) or caspase 10 inhibitor (FIG. 9H). After overnight culture, cell viability is determined by ATPLite®.

All of the 10 human malignant glioma cells tested expressed detectable levels of DR5 at the cell surface. Most expressed intermediate to high levels of DR5 as shown in FIG. 2b. Three lines, D-54MG, U373MG and CH-235MG expressed high levels of DR5 while six lines, Hs-683, U251-MG, D37-MG, U87, SMK1 and 1321N1, expressed intermediate levels of DR5. Only one cell line, H-465 expressed low levels of DR5. All three prostate cancer cell lines expressed high levels of DR5 as shown in FIG. 2c.

Figures 2, 2A, 3, 4, 5, 6, 7, 8, 9, 10:
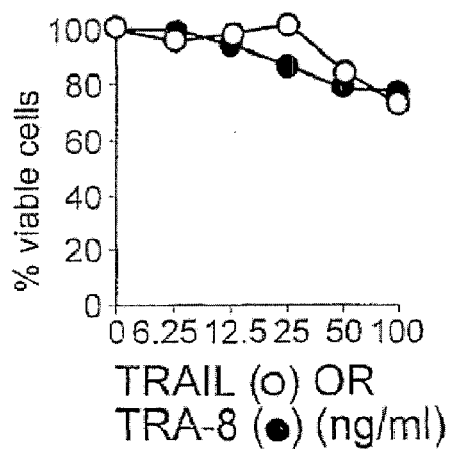
Figure 2A:
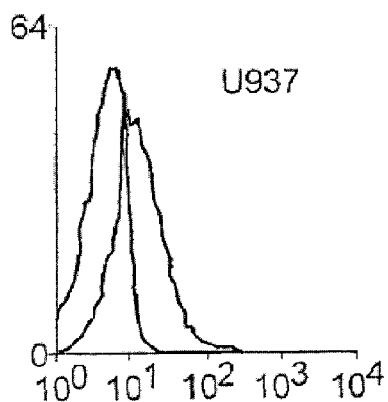
Figures 1, 2B:
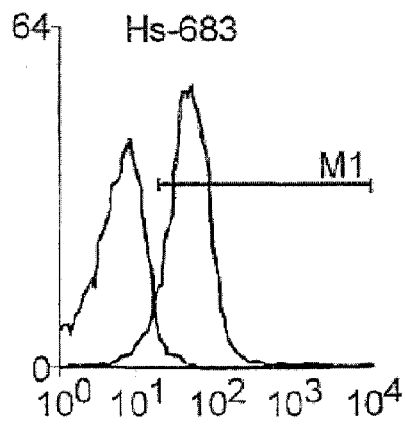
Figures 2, 2B:
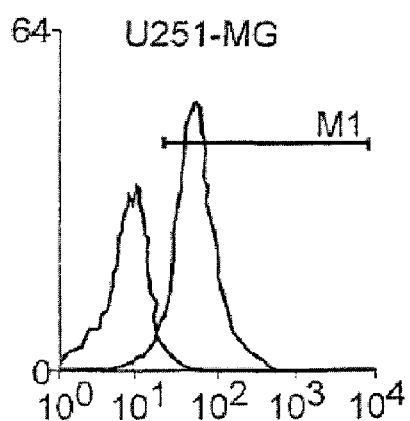
Figures 2, 2B, 3:
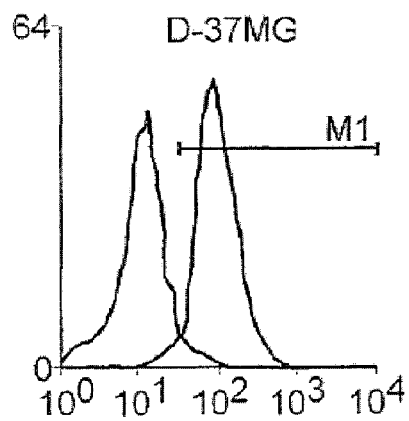
Figures 2, 2B, 3, 4:
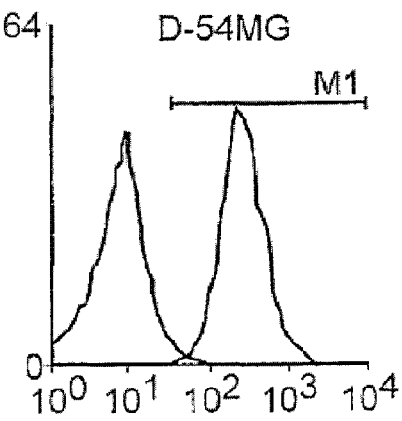
Figures 2, 2B, 3, 4, 5:
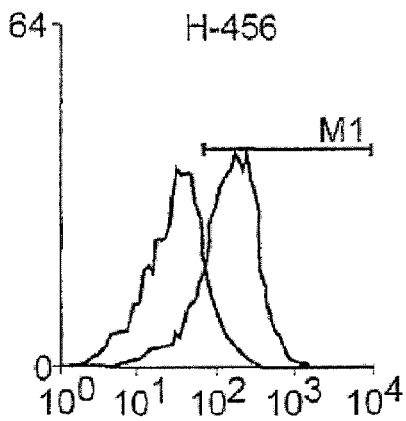
Figures 2, 2B, 3, 4, 5, 6:
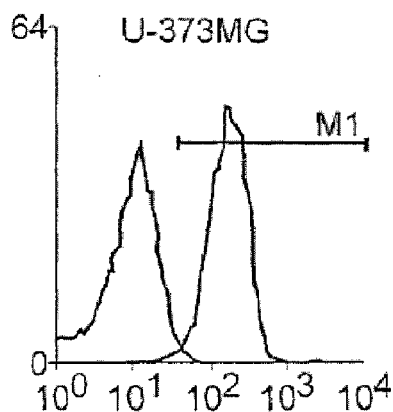
Figures 2, 2B, 3, 4, 5, 6, 7:
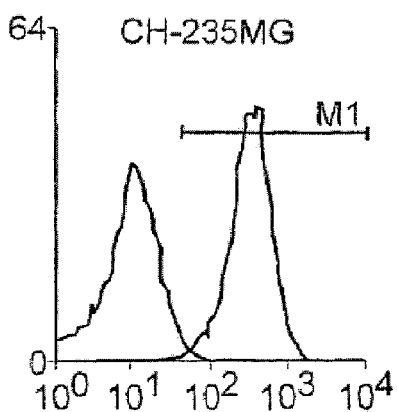
Figures 2, 2B, 3, 4, 5, 6, 7, 8:
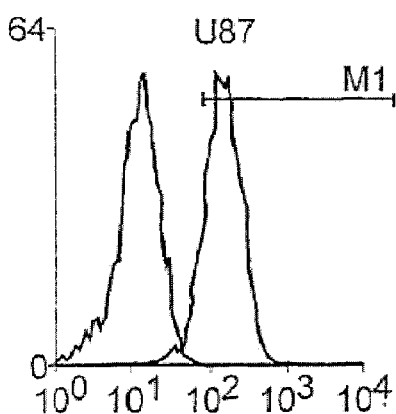
Figures 2, 2B, 3, 4, 5, 6, 7, 8, 9:
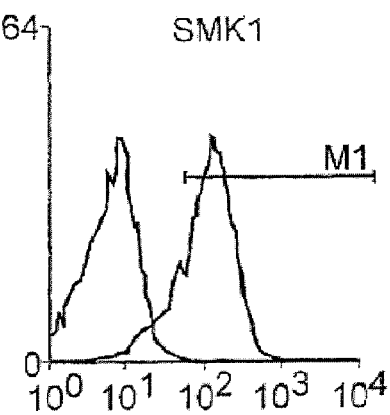
Figures 2, 2B, 3, 4, 5, 6, 7, 8, 9, 10:
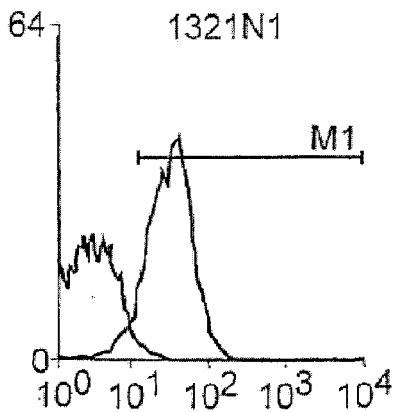
Figure 2B:
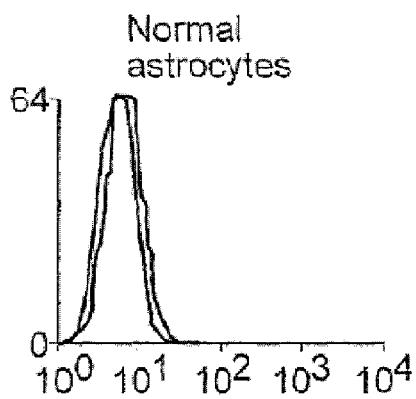
Figure 2B:
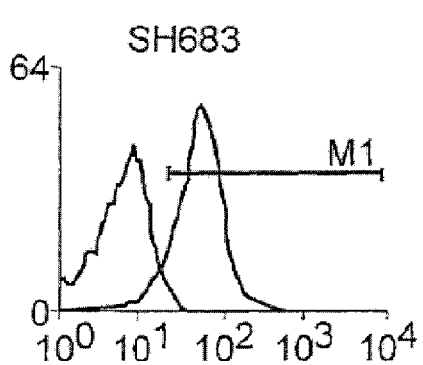
Figure 2B:
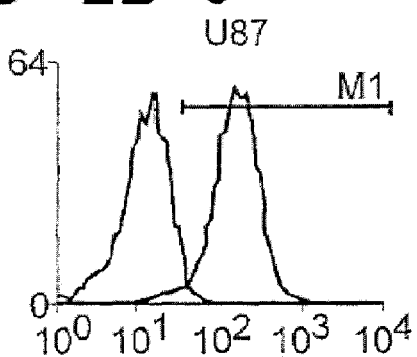
Figure 2B:
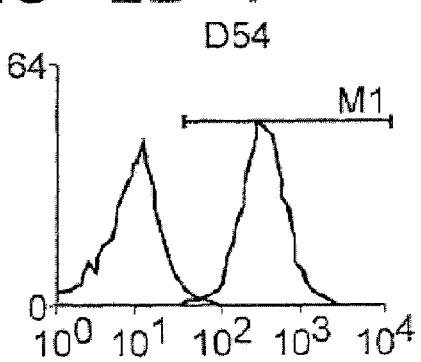
Figure 2B:
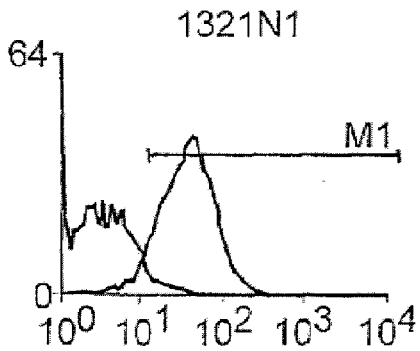
Figure 2B:
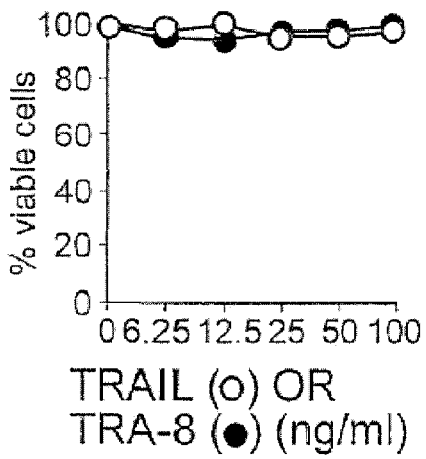
Figure 2B:
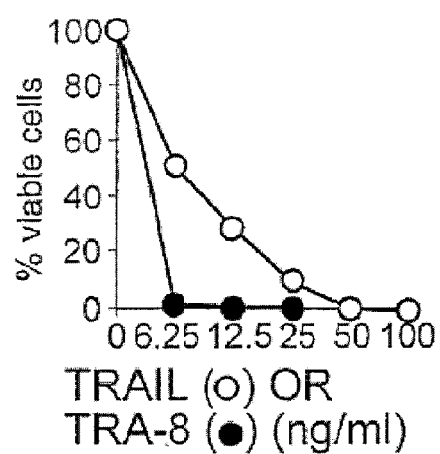
Figure 2B:
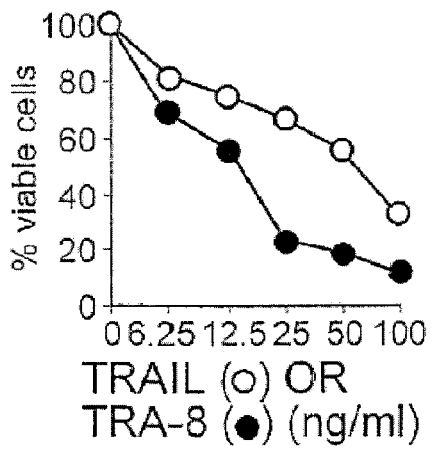
Figure 2B:
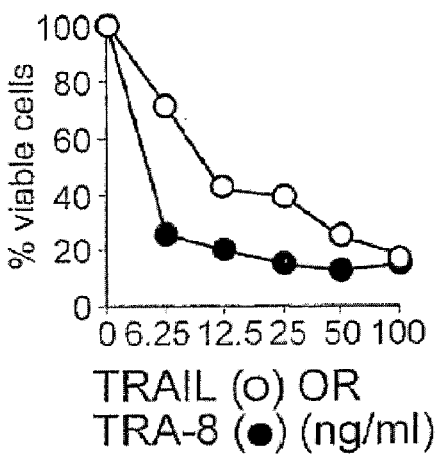
Figure 2B:
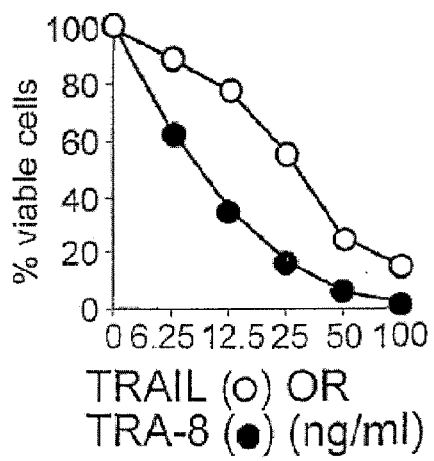
Figures 1, 2C:
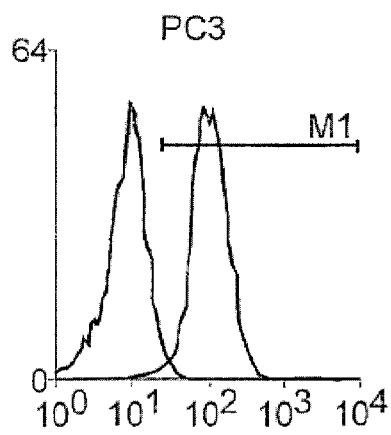
Figures 2, 2C:
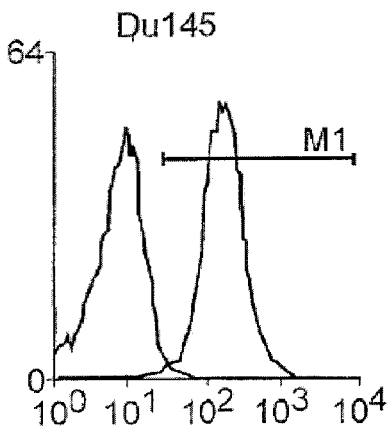
Figures 2, 2C, 3:
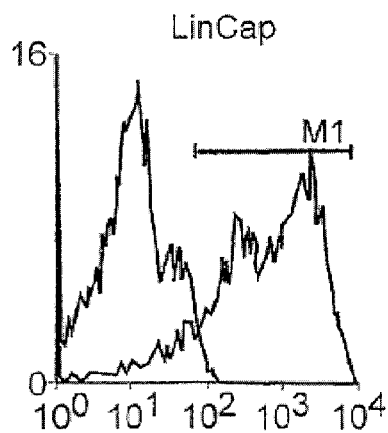
Figures 1, 2D:
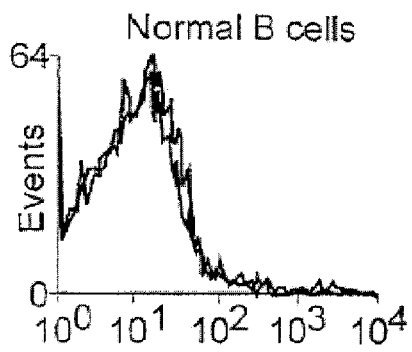
Figures 2, 2D:
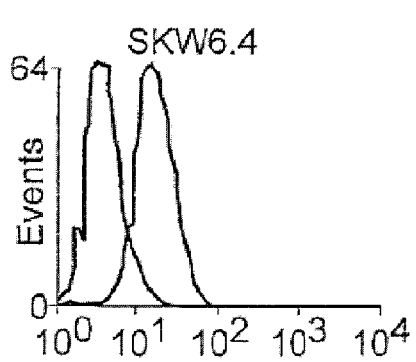
Figures 2, 2D, 3:
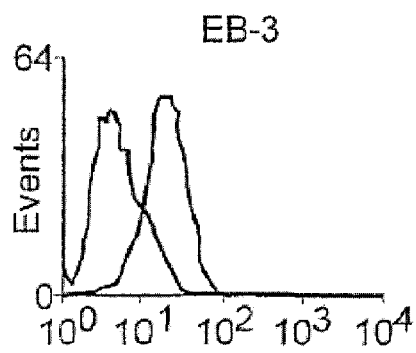
Figures 2, 2D, 3, 4:
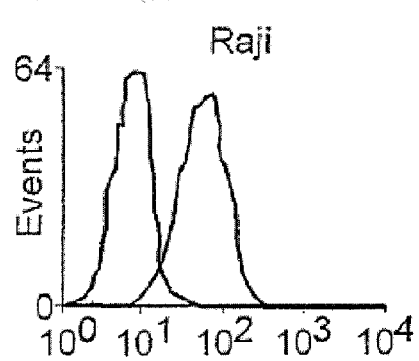
Figures 2, 2D, 3, 4, 5:
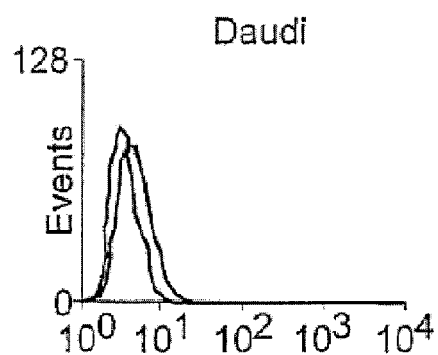
Figures 2, 2D, 3, 4, 5, 6:
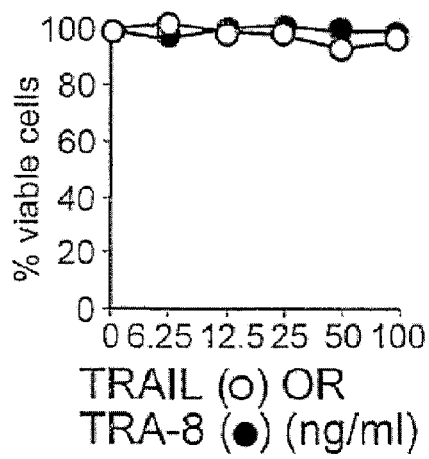
Figures 2, 2D, 3, 4, 5, 6, 7:
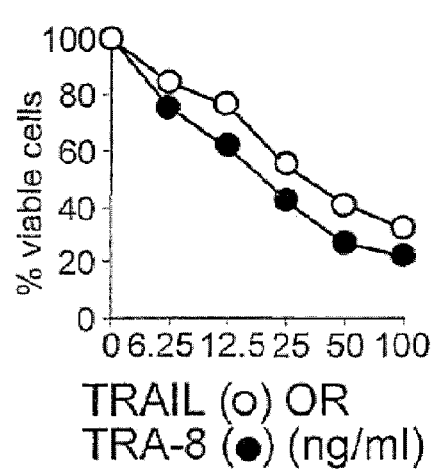
Figures 2, 2D, 3, 4, 5, 6, 7, 8:
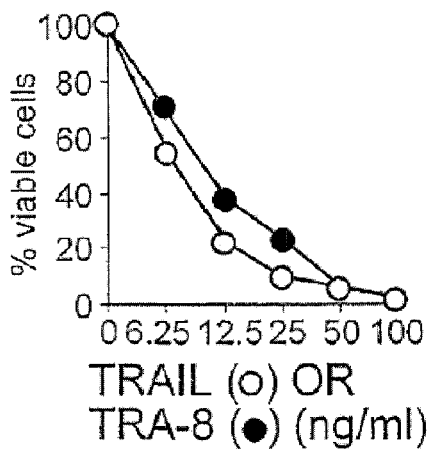
Figures 2, 2D, 3, 4, 5, 6, 7, 8, 9:
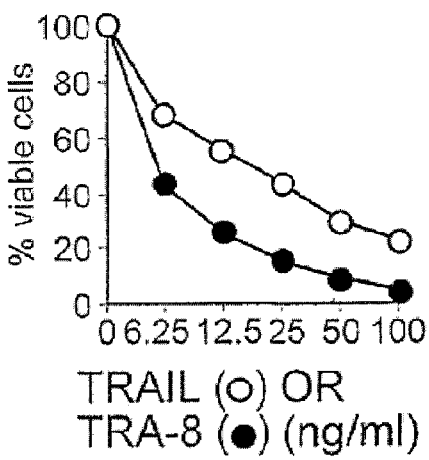
Figures 2, 2D, 3, 4, 5, 6, 7, 8, 9, 10:
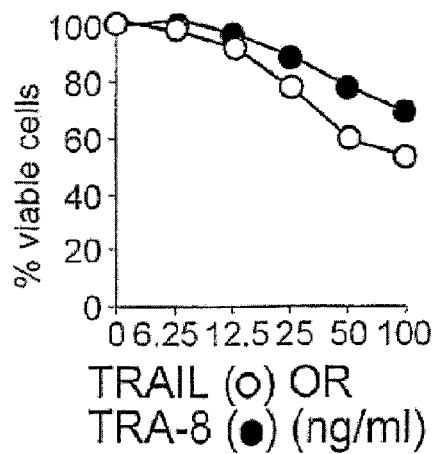

Like the normal primary T cells, primary B cells did not express significant levels of DR5 and did not undergo apoptosis after treatment with either TRAIL or TRA-8 (FIG. 2d). Three (SKW6.4, EB-3, and Raji) out of the four B lymphoma cell lines tested expressed relatively high levels of DR5 and are very susceptible to both TRAIL and TRA-8-mediated apoptosis. The fourth cell line, Daudi, expressed very low levels of DR5 and is much less susceptible to either TRAIL or TRA-8-mediated apoptosis. Although primary astrocytes did not express detectable levels of cell surface DR5 (FIG. 2b'), all four glioma cell lines tested expressed high levels of DR5. The higher level of expression of DR5 on glioma cells than on T and B cells is not accompanied by a significantly greater susceptibility to TRAIL and DR5-mediated apoptosis, suggesting that the level of cell surface expression of DR5 is not necessarily correlated with the level of apoptosis of tumor cells. RT-PCR, performed to determine message levels of DR4, DR5 and DCR2, detected message in all cells tested (Table 1). However, in general, primary normal cells expressed relatively low levels of DR5 compared to transformed tumor cells.

TABLE 1

RT-PCR analysis of TRAIL receptor expression*

| Cells | DR5 | DR4 | DcR2 |
|---|---|---|---|
| Primary T cells | <0.001 | <0.001 | 0.015 |
| Jurkat | 0.10 | 0.001 | 0.21 |
| CEM-6 | 0.50 | 0.59 | 0.25 |
| Molt-4 | 0.10 | 0.001 | 0.05 |
| H-9 | 0.73 | 0.61 | 0.07 |
| Primary B cells | <0.001 | <0.001 | 0.024 |
| SKW6.4 | 0.95 | 0.66 | 0.45 |
| EB3 | 0.40 | <0.001 | 0.35 |
| Raji | 0.55 | 0.11 | 0.45 |
| Daudi | 0.73 | 0.36 | 0.63 |
| Normal Astrocytes | 0.05 | <0.001 | 0.12 |
| SH683 | 0.56 | 0.96 | 0.14 |
| U87 | 0.44 | 0.56 | 0.21 |
| D54 | 1.15 | 0.46 | 0.12 |
| 1321N1 | 0.25 | 0.35 | 0.05 |

*Total RNA was isolated from cells and RT-PCR was performed as described in Methods. The PCR products were separated in 3% agarose gel and analyzed by the Fluor-S MAX MultiImager System (BioRad). The values are presented as a ratio relative to β-actin.

Example 8

Induction of Apoptosis in vitro in Malignant Cells

To determine whether TRA-8 induces apoptosis in transformed cells in vitro, all DR5-positive tumor cells are examined for their susceptibility to apoptosis induced either by TRA-8 or TRAIL.

Target cells ($1 \times 10^3$ per well) are cultured in 96-well plates in the presence of the indicated concentrations of soluble TRAIL plus crosslinker (Alexis) or TRA-8 at 37° C. overnight. Cell viability is determined using (1) the ATPLite® kit according to the manufacturer's instructions (Packard Instruments, Meriden, Conn.); (2) the MTT Cell proliferation/viability kit (Sigma); or (3) PI staining of dead cells and analyzed by flow cytometry. At end of culture, cells are stained with 10 µg/ml PI and PI negative cells are gated as viable cells. For analysis of condensed nuclei of hepatocytes, cells are stained with 10 ng/ml Hoechst 33352 (Molecular Probes) and analyzed by flow cytometry.

The TRA-8 antibody is capable of inducing apoptosis in the majority of the malignant human glioma cell lines (9/10), in 2 of the 3 prostate cancer cell lines, and in 2 of the 4 DR5-positive hematopoietic cell lines. It did not induce apoptosis in the Molt-4 cell line, which expressed almost undetectable cell surface levels of DR5. The levels of susceptibility of the cells to TRA-8-mediated apoptosis varied considerably among the cell lines, however.

Figure 3A:
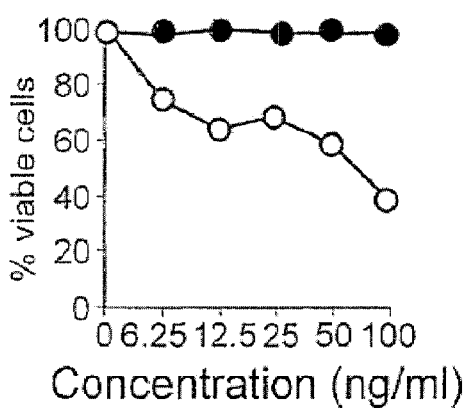
FIG. 3A'. T cell line U937 was incubated with TRA-8 or murine IgG1 isotype control antibody. Apoptosis was determined by the ATPLite® assay after overnight incubation with soluble TRAIL (open circles) or TRA-8 (closed circles).
Figures 1, 3B:
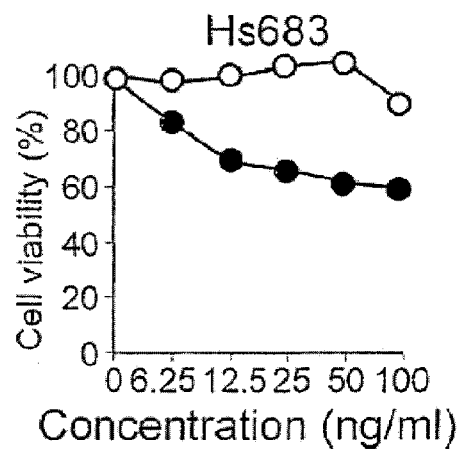
Figures 2, 3B:
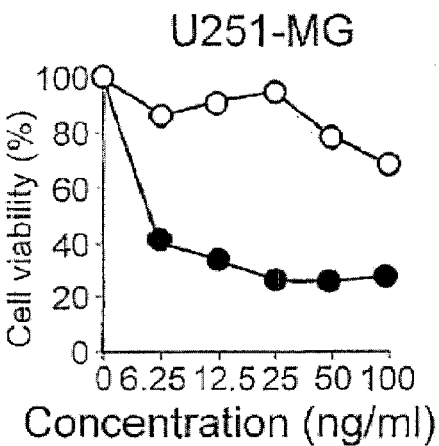
Figures 3, 3B:
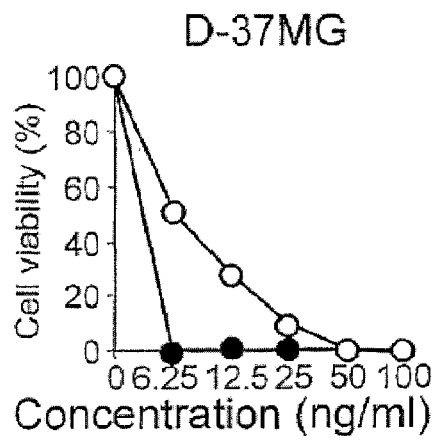
Figures 3, 3B, 4:
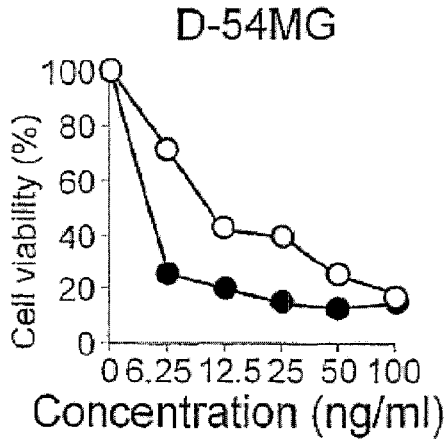
Figures 3, 3B, 4, 5:
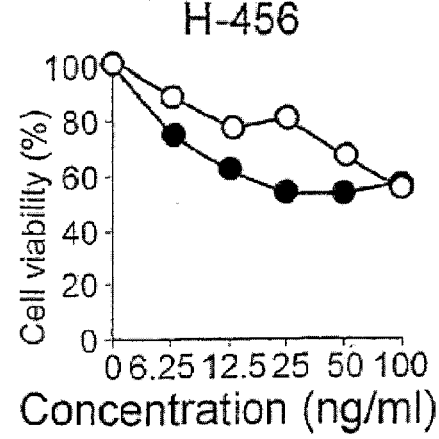
Figures 3, 3B, 4, 5, 6:
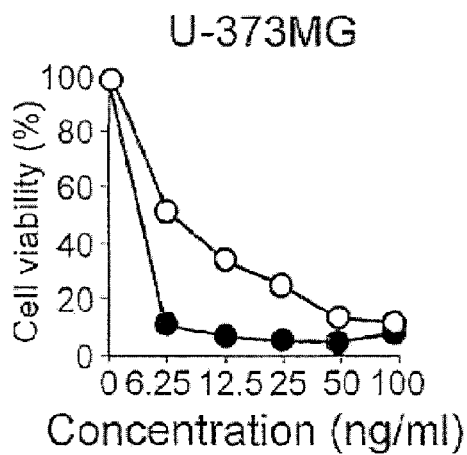
Figures 3, 3B, 4, 5, 6, 7:
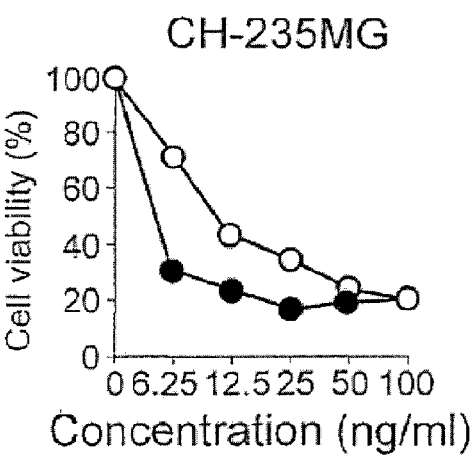
Figures 3, 3B, 4, 5, 6, 7, 8:
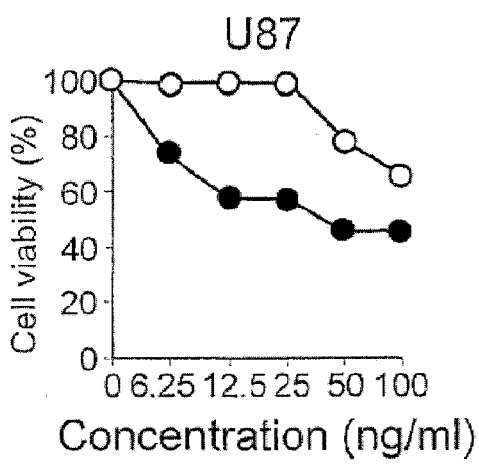
Figures 3, 3B, 4, 5, 6, 7, 8, 9:
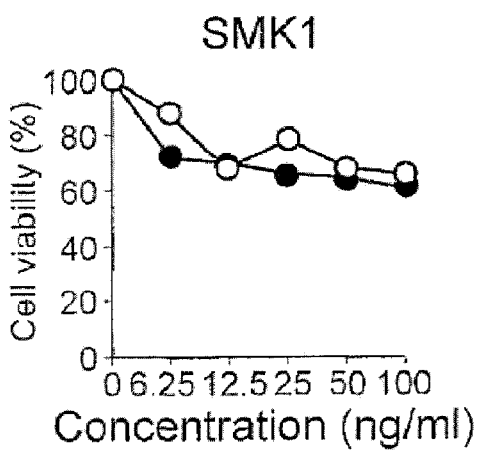
Figures 3, 3B, 4, 5, 6, 7, 8, 9, 10:
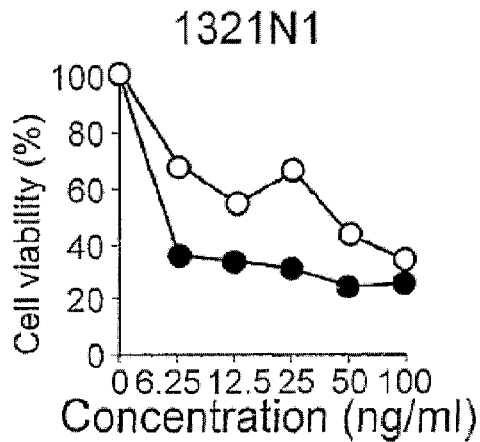
Figures 1, 3C:
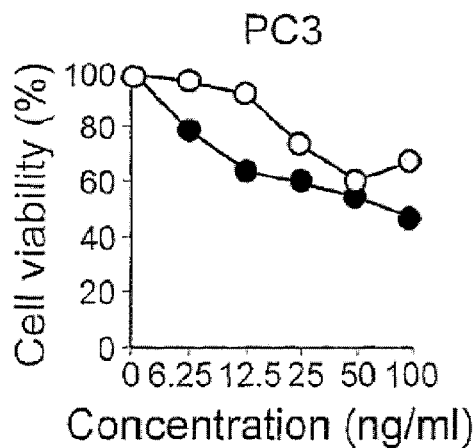
Figures 2, 3C:
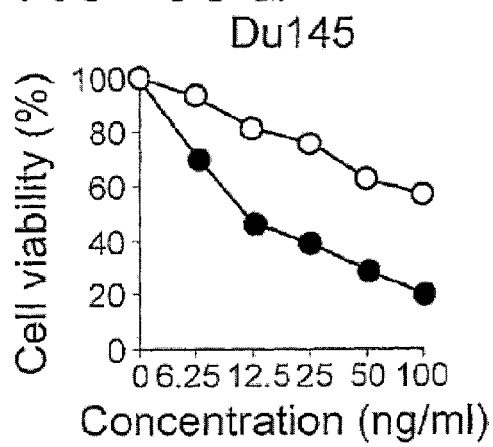
Figures 3, 3C:
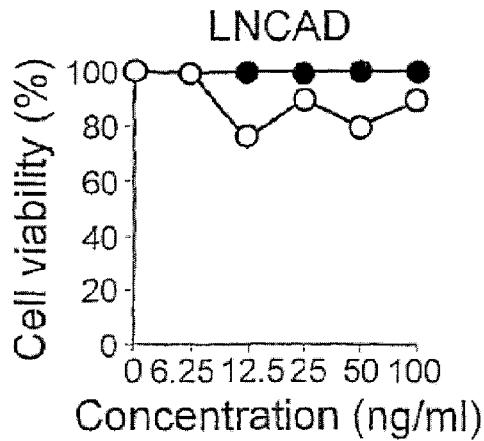
Figure 4B:
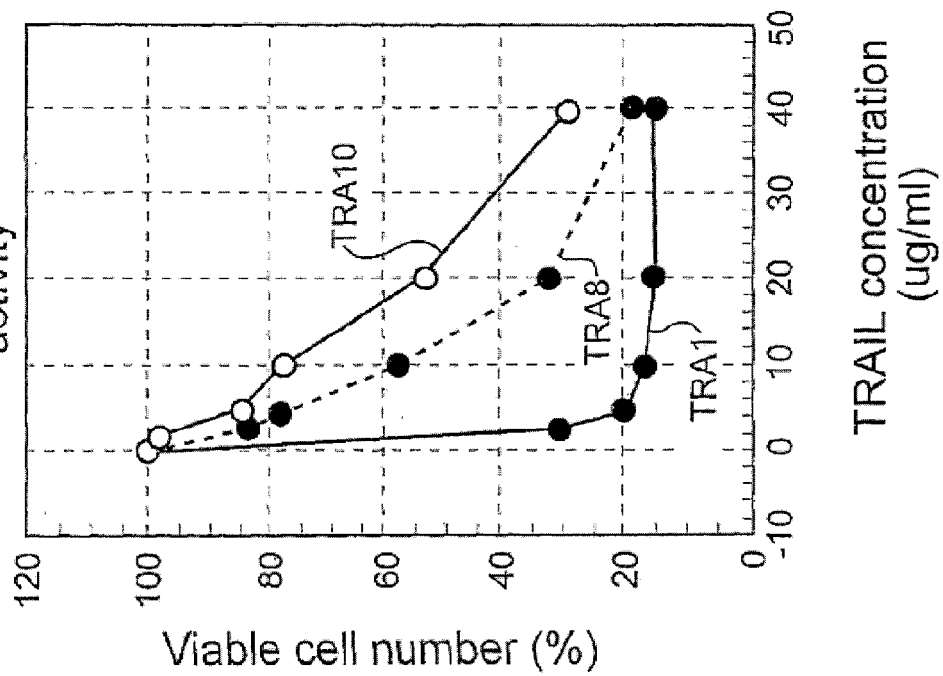
Figure 4A:
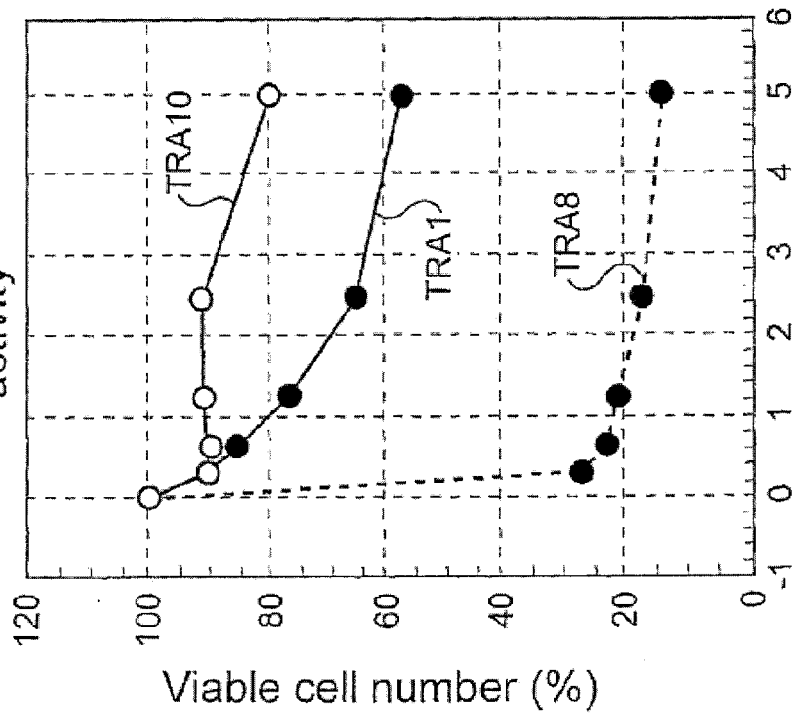

The variability of the susceptibility of the cells to TRA-8 antibody induced apoptosis suggests that although a minimal level of cell surface expression of DR5 is required, the level of cell surface expression of DR5 is not necessarily the primary determinant of susceptibility and other factors influence this process. Although all of the glioma cells generally expressed significantly higher levels of the surface DR5 than did the hematopoietic cells, glioma cell susceptibility to apoptosis induced by TRA-8 is not proportionally increased compared to the hematopoietic cells. The susceptibility of five of the glioma cell lines, D-37MG, D54-MG, U373-MG, CH235-MG and 1321N1 to TRA-8-induced apoptosis is high and is equivalent to their susceptibility to TRAIL-mediated apoptosis as shown in FIG. 3b. Two of the glioma cell lines, H-456 and SMK1, are much less susceptible to apoptosis induced by TRA-8. In the case of the H-456 cells, the surface expression of DR5 is low; however, the surface expression of DR5 on SMK1 is similar to the more susceptible cell lines, suggesting that other mechanisms might play a role in the determining the susceptibility to TRAIL-mediated apoptosis. Although all three prostate cancer cell lines expressed high levels of DR5, the Du145 cells are most sensitive to TRA-8-induced apoptosis, the PC3 cells are partially sensitive while LnCAP cells are completely resistant as shown in FIG. 3c. Among the hematopoietic cells, it is found that Jurkat and CEM-6 are very susceptible to TRA-8-apoptosis as shown in FIG. 2a although both these cell lines had been found to express low levels of DR5. Although DR5 is detectable on U937 cells, these cells are resistant to TRA-8-induced apoptosis. Similarly, although the H-9 cells expressed detectable levels of DR5, H-9 cells are resistant to apoptosis induced by TRA-8. These results implicated the existence of regulatory mechanisms that influence DR5-mediated apoptosis.

Additional surface binding anti-DR5 antibodies are produced as per the procedures of Examples 1-3. Two additional anti-DR5 antibodies designated TRA-1 and TRA-10 are studied along with TRA-8 to determine comparative ability to induce apoptosis and thereby act as an agonist or conversely block TRAIL-mediated apoptosis, thereby acting a an antagonist. Human Jurkat cells are used as a target to determine the agonist and/or antagonist activity of the three anti-DR5 antibodies denoted TRA-1, TRA-8 and TRA-10. As shown in FIG. 4, cell viability is about 90%, 70% and 20% for TRA-10, TRA-1 and TRA-8, respectively upon overnight incubation with 2.5 µg per ml. TRA-8 induced a strong apoptotic response in a dose dependent fashion while TRA-1 induced only a moderate apoptotic response and TRA-10 only induced a weak response. TRA-8 is therefore classified as an agonist anti-DR5 antibody. In FIG. 4, the viability of human Jurkat cells is shown as a dose dependent function of TRAIL-induced apoptosis. TRA-10 blocked apoptosis of human Jurkat cells to a significant extent in a low dose TRAIL-induced apoptosis study. Thus, TRA-10 is classified as an antagonist anti-DR5 antibody. TRA-1 was deposited on Apr. 20, 2000 with American Type Culture Collection, 10801 University Boulevard, Manassas, Va. 20110-2209 under Accession Number PTA-1741. TRA-10 is likewise on deposit with American Type Culture Collection under Accession Number PTA-1742.

The susceptibility of five of the glioma cell lines, D-37MG, D54-MG, U373-MG, CH235-MG and 1321N1 to TRA-8-induced apoptosis is equivalent to their susceptibility to TRAIL-mediated apoptosis as shown in FIG. 3b, indicating that TRAIL-induced apoptosis in these cells is mediated primarily through DR5. Moreover, two of the glioma cell lines, Hs683 and U251-MG, are resistant to TRAIL-induced apoptosis but partially sensitive to TRA-8-induced apoptosis, indicating that the decoy receptors function in these cells and that use of the TRA-8 antibody bypassed this regulatory mechanism. In the prostate cancer cell lines, despite the varying sensitivity to apoptosis induced by TRA-8, this paralleled the sensitivity of the cells to apoptosis induced by TRAIL, again suggesting that DR5 plays a major role of TRAIL-mediated apoptosis in the prostate cancer cells. Among the hematopoietic cells, it is found that Jurkat and CEM-6 are very susceptible to both TRA-8 and TRAIL-mediated apoptosis. The level of apoptosis induced by TRA-8 is comparable to that induced by TRAIL as shown in FIGS. 2a and 3a'. Only one of the glioma cell lines, U87, and two hematopoietic cell lines, U937 and Molt-4, exhibited sensitivity to TRAIL-induced apoptosis but are less sensitive or resistant to TRA-8-induced apoptosis. One cell line, the H-9 cell line, expressed detectable levels of DR5 but are resistant to apoptosis induced by either TRA-8 or TRAIL. While minimal levels of expression of DR5 are required for TRA-8-induced apoptosis, the level of expression of DR5 does not necessarily predict the susceptibility of the cells to TRA-8 mediated apoptosis; decoy receptors play a role in modulating TRAIL-mediated apoptosis in some cells, but does not appear to play a major role in most of the cells tested to date; as anticipated the TRA-8 antibody bypasses the effects of the decoy receptors; functional mutations of the DR5 receptor may occur in transformed cells; and, finally, intracellular regulatory mechanisms may be as important, or more important than the decoy receptors in defining the susceptibility of the cells to TRAIL and DR5-mediated apoptosis.

Previous studies have shown that the mRNA for DR5 is distributed widely in normal tissues[7]. To evaluate the expression of DR5 at the protein level, a panel of normal human tissue homogenates (Geno Technology, St. Louis, Mo.) is probed with the TRA-8 antibody in western blot analysis. Among nine normal human tissues, brain tissue is weakly positive (FIG. 5a, lane 2). DR5 protein is not detectable by TRA-8 reactivity in liver (lane 1), lung (lane 3), kidney (lane 4), spleen (lane 5), testes (lane 6), ovary (lane 7), heart (lane 8), or pancreas (lane 9). In contrast, all thirteen human cancer tissues stained positively with TRA-8 (FIG. 5b), including cancers of the ovary (lane 1), lung (lane 2), liver (lane 3), rectum (lane 4), cervix (lane 5), skin (lane 6), testes (lane 7), thyroid (lane 8), uterus (lane 10), stomach (lane 11), laryngopharynx (lane 12), and pancreas (lane 13). Moreover, in situ immunohistochemistry of normal and cancer tissues with TRA-8 confirmed that aside from a few scattered positive cells in spleen, DR5 expression in normal breast, lung and spleen tissues is not detectable (FIG. 5c). The corresponding cancer tissues including breast infiltrating ductal carcinoma, small cell lung cancer, and lymphoma reacted positively with TRA-8 (FIG. 5d). Among a total of 22 cancer tissues examined, 5 of 6 breast cancers, 2 of 2 cancers of the cervix, 4 of 5 liver cancers, 5 of 8 lymphomas, 2 of 2 lung cancers, and 2 of 2 prostate cancers reacted positively with TRA-8. These results are consistent with those of the flow cytometry analysis and indicate that cancerous tissues express higher levels of DR5 protein than do normal tissues.

Example 9

Tumoricidal Activity of TRA-8 in vivo

For various reasons, many agents that show promise in in vitro studies do not show efficacy in vivo. It is therefore important to test the efficacy of TRA-8 in an in vivo animal model. To accomplish this the TRA-8 anti-human DR5 antibody is administered to mice bearing human xenografts that express the human DR5 molecule. The mice used are 6 to 8 week-old NOD/SCID mice (Jackson Laboratory), which are inoculated subcutaneously with human astrocytoma 1321N1 cells ($1\times10^7$), or inoculated intravenously with human leukemia Jurkat cells ($1\times10^6$). At day 2 after tumor inoculation, mice are inoculated intravenously with TRA-8 (100 µg). Five days after the treatment with TRA-8, 1321N1 tumor growth is determined by the size and weight of the tumor mass. The growth of Jurkat cells is determined by the weight of the spleen and the percentage of human CD3-positive Jurkat cells in the spleen of inoculated animals. Biopsies of tumor tissues are taken and examined histologically.

Figure 6D:
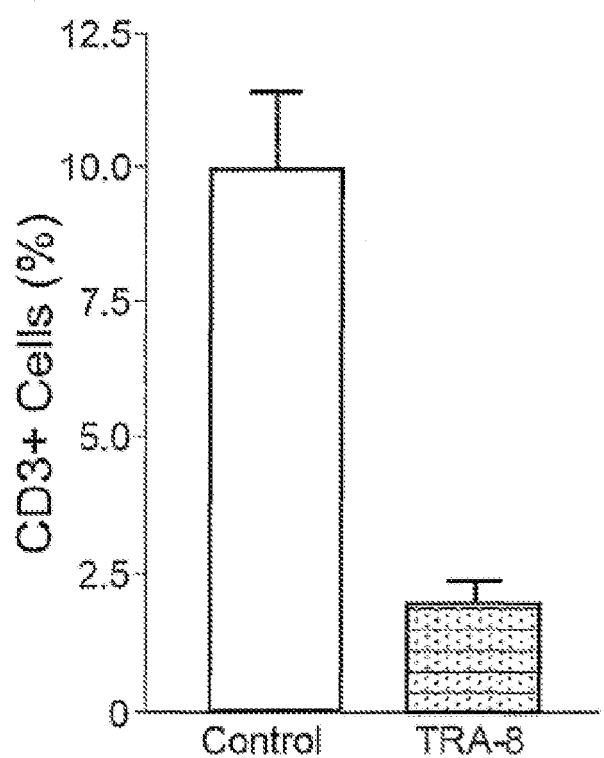
Figure 6E:
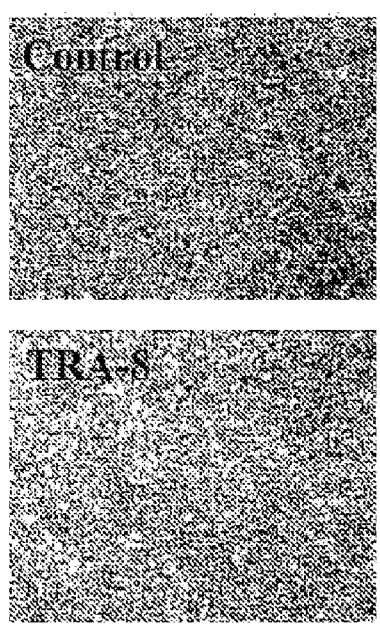

Early treatment with a single intravenous dose of 100 µg of TRA-8 at one day after tumor inoculation completely inhibited the 1321N1 cells from forming a solid tumor of (FIG. 6a). Late treatment with three doses of 100 µg TRA-8 at one week after tumor inoculation reduced tumor weight 4-fold or more (FIG. 6b). Tumor formation is not visible in animals treated with TRA-8 at an early time point (FIG. 6c, upper panel). Histologic analysis revealed dramatically degenerated tumor tissue in animals treated with TRA-8 (FIG. 6c, lower panel). Similarly, TRA-8 treatment inhibited population of the spleen by Jurkat cells as demonstrated by the scarcity of CD3-positive Jurkat cells in the spleen (FIG. 6d, 6e). Histological analysis of the implanted tumor showed a few tumor cells scattered in the soft tissue in TRA-8-treated animals while controls showed the formation of a solid tumor as shown in FIG. 6c. In the Jurkat cell model, the number of Jurkat cells in the spleens of TRA-8 treated animals is less than 2% compared to nearly 10% in the spleen of control animals as demonstrated by flow cytometry analysis as shown in FIG. 6a and in situ CD3 staining of FIG. 6c.

These results confirm the recent demonstration that systemic administration of cross-linked recombinant TRAIL inhibits growth of tumor in vivo (13). These results indicate that a single dose of TRA-8 is highly effective in the elimination of tumor cells in vivo.

As an anti-human antibody is used in a murine model, the toxicity of the TRA-8 treatment could not be assessed. However, the study of administration of TRAIL in vivo indicated that no significant toxicity is associated with this treatment (13).

Example 10

RA Synovial Cells are Susceptible to TRAIL and TRA-8-Induced Apoptosis

Most of the prior art studies of TRAIL-mediated apoptosis have focused on malignant cells. TRAIL-mediated apoptosis according to the present invention is also therapeutic in autoimmune and inflammatory conditions, such as RA.

10.1 Flow Cytometric Analysis of the Expression of Cell Surface DR5 in RA Synovial Cells The expression of DR5 on a panel of eight primary cultured synovial cells from patients with RA is compared with that on eight primary cultured synovial cells from patients with osteoarthritis (hereinafter referred to as "OA"). The eight human primary RA synovial cell cultures RA-1014, RA-1016, RA-1021, RA-512, RA-707, RA-811, RA-716, and RA-929 are kindly provided by Dr. M. Ohtsuki (Sankyo Co. Ltd., Tokyo, Japan) and cultured in DMEM supplemented with 10% FCS, penicillin, streptomycin, and glutamine. The seven OA synovial cell primary cell cultures are isolated from the synovial tissues of OA patients by a standard collagenase method and cultured under the same conditions. The passage number of all primary cells is under 10. The expression of DR5 is determined by FACs analysis as described in Example 5.

Figures 1, 7A:
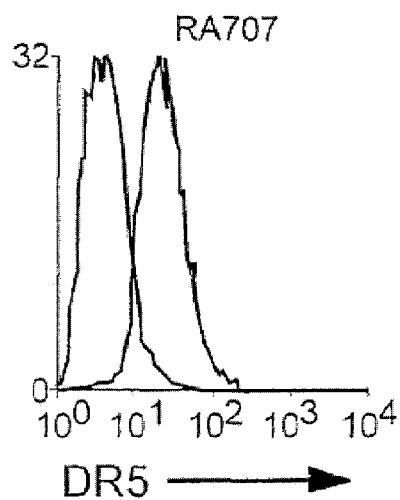
Figures 2, 7A:
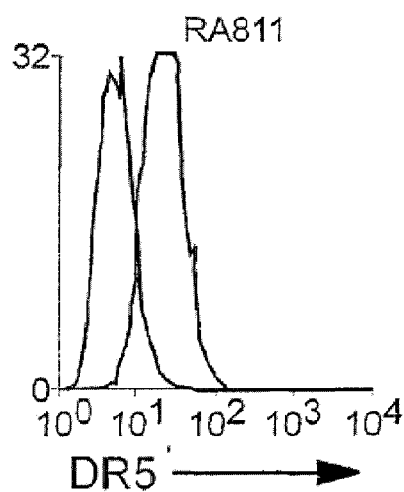
Figures 3, 7A:
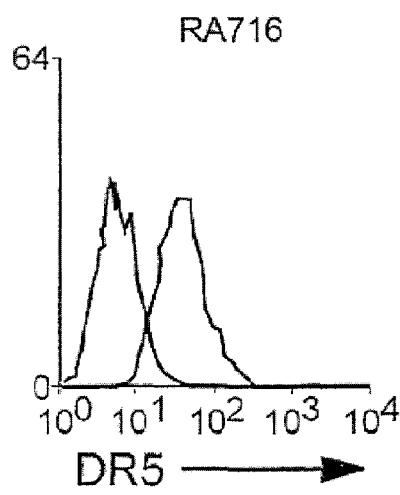
Figures 4, 7A:
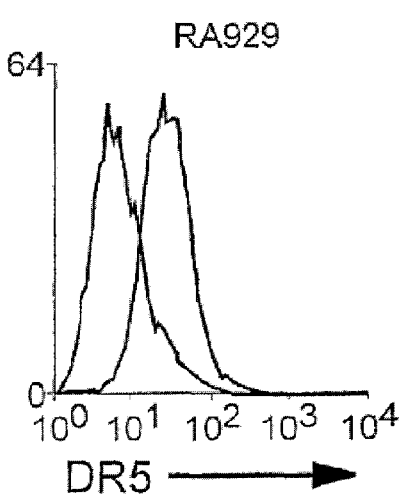
Figures 5, 7A:
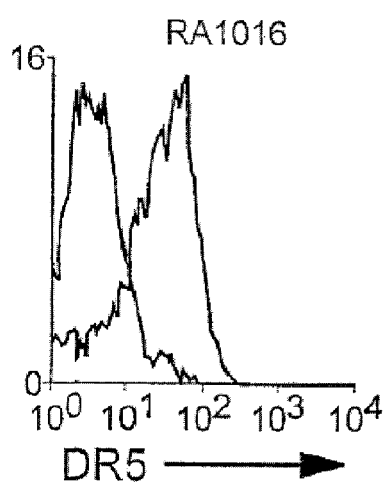
Figures 6, 7A:
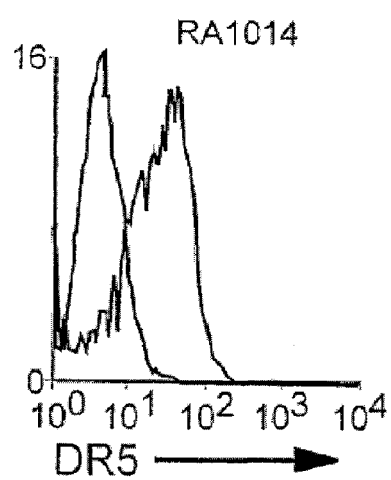
Figures 7, 7A:
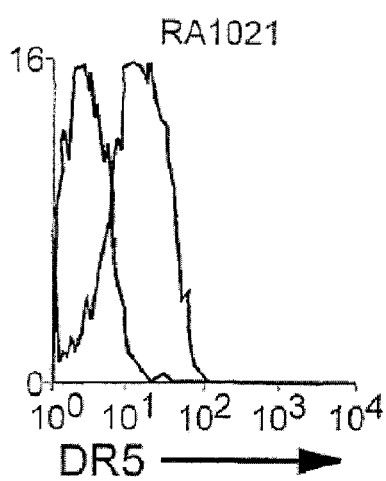
Figures 7, 7A, 8:
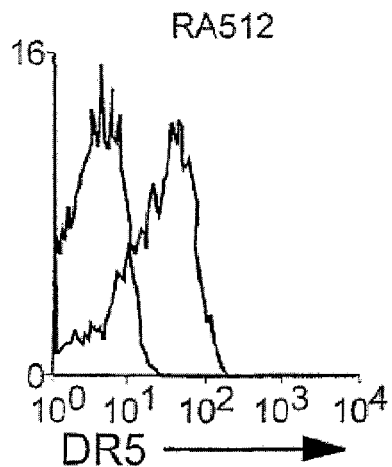
Figures 1, 7B:
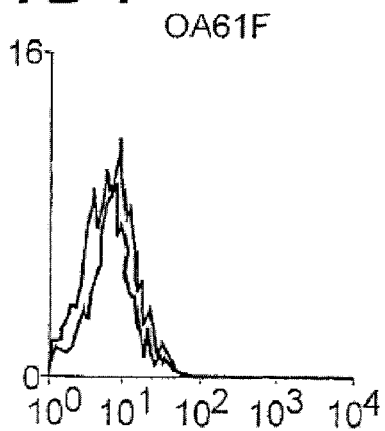
Figures 2, 7B:
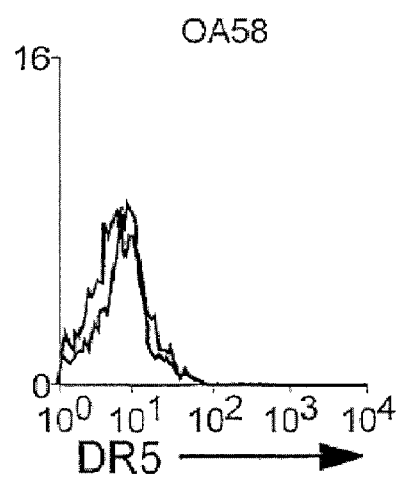
Figures 3, 7B:
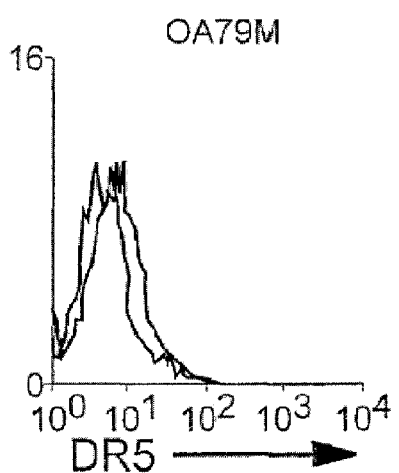
Figures 4, 7B:
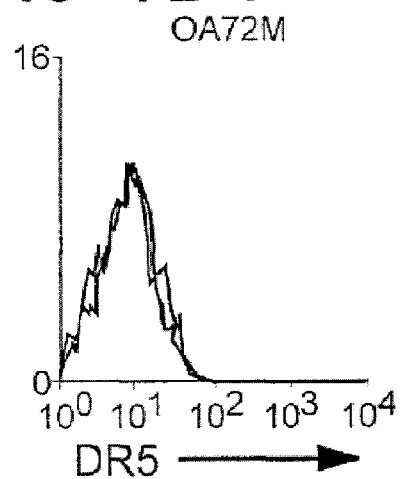
Figures 5, 7B:
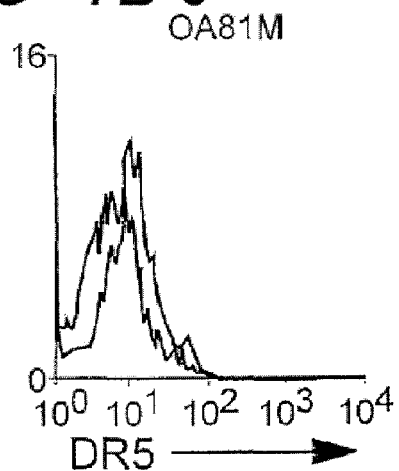
Figures 6, 7B:
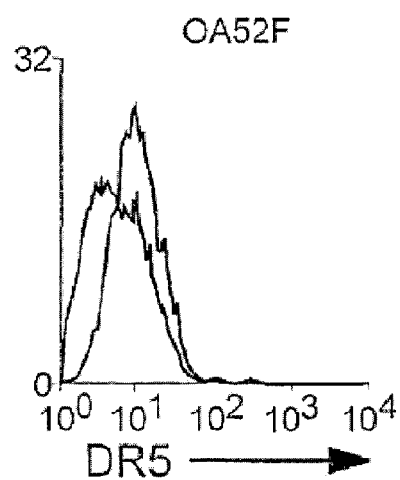
Figures 7, 7B:
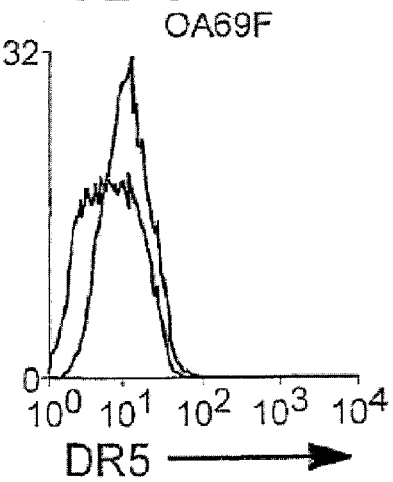

All of the primary cultures of RA cells expressed high levels of surface DR5, and there is little variation in the expression levels among these synovial cells isolated from different patients as shown in FIG. 7a. In contrast, the expression of surface DR5 on the surface of synovial cells isolated from the OA patients is very low or undetectable as per FIG. 7b. SV40-transformed synovial cell are found to express high levels of DR5 comparable with those exhibited by the RA cells. In contrast, non-transformed fibroblast cells expressed low levels of DR5 comparable to those exhibited by the OA cells in FIG. 7b.

Figures 1, 8A:
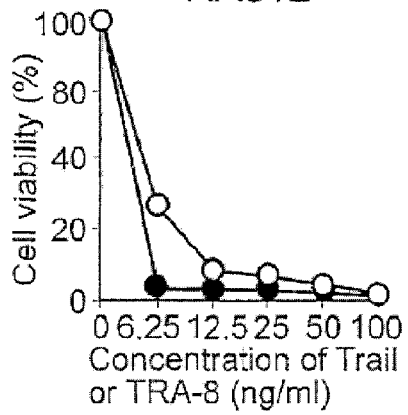
Figures 2, 8A:
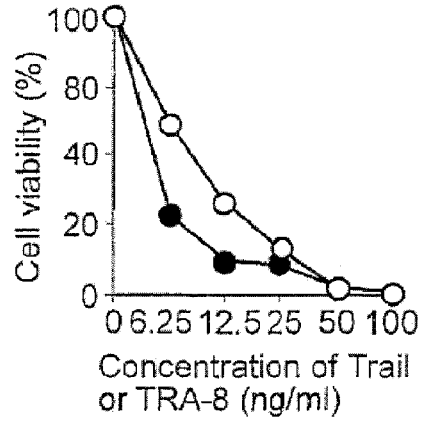
Figures 3, 8A:
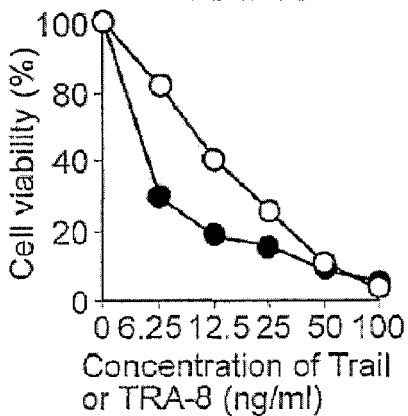
Figures 4, 8A:
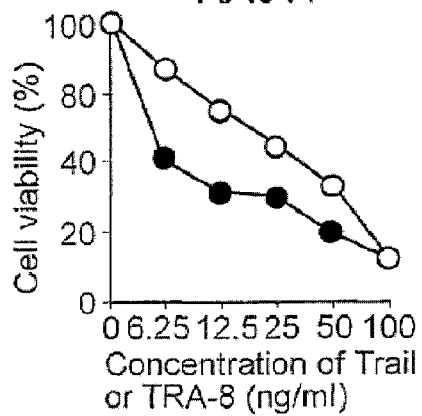
Figures 5, 8A:
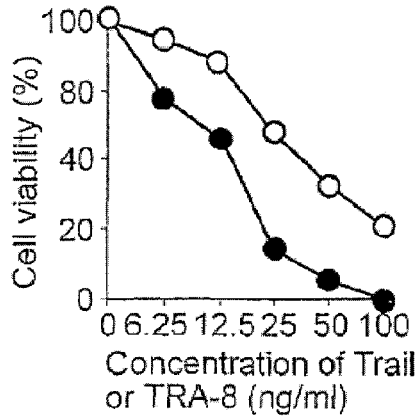
Figures 6, 8A:
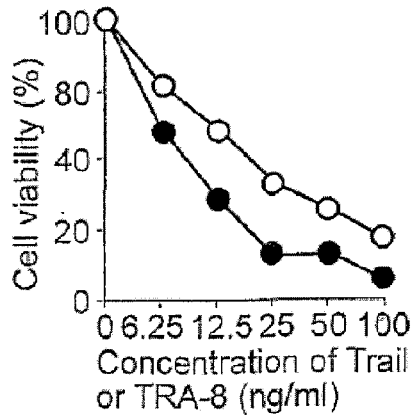
Figures 7, 8A:
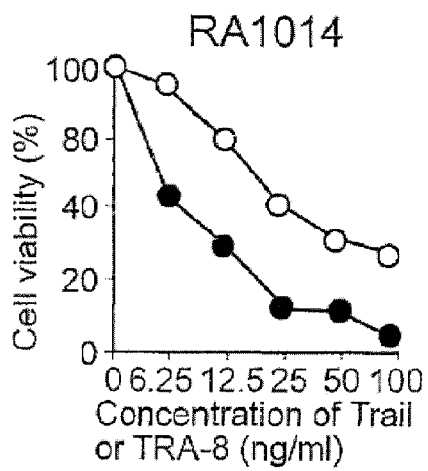
Figures 8, 8A:
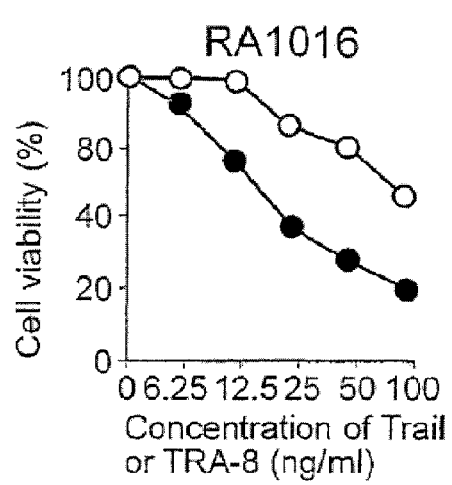
Figures 1, 8B:
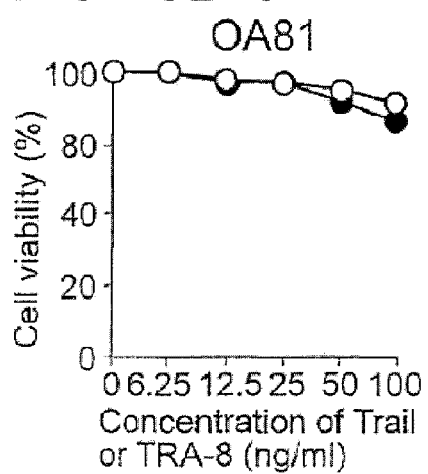
Figures 2, 8B:
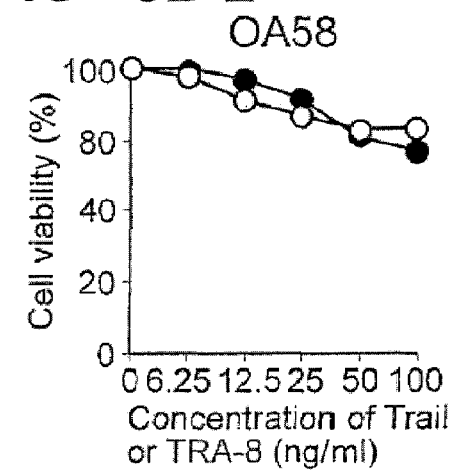
Figures 3, 8B:
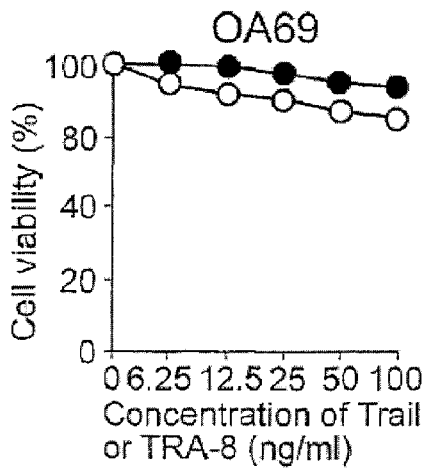
Figures 4, 8B:
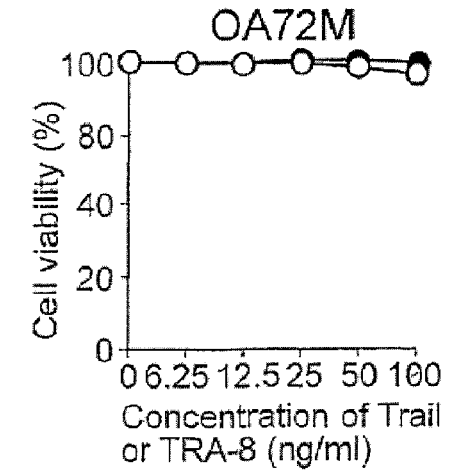
Figure 9E:
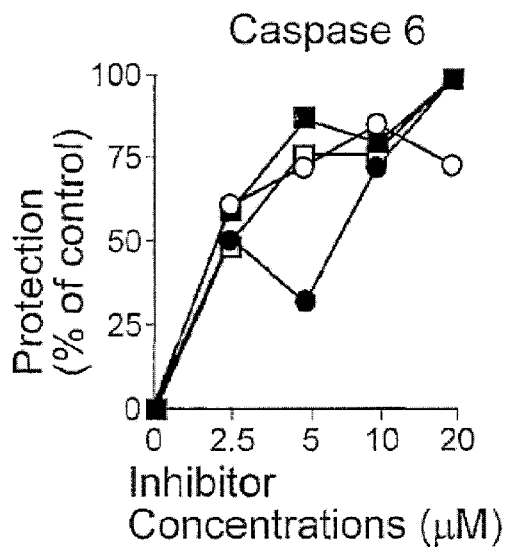
Figure 9F:
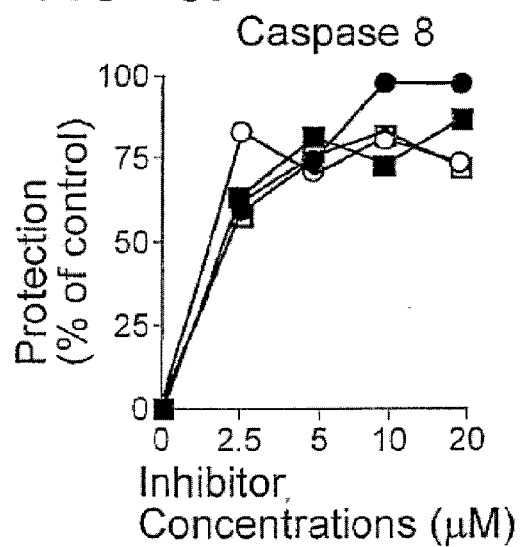
Figure 9G:
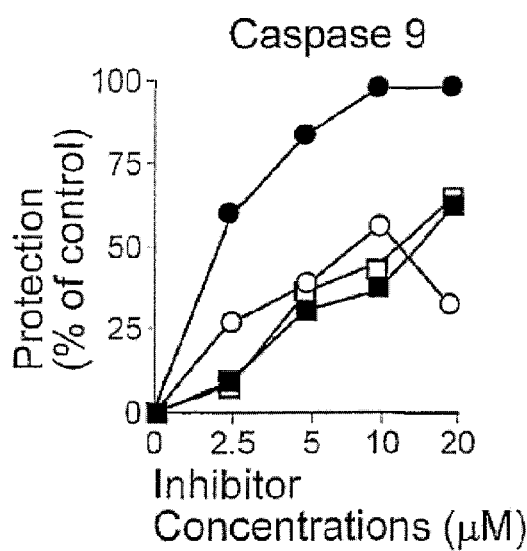
Figure 9H:
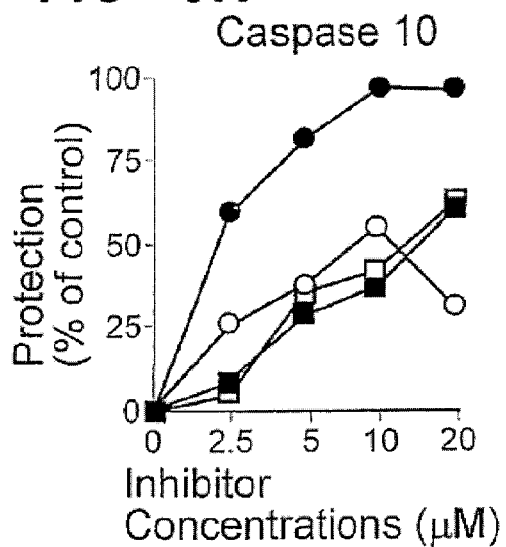
Figure 10A:
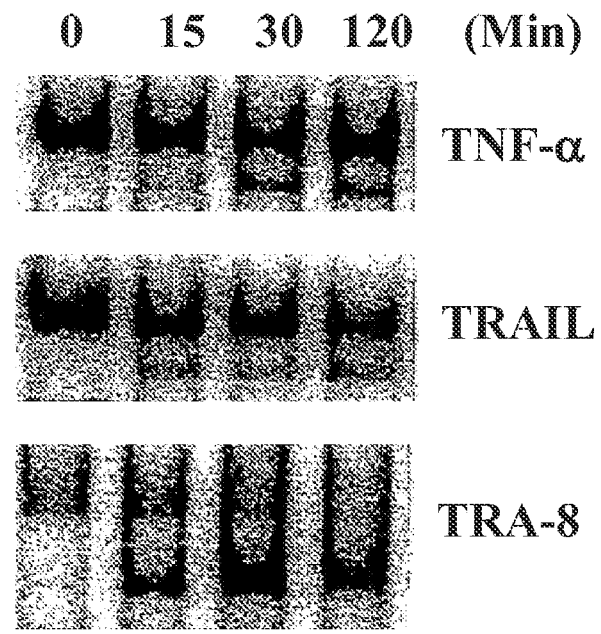
FIG. 10A is an electrophoretic gel-shift assay indicating NFkb activation. RA1016 cells are incubated with 20 ng/ml TNF-a, 50 ng/ml soluble TRAIL or 50 ng/ml TRA-8 for indicated time points before being subjected to electrophoresis.
Figure 10B:
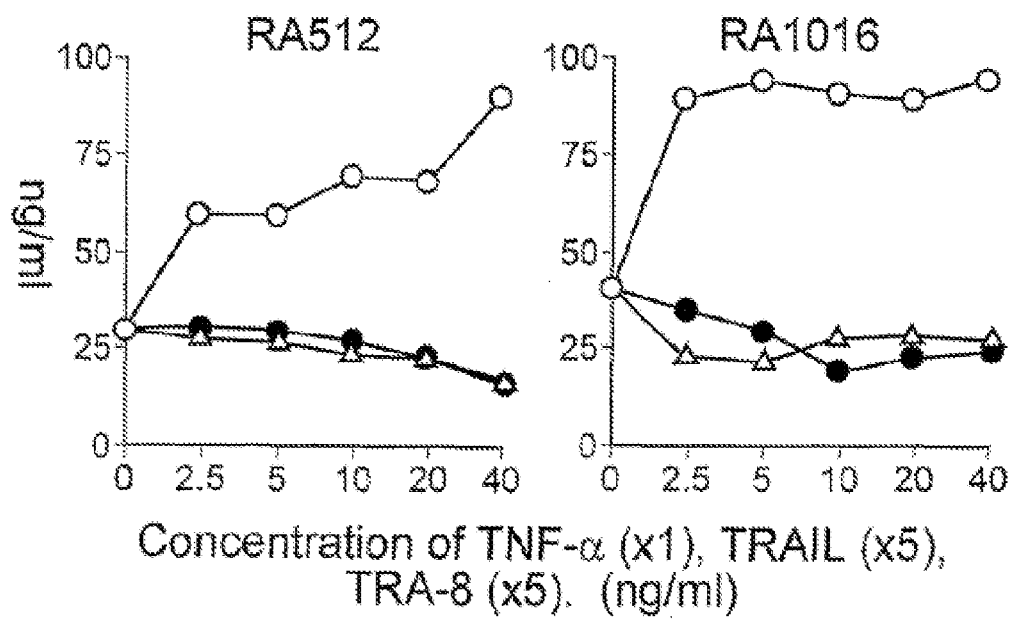
FIGS. 10B and C are graphs showing the production of MMP-1 and MMP-3. $1\times10^6$/ml of indicated RA synovial cells are incubated with the indicated concentrations of TNF-a (the open circles), TRAIL (the open triangles) or TRA-8 (the closed circle). After overnight culture, the culture supernatants are collected. The levels of MMPs in culture supernatants are determined by ELISA.
Figure 10C:
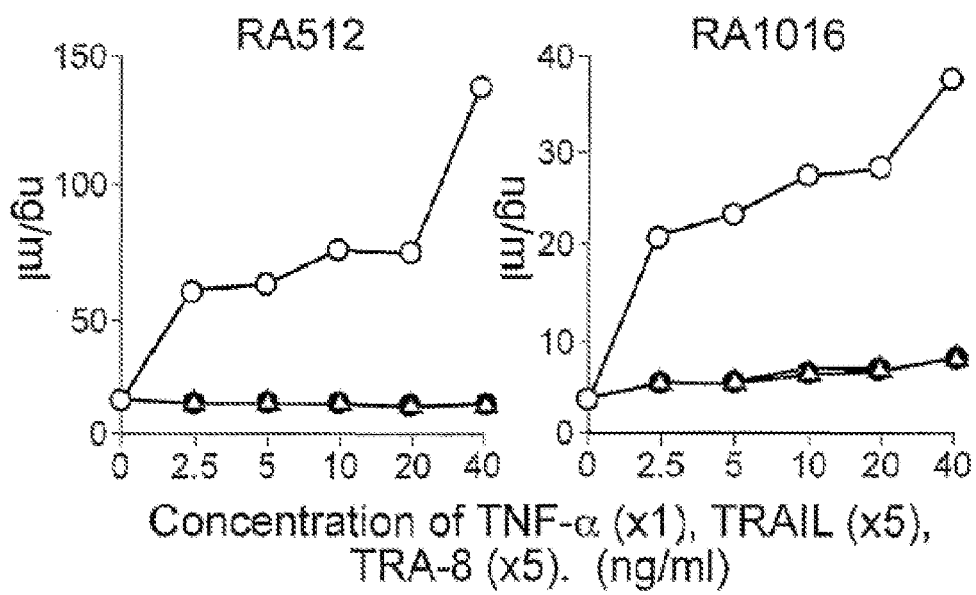

10.2 Susceptibility of RA Synovial Cells to Apoptosis Mediated by TRA-8 or TRAIL In general, all synovial cells isolated from the RA patients are susceptible to both TRAIL and anti-DR5 antibody induced apoptosis, and all OA cells are resistant to TRAIL and anti-DR5 antibody induced apoptosis as per FIG. 8a,b. These studies indicate that the TRA-8 antibody targets altered cells in preference to normal cells. Moreover, the pattern of the susceptibility or resistance to apoptosis induced by TRAIL is correlated with that induced by anti-DR5 antibody, indicating that the synovial cells primarily utilize DR5 to trigger TRAIL apoptosis.

As described for the malignant cells, the susceptibility to apoptosis induced by TRAIL or anti-DR5 antibody varied among the RA synovial cells although expressing similar levels of DR5. RA-512 and RA-707 are the most susceptible as over 80% cells are killed by concentrations of TRAIL or TRA-8 below 20 ng/ml. RA-1014, RA-811, RA-716, and RA929 are among those with the intermediate susceptibility to TRAIL or TRA-8, with nearly 100% cell death occurring in the presence of high concentrations (>50 ng/ml) of TRAIL or TRA-8. In RA-1016 and RA1021 cells, although the majority (over 60%) of cells are killed by a low dose of TRAIL or TRA-8, a portion of cells survived in the presence of high concentrations of TRAIL or TRA-8, indicating that a subpopulation of cells are resistant to TRAIL-mediated apoptosis. In contrast, all OA cells are much less susceptible to TRAIL and TRA-8 induced apoptosis. No greater than 60% cells are killed in the OA52F and OA69F even in the presence of high concentration of TRAIL or TRA-8. OA72M cells are completely resistant to TRAIL or TRA-8 induced apoptosis. The SV40 transformed synovial cells are also susceptible to TRAIL and TRA-8 induced apoptosis (data not shown). In contrast, the non-transformed fibroblast cells appeared to be resistant to TRAIL and TRA-8.

It has been shown previously that DR5 utilizes a FADD/caspase 8 dependent pathway to trigger apoptosis (44). To determine the caspase-dependence of DR5-mediated apoptosis of RA synovial cells, RA cells are cultured with TRAIL or anti-DR5 antibody in the presence of specific caspase inhibitors. Among eight caspase inhibitors tested, caspase 6, 8 and 10 inhibitors are able to inhibit apoptosis of RA synovial cells induced by both TRAIL and DR5 as shown in FIG. 9, indicating that these three caspases are involved in DR5-mediated apoptosis.

10.3 TRA-8 or TRAIL Induce NF-κb Activation in RA Synovial Cells without Increased Release of MMPs There is considerable evidence to support the concept that there are close links between the signaling of apoptosis and the signaling of proliferation (45). It has been established that DR5 is able to activate a NF-kb pathway in addition to apoptosis signaling transduction, and that NF-κb activation may be able to transduce an anti-apoptosis signal. Therefore a gel-shift assay is carried out. Cells are stimulated with 50 ng/ml of the recombinant soluble TRAIL, Fas ligand in the presence of the 1 mg/ml enhancer, or 50 ng/ml of TRA-8 for the indicated time. The nuclear extracts are prepared and incubated with the double-stained [$^{32}$P]-labeled oligo-DNA probe. The results are analyzed using the cyclone phosphaimager (TopCount NXT, Packard Instrument Company, CT). After RA synovial cells are incubated with TNF-α or TRAIL, NF-κb is activated in a time-dependent fashion. The TRA-8 antibody is able to strongly activate NF-κb. In contrast, Fas ligand is unable to induce NF-κb activation.

Thus, although TRAIL and TRA-8 antibody induce a strong apoptosis response in RA synovial cells, they also activate NF-κb, and NF-κb activation has been believed to contribute to the proinflammatory role of TNF-α in RA. Thus, it is possible that TRAIL, like TNF-α, may serve as a proinflammatory cytokine. To determine whether there is a similar biological consequence of NF-kb activation induced by TRAIL and TNF-α, the production of MMPs is determined by ELISA. Synovial cells are cultured in medium alone or with 50 ng/ml interleukin 1b, 10 ng/ml TNF-a, 50 ng/ml TRAIL, or 50 ng/ml TRA-8 overnight. The levels of the MMP-1 and MMP-3 in the culture supernatants are determined by the ELISA kits.

When RA synovial cells are incubated with a proinflammatory cytokine, TNF-α or IL-1b, the production of MMP-1, 3, and 13 is increased compared to the medium control as shown in FIG. 10 b,c. In contrast, treatment with TRAIL or anti-DR5 antibody is not associated with increased release of these MMPs.

Example 11A

Failure to Induce Hepatocellular Toxicity

For 24-hour cell viability assays, fresh normal human hepatocytes in 96-well plates were purchased from In Vitro Technology (Baltimore, Md.). The hepatocytes are cultured in the Hepatocyte Culture Medium containing 1 µg/ml of either soluble TRAIL or TRA-8. For 6-hour viability assays, normal hepatocytes or hepatocellular cancer cells are isolated from fresh surgical specimens collected from UAB Tissue Procurement Center. All reagents for isolation of human hepatocytes including hepatocytes perfusion buffer, digest medium, washing medium, and attachment medium were purchased from Gibco. The tissue slides are digested in the Hepatocyte Digest Medium at 37° C. with shaking (50 rpm) for one hour. The isolated hepatocytes are harvested by low speed centrifugation (50 g, 3 min), and washed with the Hepatocyte Washing Medium six times. Single cell suspension of hepatocytes are cultured in the Attachment Medium containing 10% FCS in 96-well Matrigel plates (BD) for six hours. Non-attached hepatocytes are removed by twice washing with pre-warmed attachment medium. Attached hepatocytes are further incubated with various concentrations of soluble TRAIL or FasL in the presence of crosslinker, or TRA-8 or CH11 for 6 hours.

Figure 11A:
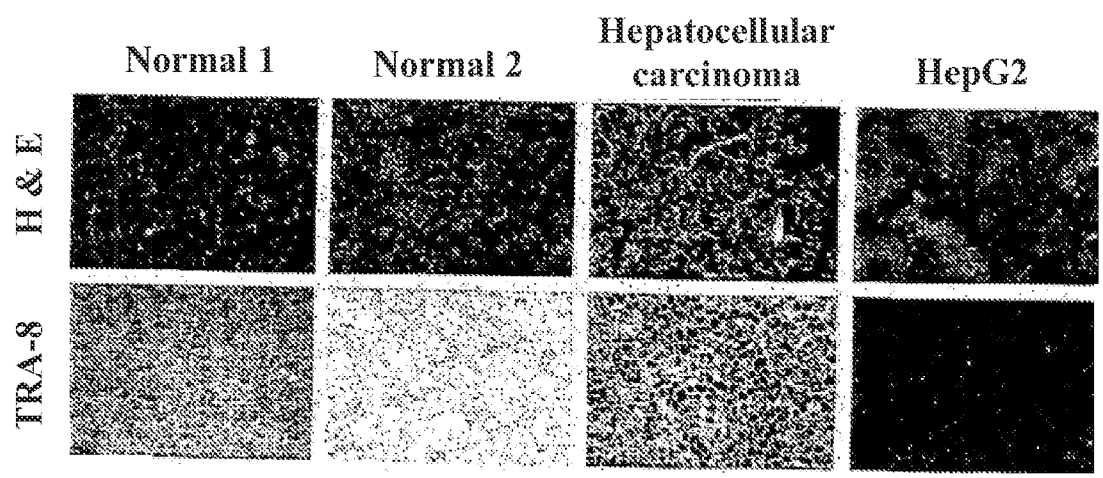
FIG. 11. TRA-8 does not induce hepatocellular toxicity. (A) Normal liver tissues do not express DR5. The paraffin sections of two normal liver tissues, one hepatocellular carcinoma tissue, and the cytospin preparation of HepG2 cells were prepared for H&E staining, and corresponding frozen sections were stained with TRA-8. (B) Flow cytometry analysis of cell surface expression of DR5. Hepatocytes, isolated from two normal liver tissues and from a case of hepatocellular carcinoma tissue, and HepG2 cells were stained with TRA-8, anti-Fas antibody (DX2) or an isotype control antibody. The solid histograms indicate TRA-8 or DX2 staining, and the open histograms are the corresponding isotype controls.

TRAIL has at least two receptors (DR4 and DR5) that are capable of inducing apoptosis. TRA-8 is used to determine whether crosslinking of DR5 alone is sufficient to induce apoptosis of normal hepatocytes. DR5 expression at the protein level is examined initially in five normal human liver tissues and five liver cancer tissues by in situ immunohistochemistry using TRA-8. Sections from the normal liver tissues showed normal architecture and cell morphology on H&E staining (FIG. 11a, left upper panels) in the absence of positive reactivity with TRA-8 for DR5 (FIG. 11a, left lower panels). In contrast, the human hepatocellular carcinoma tissue reacted positively with TRA-8 in a pattern consistent with both cell membrane and cytoplasmic presence of DR5 on the cancerous cells. The human hepatocellular carcinoma cell line HepG2 is also positive for DR5. These results are consistent among the five normal liver tissues, and only one (liver adenoma) out of five liver cancer tissues is DR5-negative. These results are consistent with the Western blot data, shown in FIG. 5a, that, as with other normal tissues, normal human liver tissue does not express significant levels of DR5 protein. Furthermore, Western blot analysis of isolated, normal human hepatocytes probed with TRA-8 does not reveal detectable levels of DR5.

Figures 1, 11B:
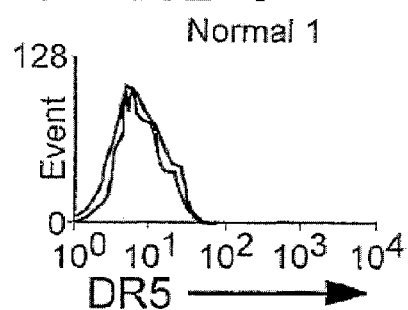
Figures 2, 11B:
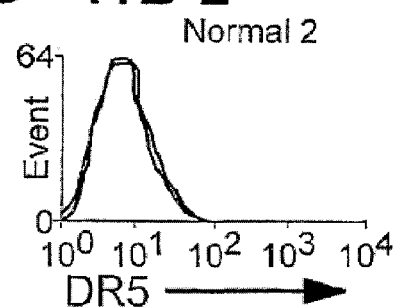
Figures 3, 11B:
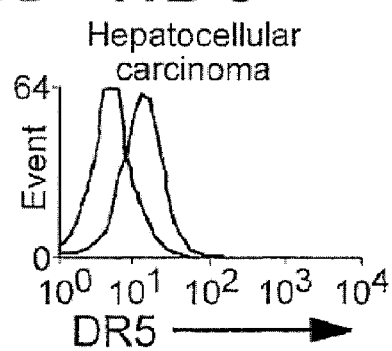
Figures 4, 11B:
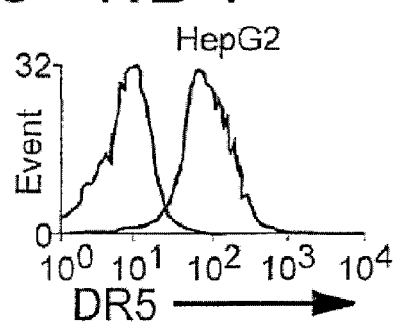
Figures 5, 11B:
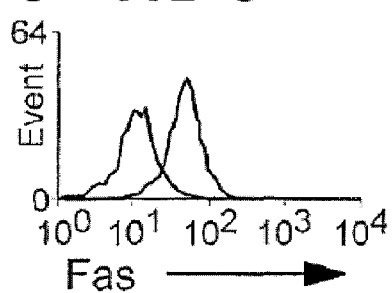
Figures 6, 11B:
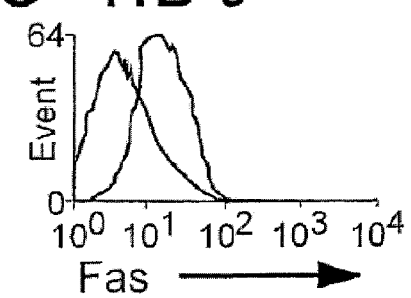
Figures 7, 11B:
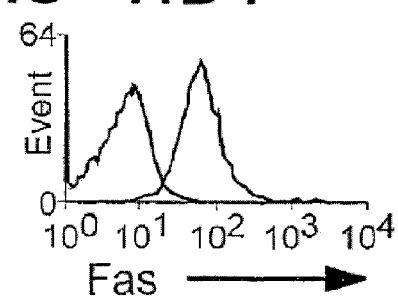
Figures 8, 11B:
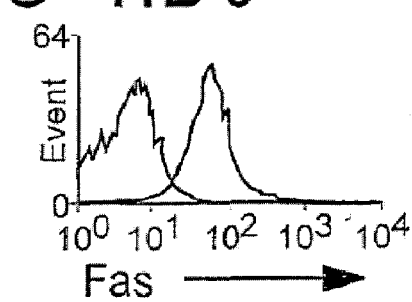

Cell surface expression of DR5 on human hepatocytes by flow cytometry analysis demonstrated that freshly prepared normal hepatocytes did not express detectable levels of cell surface DR5 (FIG. 11b, top left panels). Neither is it detected on normal human hepatocytes that had been cryopreserved or placed in short-term culture. In contrast, freshly isolated hepatocellular carcinoma cells as well as HepG2 cells express cell surface DR5. Using Fas as a comparison, the normal hepatocytes, hepatocellular carcinoma cells, and HepG2 cells all expressed equivalent levels of Fas (FIG. 11b, lower panels). These results are consistent with those obtained using in situ immunohistochemistry and Western blot and indicate that cell surface DR5 is highly expressed in cancerous liver cells but not normal hepatocytes. The presence of mRNA levels for DR4, DR5, DcR1 and DcR2 in human hepatocytes, demonstrated by RT-PCR[23], suggests that human hepatocytes might express very low levels of DR5 protein that are below the threshold for detection by TRA-8.

Figure 12A:
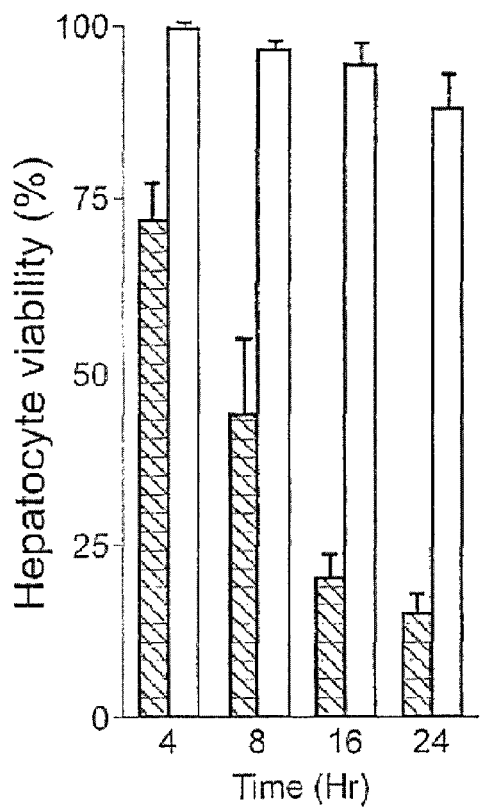
FIG. 12. TRAIL but not TRA-8 induces hepatocellular toxicity. Fresh normal human hepatocytes were maintained in Hepatocyte Culture Medium. (A) Apoptosis of hepatocytes was induced with 1 μg/ml soluble TRAIL plus crosslinker or TRA-8 for the indicated time points. Cell viability was determined by ATPLite®. The results are presented as percent viable cells compared to the medium control. The shaded bars indicate TRAIL and the black bars indicate TRA-8. (B) The condensed nuclei of hepatocytes were stained with Hoechst 33352 and analyzed by flow cytometry. (C) Effect of cycloheximide on hepatocytes apoptosis. Hepatocytes were cultured in control medium or with 1 µg/ml TRAIL or TRA-8 in the presence (closed bars) or absence (open bars) of 1 µg/ml cycloheximide for 8 hours. Cell viability was determined by ATPLite®. The results are presented as mean±SEM of triplicate cultures of two experiments. (D) A comparison of the susceptibility of normal hepatocytes to DR5 and Fas-mediated apoptosis. Freshly isolated hepatocytes were incubated with indicated concentrations of soluble TRAIL, TRA-8, soluble FasL or the anti-Fas mAb CH11 for 6 hours. Cell viability was determined by ATPLite® assay. The results are presented as the percentage of viable cells compared to medium control. For normal hepatocytes, mean±SEM of four normal individuals are presented. The results of hepatocellular carcinoma cells from one patient and HepG2 cells are presented as the average of triplicate cultures.
Figure 12B:
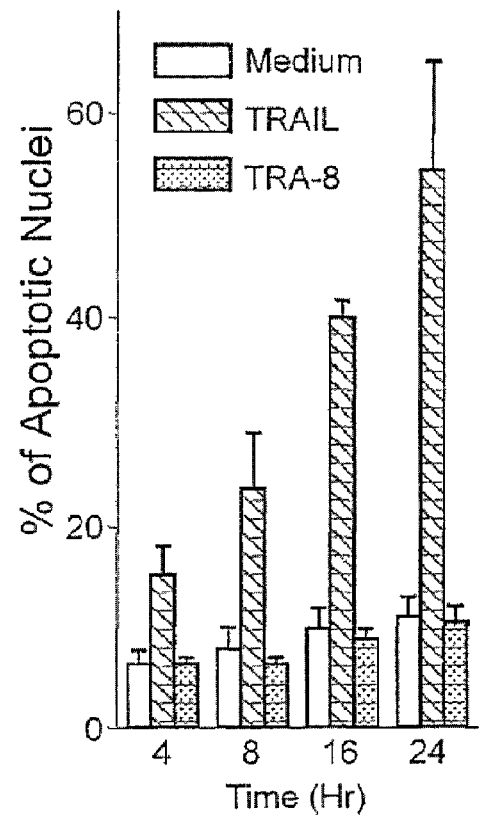
Figure 12C:
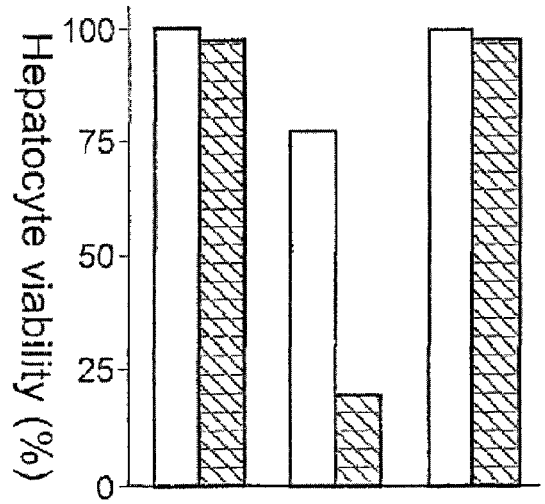
Figure 14A:
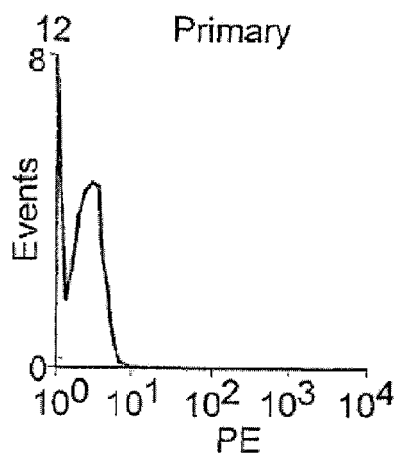
FIG. 14A is a graph of DR5 expression in un-stimulated human T cells.
Figure 14B:
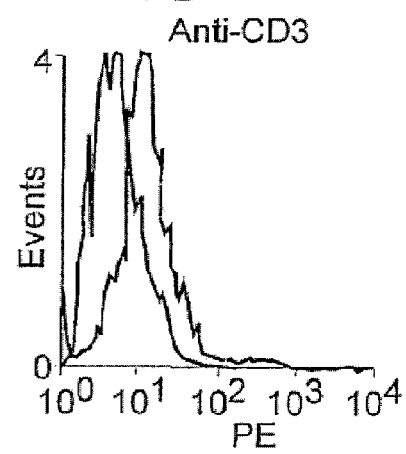
FIG. 14B is a graph of DR5 expression 48 hours after anti-CD3 stimulation.
Figure 14C:
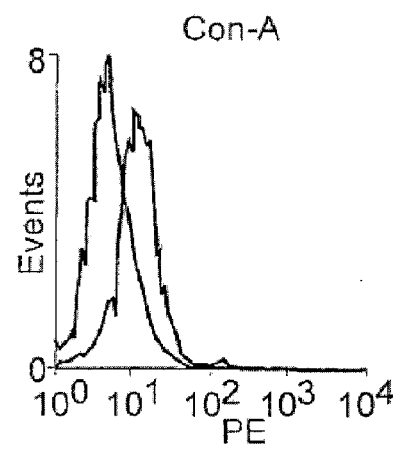
FIG. 14C is a graph of DR5 expression 48 hours after Con-A stimulation.
Figure 14D:
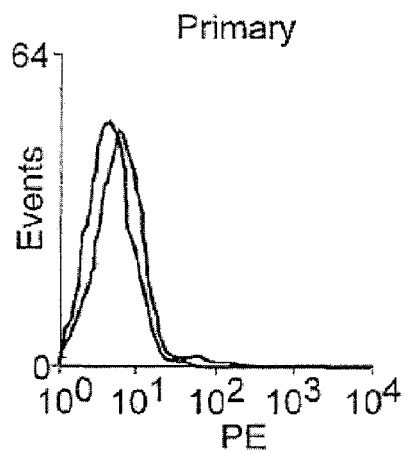
FIG. 14D is a graph of DR5 expression in un-stimulated B cells.
Figure 14E:
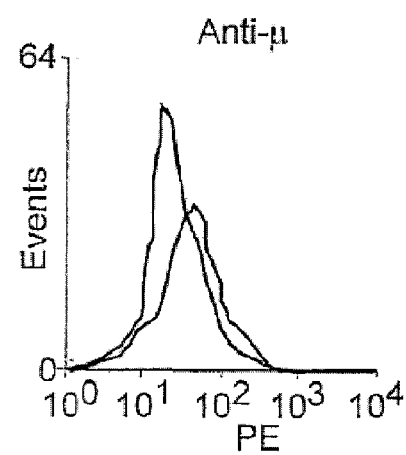
FIG. 14E is a graph of DR5 expression after anti-µ stimulation.
Figure 14F:
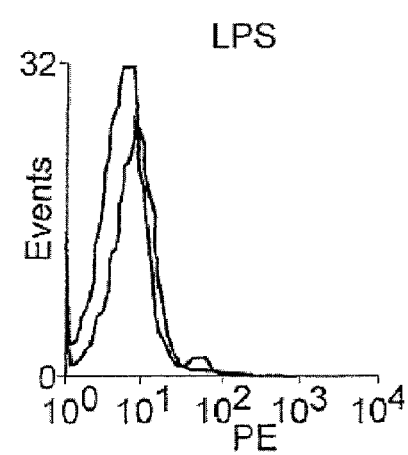
FIG. 14F is a graph of DR5 expression after LPS expression.

To determine whether TRA-8 induces hepatocellular toxicity, the susceptibility of normal human hepatocytes to apoptosis induced by TRA-8 and by soluble TRAIL plus crosslinker is examined. When normal hepatocytes are cultured in the presence of a high concentration of TRAIL, a time-dependent decrease in cell viability is observed by ATPLite® (FIG. 12a) and MTT assays. TRAIL-mediated cell death of normal hepatocytes could be seen as early as four hours after addition of TRAIL. At end of a 24-hour culture, more than 80% of the hepatocytes are killed by TRAIL. In contrast, during the same culture period, TRA-8 did not induce significant cell death in normal hepatocytes. The condensed nuclei stained with Hoechst, a characteristic of apoptosis, are increased in TRAIL-treated but not TRA-8-treated hepatocytes (FIG. 12b). The number of apoptotic hepatocytes is well correlated with decreased cell viability as determined by ATPLite® assay, suggesting that TRAIL-induced cell death of hepatocytes is mediated by apoptosis. This is confirmed by the ability of Z-VAD to inhibit TRAIL-mediated toxicity of hepatocytes. As cycloheximide is a potent apoptosis enhancer, the effect of this compound on TRAIL and TRA-8-treated hepatocytes is investigated. During a four-hour culture, cycloheximide significantly enhanced the cell death of hepatocytes induced by TRAIL, with greater than 70% hepatocytes being killed by TRAIL in the presence of cycloheximide (FIG. 12c). However, cycloheximide treatment is unable to enhance TRA-8-mediated cell death in hepatocytes. To compare the characteristics of apoptosis induced by TRA-8 with that induced by TRAIL in hepatocytes, normal hepatocytes as well as cancer cells are incubated with variable concentrations of soluble TRAIL with crosslinker or TRA-8. During a 6-hour culture period, TRAIL induced a moderate apoptotic response in normal hepatocytes. Over 20% of hepatocytes are killed in the presence of 500 ng/ml TRAIL (FIG. 12d, upper left). TRA-8-treatment of normal hepatocytes did not elicit any significant cell death over the same time period. In contrast to normal hepatocytes, primary hepatocellular carcinoma cells (FIG. 12d, upper middle) and HepG2 cells (FIG. 12d, upper right) are highly susceptible to apoptosis mediated by either TRAIL or TRA-8. Over 80% of hepatocellular carcinoma cells and nearly 100% of HepG2 cells are killed during the 8-hour culture period. These results indicate that normal hepatocytes are completely resistant to TRA-8-mediated apoptosis, and are much less susceptible to TRAIL-mediated apoptosis than are liver cancer cells. Using Fas ligand and anti-Fas antibody (CH-11), there is no significant difference in the susceptibility to Fas-mediated apoptosis among normal hepatocytes, hepatocellular carcinoma cells, and HepG2 cells (FIG. 12d, lower panels).

Comparative Example 11B

Human Membrane-Bound TRAIL Induction of Hepatitis in vivo 8-10 week-old female B6 mice are intravenously injected with $10^9$ pfu of Ad/hTRAIL with the equal number of Ad/Tet-on. Mice are fed with different concentrations of tetracycline in their drinking water immediately after inoculation of adenoviral vectors. Liver injury is determined by serum levels of AST using an AST diagnostic kit (Sigma). Expression of TRAIL is determined by Northern blot analysis.

To determine whether the membrane bound form of TRAIL induces liver damage in vivo, a recombinant adenoviral vector encoding the full length human TRAIL (Ad/hTRAIL) is constructed, the expression of which is under the control of the tetracycline-inducible promoter. Twenty-four hours after intravenous inoculation of B6 mice with Ad/hTRAIL, tetracycline-induced expression of human TRAIL is observed in the liver in a dose-dependent fashion as demonstrated by Northern blot analysis (FIG. 13a). The expression levels of TRAIL correlated well with liver damage as shown by a tetracycline-dependent increase in serum levels of transaminases, again in a dose-dependent fashion (FIG. 13b). As the inoculation with adenoviral vector per se might increase the susceptibility of hepatocytes to TRAIL-mediated apoptosis, the hepatocytes from mice inoculated with Ad/TRAIL are isolated and tested for TRAIL-mediated cell death. There is no significantly increased cell death of Ad/TRAIL infected hepatocytes compared to those from control mice (FIG. 13c, left panel). Moreover, Ad/TRAIL inoculated mice did not exhibit increased liver injury after intravenous injection of soluble human TRAIL. Thus, it follows that hepatitis induced by Ad/TRAIL is mediated by high levels of TRAIL expression in its membrane form. Histologic analysis of liver sections revealed that damage to the hepatocytes is apparent as early as 24 hours after vector inoculation (FIG. 13d), and persisted for at least 7 days (FIG. 13e). These pathologic alterations in the liver also are tetracycline-dependent and occurred in a dose-dependent manner. The early phase, within 24 hours of treatment, of TRAIL-induced liver damage is characterized by foci of necrosis. Infiltration of inflammatory cells is not observed at this stage, but hemorrhage had occurred. By day 7 after inoculation, diffuse liver damage is apparent with marked lobular disarray, severe degeneration of hepatocytes with irregularly clumped cytoplasm and large clear spaces, and prominent apoptosis and necrosis. An extensive infiltrate of mononuclear cells is a characteristic feature at this stage. These results indicate that human TRAIL in its membrane-bound form is able to induce liver damage in vivo. Despite the propensity of human TRAIL to cause severe hepatitis in mice, it did not induce a lethal response. In contrast, mice inoculated with similar tetracycline-controlled vectors encoding Fas ligand developed fulminant hepatitis with massive apoptosis and necrosis of hepatocytes accompanied by severe hemorrhage and by mortality occurring in a tetracycline dose-dependent within 72 hours of inoculation. The mortality rate reached 100% within 48 hours in those subgroups receiving 3 mg/ml or more of tetracycline. In contrast, all of the mice that received Ad/hTRAIL, regardless of the dose of tetracycline, are still alive four weeks after inoculation. Thus, it follows that, in vivo, the membrane-bound form of TRAIL is a less potent inducer of hepatocellular damage than Fas ligand. They further suggest that TRAIL might induce liver damage through a mechanism that differs from the mechanism underlying the toxicity of Fas ligand.

Example 12

Activated Human T and B Cells Express Increased Levels of DR5

To determine whether DR5 plays a role in TRAIL-mediated apoptosis of activated T cells and B cells, surface expression of DR5 on resting and activated T and B cells using TRA-8 is examined. The unstimulated human T cells in PBMC did not express significant levels of DR5 (FIG. 14). At 48 hours after either anti-CD3 or Con-A stimulation, cell surface DR5 expression is significantly increased. Similarly, the unstimulated B cells expressed very low levels of DR5. Stimulation with anti-μ but not LPS resulted in increased cell surface expression of DR5. These results indicate that both activated T and B cells express higher levels of cell surface DR5. Cells are stained with 20 μg/ml TRA-8 and PE anti-mouse IgG1.

Example 13

Activated T and B Cells Become Susceptible to TRA-8 Mediated Apoptosis

To determine whether activated T and B cells are susceptible to TRA-8-mediated apoptosis, the T cells and B cells of human PBMC are stimulated with anti-CD3 or anti-μ in vitro for 48 hours, respectively. The viable cells and proliferating blast cells are collected by gradient centrifugation, and incubated with various concentrations of TRA-8. Unstimulated T cells and B cells are not susceptible to TRA-8-mediated apoptosis (FIG. 15). Total stimulated T cells and B cells showed a moderately increased susceptibility to TRA-8-mediated apoptosis, with 20% cells being killed by TRA-8 after overnight culture. The highly proliferating blast T cells are even more susceptible to TRA-8 mediated apoptosis. More than 70% of the blast T cells could be killed by TRA-8. The blast B cells are also more susceptible to TRA-8 mediated apoptosis compared to others. These results indicate that activated T and B cells are susceptible to DR5-mediated apoptosis.

Example 14

TRA-8 Depletes Activated T Cells in Human/SCID Mice

To determine the in vivo anti-T cell efficacy of TRA-8, NOD/SCID mice are intravenously injected with 1×10$^8$ human PBMC. Normally, the human T cells in SCID mice are quickly activated in response to xenogeneic stimulation. The human PBMC/SCID mice are intraperitoneally injected with 100 μg TRA-8 or control IgG1 from the day of transfer, repeated daily for three days. Five days after transfer, the mononuclear cells are isolated from the spleen and stained with anti-human CD3 antibody, and the lymphocyte population is gated by flow cytometry analysis, and CD3 positive human T cells are analyzed. Approximately 30% of splenic lymphocytes are human T cells as determined by anti-human CD3 staining in control treated mice. However, only a few human T cells (less than 3%) are observed among the splenic lymphocytes in TRA-8 treated mice (FIG. 16). In situ histological study revealed that in the spleen of control mice, the human T cells are repopulated in the spleen with only a few apoptotic cells observed as demonstrated by TUNEL staining. In contrast, repopulation with viable human T cells is not observed in the spleen of TRA-8 treated mice, rather many apoptotic cells are observed (FIG. 17). These results demonstrate that TRA-8 has anti-T cell activity in vivo, and indicate the utility of the inventive antibodies for the treatment of GVH disease.

Example 15

Anti-Cancer Therapeutic Activity of TRA-8

15.1 DR5 Expression and Function in Human Cancer Tissues and Cell Lines i) DR5 expression in human cancer tissues by in situ staining with TRA-8. To determine whether cancer cells and tissues differentially express higher levels of DR5, a panel of human cancer tissues including over 20 breast cancers, 6 ovarian cancers, 5 colon cancers and 5 prostate cancers are stained with TRA-8 for immunohistochemistry. The majority of these cancer tissues expressed detectable DR5. The expression levels of DR5 in these cancer tissues varied. In general, cancer tissues expressed higher levels of DR5 than uninvolved tissues. In addition, DR5 expression is apparently not correlated with the mutation of p53.

ii) DR5 expression and function in human cancer cell lines (Table 2). Nine human breast cancer cell lines, three ovarian cancer lines, three colon cancer lines and three prostate cancer lines are examined for cell surface expression of DR5 and susceptibility to TRA-8-induced apoptosis in vitro. 7 of 9 breast cancer lines, 3 of 3 ovarian cancer lines, 3 of 3 colon cancer lines and 3 of 3 prostate cancer lines expressed variable levels of cell surface DR5. Of 9 breast cancer lines, three are very susceptible, three are intermediate and three are resistant to TRA-8-mediated apoptosis. All three ovarian cancer lines are very susceptible. One of three colon cancer lines is very susceptible, while two have intermediate sensitivity. Two of three prostate cancer lines have intermediate sensitivity and one is resistant.

TABLE 2

Expression and function of DR5 in human cancer cells.

| Cell line | Origin | Expression[1] | Susceptibility[2] |
|---|---|---|---|
| 2LMP | breast | + | ++++ |
| LCC6 | breast | +++ | ++++ |
| MB468 | breast | +++ | +++ |
| MB231 | breast | ++ | +++ |
| ZR-75-1 | breast | +++ | ++ |
| SKBR3 | breast | + | ++ |
| MB453 | breast | ++ | + |
| BT474 | breast | + | − |
| DY36T2 | breast | − | − |
| Caov-3 | ovary | + | ++++ |
| OVCAR-3 | ovary | ++ | ++++ |
| Skov-3 | ovary | + | +++ |
| WiDR | colon | +++ | ++++ |
| HST29 | colon | ++ | +++ |
| T84 | colon | + | ++ |
| PC3 | prostate | +++ | ++ |
| LnCap | prostate | +++ | + |
| Du-145 | prostate | +++ | + |

Note:
[1]determined by flow cytometry, cells are stained with 20 μg/ml TRA-8 and compared to control antibody.
[2]determined by ATPLite ® assay.
++++: over 80% killing, +++: killing between 60-80%, ++: killing between 40-60%, +: killing between 20-40%, − no killing.

iii) Combined cytotoxicity of TRA-8 with adriamycin. In several breast cancer lines, the effect of adriamycin on TRA8-induced apoptosis is examined. High doses of adriamycin exhibited an additive effect. However, in some of TRA-8 resistant lines, low doses of adriamycin synergistically enhance TRA-8-induced apoptosis.

iv) In vitro and in vivo binding activity of TRA-8 to human cancer cells. Using radioisotope labeled TRA-8. The binding activity of TRA-8 to a breast cancer line is examined in vitro and in vivo in SCID mice implanted with tumor. The in vitro binding activity to cancer cells is estimated as a Kd value of 3 nM, which is constant with our previous estimation using ELISA, and at least 50-fold higher than soluble TRAIL. In vivo, TRA-8 localized to implanted tumor tissues.

15.2. Therapy of Chronic Lympholytic Leukemia in NOD/SCID Mice with TRA-8

Figure 18A:
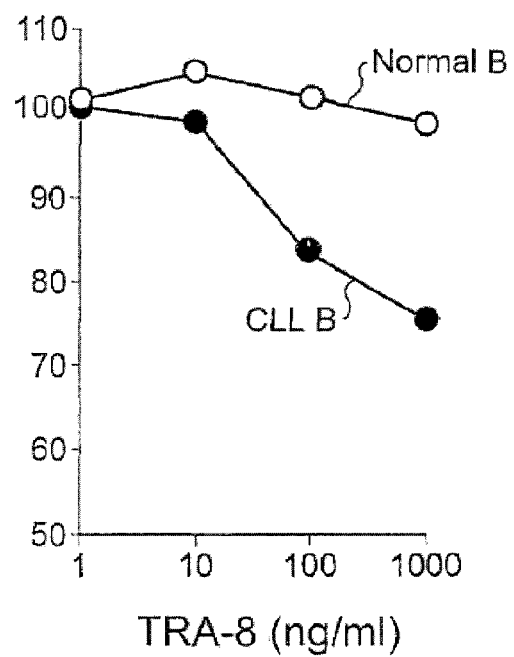
FIG. 18 shows cycotoxicity plots for chronic lympholytic leukemia (CCL) and normal B cell humans in the presence of TRA-8 (FIG. 18A), BISVIII (FIG. 18B), and the combination thereof (FIG. 18C).
Figure 18B:
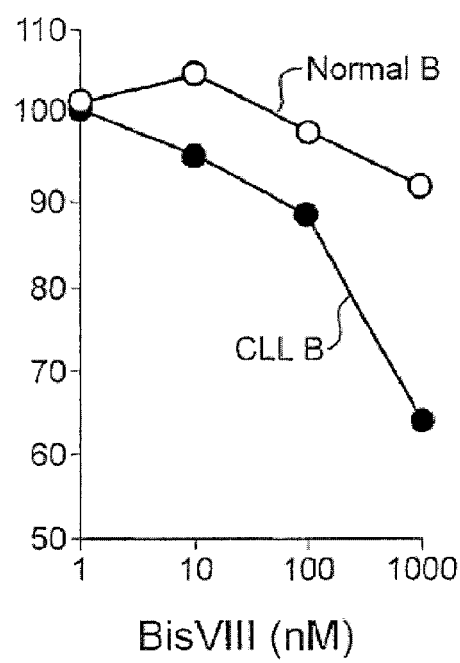
Figure 18C:
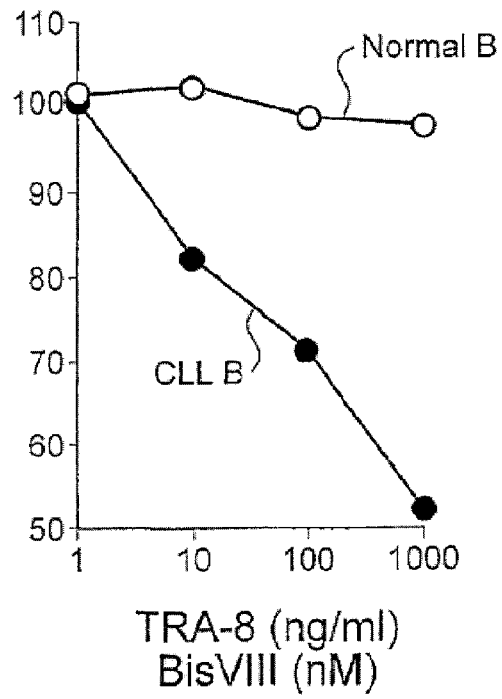

Chronic lympholytic leukemia (CLL) is a common form of B cell malignancy. Most malignant B cells in CLL are of the mature phenotype and are resistant to many apoptosis stimuli. DR5 expression and function in the B cells of five patients with CLL is examined. All patients had high counts of peripheral B cells as shown by more than 95% CD19+ B cells in PBMC. Compared to normal primary B cells, the CLL B cells of all patients had higher levels of cell surface DR5 and are more susceptible to TRA-8 induced apoptosis in vitro. Interestingly, the CLL B cells are also sensitive to bisindolemaleimide VIII (BisVIII) induced cytotoxicity. Following combined treatment with TRA-8 and BisVIII, nearly 50% of CLL B cells are killed while normal B cells remained unresponsive (FIG. 18). Transfer of CLL B cells into NOD/SCID mice resulted in about 25%-30% CD19+ B cells repopulated in the spleen of recipient mice at five days after transfer. However, three doses of 100 μg TRA-8 treatment completely eliminated CLL B cells of four out of five patients in the spleen of the recipient SCID mice. Thus, TRA-8 alone or in concert with other substances is active as a therapeutic agent for chronic lympholytic leukemia.

Example 16 cDNA Cloning (1) Determination of the N-Terminal Amino Acid Sequences of the Heavy and Light Chains of TRA-8

In order to obtain cDNAs of the heavy and light chains of TRA-8, the N-terminal amino acid sequences of the heavy and light chains of TRA-8 and cloned TRA-8 genes are determined by known techniques.

Ten μg of the solution containing the anti-human DR5 antibody TRA-8 is subjected to SDS-polyacrylamide gel electrophoresis ("SDS-PAGE"), using a gel concentration of 12% w/v, 100 V constant voltage, for 120 minutes. After electrophoresis, the gel is immersed in transfer buffer 25 mM Tris-HCl (pH 9.5), 20% methanol, 0.02% v/v SDS for 5 minutes. After this time, the protein content of the gel is transferred to a polyvinylidene difluoride membrane ("PVDF membrane"; pore size 0.45 um; Millipore, Japan), presoaked in transfer buffer, using a blotting apparatus (KS-8451; Marysol) under conditions of 10 V constant voltage, 4° C., for 14 hours.

After this time, the PVDF membrane is washed with washing buffer 25 mM NaCl, 10 mM sodium borate buffer (pH 8.0), then stained in a staining solution (50% v/v methanol, 20% v/v acetic acid and 0.05% w/v Coomassie Brilliant Blue) for 5 minutes to locate the protein bands. The PVDF membrane is then destained with 90% v/v aqueous methanol, and the bands corresponding to the heavy chain, the band with the lower mobility and light chain, the band with the higher mobility previously located on the PDVF membrane are excised and washed with deionized water.

The N-terminal amino acid sequence of the heavy and light chains are determined by the Edman automated method (Edman, P., et al., (1967), Eur. J. Biochem., 1, 80) using a gas-phase protein sequencer (PPSQ-10; Shimadzu Seisakusyo, K. K.).

The N-terminal amino acid sequence of the band corresponding to the heavy chain is determined to be:

```
                      (SEQ ID No. 4 of the Sequence Listing)
Glu-Val-Met-Leu-Val-Glu-Ser-Gly-Gly-Gly-Leu-Val- Lys-Pro-Gly-Gly-Ser-Leu-Lys-Leu;
``` and that of the band corresponding to the light chain is determined to be:

```
                      (SEQ ID No. 5 of the Sequence Listing)
Asp-Ile-Val-Met-Thr-Gln-Ser-His-Lys-Phe-Met-Ser- Thr-Ser-Val-Gly-Asp-Arg-Val-Ser.
```

Comparison of these amino acid sequences with the database of amino acid sequence of antibodies produced by Kabat et al. (Kabat E. A., et al., (1991), in "Sequences of Proteins of Immunological Interest Vol. II," U.S. Department of Health and Human Services) revealed that the heavy chain (γ1 chain) and the light chain (k chain) of TRA-8 belonged to subtypes 3d and 1, respectively.

(2) cDNA Cloning

Based on above findings, oligonucleotide primers are synthesized which would be expected to hybridize with portions of the 5'-untranslated regions and the very ends of the 3'-translated regions of the genes belonging to these mouse subtypes. Then, cDNAs encoding the heavy and light chains of TRA-8 are cloned by the following combination of reverse transcription and PCR (RT-PCR):

a) Template

The total RNA of TRA-8 hybridoma (ATCC No. PTA-1428) is extracted by using TRIzol Reagent (GIBCO BRL). The template for the PCR reaction used cDNA that is obtained by using the First-Strand cDNA synthesis kit (Amersham Pharmacia Biotech) according to the instruction manual provided with the kit.

b) PCR Primers

The following oligonucleotide primers are synthesized for the PCR:

```
5'-cagcactgaa cacggacccc-3';    (H5NCS1: SEQ ID No. 6 of the Sequence Listing)

5'-aaaggtaatt tattgagaag-3';    (H5NCS2: SEQ ID No. 7 of the Sequence Listing)

5'-cctcaccatg aacttcgggc-3';    (H5SS1: SEQ ID No. 8 of the Sequence Listing)

5'-ctgttgtatg cacatgagac-3';    (H5SS2: SEQ ID No. 9 of the Sequence Listing)

5'-gaagtgatgc tggtggagtc-3';    (H5CS1: SEQ ID No. 10 of the Sequence Listing)

5'-agtgtgaagt gatgctggtg-3';    (H5CS2: SEQ ID No. 11 of the Sequence Listing)

5'-tttaccagga gagtgggaga g-3';  (H3CR: SEQ ID No. 12 of the Sequence Listing)

5'-tgcagagaca gtgaccagag-3';    (H3VR: SEQ ID No. 13 of the Sequence Listing)

5'-tgttcaggac cagcatgggc-3';    (L5NCS1: SEQ ID No. 14 of the Sequence Listing)

5'-aagacatttt ggattctaac-3';    (L5NCS2: SEQ ID No. 15 of the Sequence Listing)

5'-tatcatgaag tctttgtatg-3';    (L5SS1: SEQ ID No. 16 of the Sequence Listing)

5'-gatggagaca cattctcagg-3';    (L5SS2: SEQ ID No. 17 of the Sequence Listing)

5'-gacattgtga tgacccagtc-3';    (L5CS: SEQ ID No. 18 of the Sequence Listing)
```

```
                                -continued
5'-ttaacactca ttcctgttga-3';    (L3CR: SEQ ID No. 19 of the Sequence Listing)
and 5'-gactgggtca tcacaatgtc-3'.    (LCSR: SEQ ID No. 20 of the Sequence Listing)
```

Unless otherwise specified, all oligonucleotides in these Examples are synthesized by Pharmacia Biotech. All oligonucleotides are stored at −20° C. after being dissolved in distilled water.

c) PCR Reaction

Composition of the PCR Reaction Solution:
- template cDNA, 5 μl of total 33 μl reaction
- primer DR5p1, 10 pmol;
- primer DR5p2, 10 pmol;
- 10× concentrated PCR buffer (provided with the kit), 10 μl;
- dNTPs (each 2.5 mM), 4 μl; and
- Taq polymerase (Promega), 5 units.

Sterile distilled water is added to the solution to a total volume of 100 μl. Unless otherwise specified, dNTPs are an equimolar mixture of dATP, dCTP, dGTP and dTTP (2.5 mM each).

The PCR reaction is conducted as follows. The solution is first heated at 94° C. for 2 minutes, after which a cycle of heating to 94° C. for 30 sec, 52° C. for 1 minute and 72° C. for 3 minutes, is repeated 40 times. After completion of this procedure, the reaction solution is heated at 72° C. for 10 minutes.

The amplified DNA fragments, thus obtained, are separated on a 1% agarose gel containing 0.25 μg/ml ethidium bromide. The bands determined to contain the desired DNA fragments are cut out using a razor blade and the DNA is recovered therefrom using the Gene Clean kit (BIO101). The DNA fragment is cloned using pGEM-T Easy vector (Promega). This is performed as follows.

The DNA fragment recovered from the PCR reaction solution, together with 50 ng of pGEM-T Easy vector (provided with the kit), is mixed with 1 μl of 10× ligase reaction buffer (6 mM Tris-HCl (pH 7.5), 6 mM magnesium chloride, 5 mM sodium chloride, 7 mM β-mercaptoethanol, 0.1 mM ATP, 2 mM DTT, 1 mM spermidine, and 0.1 mg/ml bovine serum albumin), to which 4 units of T4 DNA ligase (1 μl) has been added. The total volume of the mixture is adjusted to 10 μl with sterile deionized water, and the resulting ligase solution is incubated at 14° C. for 15 hours. After this time, 2 μl of the ligase reaction solution is added to 50 μl of competent $E.$ $coli$ strain JM109 (provided with the kit and brought to competence in accordance with the instruction manual) to which 2 μl of 0.5 M β-mercaptoethanol had been added, and the resulting mixture is kept on ice for 30 minutes, then at 42° C. for 30 seconds, and again on ice for 5 minutes. Next, 500 μl of medium containing 2% v/v tryptone, 0.5% w/v yeast extract, 0.05% w/v sodium chloride, 2.5 mM potassium chloride, 1 mM magnesium chloride, and 20 mM glucose (hereinafter referred to as "SOC" medium) is added to the culture, and the mixture is incubated for 1 hour at 37° C. with shaking. After this time, the culture is spread on an L-broth agar plate (1% v/v tryptone, 0.5% w/v yeast extract, 0.5% w/v sodium chloride, 0.1% w/v glucose, and 0.6% w/v bacto-agar (Difco)), containing 100 μg/ml. Ampicillin resistant colonies appearing on the plate are selected and scraped off with a platinum transfer loop, and cultured in L-broth medium containing 100 μg/ml ampicillin at 37° C., overnight, with shaking at 200 r.p.m. After incubation, the cells are harvested by centrifugation, from which plasmid DNA is prepared by the alkali method. The obtained plasmid is designated as plasmid pH62 for heavy chain of TRA-8 or pL28 for light chain of TRA-8.

The transformant $E.$ $coli$ strains harboring these plasmid, designated as $E.$ $coli$ JM109/pH62 and $E.$ $coli$ JM109/pL28 were deposited with International Patent Organism Depositary, National Institute of Advanced Industrial Science and Technology, 1-1, Higashi 1 chome Tsukuba-shi, Ibaraki-ken, 305-5466, Japan on Apr. 20, 2001, in accordance with the Budapest Treaty for the Deposit of Microorganisms, and were accorded the accession numbers FERM BP-7560 and FERM BP-7561, respectively. The nucleotide sequences of these DNAs encoding the heavy chain and the light chain of TRA-8 are confirmed by the dideoxy method (Sanger, F. S., et al., (1977), Proc. Natl. Acad. Sci. USA, 74:5463-5467) using 3700 DNA Analyzer (ABI PRISM®; Perkin Elmer Applied Biosystems, Japan).

The nucleotide sequences of the heavy and light chains of TRA-8 are given as SEQ ID No. 21 and No. 22 of the Sequence Listing, respectively. The amino acid sequences of the heavy and light chains of TRA-8 are given as SEQ ID No. 23 and No. 24 of the Sequence Listing, respectively. The N-terminal amino acid sequences of the heavy and light chains of TRA-8 established in above matched perfectly. Furthermore, when the amino acid sequences of the heavy and light chains are compared with the database of amino acid sequences of antibodies, it is established that, for the heavy chain, nucleotide Nos. 58 to 414 in SEQ ID No. 21 constituted the variable region, while nucleotide Nos. 415 to 1392 in SEQ ID No. 21 constituted the constant region. For the light chain, nucleotide Nos. 64 to 387 in SEQ ID No. 22 constituted the variable region, while nucleotide Nos. 388 to 702 in SEQ ID No. 22 constituted the constant region. The locations and sequences of the CDRs are also elucidated by comparing the homologies with the database. The amino acid sequences of CDR1, CDR2, and CDR3 of heavy chain of TRA-8 are shown in SEQ ID No. 25, No. 26, and No. 27, respectively. The amino acid sequences of CDR1, CDR2, and CDR3 of light chain of TRA-8 are shown in SEQ ID No. 28, No. 29, and No. 30, respectively.

Example 17

Designing a Humanized Version of the TRA-8 Antibody (1) Molecular Modeling of a Variable Region of TRA-8

Molecular modeling of the variable region of TRA-8 is performed by the method generally known as homology modeling (Methods in Enzymology, 203, 121-153, (1991)). The primary sequences of variable regions of human immunoglobulin registered in the Protein Data Bank (Nuc. Acid Res. 28, 235-242 (2000)), for which the three-dimensional structures derived from x-ray crystallography are available, are compared with the framework regions of TRA-8 determined above. As a result, 1NCD and 1HIL are selected as having the highest sequence homologies to the framework regions for the light and heavy chains of TRA-8, respectively. Three-dimensional structures of the framework regions are generated by combining the coordinates of 1NCD and 1HIL which correspond to the light and heavy chains of TRA-8, to obtain the "framework model". Using the classification defined by Chothia et al., the CDRs of TRA-8 are classified as follows; $CDRL_1$, $CDRL_2$, $CDRH_1$ and $CDRH_2$ belong to canonical classes 2,1,1,3, respectively, while CDRL₃ does not belong to any specific canonical classes. The CDR loops of CDRL₁, CDRL₂, CDRH₁, CDRH₂ are fixed to the conformations inherent to their respective canonical classes, and integrated into the framework model. CDRL₃ is assigned the conformation of cluster 8A, according to the classification of Thornton et al. (J. Mol. Biol., 263, 800-815, (1996)), and CDRH₃ is classified into k(8)C using the H3 rule (FEBS letter 455,188-197(1999)). Then representative conformations for CDRL₃ and CDRH₃ are integrated into the framework model.

Finally, energy calculations are carried out to eliminate unfavorable inter-atomic contacts, in order to obtain a probable molecular model of TRA-8's variable region in terms of energy. The above procedure is performed using the commercially available common molecular modeling system ABM (Oxford Molecular Limited, Inc.). For the molecular model obtained, the accuracy of the structure is further evaluated using the software, PROCHECK (J. Appl. Cryst. (1993), 26, 283-291).

(2) Designing the Amino Acid Sequences for Humanized TRA-8

Construction of humanized TRA-8 antibodies is performed by the method generally known as CDR grafting (Proc. Natl. Acad. Sci. USA 86, 10029-10033 (1989)). The acceptor antibody is chosen based on the amino acid homology in the framework region. The sequences of framework region in TRA-8 are compared with all the human framework sequences in the Kabat database of amino acid sequences of antibodies (Nuc. Acid Res. 29, 205-206 (2001)). As a result, mAB58'CL antibody is selected as an acceptor due to the highest sequence homology of 80% for the framework region. The amino acid residues in the framework region for mAb58'CL are aligned with that for TRA-8 and the positions where different amino acids are used are identified. The location of those residues are analyzed using the three dimensional model of TRA-8 constructed above and the donor residues which should be grafted on the acceptor are chosen by the criteria given by Queen et al. (Proc. Natl. Acad. Sci. USA 86, 10029-10033 (1989)). Humanized TRA-8 sequences are constructed as described in the following example by transferring several donor residues into acceptor antibody, mAb58'CL.

Example 18

Construction of an Expression Vector for the Heavy Chain of the Humanized Antibody (1) Construction of Plasmid Carrying the Heavy Chain Variable Region DNA of Humanized TRA-8

In order to determine the activity of humanized TRA-8, the plasmid carrying the heavy chain of humanized TRA-8 is constructed as follows. However, it is appreciated the humanization of TRA-8 is not limited to these examples.

As shown in SEQ ID No. 31 of the Sequence Listing, humanization of the amino acid sequences of the heavy chain of the mouse anti-human DR5 antibody TRA-8 entailed replacing the 13th amino acid (lysine), the 19th amino acid (lysine), the 40th amino acid (threonine), the 42nd amino acid (glutamic acid), the 44th amino acid (arginine), the 84th amino acid (serine), the 88th amino acid (serine), the 93rd amino acid (methionine), the 114th amino acid (threonine), the 115th amino acid (leucine) with glutamine, arginine, alanine, glycine, glycine, asparagine, alanine, valine, leucine, and valine, respectively.

The plasmid carrying DNA encoding heavy chain variable region of humanized TRA-8 (SEQ ID No. 31 of the Sequence Listing) are constructed as follows.

PCR is used to construct the following DNA sequences, each of which comprised described above:

The following 12 oligonucleotides are synthesized:

```
                                                     (A; SEQ ID No. 32)
5'-ttggataagc ttggcttgac ctcaccatgg gatggagctg tatcatcctc ttcttggtag caacagctac aggtgtccac-3';

(B; SEQ ID No. 33)
5'-tctgaagtaa tgctggtgga gtctggggga ggcttagtac agcctggagg gtccctgaga ctctcctgtg cagcctctgg-3';

(C; SEQ ID No. 34)
5'-attcactttc agtagttatg taatgtcttg ggttcggcag gcaccaggga agggtctgga gtgggttgca accattagta-3';

(D; SEQ ID No. 35)
5'-gtggtggtag ttacacctac tatccagaca gtgtgaaggg ccgattcacc atctccagag acaatgccaa gaacaccctg-3';

(E; SEQ ID No. 36)
5'-tatctgcaaa tgaacagtct gagagcagag gacacggctg tttattactg tgcaagaagg ggtgactcta tgattacgac-3';

(F; SEQ ID No. 37)
5'-ggactactgg ggccaaggga ccctggtcac agtctcctca gcctc cacc aagggcccat cggtc-3';

(G; SEQ ID No. 38)
5'-ctaccaagaa gaggatgata cagctccatc ccatggtgag gtcaagccaa gcttatccaa-3';

(H; SEQ ID No. 39)
5'-tctcagggac ctccaggct gtactaagcc tcccccagac tccaccagca ttacttcaga
```

-continued gtggacacct gtagctgttg-3';

(I; SEQ ID No. 40)
5'-tccagaccct tccctggtgc ctgccgaacc caagacatta cataactact gaaagtgaat ccagaggctg cacaggagag-3';

(J; SEQ ID No. 41)
5'-ctctggagat ggtgaatcgg cccttcacac tgtctggata gtaggtgtaa ctaccaccac tactaatggt tgcaacccac-3';

(K; SEQ ID No. 42)
5'-ccttcttgca cagtaataaa cagccgtgtc ctctgctctc agactgttca tttgcagata cagggtgttc ttggcattgt-3';
and (L; SEQ ID No. 43)
5'-gaccgatggg cccttggtgg aggctgagga gactgtgacc agggtccctt ggccccagta gtccgtcgta atcatagagt cacc-3'.

The following 2 PCR primers are synthesized as described above:

5'-ttggataagc ttggcttgac-3'; (P1; SEQ ID No. 44)
and

5'-gaccgatggg cccttggtgg a-3'. (P2; SEQ ID No. 45)

The synthesis of DNA encoding a polypeptide chain comprising a secretion signal sequence, a variable region of humanized TRA-8 heavy chain and the 8 amino acid residues at the N-terminus of the IgG-CH1 region is performed using a combination of PCR respectively.

The DNA fragment is prepared as follows.
Composition of the PCR Reaction Solution:
  oligonucleotide A, 10 pmol;
  oligonucleotide B, 10 pmol;
  oligonucleotide C, 10 pmol;
  oligonucleotide D, 10 pmol;
  oligonucleotide E, 10 pmol;
  oligonucleotide F, 10 pmol;
  oligonucleotide G, 10 pmol;
  oligonucleotide H, 10 pmol;
  oligonucleotide I, 10 pmol;
  oligonucleotide J, 10 pmol;
  oligonucleotide K, 10 pmol;
  oligonucleotide L, 10 pmol;
  oligonucleotide primer P1, 2 µM;
  oligonucleotide primer P2, 2 µM;
  10× Pyrobest™ buffer II, 10 µl;
  dNTP mix, 8 µl;
  Pyrobest™ DNA polymerase, 0.5 µl; and
  Redistilled water to a final volume of 50 µl.

The PCR reaction is conducted as follows. The solution is first heated at 94° C. for 5 minutes, after which a cycle of heating to 98° C. for 10 second, 55° C. for 30 second and 72° C. for 1 minute, is repeated 7 times. After completion of this procedure, the reaction solution is heated at 72° C. for 15 minutes.

An equal volume of phenol-chloroform (50% v/v phenol saturated with water, 48% v/v chloroform, 2% v/v isoamyl alcohol) is added to 200 µl of each of the PCR products, and vigorously mixed for 1 minute. After this time, the mixture is centrifuged at 10,000×g, and the aqueous layer is recovered and mixed with an equal volume of chloroform-isoamyl alcohol (96% v/v chloroform and 4% v/v isoamyl alcohol), which is again vigorously at 10,000×g and the aqueous layer is recovered. The series of steps recited in this paragraph is referred to, hereafter, as "phenol extraction").

Ethanol precipitation is then performed on the recovered aqueous layer. As used and referred to herein, "ethanol precipitation" consists of adding, with mixing, a one tenth volume of 3M sodium acetate (pH 5.2) and 2.5 volumes of 100% ethanol to the solution to be treated, and freezing the mixture using dry ice. The resulting mixture is then centrifuged at 10,000×g to recover DNA as a precipitate.

After phenol extraction and ethanol precipitation, the resulting DNA precipitate is vacuum-dried, dissolved in a minimum of redistilled water, and separated by 3% agarose gel electrophoresis. After electrophoresis, the gel is stained with a 1 µg/ml aqueous solution of ethidium bromide to allow detection of DNA under UV light. The DNA band corresponding to humanized TRA-8 DNA is cut out using a razor blade and eluted from the gel using Geneclean® Spin Kit (1310 101, CA, USA). After phenol extraction, the eluted DNA is then concentrated by centrifugation at 7,500×g, followed by ethanol precipitation, and finally dissolved in 5 µl of distilled water.

The resulting, each extracted DNA is cloned using pGEM-T Easy vector (Promega) as follows:
  The DNA fragment recovered from the PCR reaction, 5 µl;
  10× Taq polymerase buffer, 1 µl;
  dNTP mixture, 1 µl
  Taq polymerase (5 unit/ml), 1 µl; and
  redistilled water to a final volume of 10 µl.

After the above each solution is reacted at 70° C. for 30 minutes, each DNA solution and pGEM-T Easy vector are ligated using a DNA Ligation Kit Version 2.0 (Takara Shuzo Co., Ltd.) using the manufacturer's protocol.

After 4 hours incubation at 15° C., 2 µl of the incubated reaction solution is mixed with 100 µl of competent E. coli strain JM109 at a cell density of 1-2×10$^9$ cells/ml (Takara Shuzo Co., Ltd.), and the mixture is kept on ice for 30 minutes, then at 42° C. for 30 seconds, and again on ice for 1 minutes. Then, 500 µl of SOC medium (2% v/v tryptone, 0.5% w/v yeast extract, 0.05% w/v sodium chloride, 2.5 mM w/v potassium chloride, 1 mM magnesium chloride, and 20 mM glucose) is added the mixture, which is incubated for a further hour, with shaking. Transformant strains are then isolated, and plasmid DNA is prepared from the strains as described in "Molecular Cloning A Laboratory Manual". The nucleotide sequences of these DNAs encoding the heavy chain of humanized TRA-8 are confirmed by the dideoxy method (Sanger, F. S., et al., (1977), Proc. Natl. Acad. Sci. USA, 74:5463-5467) using 3700 DNA Analyzer (ABI PRISM®; Perkin Elmer Applied Biosystems, Japan).

The resulting plasmids are designated pHB14 (the plasmid carrying cDNA encoding the heavy chain of humanized TRA-8). The transformant *E coli* strain harboring these plasmid, designated as *E. coli* JM109/pHB14 was deposited with International Patent Organism Depositary, National Institute of Advanced Industrial Science and Technology, 1-1, Higashi 1 chome Tsukuba-shi, Ibaraki-ken, 305-5466, Japan on Apr. 20, 2001, in accordance with the Budapest Treaty for the Deposit of Microorganisms, and was accorded the accession number FERM BP-7556.

(2) Construction of Expression Plasmids Carrying the Heavy Chain Variable Region DNA of Humanized TRA-8

Recombinant expression vectors for animal cells are constructed by inserting the DNA encoding the heavy chain of humanized TRA-8 (cloned in above) as follows.

One µg of plasmid pSRHHH3 (European patent application EP 0-909-816-A1) carrying the heavy chain variable region of humanized anti-Fas monoclonal antibody HFE7A and human IgG1 constant region genomic DNA, an expression vector for mammalian cells, is digested with the restriction enzymes HindIII and ApaI, and separated by 3% agarose gel electrophoresis. After electrophoresis, the gel is stained with a 1 µg/ml aqueous solution of ethidium bromide to allow detection of DNA under UV light. The vector DNA bands containing human IgG1 constant region genomic DNA without the heavy chain variable region of humanized HFE7A are cut out using a razor blade and eluted from the gel using Geneclean® Spin Kit (BIO 101, CA, USA). After phenol extraction, the eluted DNA is then concentrated by centrifugation at 7,500×g, followed by ethanol precipitation, and finally dissolved in 5 µl of distilled water and then dephosphorylated using CIP. The resulting digested, dephosphorylated plasmid (100 ng) is ligated with 1 µg of the pHB14 DNA fragment containing the DNA encoding the heavy chain variable region of humanized TRA-8, which had also been digested with HindIII and ApaI, using a DNA Ligation Kit Version 2.0 (Takara Shuzo Co., Ltd.). The ligation mixture is then used to transform *E. coli* JM109, which is then plated on LB agar plates containing 50 µg/ml ampicillin.

The transformants obtained by this method are cultured in 2 ml of liquid LB medium containing 50 µg/ml ampicillin at 37° C. overnight, and plasmid DNA is subsequently extracted from the resulting culture by the alkaline-SDS method.

The extracted plasmid DNA is digested with HindIII and ApaI, and subjected to 3% w/v agarose gel electrophoresis to confirm the presence or absence of the insert of the DNA encoding the heavy chain variable region of humanized TRA-8. The insertion and orientation of the desired DNA fragment in the vector is confirmed by DNA sequencing using a gene sequence analyzer (ABI PRISM® 3700 DNA Analyzer; Applied Biosystems). The resulting expression plasmid carrying cDNA encoding the heavy chain of humanized TRA-8 is designated pHB14-1.

Example 19

Construction of an Expression Vector for the Light Chain of the Humanized Antibody (1) Construction of Vectors for the Light Chains of Humanized Versions of TRA-8 Antibody As shown in SEQ ID No. 46 of the Sequence Listing, in humanizing the amino acid sequence of the light chain of the mouse anti-human DR5 antibody TRA-8, 8th amino acid (histidine), 9th amino acid (lysine), 10th amino acid (phenylalanine), 11th amino acid (methionine), 13th amino acid (threonine), 20th amino acid (serine), 42nd amino acid (glutamine), 43rd (serine), 60th amino acid (aspartic acid), 63rd amino acid (threonine), 77th amino acid (asparagine), 78th amino acid (valine), 80th amino acid (serine) 83rd amino acid (leucine), 85th amino acid (aspartic acid), 87th amino acid (phenylalanine), and 99th amino acid (glycine) 103rd amino acid (leucine) and 108th amino acid (alanine) from the N-terminus of the amino acid sequence of the TRA-8 light chain are replaced with proline, serine, serine, leucine, alanine, threonine, lysine, alanine, serine, serine, serine, leucine, proline, phenylalanine, threonine, tyrosine, glutamine, valine and threonine respectively. The resulting sequence is designated LM2.

Expression plasmids carrying this type of humanized light chain amino acid sequences of the anti-human DR5 antibody TRA-8 is constructed as follows.

1) Synthesis of Primers for Preparing the Variable and Constant Regions of the Light Chain of Humanized TRA-8

DNA coding for the LM2 polypeptide chain (SEQ ID No. 46 of the Sequence Listing), each of which is a fusion of the variable region of humanized anti-DR5 antibody TRA-8 light chain and the constant region of the human Ig light chain (κ chain), are respectively synthesized by using combinations of PCR.

Further to 7AL1P (SEQ ID No. 47) and 7ALCN (SEQ ID No. 48), the following oligonucleotide primers are synthesized for PCR:

```
                               (HKSPR11; SEQ ID No. 49)
5'-gtcccccaca gatgcagaca aagaacttgg agattgggtc atcacaatgt caccagtgga-3';

(HKCDF11; SEQ ID No. 50)
5'-ccaagttctt tgtctgcatc agtaggagac agggtcacca tcacctgc-3';

(HKCDR12; SEQ ID No. 51)
5'-agtgtgccgg gtggatgccc agtaaatcag tagtttagga gctttccctg gtttctg-3';

(HKCDF22; SEQ ID No. 52)
5'-tgggcatcca cccggcacac tggggtccca agcaggttta gtggcagt-3';

(HKCDR22; SEQ ID No. 53)
5'-ataactacta tattgctgac agtaataggt tgcaaaatcc tccggctgca gactagagat ggt-3';
and (HKCF12; SEQ ID No. 54)
5'-cagcaatata gcagctatcg gacgttcggt caaggcacca aggtggaaat caaacggact gtg-3'.
```

2) Construction of Plasmid pCR3.1/M2-1 (Cloning of Humanized TRA-8 Light Chain)

LM2-DNA fragment as defined in SEQ ID No. 55 of the Sequence Listing coding for the amino acid sequence as defined in SEQ ID No. 46 of the same is prepared by performing 2-step PCR, inserted into a plasmid vector and cloned in *E. coli*.

a) First Step PCR

LM2-F1-DNA fragment coding for a secretion signal sequence and a portion of FRL$_1$ region with a Hind III restriction enzyme cleavage site added at the 5'-end is prepared under the following conditions. The template plasmids, pHSGHM17 and pSRPDHH, are obtained by following the description in a European patent application EP 0 909 816 A1.
Composition of the reaction solution:
  plasmid pHSGHM17 DNA (European patent application EP 0 909 816 A1), 25 ng
  oligonucleotide primer 7AL1P, 50 pmol
  oligonucleotide primer HKSPR11, 50 pmol
  dNTPs cocktail, 5 μl
  10×PCR buffer, 5 μl
  ampliTaq DNA polymerase (PerkinElmer), 2.5 units The reaction solution having the above composition is adjusted to a final volume of 50 μl by adding redistilled water and used in PCR.

PCR thermal conditions: Heating at 94° C. for 2 minutes, after which a thermal cycle of 94° C. for 1 minute, 55° C. for 1 minute and 72° C. for 2 minutes, repeated 30 times, followed by heating at 72° C. for 10 minutes.

LM2-F2-DNA fragment coding for a portion of $FRL_1$, $CDRL_1$, $FRL_2$, and $CDRL_2$ and is prepared under the following conditions.
Composition of the Reaction Solution:
  plasmid pL28 DNA, 25 ng
  oligonucleotide primer HKCDF11, 50 pmol
  oligonucleotide primer HKCDR12, 50 pmol
  dNTPs cocktail, 5 μl
  10×PCR buffer, 5 μl
  ampliTaq DNA polymerase, 2.5 units The reaction solution having the above composition is adjusted to a final volume of 50 μl by adding redistilled water and used in PCR.

PCR thermal conditions: Heating at 94° C. for 2 minutes, after which a thermal cycle of 94° C. for 1 minute, 55° C. for 1 minute and 72° C. for 2 minutes, repeated 30 times, followed by heating at 72° C. for 10 minutes.

LM2-F3-DNA fragment coding for CDRL2, $FRL_3$, and a portion of $CDRL_3$ is prepared under the following conditions.
Composition of the Reaction Solution:
  plasmid pSRPDHH DNA(European patent application EP 0 909 816 A1), 25 ng
  oligonucleotide primer HKCDF22, 50 pmol
  oligonucleotide primer HKCDR22, 50 pmol
  dNTPs cocktail, 5 μl
  10×PCR buffer, 5 μl
  ampliTaq DNA polymerase, 2.5 units The reaction solution having the above composition is adjusted to a final volume of 50 μl by adding redistilled water and used in PCR.

PCR thermal conditions: Heating at 94° C. for 2 minutes, after which a thermal cycle of 94° C. for 1 minute, 55° C. for 1 minute and 72° C. for 2 minutes, repeated 30 times, followed by heating at 72° C. for 10 minutes.

LM2-F4-DNA fragment coding for $CDRL_3$, $FRL_4$ and the constant region with an EcoR I restriction enzyme cleavage site added at the 3'-end is prepared under the following conditions.
Composition of the Reaction Solution:
  plasmid pSRPDHH DNA, 25 ng
  oligonucleotide primer HKCF12, 50 pmol
  oligonucleotide primer 7ALCN, 50 pmol
  dNTPs cocktail, 5 μl
  10×PCR buffer, 5 μl
  ampliTaq DNA polymerase, 2.5 units The reaction solution having the above composition is adjusted to a final volume of 50 μl by adding redistilled water and used in PCR.

PCR thermal conditions: Heating at 94° C. for 2 minutes, after which a thermal cycle of 94° C. for 1 minute, 55° C. for 1 minute and 72° C. for 2 minutes, repeated 30 times, followed by heating at 72° C. for 10 minutes.

The amplified DNA fragments after PCR are separated by 5% polyacrylamide gel electrophoresis. The gel after electrophoresis is stained with 1 μg/ml of ethidium bromide to detect the produced DNA under UV light. The respective DNA bands thus detected are excised with a razor b) Second Step PCR LM2-DNA in which above described LM2-F1-DNA, LM2-F2-DNA, LM2-F3-DNA and LM2-F4-DNA fragments are fused is prepared under the following conditions.
Composition of the Reaction Solution:
  Gel fragment of LM2-F1-DNA prepared in the first step PCR,
  Gel fragment of LM2-F2-DNA prepared in the first step PCR,
  Gel fragment of LM2-F3-DNA prepared in the first step PCR,
  Gel fragment of LM2-F4-DNA prepared in the first step PCR
  oligonucleotide primer 7ALIP, 50 pmol
  oligonucleotide primer 7ALCN, 50 pmol
  dNTPs cocktail, 5.0 μl
  10×PCR buffer, 5.0 μl
  ampliTaq DNA polymerase, 2.5 units The reaction solution having the above composition is adjusted to a final volume of 50 μl by adding redistilled water and used in PCR.

PCR thermal conditions: Heating at 94° C. for 2 minutes, after which a thermal cycle of 94° C. for 1 minute, 55° C. for 1 minute and 72° C. for 2 minutes, repeated 30 times, followed by heating at 72° C. for 10 minutes.

The thus prepared LM2-DNA fragment is inserted into plasmid pCR3.1DNA using Eukaryotic TA cloning Kit (Invitrogen) following the manufacturer's protocol and introduced into the competent *E. Coli* TOP10F' contained in the kit. The nucleotide sequences of these DNAs encoding the light chain of humanized TRA-8 are confirmed by the dideoxy method (Sanger, F. S., et al., (1977), Proc. Natl. Acad. Sci. USA, 74:5463-5467) using 3700 DNA Analyzer (ABI PRISM®; Perkin Elmer Applied Biosystems, Japan).

The resulting plasmids are designated pCR3.1/M2-1 (the plasmid carrying cDNA encoding the light chain variable region of humanized TRA-8 and a human Ig light chain constant region).

The obtained plasmid pCR3.1/M2-1 containing LM2-DNA fragment is digested with the restriction enzymes Hind III and EcoR I.

One μg of cloning plasmid pHSG399 DNA is digested with the restriction enzymes Hind III and EcoR I, and then dephosphorylated with CIP. The resulting dephosphorylated pHSG399 DNA and LM2-DNA fragment, that have been digested with the restriction enzymes Hind III and EcoR I, are ligated using DNA Ligation Kit Version 2.0 (Takara Syuzo, Co. Ltd.). Then, *E. coli* DH5α is transformed with the ligated DNA and spread onto LB agar medium containing 0.1 mM IPTG, 0.1% X-Gal and 50 μg/ml chloramphenicol (final concentrations). The white transformants obtained are cultured in liquid LB medium containing 50 μg/ml chloramphenicol, and plasmid DNA is extracted from the resulting culture according to the alkaline-SDS method. The extracted plasmid DNA is digested with Hind III and EcoR I, and then a clone carrying LM2-DNA fragment is selected by 1% agarose gel electrophoresis.

As a result of the above procedure, plasmid pHSG/M2-1-4 carrying a fusion fragment of the variable region of the humanized LM2 TRA-8 light chain and the constant region of human Igκ chain is obtained. The transformant *E. coli* strain harboring these plasmid, designated as *E. coli* DH5α/pHSG/M2-1-4 was deposited with International Patent Organism Depositary, National Institute of Advanced Industrial Science and Technology, 1-1, Higashi 1 chome Tsukuba-shi, Ibaraki-ken, 305-5466, Japan on Apr. 20, 2001, in accordance with the Budapest Treaty for the Deposit of Microorganisms, and was accorded the accession number FERM BP-7563.

3) Construction of Plasmid pSR/M2-1 (Expression Plasmid for Humanized LM2 TRA-8 Light Chain)

The obtained plasmid pHSG/M2-1-4 carrying a fusion fragment of the variable region of the humanized LM2 TRA-8 light chain and the constant region of human Igκ chain is digested with the restriction enzymes Hind III and EcoR I.

One μg of cloning plasmid pSRPDHH DNA (European patent application EP 0-909-816-A1) is digested with the restriction enzymes Hind III and EcoR I, and then dephosphorylated with CIP. The resulting dephosphorylated pSRPDHH DNA and HindIII-EcoRI DNA fragment obtained from pHSG/M2-1-4 are ligated using DNA Ligation Kit Version 2.0 (Takara Syuzo, Co. Ltd.). Then, *E. coli* DH5α is transformed with the ligated DNA and spread onto LB agar. The transformants obtained are cultured in liquid LB medium containing 100 μg/ml ampicillin, and plasmid DNA is extracted from the resulting culture according to the alkaline-SDS method. The insertion and orientation of the desired DNA fragment in pSRPDHH vector is confirmed by DNA sequencing using a gene sequence analyzer (ABI PRISM® 3700 DNA Analyzer; Applied Biosystems).

The resulting expression plasmid carrying cDNA encoding the light chain of humanized TRA-8 is designated pSR/M2-1.

Example 20

Production of Humanized Antibody

Transfection of COS-7 cells, i.e., a cell line derived from a monkey kidney, with the expression plasmids for the humanized TRA-8 heavy chain and the humanized TRA-8 light chain obtained above is conducted by FUGENE6 transfection reagent methods (Boehringer Mannheim Biochemica) according to the instruction manual provided with the kit.

COS-7 cells (American Type Culture Collection No. CRL-1651) are grown to semi-confluent ($3 \times 10^6$ cells/dish) in a culture dish (culture area: 57 cm$^2$; Sumitomo Bakelite) containing Dulbecco's Modified Eagle medium (hereinafter referred to as "D-MED"; Gibco BRL) supplemented with 10% fetal calf serum (hereinafter abbreviated as "FCS"; Moregate).

In the meantime, 10 μg/dish (total 5 dishes) of the humanized DR5 heavy chain expression plasmid DNA (pHA15-1) and 10 μg/dish of the humanized DR5 light chain expression plasmid DNA prepared by the alkaline-SDS method and cesium chloride density gradient centrifugation are mixed, and then precipitated with ethanol, followed by suspending in 5 μl/dish of dH$_2$O.

After 15 μl/dish of FUGENE6 Transfection regent is mixed with 180 μl/dish D-MEM without FCS, this FUGENE solution (185 μl/dish) is mixed with 5 μl/dish DNA solution containing 10 μg/dish of the humanized DR5 heavy chain expression plasmid DNA and 10 μg/dish of the humanized DR5 light chain expression plasmid DNA. After 15 minutes incubation at room temperature, the obtained plasmid suspension (200 μl) is added to the previously prepared COS-7 plates.

After incubating in 5% CO$_2$ at 37° C. for 24 hours, the culture medium is changed with D-MEM without FCS. After incubating in 5% CO$_2$ at 37° C. for 72 hours, the culture supernatant is recovered to purify the expression products in the supernatant fluids. By the method as described above, COS-7 cells are transfected with each of the following plasmid combinations:

(A): no plasmid DNA (B): cotransfection of pHB14-1 and pSR/M2-1

The culture is then centrifuged (1,000 r.p.m., 5 minutes) and collected the supernatant. The supernatant is centrifuged again (9,800 r.p.m., 15 minutes) and filtrated with 0.45 μm filter (ADVANTEC TOYO DISMIC-25cs, Cat #25CS045 AS). The purification of IgG from the filtrates are achieved using Protein G-POROS affinity chromatography (Applied Biosystems) under the following conditions:

HPLC: BioCAD 700E (Applied Biosystems)
column: ProteinG-ID sensor cartridge (column size: 2.1 mmID×30 mm LD, bed volume: 0.1 ml; Cat #2-1002-00, Applied Biosystems)
elution buffer: 0.1M Glycine-HCl (pH 2.5)
neutralization buffer: 1M Tris-HCl (pH 8.5)
detection: 280 nm
flow rate: 1 ml/min
fraction size: 0.5 ml/0.5 min
fraction tube: 1.5 ml polypropylene microtube
temperature: 4° C.

After all the filtrates are applied to column, 30 ml of PBS (Sigma, Cat #1000-3) is used to wash column. When the elution buffer is applied, fraction collector started. Each fraction microtube previously contained 55 μl of 1M NaCl, 110 μl of neutralization buffer and 74 μl of 2 mg/ml bovine serum albumin (Sigma, Cat #A-7030) in PBS. The fractions from No. 8 through No. 10 are collected and dialyzed against 1 liter PBS (pH 7.5) at 4° C. for 1 day using Slide-A lyzer (Pierce, Cat #66450). The dialysis buffer is changed twice.

Verification of the expression of the humanized antibodies and quantitative assay of the expression products in the culture supernatant fluids prepared is performed by ELISA with an antibody against anti-human IgG.

To each well of a 96-well plate (MaxiSorp™, Nunc), 100 μl of goat anti-human IgG Fc specific polyclonal antibody (Kappel) dissolved at the final concentration of 0.5 μg/ml in adsorption buffer (0.05 M sodium hydrogencarbonate, 0.02% sodium azide, pH 9.6) is added and the plate is incubated at 37° C. for 2 hours to cause adsorption of the antibody. Then, the plate is washed with 350 μl of PBS(-) containing 0.05% Tween®-20 (BioRad) (hereinafter referred to as "PBS-T") five times. To the wells after washing, the culture supernatant diluted with D-MEM containing 10% FCS is added and incubated at 37° C. for 2 hours. After washing again with PBS-T, 100 μl of alkaline phosphatase-labeled goat anti-human IgG Fc specific polyclonal antibody (Jackson Immuno Research Lab.) diluted 10,000-fold with PBS-T T is added to each well and incubated at 37° C. for 2 hours. After washing again with PBS-T, a substrate solution of p-nitrophenyl phosphate obtained from Alkaline Phosphatase Substrate kit (Bio Rad) is added according to the instruction manual provided with the kit. After incubating at 37° C. for 0.5 to 1 hour, the absorbance at 405 nm is measured. In the present experiments, human plasma immunoglobulin G subclass 1 (IgG1) (Biopure AG) diluted with D-MEM containing 10% FCS to certain concentrations is used as concentration reference samples of the humanized DR5 antibodies contained in the culture supernatant fluids.

As a result, the expression and purified products in the culture supernatant are detected specifically with the anti-human IgG antibody. The amount of human IgG antibody is 8.96 μg (800 μl).

Example 21

Apoptosis-Inducing Activity of Humanized Antibody

Jurkat cells (ATCC No. TIB-152), are used to examine the apoptosis-inducing activity of the purified humanized TRA-8 antibody.

Jurkat cells cultured in RPMI1640 medium with 10% FCS (Gibco BRL) at 37° C. for 3 days in the presence of 5% $CO_2$ are dispensed into each well of a 96-well microplate (Sumitomo Bakelite) at 50 μl per well. The humanized TRA-8 prepared in Example 20 are adjusted to have the concentration of the final product of interest of 100 ng/ml with RPMI1640 medium containing 10% FCS by estimating their concentrations in the fluids according to the method described in Example 20. Each of the solutions of the expression products thus adjusted to 100 ng/ml is used to produce serial dilutions by repeating serial 2-fold dilution with RPMI1640 containing 10% FCS. Each of the diluted humanized TRA-8 solution is added to each well at 50 μl per well. After reacting at 37° C. for 12 hours, 50 μl of 25 μM PMS (phenazine methosulfate; Sigma Chemical Co.) containing 1 mg/ml XTT (2,3-bis[2-methoxy-4-nitro-5-sulfophenyl]-2H-tetrazolium-5-carboxyaniride inner salt; Sigma Chemical Co.) is added (final concentrations of 250 μg/ml for XTT and 5 μM for PMS). After incubating for 3 hours, the absorbance at 450 nm of each well is measured to calculate the cell viability by using the reduction ability of mitochondria as the index.

The viability of the cells in each well is calculated according to the following formula:

Viability(%)=100×(a−b)/(c−b)

wherein "a" is the measurement of a test well, "b" is the measurement of a well with no cells, and "c" is the measurement of a well with no antibody added.

As a result, the expression product prepared in Example 20 (humanized TRA-8) is demonstrated to induce apoptosis in cells of T lymphoma cell line expressing human DR5 antigen.

Example 22

Reactivity of TRA-8 to Various DR5 Molecules

In order to determine the reactivity of TRA-8 to various DR5 molecules, the reactivity of TRA-8 is examined using activated lymphocytes as follows.

First, peripheral blood samples are taken from a human (30 ml), marmoset (3 ml), and cynomolgus monkey (20 ml). The blood samples had 1 ml of heparin (Novoheparin; Novo) added to them and the samples are then slowly layered over an equal volume of Ficoll-Paque PLUS solution ((Amersham Pharmacia Biotech.) specific gravity: 1.077 for all except cynomolgus monkey, which had a specific gravity of 1.072) and centrifuged at 1,700 r.p.m. for 30 minutes in order to obtain a fraction of peripheral blood mononuclear cells. This mononuclear cell fraction is washed twice with Hanks' balanced salt solution and then suspended in RPMI 1640 medium with 10% v/v FCS to a cell density of $1 \times 10^6$ cells/ml. Phytohemagglutinin-P (PHA-P, Sigma Chemicals, Co.) is added to the resulting suspension to a final concentration of 5 μg/ml and the sample incubated at 37° C. under 5% v/v $CO_2$ for 24 hours. After this time, the cells are recovered by centrifugation, washed and resuspended in RPMI 1640 medium containing 10% v/v FCS. Then, to activate the recovered cells, interleukin-2 (Amersham Pharmacia Biotech.) is added to the suspension to a final concentration of 10 units/ml, and this is incubated at 37° C. under 5% v/v $CO_2$ for 72 hours.

An amount of the activated preparation calculated to contain $1 \times 10^6$ activated lymphocyte cells is placed in a test tube and either suspended in 50 μl of 0.5, 1, 5, 10 μg/ml of TRA-8 in PBS or 50 μl of PBS alone. The resulting suspension is allowed to stand on ice for 1 hour, after which the cells are washed 3 times with aliquots of 500 μl of PBS and then suspended in 50 μl of 20 μg/ml FITC-labeled anti-mouse IgG antibody (Bioresource) in PBS. Using the cells suspended in 500 μl of PBS as controls, the fluorescence intensities are measured, using a flow cytometer (FACSCalibur; Becton Dickinson).

Distributions of cell numbers by fluorescence intensity are obtained and the proportions of the numbers of the stained cells to those of total cells are calculated. Further, each Kd value is calculated using the concentration of TRA-8 and the proportions of the numbers of the stained cells to those of total cells. Each frequency of reactivity to activated lymphocytes of human, marmoset, and cynomologus monkey is almost same. Accordingly, TRA-8 is able to bind a wide range of primate DR5 including human against which TRA-8 is originally prepared.

Example 23

Escalating Dose Study of TRA-8 in Marmosets

An escalating dose preliminary toxicity study of TRA-8 is performed using 1 male and 1 female marmoset. Three sets of single intravenous dosing, which are separated by a 7-day withdrawal period, are carried out. The dose of TRA-8 is set at 50, 250 and 1250 μg/body. Forty-eight hours after each treatment, blood is collected from the femoral vein and the plasma is prepared. Plasma aspartate aminotransferase and alanine aminotransferase activities are measured using an analyzer (FUJI DRI-CHEM: Fuji Film Medical Co., Ltd.). All blood is taken without any anesthetization. As a result, no evidences indicating hepatic injury are noted in plasma biochemical examination after each treatment.

Example 24

In vitro and in vivo Pharmacological Studies of TRA-8 Against Cancer Cells

In order to determine whether TRA-8 has the therapeutic efficacy in anti-cancer therapy, in vitro killing activity of TRA-8 using various cancer cell lines is examined as follows.

Various cancer cells ($2-8 \times 10^3$ cells/50 μl) cultured in RPMI1640 medium (for Jurkat), DMEM medium (for HCT-116), MEM-R (for WiDr), or DMEM-F12 (for COL2-Jck) obtained from Gibco BRL with 10% FCS (Gibco BRL) at 37° C. in the presence of 5% $CO_2$ are dispensed into each well of a 96-well microplate (Sumitomo Bakelite). TRA-8 are adjusted to have the concentration of the final product of interest of 100 ng/ml with medium containing 10% FCS. The TRA-8 solution (100 ng/ml) is used to produce serial dilutions by repeating serial 2-fold dilution with medium containing 10% FCS. Each of the diluted TRA-8 solution is added to each well at 50 μl per well and incubated at 37° C. After reacting at 37° C. for 72 hours, 50 μl of 25 μM PMS (phenazine methosulfate; Sigma Chemical Co.) containing 1 mg/ml XTT is added (final concentrations of 250 μg/ml for XTT and 5 μM for PMS). After incubating for 3 hours, the absorbance at 450 nm of each well is measured to calculate the cell viability by using the reduction ability of mitochondria as the index.

The viability of the cells in each well is calculated according to the following formula:

Viability(%)=100×(a−b)/(c−b)

wherein "a" is the measurement of a test well, "b" is the measurement of a well with no cells, and "c" is the measurement of a well with no antibody added.

The results are shown in Table 3, below.

TABLE 3

| Cells | ED50 (μg/ml) |
|---|---|
| Jurkat | 0.001-0.01 |
| HCT-116 | 0.004-0.02 |
| WiDr | 0.007-0.03 |
| COL2-Jck | 2.28 |

Various cancer cell lines are strongly induced apoptosis by TRA-8 under the in vitro conditions.

Furthermore, the in vivo anti-tumor effect of TRA-8 in nude mice transplanted with WiDr cells is determined, because TRA-8 is not cross-reactive with murine DR5.

TRA-8 anti-human DR5 antibody is administered to nude mice bearing human xenografts that express the human DR5 molecule. The mice used were 6 week-old BALb/c nude/nude mice (female, from Clea Japan Inc.), which were transplanted with human colon cancer cell lines WiDr (5 mm$^3$). At one day after tumor transplantation, these transplanted mice are daily treated with the intra-articular injection of TRA-8 (5 μg/body) to 14 times. WiDr tumor growth is daily determined by the size of the tumor mass. The results are shown in Table 4, below.

TABLE 4

|  | 8 days | 11 days | 15 days | 18 days | 22 days | 25 days |
|---|---|---|---|---|---|---|
| Control (PBS) SD | 196 ± 55 | 249 ± 77 | 469 ± 149 | 584 ± 230 | 833 ± 274 | 1193 ± 419 |
| TRA-8 SD | 158 ± 78 | 97 ± 30 | 155 ± 60 | 195 ± 58 | 365 ± 91 | 530 ± 135 |

In this model, while all untreated animals exhibited visible tumor growth, tumor growth in TRA-8 treated animals is inhibited as demonstrated by the size of tumor. This result indicated that TRA-8 is effective in the elimination of tumor cells in vivo.

Example 25

Combination Study of TRA-8

Human prostate cancer cell line PC-3 is obtained from American Tissue Culture Collection (ATCC) and maintained in F-12K Nutrient Mixture (21127-022, Gibco BRL) containing 10% fetal bovine serum (FBS, Hyclone), 1% L-Glutamine-200 mM (25030-149, Gibco BRL) and 0.5% Penicillin Streptomycin Solution (P-7539, Sigma). RPMI1640 medium (MED-008, IWAKI) supplemented with 10% FBS and 0.5% Penicillin Streptomycin Solution is used in the following experiment. Exponentially growing PC-3 cells are collected by trypsinization and washed twice with fresh medium. The cells are then counted, resuspended in fresh medium at a density of 5×10$^4$ cells/ml and distributed in triplicate into flat-bottomed 96 well plates (3598, Corning-Coster) in a total volume of 100 μl/well one day before the start of the experiment. A representative anti-cancer drug, Paclitaxel (169-18611, Wako) dissolved in dimethylsulfoxide (10 mg/ml) is diluted in fresh medium and then added to the 96-well plates containing the cells at 50 μl/well. The final concentrations of dimethylsulfoxide are less than 0.1%. After incubation for 24 hr at 37° C. in 5% CO$_2$ atmosphere, TRA-8 diluted in fresh medium is added to the wells. After incubation for a further 24 hr, 50 μl of Minimum Essential Medium (11095-098, Gibco BRL) containing 1 mg/ml of XTT and 25 mM of PMS is added to the wells and the plates are incubated for 6 hr. OD450 is then measured by SPECTRA MAX 250 (Molecular Devices) and the cell viability is calculated as follows.

Cell viability(%)=(OD450 for the well containing cells treated with Taxol and/or TRA-8(agent(s))−OD450 for the well containing neither cells nor agent)×100/(OD450 for the well containing cells with no agent−OD450 for the well containing neither cells nor agent)

The result of the above assay for TRA-8 combined with a representative anti-cancer drug, Paclitaxel, is followed. Paclitaxel reduced the cell viability of PC-3 cells but more than 40% of the signals indicating viable cancer cells still remained at concentrations of up to 200 nM. Notably, the addition of 0.1 ng/ml of TRA-8 greatly decreased the cell viability of the cancer cells, up to 10%, even though no reduction in cell viability is seen after a single application of TRA-8 at this concentration. This result clearly indicates that TRA-8 exhibited anti-cancer activity synergistically when combined with other anti-cancer drugs.

Example 26

Analysis of Other Type Humanized Antibodies of TRA-8

(1) Designing Humanized Antibodies

Construction of a humanized version of TRA-8 is performed by the method generally known as CDR grafting. mAB58'CL antibody is used as an acceptor as described in Reference Example 2 and the CDR regions of TRA-8 antibody is grafted on the acceptor. In the framework region, some amino acids are grafted on the acceptor from either TRA-8 or human consensus sequences by the criteria given by Queen et al. (Proc. Natl. Acad. Sci. USA 86, 10029-10033, (1989)) and humanized TRA-8 sequences are constructed as described hereinbelow.

(2) Construction of Plasmid Carrying the Heavy Chain Variable Region DNA of Other Types Humanized or Mouse TRA-8

As shown in SEQ ID No. 56 of the Sequence Listing, H1 type-humanization of the amino acid sequences of the heavy chain of the mouse anti-human DR5 antibody TRA-8 entailed replacing the 3rd amino acid (methionine), the 13th amino acid (lysine), the 19th amino acid (lysine), the 40th amino acid (threonine), the 42nd amino acid (glutamic acid), the 44th amino acid (arginine), the 84th amino acid (serine), the 88th amino acid (serine), the 93rd amino acid (methionine), the 114th amino acid (threonine), the 115th amino acid (leucine) with glutamine, glutamine, arginine, alanine, glycine, glycine, asparagine, alanine, valine, leucine, and valine, respectively.

As shown in SEQ ID No. 59 of the Sequence Listing, H3 type-humanization of the amino acid sequences of the heavy chain of the mouse anti-human DR5 antibody TRA-8 entailed replacing the 13th amino acid (lysine), the 19th amino acid (lysine), the 40th amino acid (threonine), the 42nd amino acid (glutamic acid), the 44th amino acid (arginine), the 88th amino acid (serine), the 93rd amino acid (methionine), the 114th amino acid (threonine), the 115th amino acid (leucine) with glutamine, arginine, alanine, glycine, glycine, alanine, valine, leucine, and valine, respectively.

As shown in SEQ ID No. 60 of the Sequence Listing, H4 type-humanization of the amino acid sequences of the heavy chain of the mouse anti-human DR5 antibody TRA-8 entailed replacing the 13th amino acid (lysine), the 19th amino acid (lysine), the 88th amino acid (serine), the 93rd amino acid (methionine), the 114th amino acid (threonine), the 115th amino acid (leucine) with glutamine, arginine, alanine, valine, leucine, and valine, respectively.

As shown in SEQ ID No. 61 of the Sequence Listing, the plasmid carrying the heavy chain variable region DNA of chimeric TRA-8 is designated as "M type". In addition, humanized TRA-8 described in Example 17 and 18 is designated as "H2 type".

The plasmids carrying DNA encoding heavy chain variable region of humanized or chimeric TRA-8 are constructed as follows.

PCR is used to construct the following DNA sequences, each of which comprised described above:

The following 24 oligonucleotide are synthesized:

```
                                                         (A; SEQ ID No. 32)
5'-ttggataagc ttggcttgac ctcaccatgg gatggagctg tatcatcctc ttcttggtag caacagctac aggtgtccac-3';

(B; SEQ ID No. 33)
5'-tctgaagtaa tgctggtgga gtctggggga ggcttagtac agcctggagg gtccctgaga ctctcctgtg cagcctctgg-3';

(B2; SEQ ID No. 57)
5'-tctgaagtac agctggtgga gtctggggga ggcttagtac agcctggagg gtccctgaga ctctcctgtg cagcctctgg-3';

(B3; SEQ ID No. 66)
5'-tctgaagtaa tgctggtgga gtctggggga ggcttagtaa agcctggagg gtccctgaaa ctctcctgtg cagcctctgg-3';

(C; SEQ ID No. 34)
5'-attcactttc agtagttatg taatgtcttg ggttcggcag gcaccaggga agggtctgga gtgggttgca accattagta-3';

(C2; SEQ ID No. 64)
5'-attcactttc agtagttatg taatgtcttg ggttcggcag actccagaga agaggctgga gtgggttgca accattagta-3';

(D; SEQ ID No. 35)
5'-gtggtggtag ttacacctac tatccagaca gtgtgaaggg ccgattcacc atctccagag acaatgccaa gaacacctg-3';

(E; SEQ ID No. 36)
5'-tatctgcaaa tgaacagtct gagagcagag gacacggctg tttattactg tgcaagaagg ggtgactcta tgattacgac-3';

(E2; SEQ ID No. 62)
5'-tatctgcaaa tgagcagtct gagagcagag gacacggctg tttattactg tgcaagaagg ggtgactcta tgattacgac-3';

(E3; SEQ ID No. 67)
5'-tatctgcaaa tgagcagtct gagatctgag gacacggcta tgtattactg tgcaagaagg ggtgactcta tgattacgac-3';

(F; SEQ ID No. 37)
5'-ggactactgg ggccaaggga ccctggtcac agtctcctca gcctccacc aagggcccat cggtc-
3';
```

-continued (F2; SEQ ID No. 68)
5'-ggactactgg ggccaaggga ccactctcac agtctcctca gcctccacc aagggcccat cggtc-3';

(G; SEQ ID No. 38)
5'-ctaccaagaa gaggatgata cagctccatc ccatggtgag gtcaagccaa gcttatccaa-3';

(H; SEQ ID No. 39)
5'-tctcagggac cctccaggct gtactaagcc tcccccagac tccaccagca ttacttcaga gtggacacct gtagctgttg-3';

(H2; SEQ ID No. 58)
5'-tctcagggac cctccaggct gtactaagcc tcccccagac tccaccagct gtacttcaga gtggacacct gtagctgttg-3';

(H3; SEQ ID No. 69)
5'-tttcagggac cctccaggct ttactaagcc tcccccagac tccaccagca ttacttcaga gtggacacct gtagctgttg-3';

(I; SEQ ID No. 40)
5'-tccagaccct tccctggtgc ctgccgaacc caagacatta cataactact gaaagtgaat ccagaggctg cacaggagag-3';

(I2; SEQ ID No. 65)
5'-tccagcctct tctctggagt ctgccgaacc caagacatta cataactact gaaagtgaat ccagaggctg cacaggagag-3';

(J; SEQ ID No. 41)
5'-ctctggagat ggtgaatcgg cccttcacac tgtctggata gtaggtgtaa ctaccaccac tactaatggt tgcaacccac-3';

(K; SEQ ID No. 42)
5'-ccttcttgca cagtaataaa cagccgtgtc ctctgctctc agactgttca tttgcagata cagggtgttc ttggcattgt-3';

(K2; SEQ ID No. 63)
5'-ccttcttgca cagtaataaa cagccgtgtc ctctgctctc agactgttca tttgcagata cagggtgttc ttggcattgt-3';

(K3; SEQ ID No. 70)
5'-ccttcttgca cagtaataca tagccgtgtc ctcagatctc agactgctca tttgcagata cagggtgttc ttggcattgt-3';

(L; SEQ ID No. 43)
5'-gaccgatggg cccttggtgg aggctgagga gactgtgacc agggtccctt ggccccagta gtccgtcgta atcatagagt cacc-3'
and (L2; SEQ ID No. 71)
5'-gaccgatggg cccttggtgg aggctgagga gactgtgaga gtggtccctt ggccccagta gtccgtcgta atcatagagt cacc-3'.

(P1; SEQ ID No. 44)
The following 2 PCR primers are synthesized as described above:

5'-ttggataagc ttggcttgac-3';
and (P2; SEQ ID No. 45)
5'-gaccgatggg cccttggtgg a-3'.

The synthesis of H1 type DNA encoding a polypeptide chain comprising a secretion signal sequence, a variable region of humanized TRA-8 heavy chain and the 8 amino acid residues at the N-terminus of the IgG-CH1 region is performed using a combination of PCR respectively.

The H1 type-DNA fragment is prepared as follows.
Composition of the PCR reaction solution:
  oligonucleotide A, 10 pmol;
  oligonucleotide B2, 10 pmol;
  oligonucleotide C, 10 pmol;
  oligonucleotide D, 10 pmol;
  oligonucleotide E, 10 pmol;
  oligonucleotide F, 10 pmol;
  oligonucleotide G, 10 pmol;
  oligonucleotide H2, 10 pmol;
  oligonucleotide I, 10 pmol;
  oligonucleotide J, 10 pmol;
  oligonucleotide K, 10 pmol;
  oligonucleotide L, 10 pmol;
  oligonucleotide primer P1, 2 µM;
  oligonucleotide primer P2, 2 µM;
  10× Pyrobest™ buffer II, 10 µl;
  dNTP mix, 8 µl;
  Pyrobest™ DNA polymerase, 0.5 µl; and
  Redistilled water to a final volume of 50 µl.

The PCR reaction is conducted as follows. The solution is first heated at 94° C. for 5 minutes, after which a cycle of heating to 98° C. for 10 second, 55° C. for 30 second and 72° C. for 1 minute, is repeated 7 times. After completion of this procedure, the reaction solution is heated at 72° C. for 15 minutes.

After phenol extraction and ethanol precipitation, the resulting DNA precipitate is vacuum-dried, dissolved in a minimum of redistilled water, and separated by 3% agarose gel electrophoresis. After electrophoresis, the gel is stained with a 1 µg/ml aqueous solution of ethidium bromide to allow detection of DNA under UV light. The DNA bands corresponding to H1 type-DNA is cut out using a razor blade and eluted from the gel using Geneclean® Spin Kit (BIO 101, CA, USA). After phenol extraction, the eluted DNA is then concentrated by centrifugation at 7,500×g, followed by ethanol precipitation, and finally dissolved in 5 µl of distilled water.

The synthesis of H3 type DNA encoding a polypeptide chain comprising a secretion signal sequence, a variable region of humanized TRA-8 heavy chain and the 8 amino acid residues at the N-terminus of the IgG-CH1 region is performed using a combination of PCR respectively.

The H3 type-DNA fragment is prepared as follows.
Composition of the PCR reaction solution:
  oligonucleotide A, 10 pmol;
  oligonucleotide B, 10 pmol;
  oligonucleotide C, 10 pmol;
  oligonucleotide D, 10 pmol;
  oligonucleotide E2, 10 pmol;
  oligonucleotide F, 10 pmol;
  oligonucleotide G, 10 pmol;
  oligonucleotide H, 10 pmol;
  oligonucleotide I, 10 pmol;
  oligonucleotide J, 10 pmol;
  oligonucleotide K2, 10 pmol;
  oligonucleotide L, 10 pmol;
  oligonucleotide primer P1, 2 µM;
  oligonucleotide primer P2, 2 µM;
  10× Pyrobest™ buffer II, 10 µl;
  dNTP mix, 8 µl;
  Pyrobest™ DNA polymerase, 0.5 µl; and
  Redistilled water to a final volume of 50 µl.

The PCR reaction is conducted as follows. The solution is first heated at 94° C. for 5 minutes, after which a cycle of heating to 98° C. for 10 second, 55° C. for 30 second and 72° C. for 1 minute, is repeated 7 times. After completion of this procedure, the reaction solution is heated at 72° C. for 15 minutes.

After phenol extraction and ethanol precipitation, the resulting DNA precipitate is vacuum-dried, dissolved in a minimum of redistilled water, and separated by 3% agarose gel electrophoresis. After electrophoresis, the gel is stained with a 1 µg/ml aqueous solution of ethidium bromide to allow detection of DNA under UV light. The DNA bands corresponding to H3 type-DNA is cut out using a razor blade and eluted from the gel using Geneclean® Spin Kit. After phenol extraction, the eluted DNA is then concentrated by centrifugation at 7,500×g, followed by ethanol precipitation, and finally dissolved in 5 µl of distilled water.

The synthesis of H4 type DNA encoding a polypeptide chain comprising a secretion signal sequence, a variable region of humanized TRA-8 heavy chain and the 8 amino acid residues at the N-terminus of the IgG-CH1 region is performed using a combination of PCR respectively.

The H4 type-DNA fragment is prepared as follows.
Composition of the PCR Reaction Solution:
  oligonucleotide A, 10 pmol;
  oligonucleotide B, 10 pmol;
  oligonucleotide C2, 10 pmol;
  oligonucleotide D, 10 pmol;
  oligonucleotide E2, 10 pmol;
  oligonucleotide F, 10 pmol;
  oligonucleotide G, 10 pmol;
  oligonucleotide H, 10 pmol;
  oligonucleotide I2, 10 pmol;
  oligonucleotide J, 10 pmol;
  oligonucleotide K2, 10 pmol;
  oligonucleotide L, 10 pmol;
  oligonucleotide primer P1, 2 µM;
  oligonucleotide primer P2, 2 µM;
  10×Pyrobest™ buffer II, 10 µl;
  dNTP mix, 8 µl;
  Pyrobest™ DNA polymerase, 0.5 µl; and
  Redistilled water to a final volume of 50 µl.

The PCR reaction is conducted as follows. The solution is first heated at 94° C. for 5 minutes, after which a cycle of heating to 98° C. for 10 second, 55° C. for 30 second and 72° C. for 1 minute, is repeated 7 times. After completion of this procedure, the reaction solution is heated at 72° C. for 15 minutes.

After phenol extraction and ethanol precipitation, the resulting DNA precipitate is vacuum-dried, dissolved in a minimum of redistilled water, and separated by 3% agarose gel electrophoresis. After electrophoresis, the gel is stained with a 1 µg/ml aqueous solution of ethidium bromide to allow detection of DNA under UV light. The DNA bands corresponding to H4 type-DNA is cut out using a razor blade and eluted from the gel using Geneclean® Spin Kit. After phenol extraction, the eluted DNA is then concentrated by centrifugation at 7,500×g, followed by ethanol precipitation, and finally dissolved in 5 µl of distilled water.

The synthesis of M type DNA encoding a polypeptide chain comprising a secretion signal sequence, a variable region of chimeric TRA-8 heavy chain and the 8 amino acid residues at the N-terminus of the IgG-CH1 region is performed using a combination of PCR respectively.

The M type-DNA fragment is prepared as follows.
Composition of the PCR Reaction Solution:
  oligonucleotide A, 10 pmol;
  oligonucleotide B3, 10 pmol;
  oligonucleotide C2, 10 pmol;
  oligonucleotide D, 10 pmol;
  oligonucleotide E3, 10 pmol;
  oligonucleotide F2, 10 pmol;
  oligonucleotide G, 10 pmol;
  oligonucleotide H3, 10 pmol;
  oligonucleotide I2, 10 pmol;
  oligonucleotide J, 10 pmol;
  oligonucleotide K3, 10 pmol;
  oligonucleotide L2, 10 pmol;
  oligonucleotide primer P1, 2 µM;
  oligonucleotide primer P2, 2 µM;
  10×Pyrobest™ buffer II, 10 µl;
  dNTP mix, 8 µl;
  Pyrobest™ DNA polymerase, 0.5 µl; and
  Redistilled water to a final volume of 50 µl.

The PCR reaction is conducted as follows. The solution is first heated at 94° C. for 5 minutes, after which a cycle of heating to 98° C. for 10 second, 55° C. for 30 second and 72° C. for 1 minute, is repeated 7 times. After completion of this procedure, the reaction solution is heated at 72° C. for 15 minutes.

After phenol extraction and ethanol precipitation, the resulting DNA precipitate is vacuum-dried, dissolved in a minimum of redistilled water, and separated by 3% agarose gel electrophoresis. After electrophoresis, the gel is stained with a 1 µg/ml aqueous solution of ethidium bromide to allow detection of DNA under UV light. The DNA bands corresponding to M type-DNA is cut out using a razor blade and eluted from the gel using Geneclean® Spin Kit. After phenol extraction, the eluted DNA is then concentrated by centrifugation at 7,500×g, followed by ethanol precipitation, and finally dissolved in 5 µl of distilled water.

The resulting, each extracted DNA (H1 type, H3 type, H4 type, and M type) is cloned using pGEM-T Easy vector (Promega) as follows:
  The DNA fragment recovered from the PCR reaction (H1, H3, H4 or M), 5 µl;
  10×Taq polymerase buffer, 1 µl;
  dNTP mixture, 1 µl
  Taq polymerase (5 unit/ml), 1 µl; and
  redistilled water to a final volume of 10 µl.

After the above each solution is reacted at 70° C. for 30 minutes, each DNA solution and pGEM-T Easy vector are ligated using a DNA Ligation Kit Version 2.0 (Takara Shuzo Co., Ltd.) using the manufacturer's protocol.

After 4 hours incubation at 15° C., 2 µl of the incubated reaction solution is mixed with 100 µl of competent E. coli strain JM109 at a cell density of 1-2×10$^9$ cells/ml (Takara Shuzo Co., Ltd.), and the mixture is kept on ice for 30 minutes, then at 42° C. for 30 seconds, and again on ice for 1 minute. Then, 500 µl of SOC medium (2% v/v tryptone, 0.5% w/v yeast extract, 0.05% w/v sodium chloride, 2.5 mM w/v potassium chloride, 1 mM magnesium chloride, and 20 mM glucose) is added the mixture, which is incubated for a further hour, with shaking. Transformant strains are then isolated, and plasmid DNA is prepared from the strains as described in "Molecular Cloning: A Laboratory Manual". The nucleotide sequence of this DNA encoding the heavy chain of humanized or mouse TRA-8 is confirmed by the dideoxy method, respectively (Sanger, F. S., et al., (1977), Proc. Natl. Acad. Sci. USA, 74:5463-5467) using 3700 DNA Analyzer (ABI PRISM®; Perkin Elmer Applied Biosystems, Japan).

The resulting plasmid is designated pHA15 (the plasmid carrying cDNA encoding the H1-type heavy chain of humanized TRA-8), pHC10 (the plasmid carrying cDNA encoding the H3-type heavy chain of humanized TRA-8), pHD21 (the plasmid carrying cDNA encoding the H4-type heavy chain of humanized TRA-8), and pM11 (the plasmid carrying cDNA encoding the heavy chain of chimeric TRA-8). The transformant E coli strains harboring these plasmid, designated as E. coli JM109/pHA15, E. coli JM109/pHC10, E. coli JM109/pHD21, and E. coli JM109/pM11 were deposited with International Patent Organism Depositary, National Institute of Advanced Industrial Science and Technology, 1-1, Higashi 1 chome Tsukuba-shi, Ibaraki-ken, 305-5466, Japan on Apr. 20, 2001, in accordance with the Budapest Treaty for the Deposit of Microorganisms, and was accorded the accession number FERM BP-7555, FERM BP-7557, FERM BP-7558, and FERM BP-7559, respectively.

(3) Construction of Expression Plasmids Carrying the Heavy Chain Variable Region DNA of Several Types Humanized or Mouse TRA-8

Recombinant expression vector for animal cells are constructed by inserting the DNA encoding the heavy chain of H1 type, H3 type, and H4 type humanized or M type chimeric TRA-8 (cloned in above) as follows.

One µg of plasmid pSRHHH3 (European patent application EP 0 909 816 A1) carrying the heavy chain variable region of humanized anti-Fas monoclonal antibody HFE7A and human IgG1 constant region genomic DNA, an expression vector for mammalian cells, is digested with the restriction enzymes HindIII and ApaI, and separated by 3% agarose gel electrophoresis. After electrophoresis, the gel is stained with a 1 µg/ml aqueous solution of ethidium bromide to allow detection of DNA under UV light. The vector DNA bands containing human IgG1 constant region genomic DNA without the heavy chain variable region of humanized HFE7A are cut out using a razor blade and eluted from the gel using Geneclean® Spin Kit. After phenol extraction, the eluted DNA is then concentrated by centrifugation at 7,500×g, followed by ethanol precipitation, and finally dissolved in 5 µl of distilled water and then dephosphorylated using CIP. The resulting digested, dephosphorylated plasmid (100 ng) is ligated with 1 µg of the DNA fragment of pHA15, pHC10, pHD21, or pM11 containing the DNA encoding the heavy chain variable region of humanized or chimeric TRA-8, which had also been digested with HindIII and ApaI, using a DNA Ligation Kit Version 2.0 (Takara Shuzo Co., Ltd.). The ligation mixture is then used to transform E. coli JM109, which is then plated on LB agar plates containing 50 µg/ml ampicillin.

The transformants obtained by this method are cultured in 2 ml of liquid LB medium containing 50 µg/ml ampicillin at 37° C. overnight, and plasmid DNA is subsequently extracted from the resulting culture by the alkaline-SDS method.

The extracted plasmid DNA is digested with HindIII and ApaI, and subjected to 3% w/v agarose gel electrophoresis to confirm the presence or absence of the insert of the DNA encoding the heavy chain variable region of humanized or chimeric TRA-8. The insertion and orientation of the desired DNA fragment in the vector is confirmed by DNA sequencing using a gene sequence analyzer (ABI PRISM® 3700 DNA Analyzer; Applied Biosystems). The resulting expression plasmids carrying cDNA encoding the heavy chain of humanized or chimeric TRA-8 were designated pHA15-1, pHC10-3, pHD21-1, and pM11-1, respectively.

(4) Construction of Vectors for the Humanized Light Chains (4.1) Construction of an Expression Vector for the Light Chain of the Humanized Antibody (LM1 Type)

As shown in SEQ ID No. 72 of the Sequence Listing, other humanization (LM1 type) of the amino acid sequences of the light chain of the mouse anti-human DR5 antibody TRA-8 entailed replacing the 3rd amino acid (valine), 8th amino acid (histidine), 9th amino acid (lysine), 10th amino acid (phenylalanine), 11th amino acid (methionine), 13th amino acid (threonine), 20th amino acid (serine), 42nd amino acid (glutamine), 43rd (serine), 60th amino acid (aspartic acid), 63rd amino acid (threonine), 77th amino acid (asparagine), 78th amino acid (valine), 80th amino acid (serine) 83rd amino acid (leucine), 85th amino acid (aspartic acid), 87th amino acid (phenylalanine), and 99th amino acid (glycine) 103rd amino acid (leucine) and 108th amino acid (alanine) from the N-terminus of the amino acid sequence of the TRA-8 light chain are replaced with glutamine, proline, serine, serine, leucine, alanine, threonine, lysine, alanine, serine, serine, serine, leucine, proline, phenylalanine, threonine, tyrosine, glutamine, valine and threonine respectively. The resulting sequence is designated LM1.

Expression plasmids carrying this type of humanized light chain amino acid sequences of the anti-human DR5 antibody TRA-8 (LM1 type, SEQ ID No. 72 of the Sequence Listing) are constructed as follows.

1) Synthesis of Primers for Preparing the Variable and Constant Regions of the Light Chain of Humanized TRA-8 (LM1 Type)

DNA coding for the LM1 polypeptide chain (SEQ ID No. 72 of the Sequence Listing), each of which is a fusion of the variable region of humanized anti-DR5 antibody TRA-8 light chain (LM1 type) and the constant region of the human Ig light chain (κ chain), are respectively synthesized by using combinations of PCR.

Further to 7AL1P (SEQ ID No. 47), 7ALCN (SEQ ID No. 48), HKCDF11 (SEQ ID No. 50), HKCDR12 (SEQ ID No. 51), HKCDF22 (SEQ ID No. 52), HKCDR22 (SEQ ID No. 53), and HKCF12 (SEQ ID No. 54).

The following oligonucleotide primers are synthesized for PCR:

5'-gtcccccaca gatgcagaca aagaacttgg agattgggtc atctgaatgt caccagtgga-3' (HKSPR12; SEQ ID No. 77).

2) Construction of Plasmid pCR3.1/LM1-2 (Cloning of Humanized TRA-8 Light Chain Type LM1)

LM1-DNA fragment coding for the amino acid sequence as defined in SEQ ID No. 72 of the same is prepared by performing 2-step PCR, inserted into a plasmid vector and cloned in *E. coli*.

a) First Step PCR

LM1-F1-DNA fragment coding for a secretion signal sequence and a portion of $FRL_1$ region with a Hind III restriction enzyme cleavage site added at the 5'-end is prepared under the following conditions. The template plasmids, pHSGHM17 and pSRPDHH, are obtained by following the description in a European patent application EP 0 909 816 A1.

Composition of the Reaction Solution:
plasmid pHSGHM17 DNA, 25 ng
oligonucleotide primer 7AL1P, 50 pmol
oligonucleotide primer HKSPR12, 50 pmol
dNTPs cocktail, 5 µl
10×PCR buffer, 5 µl
ampliTaq DNA polymerase (PerkinElmer), 2.5 units The reaction solution having the above composition is adjusted to a final volume of 50 µl by adding redistilled water and used in PCR.

PCR thermal conditions: Heating at 94° C. for 2 minutes, after which a thermal cycle of 94° C. for 1 minute, 55° C. for 1 minute and 72° C. for 2 minutes, repeated 30 times, followed by heating at 72° C. for 10 minutes.

LM1-F2-DNA fragment coding for a portion of $FRL_1$, $CDRL_1$, $FRL_2$, and $CDRL_2$ is prepared under the following conditions.

Composition of the Reaction Solution:
plasmid pL28 DNA, 25 ng
oligonucleotide primer HKCDF11, 50 pmol
oligonucleotide primer HKCDR12, 50 pmol
dNTPs cocktail, 5 µl
10×PCR buffer, 5 µl
ampliTaq DNA polymerase, 2.5 units The reaction solution having the above composition is adjusted to a final volume of 50 µl by adding redistilled water and used in PCR.

PCR thermal conditions: Heating at 94° C. for 2 minutes, after which a thermal cycle of 94° C. for 1 minute, 55° C. for 1 minute and 72° C. for 2 minutes, repeated 30 times, followed by heating at 72° C. for 10 minutes.

LM1-F3-DNA fragment coding for CDRL2, $FRL_3$, and a portion of $CDRL_3$ is prepared under the following conditions.

Composition of the Reaction Solution:
plasmid pSRPDHH DNA, 25 ng
oligonucleotide primer HKCDF22, 50 pmol
oligonucleotide primer HKCDR22, 50 pmol
dNTPs cocktail, 5 µl
10×PCR buffer, 5 µl
ampliTaq DNA polymerase, 2.5 units The reaction solution having the above composition is adjusted to a final volume of 50 µl by adding redistilled water and used in PCR.

PCR thermal conditions: Heating at 94° C. for 2 minutes, after which a thermal cycle of 94° C. for 1 minute, 55° C. for 1 minute and 72° C. for 2 minutes, repeated 30 times, followed by heating at 72° C. for 10 minutes.

LM1-F4-DNA fragment coding for $CDRL_3$, $FRL_4$ and the constant region with an EcoR I restriction enzyme cleavage site added at the 3'-end is prepared under the following conditions.

Composition of the Reaction Solution:
plasmid pSRPDHH DNA, 25 ng
oligonucleotide primer HKCF12, 50 pmol
oligonucleotide primer 7ALCN, 50 pmol
dNTPs cocktail, 5 µl
10×PCR buffer, 5 µl
ampliTaq DNA polymerase, 2.5 units The reaction solution having the above composition is adjusted to a final volume of 50 µl by adding redistilled water and used in PCR.

PCR thermal conditions: Heating at 94° C. for 2 minutes, after which a thermal cycle of 94° C. for 1 minute, 55° C. for 1 minute and 72° C. for 2 minutes, repeated 30 times, followed by heating at 72° C. for 10 minutes.

The amplified DNA fragments after PCR are separated by 5% polyacrylamide gel electrophoresis. The gel after electrophoresis is stained with 1 µg/ml of ethidium bromide to detect the produced DNA under UV light. The respective DNA bands thus detected are excised with a razor b) Second Step PCR LM1-DNA in which above described LM1-F1-DNA, LM1-F2-DNA, LM1-F3-DNA and LM1-F4-DNA fragments are fused is prepared under the following conditions.

Composition of the Reaction Solution:
Gel fragment of LM1-F1-DNA prepared in the first step PCR, Gel fragment of LM1-F2-DNA prepared in the first step PCR, Gel fragment of LM1-F3-DNA prepared in the first step PCR, Gel fragment of LM1-F4-DNA prepared in the first step PCR oligonucleotide primer 7AL1P, 50 pmol
oligonucleotide primer 7ALCN, 50 pmol
dNTPs cocktail, 5.0 μl
10×PCR buffer, 5.0 μl
ampliTaq DNA polymerase, 2.5 units The reaction solution having the above composition is adjusted to a final volume of 50 μl by adding redistilled water and used in PCR.

PCR thermal conditions: Heating at 94° C. for 2 minutes, after which a thermal cycle of 94° C. for 1 minute, 55° C. for 1 minute and 72° C. for 2 minutes, repeated 30 times, followed by heating at 72° C. for 10 minutes.

The thus prepared LM1-DNA fragment is inserted into plasmid pCR3.1DNA using Eukaryotic TA cloning Kit (In-Vitrogen) following the manufacturer's protocol and introduced into the competent E. Coli TOP10F' contained in the kit. The nucleotide sequences of these DNAs encoding the light chain of humanized TRA-8 (LM1 type) are confirmed by the dideoxy method (Sanger, F. S., et al., (1977), Proc. Natl. Acad. Sci. USA, 74:5463-5467) using 3700 DNA Analyzer (ABI PRISM®; Perkin Elmer Applied Biosystems, Japan).

The resulting plasmids are designated pCR3.1/LM1-2 (the plasmid carrying cDNA encoding the light chain variable region of humanized TRA-8 (LM1 type) and a human Ig light chain constant region).

The obtained plasmid pCR3.1/LM1-2 containing LM1-DNA fragment is digested with the restriction enzymes Hind III and EcoR I.

One μg of cloning plasmid pHSG399 DNA is digested with the restriction enzymes Hind III and EcoR I, and then dephosphorylated with CIP. The resulting dephosphorylated pHSG399 DNA and LM1-DNA fragment, that had been digested with the restriction enzymes Hind III and EcoR I, are ligated using DNA Ligation Kit Version 2.0 (Takara Syuzo, Co. Ltd.). Then, E. coli DH5α is transformed with the ligated DNA and spread onto LB agar medium containing 0.1 mM IPTG, 0.1% X-Gal and 50 μg/ml chloramphenicol (final concentrations). The white transformants obtained are cultured in liquid LB medium containing 50 μg/ml chloramphenicol, and plasmid DNA is extracted from the resulting culture according to the alkaline-SDS method. The extracted plasmid DNA is digested with Hind III and EcoR I, and then a clone carrying LM1-DNA fragment is selected by 1% agarose gel electrophoresis.

As a result of the above procedure, plasmid pHSG/M1-2-2 carrying a fusion fragment of the variable region of the humanized LM1 TRA-8 light chain and the constant region of human Igκ chain is obtained. The transformant E coli strain harboring these plasmid, designated as E. coli DH5α/pHSG/M1-2-2 was deposited with International Patent Organism Depositary, National Institute of Advanced Industrial Science and Technology, 1-1, Higashi 1 chome Tsukuba-shi, Ibaraki-ken, 305-5466, Japan on Apr. 20, 2001, in accordance with the Budapest Treaty for the Deposit of Microorganisms, and was accorded the accession number FERM BP-7562.

3) Construction of Plasmid pSR/LM1-2 (Expression Plasmid for Humanized LM1 TRA-8 Light Chain)

The obtained plasmid pHSG/M1-2—carrying a fusion fragment of the variable region of the humanized LM1 TRA-8 light chain and the constant region of human Igκ chain is digested with the restriction enzymes Hind III and EcoR I.

One μg of cloning plasmid pSRPDHH DNA (European patent application EP 0 909 816 A1) is digested with the restriction enzymes Hind III and EcoR I, and then dephosphorylated with CIP. The resulting dephosphorylated pSRPDHH DNA and HindIII-EcoRI DNA fragment obtained from pHSG/M1-2-2 are ligated using DNA Ligation Kit Version 2.0 (Takara Syuzo, Co. Ltd.). Then, E. coli DH5α is transformed with the ligated DNA and spread onto LB agar. The transformants obtained are cultured in liquid LB medium containing 100 μg/ml ampicillin, and plasmid DNA is extracted from the resulting culture according to the alkaline-SDS method. The insertion and orientation of the desired DNA fragment in pSRPDHH vector is confirmed by DNA sequencing using a gene sequence analyzer.

The resulting expression plasmid carrying cDNA encoding the light chain of humanized LM1 TRA-8 is designated pSR/LM1-2.

(4.2) Construction of an Expression Vector for the Light Chain of the Humanized Antibody (LM3 Type)

As shown in SEQ ID No. 73 of the Sequence Listing, other humanization (LM3 type) of the amino acid sequences of the light chain of the mouse anti-human DR5 antibody TRA-8 entailed replacing the 8th amino acid (histidine), 9th amino acid (lysine), 10th amino acid (phenylalanine), 11th amino acid (methionine), 13th amino acid (threonine), 20th amino acid (serine), 42nd amino acid (glutamine), 43rd amino acid (serine), 77th amino acid (asparagine), 78th amino acid (valine), 80th amino acid (serine) 83rd amino acid (leucine), 85th amino acid (aspartic acid), 87th amino acid (phenylalanine), 99th amino acid (glycine) 103rd amino acid (leucine) and 108th amino acid (alanine) from the N-terminus of the amino acid sequence of the TRA-8 light chain are replaced with proline, serine, serine, leucine, alanine, threonine, lysine, alanine, serine, leucine, proline, phenylalanine, threonine, tyrosine, glutamine, valine and threonine, respectively. The resulting sequence is designated LM3.

Expression plasmids carrying this type of humanized light chain amino acid sequences of the anti-human DR5 antibody TRA-8 (LM3 type, SEQ ID No. 73 of the Sequence Listing) are constructed as follows.

1) Synthesis of Primers for Preparing the Variable and Constant Regions of the Light Chain of Humanized LM3 TRA-8

DNA coding for the LM3 polypeptide chain (SEQ ID No. 73 of the Sequence Listing), each of which is a fusion of the variable region of humanized anti-DR5 antibody TRA-8 light chain and the constant region of the human Ig light chain (κ chain), are respectively synthesized by using combinations of PCR.

Further to 7AL1P (SEQ ID No. 47) and 7ALCN (SEQ ID No. 48), the following oligonucleotide primers are synthesized for PCR:

```
                                                    (MOD1F1; SEQ ID No. 78)
5'-atctagttct cagagatgga gacagacaca atcctgctat gggtgctgct gctctgggtt ccagg-3';

(MOD1R1; SEQ ID No. 79)
5'-cagcacccat agcaggattg tgtctgtctc catctctgag aactagatga gaggatgctt cttaagctt-3';
```

```
                                                              (MOD1F22; SEQ ID No. 80)
5'-ctccactggt gacattgtga tgacccaatc tccaagttct ttgtctgcat ctgtggggga cagggtc-3';

(MOD1R22; SEQ ID No. 81)
5'-acttggagat tgggtcatca caatgtcacc agtggagcct ggaacccaga gcag-3';

(MOD1F3; SEQ ID No. 82)
5'-accatcacct gcaaggccag tcaggatgtg ggtactgctg tagcctggta ccaacagaaa ccaggaa-3';

(MOD1R3; SEQ ID No. 83)
5'-tacagcagta cccacatcct gactggcctt gcaggtgatg gtgaccctgt ccccacaga tgcagacaaa
ga-3';

(MOD1F42; SEQ ID No. 84)
5'-aagcacccaa actcctcatc tattgggcat ccaccggca cactggggtc ccagataggt ttacaggcag
t-3';

(MOD1R4; SEQ ID No. 85)
5'-cccagtgtgc cgggtggatg cccaatagat gaggagtttg ggtgcttttc ctggtttctg ttggtaccag gc-3';

(MOD1F5; SEQ ID No. 86)
5'-gggtctggga cagacttcac cctcaccatc tctagtctgc agccggagga ttttgcaacc tat-
3';

(MOD1R52; SEQ ID No. 87)
5'-actagagatg gtgagggtga agtctgtccc agacccactg cctgtaaacc tatctgggac-3';

(MOD1F6; SEQ ID No. 88)
5'-tactgtcagc aatatagcag ctatcggacg ttcggtcaag gcaccaaggt ggaaatc-3';

(MOD1R6; SEQ ID No. 89)
5'-cgtccgatag ctgctatatt gctgacagta ataggttgca aaatcctccg gctgcac-3'

(MOD1F7; SEQ ID No. 90)
5'-aaacggactg tggctgcacc atctgtcttc atcttcccgc catctgatga g-3';

(MOD1R7; SEQ ID No. 91)
5'-gaagatgaag acagatggtg cagccacagt ccgtttgatt tccaccttgg tgccttgacc gaa-3';
and (LR17; SEQ ID No. 101)
5'-agatttcaac tgctcatcag atggcgggaa.
```

2) Construction of Plasmid pCR3.1/LM3-3-44 (Cloning of Humanized TRA-8 Light Chain Type LM3)

LM3-DNA fragment coding for the amino acid sequence as defined in SEQ ID No. 73 of the same is prepared by performing 2-step PCR, inserted into a plasmid vector and cloned in *E. coli*.

a) First Step PCR

LM3-F31B-DNA fragment coding for a secretion signal sequence region with a Hind III restriction enzyme cleavage site added at the 5'-end, $FRL_1$ $CDRL_1$, $FRL_2$, and $CDRL_2$, $FRL_3$, $CDRL_3$, $FRL_4$ and a portion of the constant region is prepared under the following conditions.

Composition of the Reaction Solution:
  oligonucleotide primer MOD1F1, 5 pmol
  oligonucleotide primer MOD1R1, 5 pmol
  oligonucleotide primer MOD1F22, 5 pmol
  oligonucleotide primer MOD1R22, 5 pmol
  oligonucleotide primer MOD1F3, 5 pmol
  oligonucleotide primer MOD1R3, 5 pmol
  oligonucleotide primer MOD1F42, 5 pmol
  oligonucleotide primer MOD1R4, 5 pmol
  oligonucleotide primer MOD1F5, 5 pmol
  oligonucleotide primer MOD1R52, 5 pmol
  oligonucleotide primer MOD1F6, 5 pmol
  oligonucleotide primer MOD1R6, 5 pmol
  oligonucleotide primer MOD1F7, 50 pmol
  oligonucleotide primer MOD1R7, 5 pmol
  oligonucleotide primer 7AL1P, 50 pmol
  oligonucleotide primer LR17, 50 pmol
  dNTPs cocktail, 5 µl
  10×PCR buffer, 5 µl
  ampliTaq DNA polymerase, 2.5 units The reaction solution having the above composition is adjusted to a final volume of 50 µl by adding redistilled water and used in PCR.

PCR thermal conditions: Heating at 94° C. for 2 minutes, after which a thermal cycle of 94° C. for 1 minute, 55° C. for 1 minute and 72° C. for 2 minutes, repeated 30 times, followed by heating at 72° C. for 10 minutes.

LM3-F31C-DNA fragment coding for a portion of the constant region with an Eco R I restriction enzyme cleavage site added at the 3'-end is prepared under the following conditions.

The template plasmids, pSRPDHH, is obtained by following the description in a European patent application EP 0 909 816 A1.

Composition of the Reaction Solution:
  plasmid pSRPDHH DNA, 25 ng
  oligonucleotide primer MOD1F7, 50 pmol
  oligonucleotide primer 7ALCN, 50 pmol
  dNTPs cocktail, 5 µl
  10×PCR buffer, 5 µl
  ampliTaq DNA polymerase, 2.5 units The reaction solution having the above composition is adjusted to a final volume of 50 µl by adding redistilled water and used in PCR.

PCR thermal conditions: Heating at 94° C. for 2 minutes, after which a thermal cycle of 94° C. for 1 minute, 55° C. for 1 minute and 72° C. for 2 minutes, repeated 30 times, followed by heating at 72° C. for 10 minutes.

The amplified DNA fragments after PCR are separated by 5% polyacrylamide gel electrophoresis. The gel after electrophoresis is stained with 1 µg/ml of ethidium bromide to detect the produced DNA under UV light. The respective DNA bands thus detected are excised with a razor.

b) Second Step PCR

LM3-DNA in which above described LM3-F31B-DNA, and LM3-F31C-DNA fragments are fused is prepared under the following conditions.

Composition of the Reaction Solution:

Gel fragment of LM3-F31B-DNA prepared in the first step PCR,
Gel fragment of LM3-F31C-DNA prepared in the first step PCR,
oligonucleotide primer 7AL1P, 50 pmol
oligonucleotide primer 7ALCN, 50 pmol
dNTPs cocktail, 5.0 µl
10×PCR buffer, 5.0 µl
ampliTaq DNA polymerase, 2.5 units The reaction solution having the above composition is adjusted to a final volume of 50 µl by adding redistilled water and used in PCR.

PCR thermal conditions: Heating at 94° C. for 2 minutes, after which a thermal cycle of 94° C. for 1 minute, 55° C. for 1 minute and 72° C. for 2 minutes, repeated 30 times, followed by heating at 72° C. for 10 minutes.

The thus prepared LM3-DNA fragment is inserted into plasmid pCR3.1DNA using Eukaryotic TA cloning Kit (In-Vitrogen) following the manufacturer's protocol and introduced into the competent *E. Coli* TOP10F' contained in the kit. The nucleotide sequences of these DNAs encoding the light chain of humanized LM3 TRA-8 are confirmed by the dideoxy method (Sanger, F. S., et al., (1977), Proc. Natl. Acad. Sci. USA, 74:5463-5467) using 3700 DNA Analyzer (ABI PRISM®; Perkin Elmer Applied Biosystems, Japan).

The resulting plasmids are designated pCR3.1/LM3-3-44 (the plasmid carrying cDNA encoding the light chain variable region of humanized LM3 TRA-8 and a human Ig light chain constant region).

The obtained plasmid pCR3.1/LM3-3-44 containing LM3-DNA fragment is digested with the restriction enzymes Hind III and EcoR I.

One µg of cloning plasmid pHSG399 DNA is digested with the restriction enzymes Hind III and EcoR I, and then dephosphorylated with CIP. The resulting dephosphorylated pHSG399 DNA and LM3-DNA fragment, that had been digested with the restriction enzymes Hind III and EcoR I, are ligated using DNA Ligation Kit Version 2.0 (Takara Syuzo, Co. Ltd.). Then, *E. coli* DH5α is transformed with the ligated DNA and spread onto LB agar medium containing 0.1 mM IPTG, 0.1% X-Gal and 50 µg/ml chloramphenicol (final concentrations). The white transformants obtained are cultured in liquid LB medium containing 50 µg/ml chloramphenicol, and plasmid DNA is extracted from the resulting culture according to the alkaline-SDS method. The extracted plasmid DNA is digested with Hind III and EcoR I, and then a clone carrying LM3-DNA fragment is selected by 1% agarose gel electrophoresis.

As a result of the above procedure, plasmid pHSG/M3-3-22 carrying a fusion fragment of the variable region of the humanized LM3 TRA-8 light chain and the constant region of human Igκ chain is obtained. The transformant *E coli* strain harboring these plasmid, designated as *E. coli* DH5α/pHSG/M3-3-22 was deposited with International Patent Organism Depositary, National Institute of Advanced Industrial Science and Technology, 1-1, Higashi 1 chome Tsukuba-shi, Ibaraki-ken, 305-5466, Japan on Apr. 20, 2001, in accordance with the Budapest Treaty for the Deposit of Microorganisms, and was accorded the accession number FERM BP-7564.

3) Construction of Plasmid pSR/LM3-3-44-10 (Expression Plasmid for Humanized LM3 TRA-8 Light Chain)

The obtained plasmid pHSG/M3-3-22 carrying a fusion fragment of the variable region of the humanized LM3 TRA-8 light chain and the constant region of human Igκ chain is digested with the restriction enzymes Hind III and EcoR I.

One µg of cloning plasmid pSRPDHH DNA (European patent application EP 0 909 816 A1) is digested with the restriction enzymes Hind III and EcoR I, and then dephosphorylated with CIP. The resulting dephosphorylated pSRPDHH DNA and HindIII-EcoRI DNA fragment obtained from pHSG/M3-3-22 are ligated using DNA Ligation Kit Version 2.0 (Takara Syuzo, Co. Ltd.). Then, *E. coli* DH5α is transformed with the ligated DNA and spread onto LB agar. The transformants obtained are cultured in liquid LB medium containing 100 µg/ml ampicillin, and plasmid DNA is extracted from the resulting culture according to the alkaline-SDS method. The insertion and orientation of the desired DNA fragment in pSRPDHH vector is confirmed by DNA sequencing using a gene sequence analyzer (ABI PRIDM® 3700 DNA Analyzer; Applied Biosystems).

The resulting expression plasmid carrying cDNA encoding the light chain of humanized LM3 TRA-8 is designated pSR/LM3-3-44-10.

(4.3) Construction of an Expression Vector for the Light Chain of the Humanized Antibody (LM4 Type)

As shown in SEQ ID No. 74 of the Sequence Listing, other humanization (LM4 type) of the amino acid sequences of the light chain of the mouse anti-human DR5 antibody TRA-8 entailed replacing the 8th amino acid (histidine), 9th amino acid (lysine), 10th amino acid (phenylalanine), 11th amino acid (methionine), 13th amino acid (threonine), 20th amino acid (serine), 42nd amino acid (glutamine), 43rd amino acid (serine), 77th amino acid (asparagine), 78th amino acid (valine), 80th amino acid (serine) 83rd amino acid (leucine), 85th amino acid (aspartic acid), 99th amino acid (glycine) 103rd amino acid (leucine) and 108th amino acid (alanine) from the N-terminus of the amino acid sequence of the TRA-8 light chain are replaced with proline, serine, serine, leucine, alanine, threonine, lysine, alanine, serine, leucine, proline, phenylalanine, threonine, glutamine, valine and threonine respectively. The resulting sequence is designated LM4. Expression plasmids carrying this type of humanized light chain amino acid sequences of the anti-human DR5 antibody TRA-8 (LM4 type) (SEQ ID No. 74 of the Sequence Listing) are constructed as follows.

1) Synthesis of Primers for Preparing the Variable and Constant Regions of the Light Chain of Humanized LM4 TRA-8

DNA coding for the LM4 polypeptide chain (SEQ ID No. 74 of the Sequence Listing), each of which is a fusion of the variable region of humanized anti-DR5 antibody TRA-8 light chain and the constant region of the human Ig light chain (κ chain), are respectively synthesized by using combinations of PCR.

Further to 7AL1P (SEQ ID No. 47), 7ALCN (SEQ ID No. 48), MOD1F1 (SEQ ID No. 78), MOD1R1 (SEQ ID No. 79), MOD1F22 (SEQ ID No. 80), MOD1R22 (SEQ ID No. 81), MOD1F3 (SEQ ID No. 82), MOD1R3 (SEQ ID No. 83), MOD1F42 (SEQ ID No. 84), MOD1R4 (SEQ ID No. 85), MOD1F5 (SEQ ID No. 86), MOD1R52 (SEQ ID No. 87), MOD1F7 (SEQ ID No. 90), and MOD1R7 (SEQ ID No. 91), LR17 (SEQ ID No. 101), the following oligonucleotide primers are synthesized for PCR:

(MOD1F62; SEQ ID No. 92)
5'-ttctgtcagc aatatagcag ctatcggacg ttcggtcaag gcaccaaggt ggaaatc-3'

(MOD1R62; SEQ ID No. 93)
5'-cgtccgatag ctgctatatt gctgacagaa ataggttgca aaatcctccg gctgcag-3'

2) Construction of Plasmid pCR3.1/LM4-5-3 (Cloning of Humanized TRA-8 Light Chain Type LM4)

LM4-DNA fragment coding for the amino acid sequence as defined in SEQ ID No. 74 of the same is prepared by performing 2-step PCR, inserted into a plasmid vector and cloned in *E. coli*.

a) First Step PCR

LM4-F41B-DNA fragment coding for a secretion signal sequence region with a Hind III restriction enzyme cleavage site added at the 5'-end, $FRL_1$, $CDRL_1$, $FRL_2$, and $CDRL_2$, $FRL_3$, $CDRL_3$, $FRL_4$ and a portion of the constant region is prepared under the following conditions.

Composition of the Reaction Solution:
 oligonucleotide primer MOD1F1, 5 pmol
 oligonucleotide primer MOD1R1, 5 pmol
 oligonucleotide primer MOD1F22, 5 pmol
 oligonucleotide primer MOD1R22, 5 pmol
 oligonucleotide primer MOD1F3, 5 pmol
 oligonucleotide primer MOD1R3, 5 pmol
 oligonucleotide primer MOD1F42, 5 pmol
 oligonucleotide primer MOD1R4, 5 pmol
 oligonucleotide primer MOD1F5, 5 pmol
 oligonucleotide primer MOD1R52, 5 pmol
 oligonucleotide primer MOD1F62, 5 pmol
 oligonucleotide primer MOD1R62, 5 pmol
 oligonucleotide primer MOD1F7, 50 pmol
 oligonucleotide primer MOD1R7, 5 pmol
 oligonucleotide primer 7AL1P, 50 pmol
 oligonucleotide primer LR17, 50 pmol
 dNTPs cocktail, 5 µl
 10×PCR buffer, 5 µl
 ampliTaq DNA polymerase, 2.5 units The reaction solution having the above composition is adjusted to a final volume of 50 µl by adding redistilled water and used in PCR.

PCR thermal conditions: Heating at 94° C. for 2 minutes, after which a thermal cycle of 94° C. for 1 minute, 55° C. for 1 minute and 72° C. for 2 minutes, repeated 30 times, followed by heating at 72° C. for 10 minutes.

LM4-F41C-DNA fragment coding for a portion of the constant region with an Eco R I restriction enzyme cleavage site added at the 3'-end is prepared under the following conditions.

The template plasmids, pSRPDHH, are obtained by following the description in a European patent application EP 0 909 816 A1.

Composition of the Reaction Solution:
 plasmid pSRPDHH DNA, 25 ng
 oligonucleotide primer MOD1F7, 50 pmol
 oligonucleotide primer 7ALCN, 50 pmol
 dNTPs cocktail, 5 µl
 10×PCR buffer, 5 µl
 ampliTaq DNA polymerase, 2.5 units The reaction solution having the above composition is adjusted to a final volume of 50 µl by adding redistilled water and used in PCR.

PCR thermal conditions: Heating at 94° C. for 2 minutes, after which a thermal cycle of 94° C. for 1 minute, 55° C. for 1 minute and 72° C. for 2 minutes, repeated 30 times, followed by heating at 72° C. for 10 minutes.

The amplified DNA fragments after PCR are separated by 5% polyacrylamide gel electrophoresis. The gel after electrophoresis is stained with 1 µg/ml of ethidium bromide to detect the produced DNA under UV light. The respective DNA bands thus detected are excised with a razor blade.

b) Second Step PCR

LM4-DNA in which above described LM4-F41B-DNA, and LM4-F41C-DNA fragments are fused is prepared under the following conditions.

Composition of the Reaction Solution:
 Gel fragment of LM4-F41B-DNA prepared in the first step PCR,
 Gel fragment of LM4-F41C-DNA prepared in the first step PCR,
 oligonucleotide primer 7AL1P, 50 pmol
 oligonucleotide primer 7ALCN, 50 pmol
 dNTPs cocktail, 5.0 µl
 10×PCR buffer, 5.0 µl
 ampliTaq DNA polymerase, 2.5 units The reaction solution having the above composition is adjusted to a final volume of 50 µl by adding redistilled water and used in PCR.

PCR thermal conditions: Heating at 94° C. for 2 minutes, after which a thermal cycle of 94° C. for 1 minute, 55° C. for 1 minute and 72° C. for 2 minutes, repeated 30 times, followed by heating at 72° C. for 10 minutes.

The thus prepared LM4-DNA fragment is inserted into plasmid pCR3.1DNA using Eukaryotic TA cloning Kit (In-Vitrogen) following the manufacturer's protocol and introduced into the competent *E. Coli* TOP10F' contained in the kit. The nucleotide sequences of these DNAs encoding the light chain of humanized LM4 TRA-8 are confirmed by the dideoxy method (Sanger, F. S., et al., (1977), Proc. Natl. Acad. Sci. USA, 74:5463-5467) using 3700 DNA Analyzer (ABI PRISM®; Perkin Elmer Applied Biosystems, Japan).

The resulting plasmids are designated pCR3.1/LM4-5-3 (the plasmid carrying cDNA encoding the light chain variable region of humanized LM4 TRA-8 and a human Ig light chain constant region).

The obtained plasmid pCR3.1/LM4-5-3 containing LM4-DNA fragment is digested with the restriction enzymes Hind III and EcoR I.

One µg of cloning plasmid pHSG399 DNA is digested with the restriction enzymes Hind III and EcoR I, and then dephosphorylated with CIP. The resulting dephosphorylated pHSG399 DNA and LM4-DNA fragment, that had been digested with the restriction enzymes Hind III and EcoR I, are ligated using DNA Ligation Kit Version 2.0 (Takara Syuzo, Co. Ltd.). Then, *E. coli* DH5α is transformed with the ligated DNA and spread onto LB agar medium containing 0.1 mM IPTG, 0.1% X-Gal and 50 µg/ml chloramphenicol (final concentrations). The white transformants obtained are cultured in liquid LB medium containing 50 µg/ml chloramphenicol, and plasmid DNA is extracted from the resulting culture according to the alkaline-SDS method. The extracted plasmid DNA is digested with Hind III and EcoR I, and then a clone carrying LM4-DNA fragment is selected by 1% agarose gel electrophoresis.

As a result of the above procedure, plasmid pHSG/M4-5-3-1 carrying a fusion fragment of the variable region of the humanized LM4 TRA-8 light chain and the constant region of human Igκ chain is obtained. The transformant *E coli* strain harboring these plasmid, designated as *E. coli* DH5α/pHSG/M4-5-3-1 was deposited with International Patent Organism Depositary, National Institute of Advanced Industrial Science and Technology, 1-1, Higashi 1 chome Tsukuba-shi, Ibaraki-ken, 305-5466, Japan on Apr. 20, 2001, in accordance with the Budapest Treaty for the Deposit of Microorganisms, and was accorded the accession number FERM BP-7565.

3) Construction of Plasmid pSR/LM4-5-3-3 (Expression Plasmid for Humanized LM4 TRA-8 Light Chain)

The obtained plasmid pHSG/M4-5-3-1 carrying a fusion fragment of the variable region of the humanized LM4 TRA-8 light chain and the constant region of human Igκ chain is digested with the restriction enzymes Hind III and EcoR I.

One μg of cloning plasmid pSRPDHH DNA (European patent application EP 0 909 816 A1) is digested with the restriction enzymes Hind III and EcoR I, and then dephosphorylated with CIP. The resulting dephosphorylated pSRPDHH DNA and HindIII-EcoRI DNA fragment obtained from pHSG/M4-5-3-1 are ligated using DNA Ligation Kit Version 2.0 (Takara Syuzo, Co. Ltd.). Then, *E. coli* DH5α is transformed with the ligated DNA and spread onto LB agar. The transformants obtained are cultured in liquid LB medium containing 100 μg/ml ampicillin, and plasmid DNA is extracted from the resulting culture according to the alkaline-SDS method. The insertion and orientation of the desired DNA fragment in pSRPDHH vector is confirmed by DNA sequencing using a gene sequence analyzer (ABI PRISM® 3700 DNA Analyzer; Applied Biosystems).

The resulting expression plasmid carrying cDNA encoding the light chain of humanized LM4 TRA-8 is designated pSR/LM4-5-3-3.

(4.4) Construction of an Expression Vector for the Light Chain of the Humanized Antibody (LM5 Type)

As shown in SEQ ID No. 75 of the Sequence Listing, other humanization (LM5 type) of the amino acid sequences of the light chain of the mouse anti-human DR5 antibody TRA-8 entailed replacing the 8th amino acid (histidine), 9th amino acid (lysine), 10th amino acid (phenylalanine), 11th amino acid (methionine), 13th amino acid (threonine), 20th amino acid (serine), 42nd amino acid (glutamine), 43rd amino acid (serine), 77th amino acid (asparagine), 78th amino acid (valine), 80th amino acid (serine) 83rd amino acid (leucine), 103rd amino acid (leucine) and 108th amino acid (alanine) from the N-terminus of the amino acid sequence of the TRA-8 light chain are replaced with proline, serine, serine, leucine, alanine, threonine, lysine, alanine, serine, leucine, proline, phenylalanine, valine and threonine respectively. The resulting sequence is designated LM5.

Expression plasmids carrying this type of humanized light chain amino acid sequences of the anti-human DR5 antibody TRA-8 (LM5 type) (SEQ ID No. 75 of the Sequence Listing) is constructed as follows.

1) Synthesis of Primers for Preparing the Variable and Constant Regions of the Light Chain of Humanized LM5 TRA-8

DNA coding for the LM5 polypeptide chain (SEQ ID No. 75 of the Sequence Listing), each of which is a fusion of the variable region of humanized anti-DR5 antibody TRA-8 light chain and the constant region of the human Ig light chain (κ chain), are respectively synthesized by using combinations of PCR.

Further to 7AL1P (SEQ ID No. 47), 7ALCN (SEQ ID No. 48), MOD1F1 (SEQ ID No. 78), MOD1R1 (SEQ ID No. 79), MOD1F22 (SEQ ID No. 80), MOD1R22 (SEQ ID No. 81), MOD1F3 (SEQ ID No. 82), MOD1R3 (SEQ ID No. 83), MOD1F42 (SEQ ID No. 84), MOD1R4 (SEQ ID No. 85), MOD1R52 (SEQ ID No. 87), MOD1F7 (SEQ ID No. 90), and LR17 (SEQ ID No. 101), the following oligonucleotide primers are synthesized for PCR:

```
                                (MOD1F52; SEQ ID No. 94)
5'-gggtctggga cagacttcac cctcaccatc tctagtctgc agccggagga ttttgcagat tat-3'

(MOD1F63; SEQ ID No. 95)
5'-ttctgtcagc aatatagcag ctatcggacg ttcggtggag gcaccaaggt ggaaatc-3'

(MOD1R63; SEQ ID No. 96)
5'-cgtccgatag ctgctatatt gctgacagaa ataatctgca aaatcctccg gctgcag-3'

(MOD1R72; SEQ ID No. 102)
5'-gaagatgaag acagatggtg cagccacagt ccgtttgatt tccaccttgg tgcctccacc gaa-3'
```

2) Construction of Plasmid pCR3.1/LM5-3-42 (Cloning of Humanized TRA-8 Light Chain Type LM5)

LM5-DNA fragment coding for the amino acid sequence as defined in SEQ ID No. 75 of the same is prepared by performing 2-step PCR, inserted into a plasmid vector and cloned in *E. coli*.

a) First Step PCR

LM5-F51B-DNA fragment coding for a secretion signal sequence region with a Hind III restriction enzyme cleavage site added at the 5'-end, $FRL_1$, $CDRL_1$, $FRL_2$, $CDRL_2$, $FRL_3$, $CDRL_3$, $FRL_4$ and a portion of the constant region is prepared under the following conditions.

Composition of the Reaction Solution:
    oligonucleotide primer MOD1F1, 5 pmol
    oligonucleotide primer MOD1R1, 5 pmol
    oligonucleotide primer MOD1F22, 5 pmol
    oligonucleotide primer MOD1R22, 5 pmol
    oligonucleotide primer MOD1F3, 5 pmol
    oligonucleotide primer MOD1R3, 5 pmol
    oligonucleotide primer MOD1F42, 5 pmol
    oligonucleotide primer MOD1R4, 5 pmol
    oligonucleotide primer MOD1F52, 5 pmol
    oligonucleotide primer MOD1R52, 5 pmol
    oligonucleotide primer MOD1F63, 5 pmol
    oligonucleotide primer MOD1R63, 5 pmol
    oligonucleotide primer MOD1F7, 50 pmol
    oligonucleotide primer MOD1R72, 5 pmol
    oligonucleotide primer 7AL1P, 50 pmol
    oligonucleotide primer LR17, 50 pmol
    dNTPs cocktail, 5 μl
    10×PCR buffer, 5 μl
    ampliTaq DNA polymerase, 2.5 units The reaction solution having the above composition is adjusted to a final volume of 50 μl by adding redistilled water and used in PCR.

PCR thermal conditions: Heating at 94° C. for 2 minutes, after which a thermal cycle of 94° C. for 1 minute, 55° C. for 1 minute and 72° C. for 2 minutes, repeated 30 times, followed by heating at 72° C. for 10 minutes.

LM5-F51C-DNA fragment coding for a portion of the constant region with an Eco R I restriction enzyme cleavage site added at the 3'-end is prepared under the following conditions. The template plasmids, pSRPDHH, is obtained by following the description in an European patent application EP 0 909 816 A1.

Composition of the Reaction Solution:
plasmid pSRPDHH DNA, 25 ng
oligonucleotide primer MOD1F7, 50 pmol
oligonucleotide primer 7ALCN, 50 pmol
dNTPs cocktail, 5 µl
10×PCR buffer, 5 µl
ampliTaq DNA polymerase, 2.5 units The reaction solution having the above composition is adjusted to a final volume of 50 µl by adding redistilled water and used in PCR.

PCR thermal conditions: Heating at 94° C. for 2 minutes, after which a thermal cycle of 94° C. for 1 minute, 55° C. for 1 minute and 72° C. for 2 minutes, repeated 30 times, followed by heating at 72° C. for 10 minutes.

The amplified DNA fragments after PCR are separated by 5% polyacrylamide gel electrophoresis. The gel after electrophoresis is stained with 1 µg/ml of ethidium bromide to detect the produced DNA under UV light. The respective DNA bands thus detected are excised with a razor blade.

b) Second Step PCR

LM5-DNA in which above described LM5-F51B-DNA, and LM5-F51C-DNA fragments are fused is prepared under the following conditions.

Composition of the Reaction Solution:
Gel fragment of LM5-F51B-DNA prepared in the first step PCR,
Gel fragment of LM5-F51C-DNA prepared in the first step PCR,
oligonucleotide primer 7AL1P, 50 pmol
oligonucleotide primer 7ALCN, 50 pmol
dNTPs cocktail, 5.0 µl
10×PCR buffer, 5.0 µl
ampliTaq DNA polymerase, 2.5 units The reaction solution having the above composition is adjusted to a final volume of 50 µl by adding redistilled water and used in PCR.

PCR thermal conditions: Heating at 94° C. for 2 minutes, after which a thermal cycle of 94° C. for 1 minute, 55° C. for 1 minute and 72° C. for 2 minutes, repeated 30 times, followed by heating at 72° C. for 10 minutes.

The thus prepared LM5-DNA fragment is inserted into plasmid pCR3.1DNA using Eukaryotic TA cloning Kit (InVitrogen) following the manufacturer's protocol and introduced into the competent E. Coli TOP10F' contained in the kit. The nucleotide sequences of these DNAs encoding the light chain of humanized LM5 TRA-8 are confirmed by the dideoxy method (Sanger, F. S., et al., (1977), Proc. Natl. Acad. Sci. USA, 74:5463-5467) using DNA analyzer.

The resulting plasmids are designated pCR3.1/LM5-3-42 (the plasmid carrying cDNA encoding the light chain variable region of humanized LM5 TRA-8 and a human Ig light chain constant region).

The obtained plasmid pCR3.1/LM5-3-42 containing LM5-DNA fragment is digested with the restriction enzymes Hind III and EcoR I.

One µg of cloning plasmid pHSG399 DNA is digested with the restriction enzymes Hind III and EcoR I, and then dephosphorylated with CIP. The resulting dephosphorylated pHSG399 DNA and LM5-DNA fragment, that had been digested with the restriction enzymes Hind III and EcoR I, are ligated using DNA Ligation Kit Version 2.0 (Takara Syuzo, Co. Ltd.). Then, E. coli DH5α is transformed with the ligated DNA and spread onto LB agar medium containing 0.1 mM IPTG, 0.1% X-Gal and 50 µg/ml chloramphenicol (final concentrations). The white transformants obtained are cultured in liquid LB medium containing 50 µg/ml chloramphenicol, and plasmid DNA is extracted from the resulting culture according to the alkaline-SDS method. The extracted plasmid DNA is digested with Hind III and EcoR I, and then a clone carrying LM5-DNA fragment is selected by 1% agarose gel electrophoresis.

As a result of the above procedure, plasmid pHSG/M5-3-27 carrying a fusion fragment of the variable region of the humanized LM5 TRA-8 light chain and the constant region of human Igκ chain is obtained.

3) Construction of Plasmid pSR/LM5-3-27-1 (Expression Plasmid for Humanized LM5 TRA-8 Light Chain)

The obtained plasmid pHSG/M5-3-27 carrying a fusion fragment of the variable region of the humanized LM5 TRA-8 light chain and the constant region of human Igκ chain is digested with the restriction enzymes Hind III and EcoR I.

One µg of cloning plasmid pSRPDHH DNA (European patent application EP 0 909 816 A1) is digested with the restriction enzymes Hind III and EcoR I, and then dephosphorylated with CIP. The resulting dephosphorylated pSRPDHH DNA and HindIII-EcoRI DNA fragment obtained from pHSG/M5-3-27 are ligated using DNA Ligation Kit Version 2.0 (Takara Syuzo, Co. Ltd.). Then, E. coli DH5α is transformed with the ligated DNA and spread onto LB agar. The transformants obtained are cultured in liquid LB medium containing 100 µg/ml ampicillin, and plasmid DNA is extracted from the resulting culture according to the alkaline-SDS method. The insertion and orientation of the desired DNA fragment in pSRPDHH vector is confirmed by DNA sequencing using a gene sequence analyzer (ABI PRISM® 3700 DNA Analyzer; Applied Biosystems).

The resulting expression plasmid carrying cDNA encoding the light chain of humanized LM5 TRA-8 is designated pSR/LM5-3-27-1.

(4.5) Construction of an Expression Vector for the Light Chain of the Humanized Antibody(Chimera Type)

The sequence shown in SEQ ID No. 76 of the Sequence Listing, the amino acid sequence of the light chain of chimera type TRA-8, is designated LM6.

Expression plasmids carrying this type of humanized light chain amino acid sequences of the anti-human DR5 antibody TRA-8 (LM6 type) (SEQ ID No. 75 of the Sequence Listing) is constructed as follows.

1) Synthesis of Primers for Preparing the Variable and Constant Regions of the Light Chain of Humanized LM6 TRA-8

DNA coding for the LM6 polypeptide chain (SEQ ID No. 75 of the Sequence Listing), each of which is a fusion of the variable region of mouse anti-DR5 antibody TRA-8 light chain (LM6 type) and the constant region of the human Ig light chain (κ chain), are respectively synthesized by using combinations of PCR.

Further to 7AL1P (SEQ ID No. 47) and 7ALCN (SEQ ID No. 48), the following oligonucleotide primers are synthesized for PCR:

```
                                      (HKSPR13; SEQ ID No. 97)
5'-tgatgtggac atgaatttgt gagactgggt catcacaatg tcaccagtgg a-3';

(MVF11; SEQ ID No. 98)
5'-tgggttccag gctccactgg tgacattgtg atgacccagt ctcacaaatt c-3';

(MVR11; SEQ ID No. 99)
5'-aagacagatg gtgcagccac agcccgtttg atttccagct tggtgcctc-3';
and
```

-continued (MCF11; SEQ ID No. 100)
5'-aagctggaaa tcaaacgggc tgtggctgca ccatctgtct tcatc-3'.

2) Construction of Plasmid pCR3.1/LM6-1-16 (Cloning of Humanized TRA-8 Light Chain Type LM6)

LM6-DNA fragment coding for the amino acid sequence as defined in SEQ ID No. 75 of the same is prepared by performing 2-step PCR, inserted into a plasmid vector and cloned in *E. coli*.

a) First Step PCR

LM6-F1-DNA fragment coding for a secretion signal sequence and a portion of $FRL_1$ region with a Hind III restriction enzyme cleavage site added at the 5'-end is prepared under the following conditions. The template plasmids, pHSGHM17 and pSRPDHH, are obtained by following the description in a European patent application EP 0 909 816 A1.
Composition of the Reaction Solution:
  plasmid pHSGHM17 DNA, 25 ng
  oligonucleotide primer 7AL1P, 50 pmol
  oligonucleotide primer HKSPR13, 50 pmol
  dNTPs cocktail, 5 μl
  10×PCR buffer, 5 μl
  ampliTaq DNA polymerase (PerkinElmer), 2.5 units
The reaction solution having the above composition is adjusted to a final volume of 50 μl by adding redistilled water and used in PCR.

PCR thermal conditions: Heating at 94° C. for 2 minutes, after which a thermal cycle of 94° C. for 1 minute, 55° C. for 1 minute and 72° C. for 2 minutes, repeated 30 times, followed by heating at 72° C. for 10 minutes.

LM6-F2-DNA fragment coding for a portion of $FRL_1$, $CDRL_1$, $FRL_2$, $CDRL_2$, $FRL_3$, $CDRL_3$, $FRL_4$ and a portion of the constant region is prepared under the following conditions.
Composition of the Reaction Solution:
  plasmid pL28 DNA, 25 ng
  oligonucleotide primer MVF11, 50 pmol
  oligonucleotide primer MVR12, 50 pmol
  dNTPs cocktail, 5 μl
  10×PCR buffer, 5 μl
  ampliTaq DNA polymerase, 2.5 units
The reaction solution having the above composition is adjusted to a final volume of 50 μl by adding redistilled water and used in PCR.

PCR thermal conditions: Heating at 94° C. for 2 minutes, after which a thermal cycle of 94° C. for 1 minute, 55° C. for 1 minute and 72° C. for 2 minutes, repeated 30 times, followed by heating at 72° C. for 10 minutes.

LM6-F3-DNA fragment coding for a portion of $FRL_4$ and the constant region with an EcoR I restriction enzyme cleavage site added at the 3'-end is prepared under the following conditions.
Composition of the Reaction Solution:
  plasmid pSRPDHH DNA, 25 ng
  oligonucleotide primer MCF11, 50 pmol
  oligonucleotide primer 7ALCN, 50 pmol
  dNTPs cocktail, 5 μl
  10×PCR buffer, 5 μl
  ampliTaq DNA polymerase, 2.5 units
The reaction solution having the above composition is adjusted to a final volume of 50 μl by adding redistilled water and used in PCR.

PCR thermal conditions: Heating at 94° C. for 2 minutes, after which a thermal cycle of 94° C. for 1 minute, 55° C. for 1 minute and 72° C. for 2 minutes, repeated 30 times, followed by heating at 72° C. for 10 minutes.

The amplified DNA fragments after PCR are separated by 5% polyacrylamide gel electrophoresis. The gel after electrophoresis is stained with 1 μg/ml of ethidium bromide to detect the produced DNA under UV light. The respective DNA bands thus detected are excised with a razor blade.

b) Second Step PCR

LM6-DNA in which above described LM6-F1-DNA, LM6-F2-DNA, and LM6-F3-DNA fragments are fused is prepared under the following conditions.
Composition of the Reaction Solution:
  Gel fragment of LM6-F1-DNA prepared in the first step PCR,
  Gel fragment of LM6-F2-DNA prepared in the first step PCR,
  Gel fragment of LM6-F3-DNA prepared in the first step PCR,
  oligonucleotide primer 7AL1P, 50 pmol
  oligonucleotide primer 7ALCN, 50 pmol
  dNTPs cocktail, 5.0 μl
  10×PCR buffer, 5.0 μl
  ampliTaq DNA polymerase, 2.5 units
The reaction solution having the above composition is adjusted to a final volume of 50 μl by adding redistilled water and used in PCR.

PCR thermal conditions: Heating at 94° C. for 2 minutes, after which a thermal cycle of 94° C. for 1 minute, 55° C. for 1 minute and 72° C. for 2 minutes, repeated 30 times, followed by heating at 72° C. for 10 minutes.

The thus prepared LM6-DNA fragment is inserted into plasmid pCR3.1DNA using Eukaryotic TA cloning Kit (Invitrogen) following the manufacturer's protocol and introduced into the competent *E. Coli* TOP10F' contained in the kit. The nucleotide sequences of these DNAs encoding the light chain of humanized TRA-8 are confirmed by the dideoxy method using a DNA analyzer.

The resulting plasmids are designated pCR3.1/LM6-1-16 (the plasmid carrying cDNA encoding the light chain variable region of mouse TRA-8 and a human 1g light chain constant region).

The obtained plasmid pCR3.1/LM6-1-16 containing LM6-DNA fragment is digested with the restriction enzymes Hind III and EcoR I.

One μg of cloning plasmid pHSG399 DNA is digested with the restriction enzymes Hind III and EcoR I, and then dephosphorylated with CIP. The resulting dephosphorylated pHSG399 DNA and LM6-DNA fragment, that had been digested with the restriction enzymes Hind III and EcoR I, are ligated using DNA Ligation Kit Version 2.0 (Takara Syuzo, Co. Ltd.). Then, *E. coli* DH5α is transformed with the ligated DNA and spread onto LB agar medium containing 0.1 mM IPTG, 0.1% X-Gal and 50 μg/ml chloramphenicol (final concentrations). The white transformants obtained are cultured in liquid LB medium containing 50 μg/ml chloramphenicol, and plasmid DNA is extracted from the resulting culture according to the alkaline-SDS method. The extracted plasmid DNA is digested with Hind III and EcoR I, and then a clone carrying LM6-DNA fragment is selected by 1% agarose gel electrophoresis.

As a result of the above procedure, plasmid pHSG/M6-1-4-1 carrying a fusion fragment of the variable region of the mouse TRA-8 light chain and the constant region of human Igκ chain is obtained. The transformant *E coli* strain harboring these plasmid, designated as *E. coli* DH5α/pHSG/M6-1-4-1 was deposited with International Patent Organism Depositary, National Institute of Advanced Industrial Science and Technology, 1-1, Higashi 1 chome Tsukuba-shi, Ibaraki-ken, 305-5466, Japan on Apr. 20, 2001, in accordance with the Budapest Treaty for the Deposit of Microorganisms, and was accorded the accession number FERM BP-7566.

3) Construction of Plasmid pSR/LM6-1-4-6(Expression Plasmid for Chimera Type LM6 TRA-8 Light Chain)

The obtained plasmid pHSG/LM6-1-4-1 carrying a fusion fragment of the variable region of the mouse TRA-8 light chain and the constant region of human Igκ chain is digested with the restriction enzymes Hind III and EcoR I.

One µg of cloning plasmid pSRPDHH DNA is digested with the restriction enzymes Hind III and EcoR I, and then dephosphorylated with CIP. The resulting dephosphorylated pSRPDHH DNA and HindIII-EcoRI DNA fragment obtained from pHSG/LM6-1-4-1 are ligated using DNA Ligation Kit Version 2.0 (Takara Syuzo, Co. Ltd.). Then, E. coli DH5α is transformed with the ligated DNA and spread onto LB agar. The transformants obtained are cultured in liquid LB medium containing 100 µg/ml ampicillin, and plasmid DNA is extracted from the resulting culture according to the alkaline-SDS method. The insertion and orientation of the desired DNA fragment in the vector is confirmed by DNA sequencing using a gene sequence analyzer.

The resulting expression plasmid carrying cDNA encoding the light chain of TRA-8 (chimera type) is designated pSR/LM6-1-4-6.

(5) Production of Several Types-Humanized or Chimeric TRA-8 Antibody

Transfection of COS-7 cells is conducted by FUGENE6 transfection reagent methods (Boehringer Mannheim Biochemica) according to the instruction manual provided with the kit.

COS-7 cells (American Type Culture Collection No. CRL-1651) are grown to semi-confluent ($3\times10^6$ cells/dish) in a culture dish (culture area: 57 $cm^2$; Sumitomo Bakelite) containing Dulbecco's Modified Eagle medium (hereinafter referred to as "D-MED"; Gibco BRL) supplemented with 10% fetal calf serum (hereinafter abbreviated as "FCS"; Moregate).

In the meantime, 10 µg/dish (total 5 dishes) of the humanized DR5 heavy chain expression plasmid DNA (pHA15-1) and 10 µg/dish of the humanized DR5 light chain expression plasmid DNA prepared by the alkaline-SDS method and cesium chloride density gradient centrifugation are mixed, and then precipitated with ethanol, followed by suspending in 5 µl/dish of $dH_2O$.

After 15 µl/dish of FUGENE6 Transfection regent is mixed with 180 µl/dish D-MEM without FCS, this FUGENE solution (185 µl/dish) is mixed with 5 µl/dish DNA solution containing 10 µg/dish of the humanized DR5 heavy chain expression plasmid DNA and 10 µg/dish of the humanized DR5 light chain expression plasmid DNA. After 15 minutes incubation at room temperature, the obtained plasmid suspension (200 µl) is added to the previously prepared COS-7 plates. After incubating in 5% $CO_2$ at 37° C. for 24 hours, the culture medium is changed with D-MEM without FCS. After incubating in 5% $CO_2$ at 37° C. for 72 hours, the culture supernatant is recovered to purify the expression products in the supernatant fluids. By the method as described above, COS-7 cells are transfected with each of the following plasmid combinations:

(A): cotransfection of pHA15-1 and pSR/LM1-2 (H1L1)
(B): cotransfection of pHB14-1 and pSR/M2-1 (H2L2)
(C): cotransfection of pHB14-1 and pSR/LM3-3-44-10 (H2L3)
(D): cotransfection of pHB14-1 and pSR/LM4-5-3-3 (H2L4)
(E): cotransfection of pHC10-3 and pSR/M2-1 (H3L2)
(F): cotransfection of pHC10-3 and pSR/LM3-3-44-10 (H3L3)
(G): cotransfection of pHC10-3 and pSR/LM4-5-3-3 (H3L4)
(H): cotransfection of pHD21-1 and pSR/LM5-3-27-1 (H4L5)
(I): cotransfection of pM11-1 and pSR/LM6-1-4-6 (Chimera)

The culture is then centrifuged (3,500 r.p.m., 15 minutes) and collected the supernatant. The supernatant is filtrated with 0.45 µm filter (ADVANTEC TOYO DISMIC-25cs, Cat #25CS045 AS). The purification of IgG from the filtrates are achieved using Protein G-POROS affinity chromatography (Applied Biosystems) under the following conditions:

HPLC system: BioCAD 700E (Applied Biosystems)
column: ProteinG-ID sensor cartridge
(column size: 2.1 mmID×30 mm LD, bed volume: 0.1 ml; Applied Biosystems)
elution buffer: 0.1 M Glycine-HCl (pH 2.5)
neutralization buffer: 1 M Tris-HCl (pH 8.5)
detection: 280 nm
flow rate: 1 ml/min
fraction size: 0.5 ml/0.5 min
fraction tube: 1.5 ml polypropylene microtube
temperature: 4° C.

After all the filtrates are applied to column, 50 ml of PBS (Sigma, Cat #1000-3) is used to wash column. When the elution buffer is applied, fraction collector started. Each fraction microtube previously contained 55 µl of 1 M NaCl, 110 µl of neutralization buffer and 74 µl of 2 mg/ml bovine serum albumin (Sigma, Cat #A-7030) in PBS. The fractions from No. 7 through No. 8 are collected.

Verification of the expression of the humanized antibodies and quantitative assay of the expression products in the culture supernatant fluids prepared is performed by ELISA with an antibody against anti-human IgG.

To each well of a 96-well plate (MaxiSorp, Nunc), 100 µl of goat anti-human IgG Fc specific polyclonal antibody (Kappel) dissolved at the final concentration of 0.5 µg/ml in adsorption buffer (0.05 M sodium hydrogencarbonate, 0.02% sodium azide, pH 9.6) is added and the plate is incubated at 37° C. for 2 hours to cause adsorption of the antibody. Then, the plate is washed with 350 µl of PBS-T five times. To the wells after washing, the culture supernatant diluted with D-MEM containing 10% FCS is added and incubated at 37° C. for 2 hours. After washing again with PBS-T, 100 µl of alkaline phosphatase-labeled goat anti-human IgG Fc specific polyclonal antibody (Jackson Immuno Research Lab.) diluted 10,000-fold with PBS-T is added to each well and incubated at 37° C. for 2 hours. After washing again with PBS-T, a substrate solution of p-nitrophenyl phosphate obtained from Alkaline Phosphatase Substrate kit (Bio Rad) is added according to the instruction manual provided with the kit. After incubating at 37° C. for 0.5 to 1 hour, the absorbance at 405 nm is measured. In the present experiments, human plasma immunoglobulin G subclass 1 (IgG1) (Biopure AG) diluted with D-MEM containing 10% FCS to certain concentrations is used as concentration reference samples of the humanized DR5 antibodies contained in the culture supernatant fluids.

As a result, the expression and purified products in the culture supernatant are detected specifically with the anti-human IgG antibody. The final concentration of human IgG antibody is 44.03 µg/ml (H1L1), 39.8 µg/ml (H2L2), 26.7 µg/ml (H2L3), 41.0 µg/ml (H2L4), 39.3 µg/ml (H3L2), 24.7

µg/ml (H3L3), 21.5 µg/ml (H3L4), 16.7 µg/ml (H4L5) and 18.3 µg/ml (chimera), respectively.

(6) Apoptosis-Inducing Activity of Several Types Humanized Antibody or Chimeric Antibody Jurkat cells (ATCC No. TIB-152), are used to examine the apoptosis-inducing activity of the purified humanized TRA-8 antibody.

Jurkat cells cultured in RPMI1640 medium with 10% FCS (Gibco BRL) at 37° C. for 3 days in the presence of 5% $CO_2$ are dispensed into each well of a 96-well microplate (Sumitomo Bakelite) at 50 µl per well. The humanized TRA-8 prepared in this Example 26 are adjusted to have the concentration of the final product of interest of 100 ng/ml with RPMI1640 medium containing 10% FCS by estimating their concentrations in the fluids according to the method described in Example 26. Each of the solutions of the expression products thus adjusted to 100 ng/ml is used to produce serial dilutions by repeating serial 2-fold dilution with RPMI1640 containing 10% FCS. Each of the diluted humanized TRA-8 solution (H1L1, H2L2, H2L3, H2L4, H3L3, H3L4 or H4L5) is added to each well at 50 µl per well. After reacting at 37° C. for 12 hours, 50 µl of 25 µM PMS containing 1 mg/ml XTT is added (final concentrations of 250 µg/ml for XTT and 5 µM for PMS). After incubating for 3 hours, the absorbance at 450 nm of each well is measured to calculate the cell viability by using the reduction ability of mitochondria as the index.

The viability of the cells in each well is calculated according to the following formula:

$$\text{Viability}(\%) = 100 \times (a-b)/(c-b)$$

wherein "a" is the measurement of a test well, "b" is the measurement of a well with no cells, and "c" is the measurement of a well with no antibody added.

As a result, the tested humanized antibodies are demonstrated to induce apoptosis in cells of T lymphoma cell line expressing human DR5 antigen.

Furthermore, the apoptosis-inducing activity of humanized TRA-8 to PC-3 is examined by adding taxol according to the method described in Example 25.

Human prostate cancer cell line PC-3 (ATCC No. CRL-1435) is obtained from American Tissue Culture Collection (ATCC) and maintained in F-12K Nutrient Mixture (21127-022, Gibco BRL) containing 10% fetal bovine serum (FBS, Hyclone), 1% L-Glutamine-200 mM (25030-149, Gibco BRL) and 0.5% Penicillin Streptomycin Solution (P-7539, Sigma). RPMI1640 medium (MED-008, IWAKI) supplemented with 10% FBS and 0.5% Penicillin Streptomycin Solution is used in the following experiment. Exponentially growing PC-3 cells are collected by trypsinization and washed twice with fresh medium. The cells are then counted, resuspended in fresh medium at a density of $5 \times 10^4$ cells/ml and distributed in triplicate into flat-bottomed 96 well plates (3598, Corning-Coster) in a total volume of 100 µl/well one day before the start of the experiment. A representative anticancer drug, Paclitaxel (169-18611, Wako) dissolved in dimethylsulfoxide (10 mg/ml) is diluted in fresh medium and then added to the 96-well plates containing the cells at 50 µl/well. The final concentrations of dimethylsulfoxide are less than 0.1%. After incubation for 24 hr at 37° C. in 5% $CO_2$ atmosphere, humanized TRA-8 antibody (H1L1, H2L2, H2L3, H2L4, H3L2, H3L3, H3L4 or H4L5) diluted in fresh medium is added to the wells. After incubation for a further 24 hr, 50 µl of Minimum Essential Medium (11095-098, Gibco BRL) containing 1 mg/ml of XTT and 25 mM of PMS is added to the wells and the plates are incubated for 6 hr. OD450 is then measured by ARVO HTS 1420 Multilabel Counter (Wallac Berthold) and the cell viability is calculated as follows.

Cell viability(%)=(OD450 for the well containing cells treated with Taxol and humanized TRA-8 (agent(s))−OD450 for the well containing neither cells nor agent)×100/(OD450 for the well containing cells with no agent−OD450 for the well containing neither cells nor agent)

As a result, the tested humanized antibodies are demonstrated to induce apoptosis in human prostate cancer cells expressing human DR5 antigen.

Any patents or publications mentioned in the specification are indicative of the level of those skilled in the art to which the invention pertains. These patents and publications are herein incorporated by reference to the same extent as if each individual publication was specifically and individually indicated to be incorporated by reference.

The present invention is not limited in scope by the above-referenced deposit or the embodiments disclosed in the examples which are intended as illustrations of a few aspects of the invention and any embodiments which are functionally equivalent are within the scope of this invention. Various modifications of the invention in addition to those shown and described herein will become apparent to those skilled in the art and are intended to fall within the scope of the appended claims.

REFERENCES

1. Wiley S R, Schooley K, Smolak P J, Din W S, Huang C P, Nicholl J K, Sutherland G R, Smith T D, Rauch C, Smith C A, et al. Immunity 1995 December; 3(6):673-82
2. Pan G, O'Rourke K, Chinnaiyan A M, Gentz R, Ebner R, Ni J, Dixit V M Science 1997 Apr. 4; 276(5309):111-3
3. Walczak H, Degli-Esposti M A, Johnson R S, Smolak P J, Waugh J Y, Boiani N, Timour M S, Gerhart M J, Schooley K A, Smith C A, Goodwin R G, Rauch C T. EMBO J 1997 Sep. 1; 16(17):5386-97
4. MacFarlane M, Ahmad M, Srinivasula S M, Fernandes-Alnemri T, Cohen G M, Alnemri E S. J Biol Chem 1997 Oct. 10; 272(41):25417-20.
5. Degli-Esposti M A, Dougall W C, Smolak P J, Waugh J Y, Smith C A, Goodwin R G. Immunity 1997 December; 7(6):813-20
6. Chaudhary P M, Eby M, Jasmin A, Bookwalter A, Murray J, Hood L. Immunity 1997 December; 7(6):821-30
7. Schneider P, Thome M, Burns K, Bodmer J L, Hofmann K, Kataoka T, Holler N, Tschopp J. Immunity 1997 December; 7(6):831-6
8. Degli-Esposti M A, Smolak P J, Walczak H, Waugh J, Huang C P, DuBose R F, Goodwin R G, Smith C A. J Exp Med 1997 Oct. 6; 186(7):1165-70
9. Sheridan J P, Marsters S A, Pitti R M, Gurney A, Skubatch M, Baldwin D, Ramakrishnan L, Gray C L, Baker K, Wood W I, Goddard A D, Godowski P, Ashkenazi A. Science 1997 Aug. 8; 277(5327):818-21
10. Pan G, Ni J, Wei Y F, Yu G, Gentz R, Dixit V M. Science 1997 Aug. 8; 277(5327):815-818
11. Marsters S A, Sheridan J P, Pitti R M, Huang A, Skubatch M, Baldwin D, Yuan J, Gurney A, Goddard A D, Godowski P, Ashkenazi A. Curr Biol 1997 Dec. 1; 7(12):1003-6
12. Emery J G, McDonnell P, Burke M B, Deen K C, Lyn S, Silverman C, Dul E, Appelbaum E R, Eichman C, DiPrinzio R, Dodds R A, James I E, Rosenberg M, Lee J C, Young P R. J Biol Chem 1998 Jun. 5; 273(23):14363-7

13. Walczak H, Miller R E, Ariail K, Gliniak B, Griffith T S, Kubin M, Chin W, Jones J, Woodward A, Le T, Smith C, Smolak P, Goodwin R G, Rauch C T, Schuh J C, Lynch D H. Nat Med 1999 February; 5(2):157-63
14. Gazitt Y. Leukemia 1999 November; 13(11):1817-24
15. Rieger J, Naumann U, Glaser T, Ashkenazi A, Weller M. FEBS Lett 1998 May 1; 427(1):124-8
16. Jeremias I, Herr I, Boehler T, Debatin K M. Eur J Immunol 1998 January; 28(1):143-52
17. Martinez-Lorenzo M J, Alava M A, Gamen S, Kim K J, Chuntharapai A, Pineiro A, Naval J, And A. Eur J Immunol 1998 September; 28(9):2714-25
18. Phillips T A, Ni J, Pan G, Ruben S M, Wei Y F, Pace J L, Hunt J S. J Immunol 1999 May 15; 162(10):6053-9
19. Kayagaki N, Yamaguchi N, Nakayama M, Takeda K, Akiba H, Tsutsui H, Okamura H, Nakanishi K, Okumura K, Yagita H. J Immunol 1999 Aug. 15; 163(4):1906-13
20. Johnsen A C, Haux J, Steinkjer B, Nonstad U, Egeberg K, Sundan A, Ashkenazi A, Espevik T. Cytokine 1999 September; 11(9):664-72
21. Zamai L, Ahmad M, Bennett I M, Azzoni L, Alnemri E S, Perussia B. J Exp Med 1998 Dec. 21; 188(12):2375-80
22. Fanger N A, Maliszewski C R, Schooley K, Griffith T S. J Exp Med 1999 Oct. 18; 190(8):1155-64
23. Griffith T S, Wiley S R, Kubin M Z, Sedger L M, Maliszewski C R, Fanger N A. J Exp Med 1999 Apr. 19; 189(8):1343-54
24. Griffith T S, Rauch C T, Smolak P J, Waugh J Y, Boiani N, Lynch D H, Smith C A, Goodwin R G, Kubin M Z. J. Immunology 1999 162: 2597-2605
25. Albani S and Carson D A, 1997 Arthritis and allied conditions, a textbook of rheumatology, 13$^{th}$ edition, volume 2, 979-992.
26. Fujisawa K, Asahara H, Okamoto K, Aono H, Hasunuma T, Kobata T, Iwakura Y, Yonehara S, Sumida T, and Nishioka K. J. Clin. Invest. 1996 98(2): 271-278
27. Zhang H, Yang Y, Horton J L, Samoilova E B, Judge T A, Turka L A, Wilson J M, and Chen Y. 1997 J. Clin. Invest. 100(8), 1951-1957.
28. Roth W, Isenmann S, Naumann U, Kugler S, Bahr M, Dichgans J, Ashkenazi A, Weller M. Locoregional. Biochem Biophys Res Commun 1999 Nov. 19; 265(2):479-83
29. Chinnaiyan A M, Prasad U, Shankar S, Hamstra D A, Shanaiah M, Chenevert T L, Ross B D, Rehemtulla A. Proc. Natl. Acad. Sci. 2000 Feb. 15; 97(4): 1754-1759
30. Arai T, Akiyama Y, Okabe S, Saito K, Iwai T, Yuasa Y. Cancer Lett 1998 Nov. 27; 133(2):197-204
31. Lee S H, Shin M S, Kim H S, Lee H K, Park W S, Kim Y, Lee J H, Han S Y, Park J Y, Oh R R, Jang J J, Han J Y, Lee J Y, Yoo N J. Cancer Res 1999 Nov. 15; 59(22):5683-5686
32. Pai S I, Wu G S, Ozoren N, Wu L, Jen J, Sidransky D, El-Deiry W S. 1998 Cancer Res August 15; 58(16):3513-3518
33. Maniatis et al., 1982, Molecular Cloning, a Laboratory Manual, Cold Spring Harbor Laboratory, Cold Spring Harbor, N.Y.
34. Schroff et al., 1985 Cancer Res., 45, 879-885.
35. Yelton, D. E., et al., 1978 Current Topics in Microbiology and Immunology, 81, 1-7
36. Kohler, G., et al., 1976 European J. Immunology, 6, 511-519
37. Shulman, M., et al., 1978 Nature, 276. 269-270
38. Kearney, J. F., et al., 1979 J. Immunology, 123, 1548-1550
39. Horibata, K. and Harris, A. W., 1975 Nature, 256, 495-497
40. Sheridan J P, Marsters S A, Pith R M, Gurney A, Skubatch M, Baldwin D, Ramakrishinan, Gray C L, Baker K, Wood W I, Goddard A D, Godowski P, and Ashkenazi A, 1997 Science, 277, 818-821.
41. Cheng J et al., 1994 Science, 263, 1759-1762
42. Bendele A M et al., 1999 Clin Exp Rheumatol, 17(5), 553-560
43. Sheridan J P, Marsters A S, Pitti R M, Gurney A, Skubatch M, Baldwin D, Ramakrishnan L, Gray C J, Baker K, Wood W I, Goddard A D, Godowski P, and Ashkenazi A. 1997 Science, 277, 818-821.
44. Schneider P, Thome M, Burns K, Bodmer J L, Hofmann K, Kataoka T, Holler N, Tschopp J., 1997 Immunity December; 7(6): 831-836.
45. Kennedy N J, Kataoka T, Tschopp J, and Budd R C. 1999 J. Exp. Med. 1891-1896.
46. Miiler-Ladner U, Gay R E, and Gay S, 1997 Arthritis and allied conditions, a textbook of rheumatology, 13$^{th}$ edition, Volume 1, 243-254.

What is claimed is:

1. A purified antibody which specifically binds TRAIL receptor DR5, wherein the antibody:
   (a) has apoptosis-inducing activity in vitro in the absence of secondary crosslinking in target cells expressing DR5, wherein the apoptosis-inducing activity in vitro is characterized by less than 70% target cell viability at an antibody concentration of at least 2.5 µg/ml;
   (b) has tumoricidal activity in vivo against tumor cells expressing DR5;
   (c) does not bind TRAIL receptor DR4, DcR1, or DcR2;
   (d) is a monoclonal antibody; and
   (e) does not block TRAIL-induced apoptosis.

2. The purified antibody of claim 1, wherein the antibody is a humanized antibody.

3. The purified antibody of claim 1, wherein the antibody is a human antibody.

4. The purified antibody of claim 1, wherein the DR5 is human DR5.

5. The purified antibody of claim 1, wherein the antibody has the same epitope specificity as an antibody produced by mouse-mouse hybridoma TRA-1 having ATCC Accession Number PTA-1741.

6. The purified antibody of claim 1, wherein the antibody is a monoclonal antibody produced by the mouse-mouse hybridoma TRA-1 having ATCC Accession Number PTA-1741.

7. The purified antibody of claim 1, wherein the apoptosis-inducing activity is characterized by less than 60% target cell viability at an antibody concentration of 5 µg/ml.

8. The purified antibody of claim 1, wherein the apoptosis-inducing activity is characterized by less than 20% target cell viability at an antibody concentration of 2.5 µg/ml.

9. A composition comprising the antibody of claim 1 and a pharmaceutically acceptable carrier.

10. The composition of claim 9, wherein the antibody is present at a concentration from 0.2 ng to 2000 ng/ml of the carrier.

11. A kit comprising the antibody of claim 1 in a container.

12. A method for selectively inducing apoptosis of target cells expressing DR5, comprising the step of contacting the target cells expressing DR5 with the antibody of claim 1, wherein the antibody selectively induces apoptosis of the target cells expressing DR5.

13. A method for treating cancer in a subject, comprising administering to the subject a composition comprising a pharmaceutically effective amount of the antibody of claim 1, wherein the composition comprising the pharmaceutically effective amount of the antibody selectively induces cell death of cancer cells expressing DR5.

14. The method of claim 13, wherein the composition further comprises a chemotherapeutic agent.

15. The method of claim 14, wherein the chemotherapeutic agent is selected from the group consisting of paclitaxel, doxorubicin, cycloheximide, carboplatin, chlorambucil, cisplatin, colchicine, cyclophosphamide, etoposide, 5-fluorouracil, mitomycin, vincristine, vinblastine, daunorubicin, dactinomycin, melphalan, floxuridine, teniposide, 6-thioguanine, diethylstilbestrol, and methotrexate.

16. The method of claim 13, further comprising administering radiation therapy to the subject.

17. A method for treating a condition associated with downregulated apoptosis compared to normal conditions comprising administering to the subject a composition comprising a pharmaceutically effective amount of the antibody of claim 1, wherein the composition selectively increases apoptosis in the subject.

18. The method of claim 17, wherein the composition further comprises a chemotherapeutic agent.

19. The method of claim 18, wherein the chemotherapeutic agent is selected from the group consisting of paclitaxel, doxorubicin, cycloheximide, carboplatin, chlorambucil, cisplatin, colchicine, cyclophosphamide, etoposide, 5-fluorouracil, mitomycin, vincristine, vinblastine, daunorubicin, dactinomycin, melphalan, floxuridine, teniposide, 6-thioguanine, diethylstilbestrol, and methotrexate.

20. A method of treating an autoimmune or inflammatory condition in a subject, comprising administering to the subject a composition comprising a pharmaceutically effective amount of the antibody of claim 1, wherein the composition comprising the pharmaceutically effective amount of the antibody selectively induces cell death of target cells expressing DR5 associated with the autoimmune or inflammatory condition.

\* \* \* \* \*